US011453710B2

(12) United States Patent
Winston et al.

(10) Patent No.: US 11,453,710 B2
(45) Date of Patent: *Sep. 27, 2022

(54) ACTIVATABLE INTERLEUKIN 12 POLYPEPTIDES AND METHODS OF USE THEREOF

(71) Applicant: Werewolf Therapeutics, Inc., Cambridge, MA (US)

(72) Inventors: William Winston, West Newton, MA (US); Daniel Hicklin, Montclair, NJ (US); Vinay Bhaskar, San Francisco, CA (US); Luke Evnin, San Francisco, CA (US); Patrick Baeuerle, Gauting (DE); Jose Andres Salmeron Garcia, Westminster, MA (US); Heather Brodkin, West Newton, MA (US); Cynthia Seidel-Dugan, Belmont, MA (US)

(73) Assignee: Werewolf Therapeutics, Inc., Cambridge, MA (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/880,624

(22) Filed: May 21, 2020

(65) Prior Publication Data
US 2020/0283489 A1 Sep. 10, 2020

Related U.S. Application Data

(63) Continuation of application No. 16/438,166, filed on Jun. 11, 2019, now Pat. No. 10,696,723, which is a continuation-in-part of application No. PCT/US2019/032322, filed on May 14, 2019.

(60) Provisional application No. 62/756,507, filed on Nov. 6, 2018, provisional application No. 62/756,515, filed on Nov. 6, 2018, provisional application No. 62/756,504, filed on Nov. 6, 2018, provisional application No. 62/671,225, filed on May 14, 2018.

(51) Int. Cl.
C07K 14/54 (2006.01)
C07K 16/28 (2006.01)

(52) U.S. Cl.
CPC ...... C07K 14/5434 (2013.01); C07K 16/2866 (2013.01); C07K 2317/55 (2013.01); C07K 2317/569 (2013.01); C07K 2317/622 (2013.01); C07K 2319/31 (2013.01); C07K 2319/50 (2013.01)

(58) Field of Classification Search
CPC .......................... C07K 14/5434; A61K 38/208
See application file for complete search history.

(56) References Cited

U.S. PATENT DOCUMENTS

| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland |
| 4,816,567 A | 3/1989 | Cabilly et al. |
| 4,927,762 A | 5/1990 | Darfier |
| 4,965,199 A | 10/1990 | Capon et al. |
| 5,089,261 A | 2/1992 | Nitecki et al. |
| 5,122,464 A | 6/1992 | Wilson et al. |
| 5,122,469 A | 6/1992 | Mather et al. |
| 5,208,020 A | 5/1993 | Chari et al. |
| 5,264,365 A | 11/1993 | Georgiou |
| 5,416,064 A | 5/1995 | Chari et al. |
| 5,508,192 A | 4/1996 | Georgiou et al. |
| 5,571,894 A | 11/1996 | Weis et al. |
| 5,587,458 A | 12/1996 | King et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,712,374 A | 1/1998 | Kunstmann et al. |
| 5,714,586 A | 2/1998 | Kunstmann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |

(Continued)

FOREIGN PATENT DOCUMENTS

| DE | 19701141 C1 | 4/1998 |
| EP | 0547163 B1 | 2/2002 |

(Continued)

OTHER PUBLICATIONS

Frelinger et al (2019), ournal of Interferon Cytokine Research, vol. 39, No. 4, pp. 233-245.*
Xue et al., "A tumor-specific pro-IL-12 activates preexisting cytotoxic T cells to control established tumors" Science Immunology, vol. 7, pp. 1-14 (2022).
Xue et al., "Supplementary Materials for A tumor-specific pro-IL-12 activates preexisting cytotoxic T cells to control established tumors" Science Immunology, vol. 7, pp. 1-26, (2022).

(Continued)

*Primary Examiner* — Prema M Mertz
(74) *Attorney, Agent, or Firm* — Hogan Lovells US LLP

(57) ABSTRACT

The disclosure features fusion proteins that are conditionally active variants of IL-12. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g., a steric blocking polypeptide, in sequence to the active cytokine, the cytokine can bind its receptor and effect signaling.

16 Claims, 27 Drawing Sheets

Specification includes a Sequence Listing.

(56) References Cited

U.S. PATENT DOCUMENTS

| | | |
|---|---|---|
| 5,780,588 A | 7/1998 | Pettit et al. |
| 5,834,597 A | 11/1998 | Tso et al. |
| 5,869,046 A | 2/1999 | Presta et al. |
| 5,877,296 A | 3/1999 | Hamann et al. |
| 5,891,693 A | 4/1999 | Bebbington et al. |
| 5,939,598 A | 8/1999 | Kucherlapati et al. |
| 6,027,888 A | 2/2000 | Georgiou et al. |
| 6,075,181 A | 6/2000 | Kucherlapati et al. |
| 6,083,715 A | 7/2000 | Georgiou et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,248,516 B1 | 6/2001 | Winter et al. |
| 6,399,219 B1 | 6/2002 | Welty et al. |
| 6,602,684 B1 | 8/2003 | Umana et al. |
| 6,630,579 B2 | 10/2003 | Chari et al. |
| 6,670,147 B1 | 12/2003 | Heidtman et al. |
| 6,821,505 B2 | 11/2004 | Ward et al. |
| 6,942,853 B2 | 9/2005 | Chernajovsky et al. |
| 7,498,298 B2 | 3/2009 | Doronina et al. |
| 7,514,073 B2 | 4/2009 | Epstein et al. |
| 8,399,219 B2 | 3/2013 | Stagliano et al. |
| 8,563,269 B2 | 10/2013 | Stagliano et al. |
| 8,734,774 B2 | 5/2014 | Frelinger et al. |
| 8,809,504 B2 | 8/2014 | Lauermann et al. |
| 8,969,538 B2 | 3/2015 | Rosen et al. |
| 8,993,266 B2 | 3/2015 | Stagliano et al. |
| 9,206,243 B2 | 12/2015 | Monzon et al. |
| 9,309,510 B2 | 4/2016 | La Porte et al. |
| 9,453,078 B2 | 9/2016 | Stagliano et al. |
| 9,487,590 B2 | 11/2016 | West et al. |
| 9,517,276 B2 | 12/2016 | Lowman et al. |
| 9,540,440 B2 | 1/2017 | Lowman et al. |
| 9,644,016 B2 | 5/2017 | Stagliano et al. |
| 9,708,412 B2 | 7/2017 | Baeuerle et al. |
| 9,737,623 B2 | 8/2017 | Desnoyers et al. |
| 9,856,314 B2 | 1/2018 | Lowman et al. |
| 9,861,705 B2 | 1/2018 | Bossard et al. |
| 9,889,211 B2 | 2/2018 | Lowman et al. |
| 10,059,762 B2 | 8/2018 | Stagliano et al. |
| 10,077,300 B2 | 9/2018 | Daugherty et al. |
| 10,100,106 B2 | 10/2018 | Dubridge et al. |
| 10,138,272 B2 | 11/2018 | Moore et al. |
| 10,179,817 B2 | 1/2019 | Sagert et al. |
| 10,233,244 B2 | 3/2019 | Sagert et al. |
| 10,301,380 B2 | 3/2019 | West et al. |
| 10,261,083 B2 | 4/2019 | Vasiljeva et al. |
| 10,696,723 B2 * | 6/2020 | Winston ............... C07K 14/55 |
| 2002/0164328 A1 | 11/2002 | Shinkawa et al. |
| 2003/0139575 A1 | 7/2003 | Gillies et al. |
| 2003/0157108 A1 | 8/2003 | Presta et al. |
| 2003/0190311 A1 | 10/2003 | Dall'Acqua et al. |
| 2004/0014652 A1 | 1/2004 | Trouet et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0132140 A1 | 7/2004 | Satoh et al. |
| 2004/0136952 A1 | 7/2004 | Bhaskaran et al. |
| 2005/0014934 A1 | 1/2005 | Hinton et al. |
| 2006/0166329 A1 | 7/2006 | Rosen et al. |
| 2006/0205926 A1 | 9/2006 | Ross et al. |
| 2006/0236411 A1 | 10/2006 | Dreher et al. |
| 2007/0048282 A1 | 3/2007 | Rosen et al. |
| 2007/0269422 A1 | 11/2007 | Beimaert et al. |
| 2010/0254944 A1 | 10/2010 | Subramanian et al. |
| 2011/0190209 A1 | 8/2011 | Culbertson et al. |
| 2013/0064788 A1 | 3/2013 | Barnes et al. |
| 2015/0079088 A1 | 3/2015 | Lowman et al. |
| 2015/0087810 A1 | 3/2015 | Moore et al. |
| 2016/0152686 A1 | 6/2016 | Camphausen et al. |
| 2016/0194399 A1 | 7/2016 | Irving et al. |
| 2016/0289324 A1 | 10/2016 | Moore et al. |
| 2016/0311903 A1 | 10/2016 | West et al. |
| 2016/0354472 A1 | 12/2016 | Merchant et al. |
| 2016/0355587 A1 | 12/2016 | West et al. |
| 2017/0044259 A1 | 2/2017 | Tipton et al. |
| 2017/0096472 A1 | 4/2017 | Rosen et al. |
| 2017/0240608 A1 | 8/2017 | Stagliano et al. |
| 2018/0016316 A1 | 1/2018 | Garcia et al. |
| 2018/0134789 A1 | 5/2018 | Baeuerle et al. |
| 2018/0200346 A1 | 7/2018 | Ballance et al. |
| 2018/0303952 A1 | 10/2018 | Sagert et al. |
| 2018/0344810 A1 | 12/2018 | Addepalli et al. |
| 2019/0008978 A1 | 1/2019 | Huang et al. |
| 2019/0016814 A1 | 1/2019 | Humphrey et al. |
| 2019/0117789 A1 | 4/2019 | Carman et al. |
| 2019/0135943 A1 | 5/2019 | Boustany et al. |
| 2019/0225702 A1 | 7/2019 | Baeuerle et al. |

FOREIGN PATENT DOCUMENTS

| | | |
|---|---|---|
| EP | 1867660 A1 | 12/2007 |
| EP | 2639241 A2 | 9/2013 |
| EP | 3134102 A4 | 11/2017 |
| EP | 3792277 A1 | 3/2021 |
| WO | 1987/00195 | 1/1987 |
| WO | 1990/03430 | 4/1990 |
| WO | 1991/01743 | 2/1991 |
| WO | 1993/08829 | 5/1993 |
| WO | 1993/16185 | 8/1993 |
| WO | 1994/11026 | 5/1994 |
| WO | 199429351 | 12/1994 |
| WO | 1996027011 | 9/1996 |
| WO | 1997/30087 | 8/1997 |
| WO | 1998/58964 | 12/1998 |
| WO | 1999/22764 | 5/1999 |
| WO | 1999/51642 | 10/1999 |
| WO | 2000/61739 | 10/2000 |
| WO | 2001/30460 A1 | 5/2001 |
| WO | 2001/079271 A1 | 10/2001 |
| WO | 2002022833 A1 | 3/2002 |
| WO | 2002/43478 | 6/2002 |
| WO | 2002076489 | 10/2002 |
| WO | 2003/011878 | 2/2003 |
| WO | 2003/59934 A2 | 7/2003 |
| WO | 2003/084570 | 10/2003 |
| WO | 2003/085119 | 10/2003 |
| WO | 2004/041865 | 5/2004 |
| WO | 2004/056312 | 7/2004 |
| WO | 2005/035586 | 4/2005 |
| WO | 2005/035778 | 4/2005 |
| WO | 2005/053742 | 6/2005 |
| WO | 2006/106905 A1 | 10/2006 |
| WO | 2006110728 | 10/2006 |
| WO | 2008/147530 A1 | 12/2008 |
| WO | 2009103965 A1 | 8/2009 |
| WO | 2010020766 A2 | 2/2010 |
| WO | 2011/011797 A2 | 1/2011 |
| WO | 2011/124718 | 10/2011 |
| WO | 2011123683 A2 | 10/2011 |
| WO | 2012/059486 | 5/2012 |
| WO | 2013163631 A2 | 10/2013 |
| WO | 20131771897 A2 | 11/2013 |
| WO | 2014100014 A1 | 6/2014 |
| WO | 2014/120555 A1 | 8/2014 |
| WO | 2015066279 A3 | 5/2015 |
| WO | 2016/200645 A1 | 12/2016 |
| WO | 2017156178 A1 | 9/2017 |
| WO | 2018/071918 | 4/2018 |
| WO | 2018071777 A1 | 4/2018 |
| WO | 2018136725 A1 | 4/2018 |
| WO | 2018160877 A1 | 9/2018 |
| WO | 2018160754 A3 | 10/2018 |
| WO | 2018/085555 A8 | 11/2018 |
| WO | 2018204528 A1 | 11/2018 |
| WO | 2018213341 A1 | 11/2018 |
| WO | 2018236701 A1 | 12/2018 |
| WO | 2019/014586 A1 | 1/2019 |
| WO | 2019/018828 A1 | 1/2019 |
| WO | 2019036031 A2 | 2/2019 |
| WO | 2019094396 A1 | 5/2019 |
| WO | 2019/173832 A2 | 9/2019 |
| WO | 2019/214757 A1 | 11/2019 |

(56) References Cited

FOREIGN PATENT DOCUMENTS

| WO | 2019/222294 A1 | 11/2019 |
| WO | 2019/222295 A1 | 11/2019 |
| WO | 2019/246392 | 12/2019 |
| WO | 2020/069398 A1 | 4/2020 |
| WO | 2020/252264 A1 | 12/2020 |
| WO | 2021/016599 A1 | 1/2021 |
| WO | 2021/030483 A1 | 2/2021 |
| WO | 2021202673 A1 | 7/2021 |
| WO | 2021202675 A1 | 7/2021 |
| WO | 2021202678 A1 | 10/2021 |

OTHER PUBLICATIONS

Cao, et al., "Next generation of tumor-activating type I IFN enhances anti-tumor immune responses to overcome therapy resistance", Nature Communications, 12:5866, pp. 1-11 (2021).

Lin et al., Targeting Drug Conjugates to the Tumor Microenvironment: Probody Drug Conjugates, Innovations for Next-Generation Antibody-Drug Conjugates, 2018, 281-298, Humana Press, USA.

Wong et al., In vivo imaging of protease activity by Probody therapeutic activation, Biochimie, Nov. 4, 2015, 62-67, vol. 122, Elsevier, USA.

Desnoyers et al., Tumor-Specific Activation of an EGFR-Targeting Probody Enhances Therapeutic Index, Science Translational Medicine, Oct. 16, 2013, , vol. 5, Issue 207, American Association for the Advancement of Science, USA.

Lebeau et al., Imaging a functional tumorigenic biomarker in the transformed epithelium, PNAS, Jan. 2, 2013, 93-98, vol. 110, Issue 1, National Academy of Sciences, USA.

Jabaiah et al., Identification of protease exosite-interacting peptides that enhance substrate cleavage kinetics, Biol Chem., Sep. 2012, 933-941, vol. 393, Issue 9, ASBMB Publications, USA.

Erster et al., Site-specific targeting of antibody activity in vivo mediated by disease-associated proteases, Journal of Controlled Release, Aug. 10, 2012, 804-812, vol. 161, Issue 3, Elsevier, USA.

Drag et al., Emerging principles in protease-based drug discovery, Nat Rev Drug Discov., Nov. 5, 2010, 690-701, vol. 9, Issue 9, Springer Nature, USA.

Boulware et al., Evolutionary optimization of peptide substrates for proteases that exhibit rapid hydrolysis kinetics, Biotechnol Bioeng., Jun. 15, 2010, 339-46, vol. 106, Issue 3, Wiley, USA.

Darragh et al., Specific targeting of proteolytic activity for tumor detection in vivo, Cancer Res., Feb. 15, 2010, 1505-1512, vol. 70, Issue 5, AACR, USA.

Agard et al., Methods for the proteomic identification of protease substrates, Curr Opin Chem Biol., Dec. 2009, 503-509, vol. 12, Issue 5-6, Elsevier, USA.

Ulisse et al., The urokinase plasminogen activator system: a target for anti-cancer therapy, Curr Cancer Drug Targets, Feb. 2009, 32-71, vol. 9, Issue 1, Bentham Science.

Vartak et al. Matrix metalloproteases: underutilized targets for drug discovery, J Drug Targe, Jan. 2007, 1-20, vol. 15, Issue 1, Taylor & Francis, UK.

Uhland, Matriptase and its putative role in cancer, Cell Mol Life Sci., Dec. 2006, 2968-2978, vol. 63, Issue 24, Springer.

Boulware et al., Protease specificity determination by using cellular libraries of peptide substrates (CLIPS), PNAS, May 16, 2006, 7583-7588, vol. 103, Issue 20, National Academy of Sciences, USA.

Rice et al., Bacterial display using circularly permuted outer membrane protein OmpX yields high affinity peptide ligands, Protein Sci., 825-836, Apr. 2006, vol. 15, Issue 4, Wiley.

Declerck et al., Proteases, extracellular matrix, and cancer: a workshop of the path B study section, Am J Pathol., Apr. 2004, 1131-1139, vol. 164, Issue 4, Elsevier, USA.

Geletu et al., Effect of Caveolin-1 upon Stat3-ptyr705 levels in breast and lung carcinoma cells., Biochem Cell Biol., Apr. 15, 2019, 1-19, Canadian Science Publishing.

Vasiljeva et al., The multifaceted roles of tumor-associated proteases and harnessing their activity for prodrug activation, Biological Chemistry, Apr. 22, 2019, Walter de Gruyter GmbH.

Giesen et al., 8O89Zr-labeled anti-PD-L1 CX-072 PET imaging in human xenograft and syngeneic tumors, Annals of Oncology, Feb. 27, 2019, vol. 30, Issue Supplement 1, Oxford Academic.

Zhao et al., FGFR1β is a driver isoform of FGFR1 alternative splicing in breast cancer cells, Oncotarget, Jan. 1, 2019, 30-44, vol. 10, Issue 1, Impact Journals, LLC.

Osorio et al., Understanding and quantifying the immune microenvironment in hepatocellular carcinoma, Transl Gastroenterol Hepatol. Dec. 24, 2018, 3:107, AME Publishing Company.

Zavrsnik et al., Cystatin C deficiency suppresses tumor growth in a breast cancer model through decreased proliferation of tumor cells, Oncotarget, Apr. 24, 2017, 73793-73809, vol. 8, Issue 43, Impact Journals, LLC.

Desnoyers et al., Tumor-specific activation of an EGFR-targeting probody enhances therapeutic index, Sci Transl Med., Oct. 16, 2013, 1-11, vol. 5, Issue 207, AAAS.

Irving et al., A Clue to Antigen Receptor Tails, J Immunol, May 1, 2014, 4013-4014, vol. 192, Issue 9, The American Association of Immunologists, Inc., USA.

Polu et al., Probody therapeutics for targeting antibodies to diseased tissue, May 20, 2014, Expert Opinion on Biological Therapy, 1049-1053, vol. 14, Issue 8, Taylor & Francis Online.

Lebeau et al., Imaging Active Urokinase Plasminogen Activator in Prostate Cancer, Cancer Res, 1225-1235, vol. 75, Issue 7, AACR, USA.

Pandya et al., PKCα Attenuates Jagged-1-Mediated Notch Signaling in ErbB-2-Positive Breast Cancer to Reverse Trastuzumab Resistance, Clin Cancer Res, 175-186, Jan. 1, 2016, vol. 22 Issue 1, AACR, USA.

Hoos et al., CCR 20th Anniversary Commentary: Immune-Related Response Criteria—Capturing Clinical Activity in Immuno-Oncology, Clin Cancer Res. Nov. 15, 2015, 4989-4991, vol. 21, Issue 22, American Association of Cancer Research, USA.

Adusumilli et al., New Cancer Immunotherapy Agents in Development: a report from an associated program of the 31stAnnual Meeting of the Society for Immunotherapy of Cancer, J Immunother Cancer, Jun. 20, 2017, 1-9, vol. 5, Issue 50, BioMed Central, USA.

Afonina et al., Proteolytic Processing of Interleukin-1 Family Cytokines: Variations on a Common Theme, Immunity Review Jun. 16, 2015, 991-1004, vol. 42, Issue 6, Elsevier, USA.

Halin et al., Synergistic Therapeutic Effectsofa Tumor Targeting Antibody Fragment, Fused to Interleukin 12 and to Tumor Necrosis Factor α, Cancer Research, Jun. 2003, 3202-3210, vol. 63, Issue 12, AACR, USA.

Deluca et al., Potentiation of PD-L1 blockade with a potency-matched dual cytokine-antibody fusion protein leads to cancer eradication in BALB/c-derived tumors but not in other mouse strains, Cancer Immunol Immunother, Sep. 6, 2018, 1381-1391, vol. 67, Issue 9, Springer.

Fercher et al., Evolution of the magic bullet: Single chain antibody fragments for the targeted delivery of immunomodulatory proteins, Exp Biol Med, Jan. 2018, 166-183, vol. 243, Issue 2, Sage Journals.

De Luca et al., Potency-matched Dual Cytokine-Antibody Fusion Proteins for Cancer Therapy. Mol Cancer Ther, Nov. 2017, 2442-2451, vol. 16, Issue 11, AACR, USA.

Kim et al., Novel immunocytokine IL12-SS1 (Fv) inhibits mesothelioma tumor growth in nude mice, PLoS One, Nov. 15, 2013, 1-11, vol. 8, Issue 11, PLOS.

Pedretti et al., Combination of temozolomide with immunocytokine F16-IL2 for the treatment of glioblastoma, Br J Cancer, Sep. 7, 2010, 827-836, vol. 103, Issue 6, SpringerNature, UK.

Kaspar et al., The antibody-mediated targeted delivery of interleukin-15 and GM-CSF to the tumor neovasculature inhibits tumor growth and metastasis, Cancer Res, May 15, 2007, 4940-4098, vol. 67 Issue 10, AACR. USA.

Mitsiades et al., Matrix Metalloproteinase-7-mediated Cleavage of Fas Ligand Protects Tumor Cells from Chemotherapeutic Drug Cytotoxicity, Cancer Research, Jan. 15, 2001, 577-581, vol. 61, AACR, USA.

(56) References Cited

OTHER PUBLICATIONS

John Puskas et al., Development of an attenuated interleukin-2 fusion protein that can be activated by tumour-expressed proteases, Jun. 23, 2011, Immunology, vol. 133, No. 2, pp. 206-220.
Denise Skrombolas et al., Challenges and developing solutions for increasing the benefits of IL-2 treatment in tumor therapy, Expert Review of Clinical Immunology, vol. 10, No. 2, Feb. 1, 2014, pp. 207-217.
William R. Strohl, Fusion Proteins for Half-Life Extension of Biologies as a Strategy to Make Biobetters, Biodrugs, vol. 29, No. 4, Jul. 16, 2015, pp. 215-239.
Rodrigo Vazquez-Lombardi et al., Molecular Engineering of Therapeutic Cytokines, Antibodies, vol. 2 No. 3, Jul. 3, 2013, pp. 426-451.
Bernett et al., "Potency-reduced IL 15/IL 15Ra heterodimeric Fe-fusions display enhanced in vivo activity through increased exposure," Xencor, AACR (2018) Abstract #5565.
Caescu et al., "Active site determinants of substrate recognition by the metalloproteinases TACE and ADAM10," Biochem. J., 424(1):79-88 (2010).
Lindmark et al., "Binding of immunoglobulins to protein A and immunoglobulin levels in mammalian sera," J. Immunol. Meth., 62:1-13 (1983).
Arie et al. "Chaperone function of FkpA, a heat shock prolyl isomerase, in the periplasm of *Escherichia coli*,", Mol. Micro biol. 39:199-210 (2001).
Atwell et al., "Stable heterodimers from remodeling the domain interface of a homodimer using a phage display library," J. Mol. Biol., 270(1):26-35 (1997).
Bachmann, Cellular and Molecular Biology, vol. 2 (Washington, D.C.: American Society for Microbiology), pp. 1190-1219 (1987_.
Barnes et al., "Methods for growth of cultured cells in serum-free medium," Anal. Biochem. 102:255 (1980).
Bass et al., "Hormone phage: an enrichment method for variant proteins with altered binding properties," Proteins, 8:309-314 (1990).
Boerner et al., "Production of antigen-specific human monoclonal antibodies from in vitro-primed human splenocytes," J. Immunol., 147: 86 (1991).
Brennan et al., "Preparation of bispecific antibodies by chemical recombination of monoclonal immunoglobulin G1 fragments," Science, 229:81 (1985).
Brodeur et al.. Monoclonal Antibody Production Techniques and Applications, pp. 51-63 Marcel Dekker, Inc., New York, (1987).
Carter et al., "High level *Escherichia coli* expression and production of a bivalent humanized antibody fragment," BiofTechnology 10:163-167 (1992).
Carter et al., "Bispecific human IgG by design," J. Immunol. Methods, 248: 7-15 (2001).
Chapman et al. "Therapeutic antibody fragments with prolonged in vivo half-lives," Nature Biotechnol., 17:780-783 (1999).
Chari et al., "Immunoconjugates containing novel maytansinoids: promising anticancer drugs," Cancer Res. 52:127-131 (1992).
Chen et al., "Chaperone activity of DsbC," J. Biol Chem. 274:19601-19605 (1999).
Choe et al., "Fe-Binding Ligands of Immunoglobulin G: An Overview of High Affinity Proteins and Peptides," Materials 9(12): 994 (2016).
Cunningham and Wells ,"High-resolution epitope mapping of hGH-receptor interactions by alanine-scanning mutagenesis," Science, 244:1081-1085 (1989).
Davies et al., "Antibody-antigen complexes," Annual Rev Biochem. 59:439-473, (1990).
Dennis et al., "Albumin binding as a general strategy for improving the pharmacokinetics of proteins," JBC 277(38): 35035-35043 (2002).
Dubowchik et al., "Doxorubicin Immunoconjugates Containing Bivalent, Lysosomally-Cleavable Dipeptide Linkages," Bioorg. & Med. Chem. Letters 12:1529-1532 (2002).
Duncan and Winter, "The binding site for C1q on IgG," Nature 322:738-40 (1988).

Damodaran, "Protein PEGylation: An overview of chemistry and process considerations," European Pharmaceutical Review, 15(1): 18-26 (2010).
Firan, M., et al., "The MHC class I-related receptor, FcRn, plays an essential role in the maternofetal transfer of y-globulin in humans," Int. Immunol. 13: 993-1002 (2001).
Fishwild, D. et al.,"High-avidity human IgG kappa monoclonal antibodies from a novel strain of minilocus transgenic mice," Nature Biotechnology 14: 845-851 (1996).
Graham et al., "Characteristics of a human cell line transformed by DNA from human adenovirus type 5," J. Gen Virol. 36:59 (1977).
Gunasekaran et al., "Enhancing antibody Fe heterodimer formation through electrostatic steering effects: applications to bispecific molecules and monovalent IgG," J Biol Chem., 285(25): 19637-19646 (2010).
Guss et al., "Structure of the IgG-binding regions of streptococcal protein G.," EMBO J. 5:15671575 (1986).
Guyer et al., "Immunoglobulin Binding by Mouse Intestinal Epithelial Cell Receptors," J. Immunol. 117:587 (1976).
Ham et al., "Media and Growth Requirements," Meth. Enz. 58:44 (1979).
Hara et al., "Overproduction of Penicillin-Binding Protein 7 Suppresses Thermosensitive Growth Defect at Low Osmolarty due to an spr Mutation of *Escherichia coli*," Microbial Drug Resistance, 2:63-72 (1996).
Hinman et al., "Preparation and characterization of monoclonal antibody conjugates of the calicheamicins: a novel and potent family of antitumor antibiotics," Cancer Res. 53:3336-3342 (1993).
Hudson et al., "Engineered antibodies," Nat. Med., 9:129-134 (2003).
Idusogie et al., "Mapping of the C1q Binding Site on Rituxan, a Chimeric Antibody with a Human IgG1 Fe," J. Immunol., 164:4178-4184, (2000).
Imai-Nishiya et al., "Double knockdown of a1 ,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol., 7:84, 13 pages (2007).
Jefferis et al., "Human immunoglobulin allotypes: Possible implications for immunogenicity," mAbs, 1 (4):332-8 (2009).
Jeffrey et al., "Dipeptide-based highly potent doxorubicin antibody conjugates," Bioorganic & Med. Chem. Letters, 16:358-362 (2006).
Jones et al., "Replacing the complementarity-determining regions in a human antibody with those from a mouse," Mature, 321 :522-525 (1986).
Kim et al., "Localization of the site of the murine IgG1 molecule that is involved in binding to the murine intestinal Fe receptor," European Journal of Immunology, 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem., 45:4336-4343 (2002).
Klein et al., "Progress in overcoming the chain association issue in bispecific heterodimeric IgG antibodies," MAbs, 4 (6):653-663 (2012).
Kontermann et al., "Bispecific antibodies," Drug Discovery Today, 20(7) :838-84 7 (2015).
Kozbor et al., "A human hybrid myeloma for production of human monoclonal antibodies," J. Immunol., 133:3001-5 (1984).
Kratz et al., "Prodrugs of anthracyclines in cancer chemotherapy," Current Med. Chem. 13:477-523 (2006).
Krieg et al., "Improved IL-2 immunotherapy by selective stimulation of IL-2 receptors on lymphocytes and endothelial cells," PNAS, 107(26):11906-11911 (2010).
Lehninger, in Biochemistry, second ed., pp. 73-75, Worth Publishers, New York (1975).
Lode et al., "Targeted Therapy with a Novel Enediyene Antibiotic Calicheamicin theta(I) Effectively Suppresses Growth and Dissemination of Liver Metastases in a Syngeneic Model of Murine Neuroblastoma," Cancer Res., 58:2925-2928 (1998).
Puskas et al, "Development of an attenuated interleukin-2 fusion protein that can be activated by tumour-expressed proteases" Immunology, vol. 133(2), Mar. 23, 2011-Jun. 23, 2011, 206-220.

(56) References Cited

OTHER PUBLICATIONS

Gillies, et al "Improved circulating half-life and efficacy of an antibody-interleukin 2 immunocytokine based on reduced intracellular proteolysis" Clinical Cancer Research, the American Association for Cancer Research, US, 8(1) Jan. 2002, 210-216.
Helguera, et al "Antibody-Cytokine fusion proteins: Harnessing the combined power of cytokines and antibodies for cancer therapy" Clinical immunology 105 Dec. 3, 2002, 233-246.
Penichet et al "Antibody-IL-2 fusion proteins: a novel strategy for immune protection" Human Antibodies 1997, 106-118.
Wang et al Structure of the Quaternary Complex of Interleukin-2 with its alpha, beta, and gamma-c receptors. Science Nov. 18, 2005 vol. 310, 1159-1163.
Lasek et al "Interleukin 12: still a promising candidate for tumor immunotherapy?" Cancer Immunol Immunother (2014) 63:419-435.
Montepaone et al "Profile of ustekinumab and its potential in the treatment of active psoriatic arthritis" Open Access Rheumatol. 2014; 6: 7-13.
Gerber et al Preferential attachment of peritoneal tumor metastases to omental immune aggregates and possible role of a unique vascular microenvironment in metastatic survival and growth. Am J Pathol 169(5): 1739-1752.
Marks-Konczalik et al "IL-2-induced cell death is inhibited in IL-15 transgenic mice." PNAS 2000; 97(21): 11445-11450.
Sadlack et al. "Ulcerative colitis-like disease in mice with a disrupted interleukin 2 gene." Cell 1993; 75: 253-261.
Rochman et al. "New insights into the regulation of T cells by gamma-c family cytokines." Nat Rev Immunol 2009; 9 (7): 480.
Hemar et al. "Endocytosis of Interleukin 2 receptors in human T lymphocytes: distinct intracellular localization and fate of the receptor alpha, beta, and gamma chains." J. Cell Biol. 1995; 129(1): 55-64.
Gao et al. "High-throughput screening using patient-derived tumor xenografts to predict clinical trial drug response." Nature Medicine 2015; 21(11): 1318-1325.
Suzuki et al. "Deregulated T cell activation and autoimmunity in Mice lacking interleukin-2 Receptor Beta." Science 1995; 268: 1472-1476.
Koreth et al. "Interleukin-2 and Regulatory T Cells in Graft-versus-host disease." N. Engl. J. Med. 2011; 365(22): 2055-2066.
Saadoun, et al. "Regulatory T-Cell Responses to Low-Dose Interleukin-2 in HCV-Induced Vasculitis." N. Engl. J. Med. 2011; 365(22): 2067-2077.
Smith, T.F. and Waterman, M.S. "Comparison of biosequences." Advances in applied mathermatics 1981; 2: 482-489.
Willerford, et al. "Interleukin-2 receptor alpha chain regulates the size and content of the peripheral lymphoid compartment." Immunity 1995; 3: 521-530.
Yu, A and Malek, T.R. "The Proteosome regulates receptor-mediated endocytosis of interleukin-2" The Journal of Biological Chemistry 2001; 276(1): 381-385.
Bessard et al. High antitumor activity of RLI, an interleukin-15 (IL-15)-IL-15 receptor alpha fusion protein, in metastatic melanoma and colorectal cancer. Mol Cancer Ther 2009; 8(9): 2736-2745.
Desbois et al IL-15 Trans-signaling with the superagonist RLI Promotes Effector/Memory CD8+ T cell responses and enhances antitumor activity of PD-1 antagonists. 2016 J Immunol 1-11.
Malek, T.R. and Castro, I. Interleukin-2 receptor signaling: at the interface between tolerance and immunity. Immunity 2010 33(2): 153-165.
Berger et al "An Operational definition of epigenetics." Genes Dev 2009; 23: 781-783.
Klatzmann, D and Abbas, A.K. "The promise of low-dose interleukin-2 therapy for autoimmune and inflammatory diseases." Nat. Rev. Immunol. 2015; 15: 283-294.
Oh et al "IL-15 as a mediator of CD4+ help for CD8+ T cell longevity and avoidance of TRAIL-mediated apoptosis." PNAS 2008; 105(13): 5201-5206.

Berger et al "Safety and immunologic effects of IL-15 administration in nonhuman primates." Blood 2009; 114(12): 2417-2426.
Conlon et al "Redistribution, hyperproliferation, activation of natural killer cells and CD8 T cells, and cytokine production during first-in-human clinical trial of recombinant human interleukin-15 in patients with cancer." J Clin Oncol 2015; 33(1): 74-82.
Jana et al "Interleukin-12 (IL-12), but not IL-23, induces the expression of IL-7 in microglia and macrophages: implications for multiple sclerosis." Immunology 2013; 141: 549-563.
Trinchieri et al "The IL-2 family of heterodimeric cytokines: new players in the regulation of T cell responses." Immunity 2003; 19: 641-644.
Skrombolas, et al "Development of protease activated interleukin-12 cytokine fusion proteins for tumor immunotherapy (TUM7P. 946)," The Journal of Immunology; 203:28, 192 (1 Supplement) (2014).
Skrombolas, etl al "Development of an Interleukin-12 Fusion Protein That Is Activated by Cleavage with Matrix Metalloproteinase 9," Journal of Interferon & Cytokine Research, 39(4):233-245 (2019).
Lonberg, et al., "Antigen-specific human antibodies from mice comprising four distinct genetic modifications," Nature 368:856-859 (1994).
Mather et al., "Culture of testicular cells in hormone-supplemented serum-free medium," Annals N.Y. Acad. Sci., 383:44-68 (1982).
Mather, "Establishment and characterization of two distinct mouse testicular epithelial cell lines," Biol. Reprod. 23:243-251 (1980).
Merchant et al., "An efficient route to human bispecific IgG," Nat. Biotechnol., 16(7):677-681 (1988).
Milstein et al., "Hybrid hybridomas and their use in immunohistochemistry," Nature, 305:537 (1983).
Moore et al. "A novel bispecific antibody format enables simultaneous bivalent and monovalent co-engagement of distinct target antigens," MAbs., 3(6): 546-557 (2011).
Mori et al., "Engineering Chinese hamster ovary cells to maximize effector function of produced antibodies using FUT8 siRNA," Biotechnol. Bioeng. 88(7):901-908 (2004).
Morimoto et al., "Single-step purification of F(ab12 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).
Nagy et al., ("Stability of cytotoxic luteinizing hormone-releasing hormone conjugate (AN-152) containing doxorubicin 14-O-hemiglutarate in mouse and human serum in vitro: Implications for the design of preclinical studies," Proc. Natl. Acad. Sci. USA, 97:829-834 (2000).
Nilvebrant et al., "The albumin-binding domain as a scaffold for protein engineering," Comput. Struct. Biotechnol. J., 6:e201303009, 8 pages (2013).
Nygren et al., "Analysis and use of the serum albumin binding domains of streptococcal protein G," J. Mal. Recogn., 1 (2):69-74 (1988).
Okazaki et al., "Fucose depletion from human IgG1 oligosaccharide enhances binding enthalpy and association rate between IgG1 and FcgammaRllla," J. Mal. Biol., 336:1239-1249 (2004).
Omasa et al., "Decrease in antithrombin III fucosylation by expressing GDP-fucose transporter siRNA in Chinese hamster ovary cells," J. Biosci. Bioeng., 106(2):168-173 (2008).
Podust et al., "Extension of in vivo half-life of biologically active molecules by XTEN protein polymers," J. Controlled Release, 240:52-66 (2016).
Proba et al., "Functional antibody single-chain fragments from the cytoplasm of *Escherichia coli*: influence of thioredoxin reductase (TrxB)," Gene, 159:203-207 (1995).
Ramm et al., "The periplasmic *Escherichia coli* peptidylprolyl cis, trans-isomerase FkpA II. Isomerase-independent chaperone activity in vitro," J. Biol. Chem., 275:17106-17113 (2000).
Reyes et al., "Expression of human 13-interferon cDNA under the control of a thymidine kinase promoter from herpes simplex virus," Nature, 297:598-601 (1982).
Riechmann et al.,"Reshaping human antibodies for therapy," Nature, 332:323-327 (1988).

(56) References Cited

OTHER PUBLICATIONS

Ridgway et al., "Knobs-into-holes' engineering of antibody CH3 domains for heavy chain heterodimerization," Protein Eng., 9(7):617-621 (1996).

Ripka et al., "Two Chinese hamster ovary glycosylation mutants affected in the conversion of GDP-man nose to GDP-fucose," Arch. Biochem. Biophys., 249:533-545 (1986).

Roux et al., "Comparisons of the ability of human IgG3 hinge mutants, IgM, IgE, and IgA2, to form small immune complexes: a role for flexibility and geometry," J Immunol, 161:4083-90 (1998).

Sali et al . . . "Characterization of a Novel Human-Specific STING Agonist that Elicits Antiviral Activity Against Emerging Alphaviruses," PloS Pathog., 11(12):e1005324, 30 pages (2015).

Schlapschy et al., "PASylation: a biological alternative to PEGylation for extending the plasma half-life of pharmaceutically active proteins," Protein Eng. Des. Sel., 26(8):489-501 (2013).

Shields et al., High resolution mapping of the binding site on human IgG1 for Fc gamma RI, Fc gamma RII, Fc gamma RIii, and FcRn and design of IgG1 variants with improved binding to the Fc gamma R, J. Biol. Chem., 276:6591-6604. (2001).

Shields et al., "Lack of fucose on human IgG1 N-linked oligosaccharide improves binding to human Fcgamma RIii and antibody-dependent cellular toxicity," J. Biol. Chem., 277(30):26733-40 (2002).

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-73 (2003).

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-3473 (2003).

Simmons et al., "Expression of full-length immunoglobulins in *Escherichia coli*: rapid and efficient production of aglycosylated antibodies," J. Immunol. Methods, 263:133-147 (2002).

Sola et al. "Modulation of protein biophysical properties by chemical glycosylation: biochemical insights and biomedical implications," Cell. Mol. Life Sci., 64(16):2133-2152 (2007).

Sola et al., "Effects of Glycosylation on the Stability of Protein Pharmaceuticals," J. Pharm. Sci., 98(4):1223-1245 (2009).

Sties et al. (eds), Basic and Clinical Immunology, 8th Edition, Appleton & Lange, Nmwalk, CT, p. 71 and Chapter 6 (1994).

Suresh et al., "Bispecific monoclonal antibodies from hybrid hybridomas," Methods in Enzymology, 121:210-228 (1986).

Tomizuka et al., "Double trans-chromosomic mice: Maintenance of two individual human chromosome fragments containing Ig heavy and K loci and expression of fully human antibodies," Proc. Natl. Acad. Sci. USA, 97:722-727 (2000).

Torgov et al., "Generation of an Intensely Potent Anthracycline by a Monoclonal Antibody-[3-Galactosidase Conjugate," Bioconj. Chem., 16:717-721 (2005).

Traunecker et al., "Bispecific single chain molecules (Janusins) target cytotoxic lymphocytes on HIV infected cells," EMBO J., 10:3655-3656 (1991).

Urlaub et al., "Isolation of Chinese hamster cell mutants deficient in dihydrofolate reductase activity," Proc. Natl. Acad. Sci. USA, 77:4216-4220 (1980).

Verhoeven et al., "Reshaping human antibodies: grafting an antilysozyme activity," Science, 239:1534-1536 (1988).

Vitetta et al., "Redesigning nature's poisons to create anti-tumor reagents," Science, 238:1098-1104 (1987).

Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng., 87:614-22 (2004).

Yamane-Ohnuki et al., "Production of therapeutic antibodies with controlled fucosylation," MAbs, 1 (3):230-236 (2009).

Yaniv, "Enhancing elements for activation of eukaryotic promoters," Nature 297:17-18 (1982).

Yeung et al., "Engineering Human IgG1 Affinity to Human Neonatal Fc Receptor: Impact of Affinity Improvement on Pharmacokinetics in Primates," J. Immunol., 182:7667-7671 (2009).

Zapata et al., "Engineering linear F(ab')2 fragments for efficient production in *Escherichia coli* and enhanced antiproliferative activity," Protein Eng., 8(10):1057-1062 (1995).

\* cited by examiner

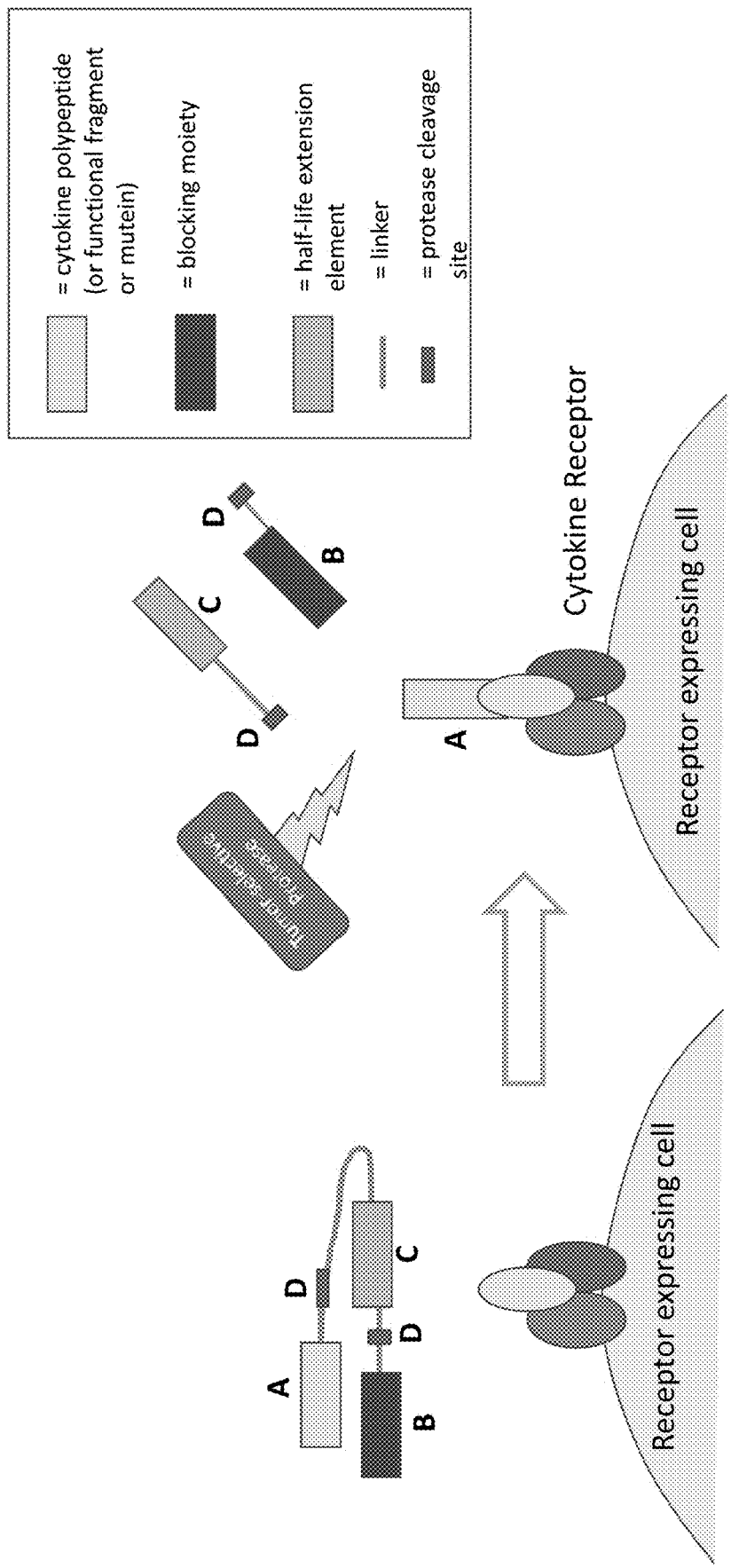

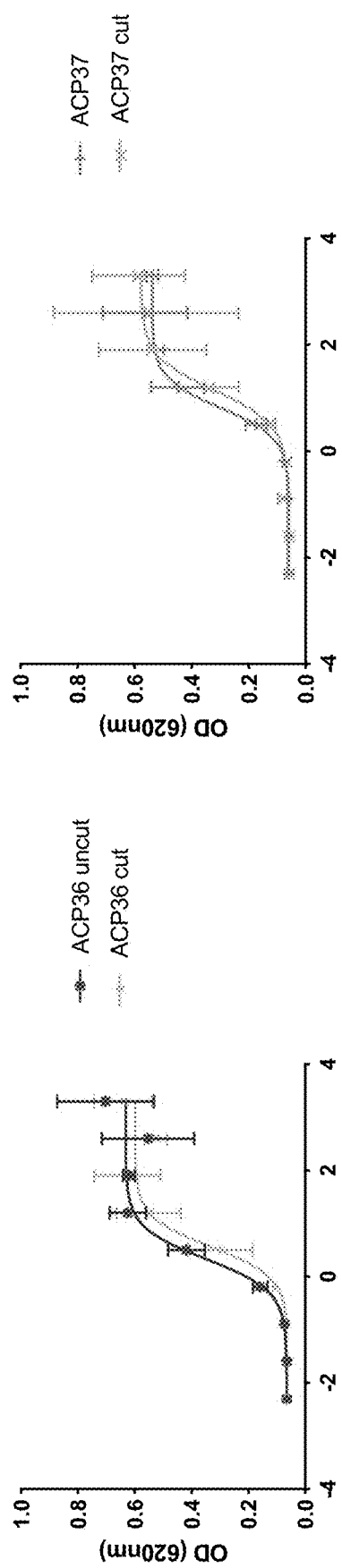
FIG. 11a ACP36 − HSA
FIG. 11b ACP36 + HSA
FIG. 11c ACP37 − HSA
FIG. 11d ACP37 + HSA

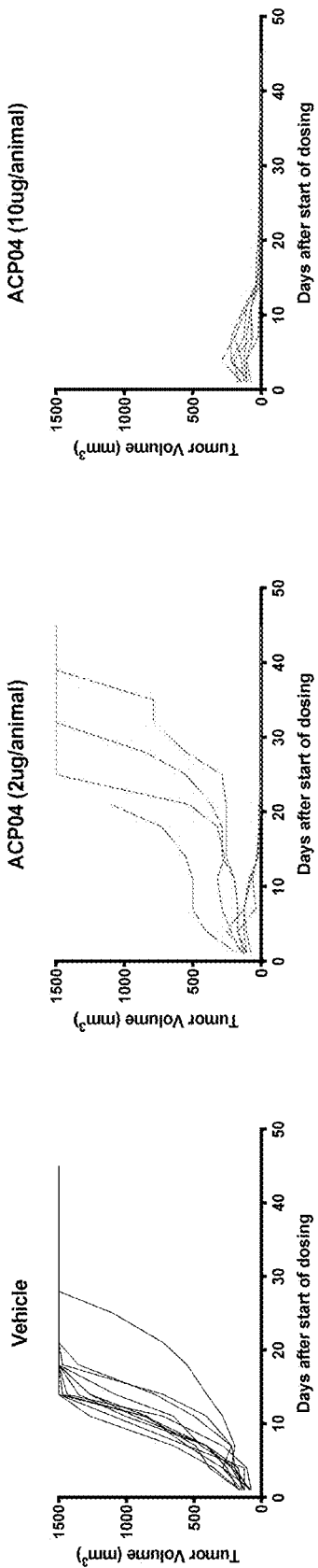
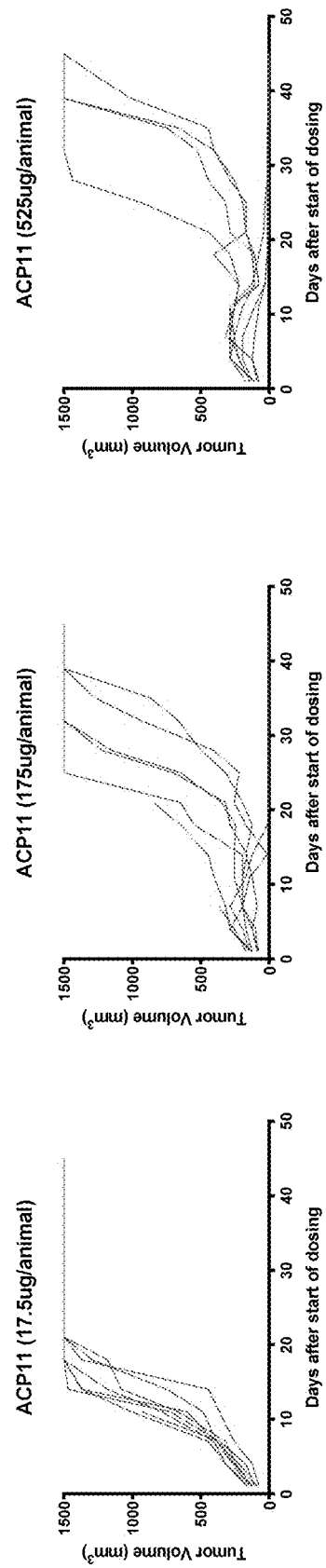
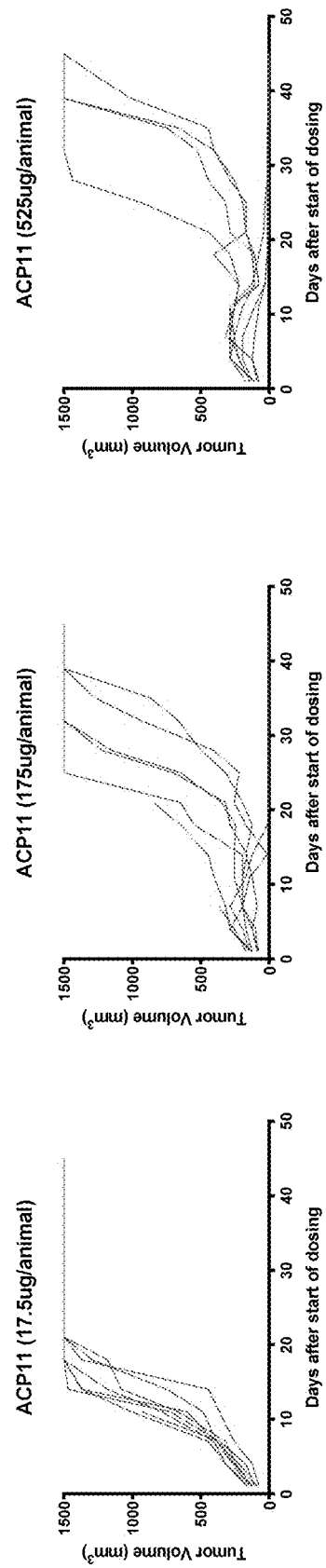
FIG. 14a, FIG. 14b, FIG. 14c, FIG. 14d, FIG. 14e, FIG. 14f

Differential Activity Supported by Various In Vitro Assays
250X Differential in CD3 Binding (ELISA)
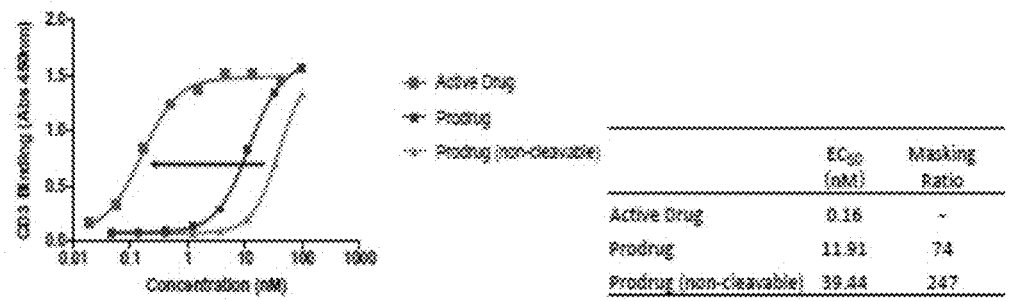
>1000X Differential in Human Primary T Cell Binding (FACS)
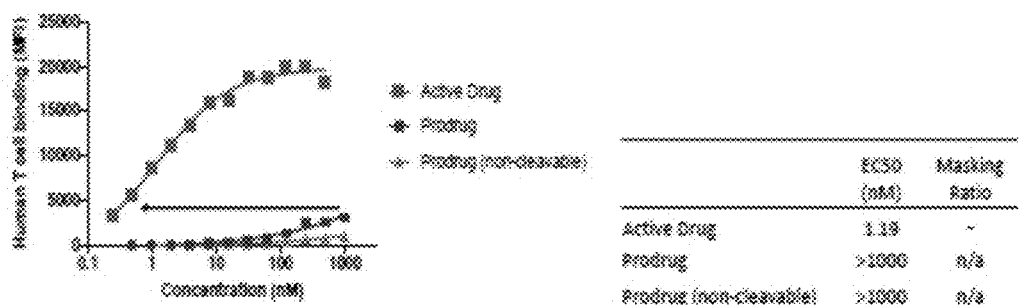
550X Differential in T Cell Killing Activity (TDCC)
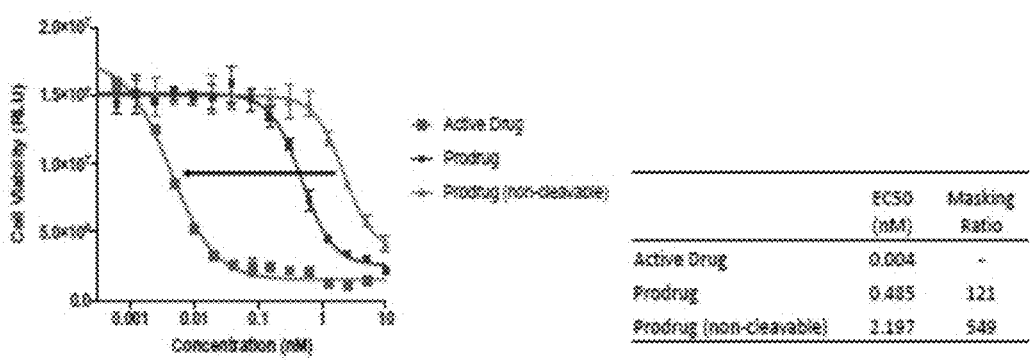
- Plug-and-play; masking demonstrated with >20 binders to 5 different targets
FIG. 16

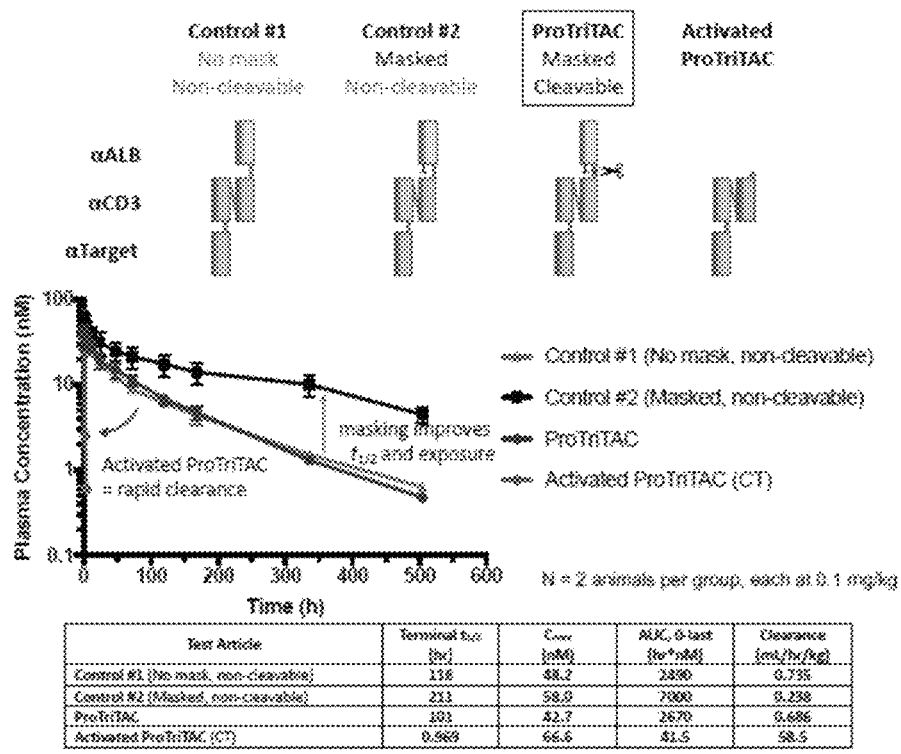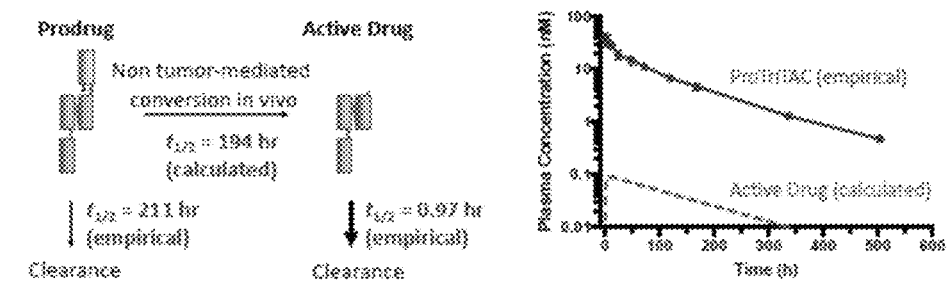
FIG. 20

SEQUENCE LISTING

```
<160> NUMBER OF SEQ ID NOS: 92

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

-continued

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Gly Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Gly Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Cys Leu Ser Val Phe
465                 470                 475                 480
```

```
Leu Asn Gln Leu Cys Val Leu His Glu Lys Thr Pro Val Ser Asp Arg
            485                 490                 495

Val Thr Lys Cys Cys Thr Glu Ser Leu Val Asn Gly Arg Pro Cys Phe
        500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 2
<211> LENGTH: 8
<212> TYPE: PRT
<213> ORGANISM: Unknown
<220> FEATURE:
<223> OTHER INFORMATION: Description of Unknown:
      MMP7 cleavage domain sequence

<400> SEQUENCE: 2

Lys Arg Ala Leu Gly Leu Pro Gly
1               5

<210> SEQ ID NO 3
<211> LENGTH: 40
<212> TYPE: PRT
<213> ORGANISM: Unknown
<220> FEATURE:
<223> OTHER INFORMATION: Description of Unknown:
      MMP7 cleavage domain sequence

<400> SEQUENCE: 3

Asp Glu Asp Glu Asp Glu Asp Glu Asp Glu Asp Glu Asp Glu Asp Glu
1               5                   10                  15

Arg Pro Leu Ala Leu Trp Arg Ser Asp Arg Asp Arg Asp Arg Asp Arg
            20                  25                  30

Asp Arg Asp Arg Asp Arg Asp Arg
        35                  40

<210> SEQ ID NO 4
<211> LENGTH: 5
<212> TYPE: PRT
<213> ORGANISM: Unknown
<220> FEATURE:
<223> OTHER INFORMATION: Description of Unknown:
      MMP9 cleavage domain sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (5)..(5)
```

```
<223> OTHER INFORMATION: Ser or Thr

<400> SEQUENCE: 4

Pro Arg Xaa Xaa Xaa
1               5

<210> SEQ ID NO 5
<211> LENGTH: 5
<212> TYPE: PRT
<213> ORGANISM: Unknown
<220> FEATURE:
<223> OTHER INFORMATION: Description of Unknown:
      MMP9 cleavage domain sequence

<400> SEQUENCE: 5

Leu Glu Ala Thr Ala
1               5

<210> SEQ ID NO 6
<211> LENGTH: 10
<212> TYPE: PRT
<213> ORGANISM: Unknown
<220> FEATURE:
<223> OTHER INFORMATION: Description of Unknown:
      MMP11 cleavage domain sequence

<400> SEQUENCE: 6

Gly Gly Ala Ala Asn Leu Val Arg Gly Gly
1               5                   10

<210> SEQ ID NO 7
<211> LENGTH: 10
<212> TYPE: PRT
<213> ORGANISM: Unknown
<220> FEATURE:
<223> OTHER INFORMATION: Description of Unknown:
      MMP14 cleavage domain sequence

<400> SEQUENCE: 7

Ser Gly Arg Ile Gly Phe Leu Arg Thr Ala
1               5                   10

<210> SEQ ID NO 8
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 8

Pro Leu Gly Leu Ala Gly
1               5

<210> SEQ ID NO 9
<211> LENGTH: 6
<212> TYPE: PRT
<213> ORGANISM: Unknown
<220> FEATURE:
<223> OTHER INFORMATION: Description of Unknown:
      MMP cleavage domain sequence
<220> FEATURE:
<221> NAME/KEY: MOD_RES
<222> LOCATION: (6)..(6)
<223> OTHER INFORMATION: Any amino acid
```

```
<400> SEQUENCE: 9

Pro Leu Gly Leu Ala Xaa
1               5

<210> SEQ ID NO 10
<211> LENGTH: 6
<212> TYPE: PRT
<213> ORGANISM: Unknown
<220> FEATURE:
<223> OTHER INFORMATION: Description of Unknown:
      MMP cleavage domain sequence
<220> FEATURE:
<221> NAME/KEY: MOD_RES
<222> LOCATION: (4)..(4)
<223> OTHER INFORMATION: Cys(me)

<400> SEQUENCE: 10

Pro Leu Gly Cys Ala Gly
1               5

<210> SEQ ID NO 11
<211> LENGTH: 8
<212> TYPE: PRT
<213> ORGANISM: Unknown
<220> FEATURE:
<223> OTHER INFORMATION: Description of Unknown:
      MMP cleavage domain sequence

<400> SEQUENCE: 11

Glu Ser Pro Ala Tyr Tyr Thr Ala
1               5

<210> SEQ ID NO 12
<211> LENGTH: 6
<212> TYPE: PRT
<213> ORGANISM: Unknown
<220> FEATURE:
<223> OTHER INFORMATION: Description of Unknown:
      MMP cleavage domain sequence

<400> SEQUENCE: 12

Arg Leu Gln Leu Lys Leu
1               5

<210> SEQ ID NO 13
<211> LENGTH: 7
<212> TYPE: PRT
<213> ORGANISM: Unknown
<220> FEATURE:
<223> OTHER INFORMATION: Description of Unknown:
      MMP cleavage domain sequence

<400> SEQUENCE: 13

Arg Leu Gln Leu Lys Ala Cys
1               5

<210> SEQ ID NO 14
<211> LENGTH: 7
<212> TYPE: PRT
<213> ORGANISM: Unknown
<220> FEATURE:
<223> OTHER INFORMATION: Description of Unknown:
      MMP2, MMP9, MMP14 cleavage domain sequence
<220> FEATURE:
<221> NAME/KEY: MOD_RES
<222> LOCATION: (3)..(3)
<223> OTHER INFORMATION: Cit
<220> FEATURE:
```

```
<221> NAME/KEY: MOD_RES
<222> LOCATION: (5)..(5)
<223> OTHER INFORMATION: Hof

<400> SEQUENCE: 14

Glu Pro Xaa Gly Xaa Tyr Leu
1               5

<210> SEQ ID NO 15
<211> LENGTH: 5
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 15

Ser Gly Arg Ser Ala
1               5

<210> SEQ ID NO 16
<211> LENGTH: 4
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 16

Asp Ala Phe Lys
1

<210> SEQ ID NO 17
<211> LENGTH: 5
<212> TYPE: PRT
<213> ORGANISM: Unknown
<220> FEATURE:
<223> OTHER INFORMATION: Description of Unknown:
      Urokinase plasminogen activator (uPA) cleavage domain
      sequence

<400> SEQUENCE: 17

Gly Gly Gly Arg Arg
1               5

<210> SEQ ID NO 18
<211> LENGTH: 4
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 18

Gly Phe Leu Gly
1

<210> SEQ ID NO 19
<211> LENGTH: 4
<212> TYPE: PRT
<213> ORGANISM: Unknown
<220> FEATURE:
<223> OTHER INFORMATION: Description of Unknown:
      Lysosomal Enzyme cleavage domain sequence
```

```
<400> SEQUENCE: 19

Ala Leu Ala Leu
1

<210> SEQ ID NO 20
<211> LENGTH: 2
<212> TYPE: PRT
<213> ORGANISM: Unknown
<220> FEATURE:
<223> OTHER INFORMATION: Description of Unknown:
      Lysosomal Enzyme cleavage domain sequence

<400> SEQUENCE: 20

Phe Lys
1

<210> SEQ ID NO 21
<211> LENGTH: 3
<212> TYPE: PRT
<213> ORGANISM: Unknown
<220> FEATURE:
<223> OTHER INFORMATION: Description of Unknown:
      Cathepsin B cleavage domain sequence

<400> SEQUENCE: 21

Asn Leu Leu
1

<210> SEQ ID NO 22
<211> LENGTH: 5
<212> TYPE: PRT
<213> ORGANISM: Unknown
<220> FEATURE:
<223> OTHER INFORMATION: Description of Unknown:
      Cathepsin D cleavage domain sequence
<220> FEATURE:
<221> NAME/KEY: MOD_RES
<222> LOCATION: (3)..(3)
<223> OTHER INFORMATION: Cys(Et)

<400> SEQUENCE: 22

Pro Ile Cys Phe Phe
1               5

<210> SEQ ID NO 23
<211> LENGTH: 8
<212> TYPE: PRT
<213> ORGANISM: Unknown
<220> FEATURE:
<223> OTHER INFORMATION: Description of Unknown:
      Cathepsin K cleavage domain sequence

<400> SEQUENCE: 23

Gly Gly Pro Arg Gly Leu Pro Gly
1               5

<210> SEQ ID NO 24
<211> LENGTH: 6
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 24

His Ser Ser Lys Leu Gln
1               5
```

```
<210> SEQ ID NO 25
<211> LENGTH: 7
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 25

His Ser Ser Lys Leu Gln Leu
1               5

<210> SEQ ID NO 26
<211> LENGTH: 9
<212> TYPE: PRT
<213> ORGANISM: Unknown
<220> FEATURE:
<223> OTHER INFORMATION: Description of Unknown:
      Prostate Specific Antigen cleavage domain sequence

<400> SEQUENCE: 26

His Ser Ser Lys Leu Gln Glu Asp Ala
1               5

<210> SEQ ID NO 27
<211> LENGTH: 10
<212> TYPE: PRT
<213> ORGANISM: Unknown
<220> FEATURE:
<223> OTHER INFORMATION: Description of Unknown:
      Herpes Simplex Virus Protease cleavage domain sequence

<400> SEQUENCE: 27

Leu Val Leu Ala Ser Ser Ser Phe Gly Tyr
1               5                   10

<210> SEQ ID NO 28
<211> LENGTH: 10
<212> TYPE: PRT
<213> ORGANISM: Unknown
<220> FEATURE:
<223> OTHER INFORMATION: Description of Unknown:
      HIV Protease cleavage domain sequence

<400> SEQUENCE: 28

Gly Val Ser Gln Asn Tyr Pro Ile Val Gly
1               5                   10

<210> SEQ ID NO 29
<211> LENGTH: 10
<212> TYPE: PRT
<213> ORGANISM: Unknown
<220> FEATURE:
<223> OTHER INFORMATION: Description of Unknown:
      CMV Protease cleavage domain sequence

<400> SEQUENCE: 29

Gly Val Val Gln Ala Ser Cys Arg Leu Ala
1               5                   10

<210> SEQ ID NO 30
<211> LENGTH: 4
<212> TYPE: PRT
<213> ORGANISM: Unknown
<220> FEATURE:
<223> OTHER INFORMATION: Description of Unknown:
      Thrombin cleavage domain sequence
```

```
<220> FEATURE:
<221> NAME/KEY: MOD_RES
<222> LOCATION: (2)..(2)
<223> OTHER INFORMATION: 2-carboxy piperdine

<400> SEQUENCE: 30

Phe Xaa Arg Ser
1

<210> SEQ ID NO 31
<211> LENGTH: 6
<212> TYPE: PRT
<213> ORGANISM: Unknown
<220> FEATURE:
<223> OTHER INFORMATION: Description of Unknown:
      Thrombin cleavage domain sequence

<400> SEQUENCE: 31

Asp Pro Arg Ser Phe Leu
1               5

<210> SEQ ID NO 32
<211> LENGTH: 6
<212> TYPE: PRT
<213> ORGANISM: Unknown
<220> FEATURE:
<223> OTHER INFORMATION: Description of Unknown:
      Thrombin cleavage domain sequence

<400> SEQUENCE: 32

Pro Pro Arg Ser Phe Leu
1               5

<210> SEQ ID NO 33
<211> LENGTH: 4
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 33

Asp Glu Val Asp
1

<210> SEQ ID NO 34
<211> LENGTH: 5
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 34

Asp Glu Val Asp Pro
1               5

<210> SEQ ID NO 35
<211> LENGTH: 8
<212> TYPE: PRT
<213> ORGANISM: Unknown
<220> FEATURE:
<223> OTHER INFORMATION: Description of Unknown:
      Caspase-3 cleavage domain sequence

<400> SEQUENCE: 35

Lys Gly Ser Gly Asp Val Glu Gly
1               5
```

```
<210> SEQ ID NO 36
<211> LENGTH: 6
<212> TYPE: PRT
<213> ORGANISM: Unknown
<220> FEATURE:
<223> OTHER INFORMATION: Description of Unknown:
      Interleukin 1beta converting enzyme cleavage domain
      sequence

<400> SEQUENCE: 36

Gly Trp Glu His Asp Gly
1               5

<210> SEQ ID NO 37
<211> LENGTH: 7
<212> TYPE: PRT
<213> ORGANISM: Unknown
<220> FEATURE:
<223> OTHER INFORMATION: Description of Unknown:
      Enterokinase cleavage domain sequence

<400> SEQUENCE: 37

Glu Asp Asp Asp Asp Lys Ala
1               5

<210> SEQ ID NO 38
<211> LENGTH: 9
<212> TYPE: PRT
<213> ORGANISM: Unknown
<220> FEATURE:
<223> OTHER INFORMATION: Description of Unknown:
      FAP cleavage domain sequence

<400> SEQUENCE: 38

Lys Gln Glu Gln Asn Pro Gly Ser Thr
1               5

<210> SEQ ID NO 39
<211> LENGTH: 6
<212> TYPE: PRT
<213> ORGANISM: Unknown
<220> FEATURE:
<223> OTHER INFORMATION: Description of Unknown:
      Kallikrein 2 cleavage domain sequence

<400> SEQUENCE: 39

Gly Lys Ala Phe Arg Arg
1               5

<210> SEQ ID NO 40
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 40

Asp Ala Phe Lys
1

<210> SEQ ID NO 41
<211> LENGTH: 4
<212> TYPE: PRT
<213> ORGANISM: Unknown
```

<220> FEATURE:
<223> OTHER INFORMATION: Description of Unknown:
      Plasmin cleavage domain sequence

<400> SEQUENCE: 41

Asp Val Leu Lys
1

<210> SEQ ID NO 42
<211> LENGTH: 4
<212> TYPE: PRT
<213> ORGANISM: Unknown
<220> FEATURE:
<223> OTHER INFORMATION: Description of Unknown:
      Plasmin cleavage domain sequence

<400> SEQUENCE: 42

Asp Ala Phe Lys
1

<210> SEQ ID NO 43
<211> LENGTH: 7
<212> TYPE: PRT
<213> ORGANISM: Unknown
<220> FEATURE:
<223> OTHER INFORMATION: Description of Unknown:
      TOP cleavage domain sequence

<400> SEQUENCE: 43

Ala Leu Leu Leu Ala Leu Leu
1               5

<210> SEQ ID NO 44
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
        290                 295                 300

Cys Ser Gly Gly Gly Ser Gly Gly Gly Ser Gly Gly Gly Gly
305                 310                 315                 320

Ser Arg Val Ile Pro Val Ser Gly Pro Ala Arg Cys Leu Ser Gln Ser
            325                 330                 335

Arg Asn Leu Leu Lys Thr Thr Asp Asp Met Val Lys Thr Ala Arg Glu
        340                 345                 350

Lys Leu Lys His Tyr Ser Cys Thr Ala Glu Asp Ile Asp His Glu Asp
        355                 360                 365

Ile Thr Arg Asp Gln Thr Ser Thr Leu Lys Thr Cys Leu Pro Leu Glu
        370                 375                 380

Leu His Lys Asn Glu Ser Cys Leu Ala Thr Arg Glu Thr Ser Ser Thr
385                 390                 395                 400

Thr Arg Gly Ser Cys Leu Pro Pro Gln Lys Thr Ser Leu Met Met Thr
            405                 410                 415

Leu Cys Leu Gly Ser Ile Tyr Glu Asp Leu Lys Met Tyr Gln Thr Glu
            420                 425                 430

Phe Gln Ala Ile Asn Ala Ala Leu Gln Asn His Asn His Gln Gln Ile
            435                 440                 445

Ile Leu Asp Lys Gly Met Leu Val Ala Ile Asp Glu Leu Met Gln Ser
        450                 455                 460

Leu Asn His Asn Gly Glu Thr Leu Arg Gln Lys Pro Pro Val Gly Glu
465                 470                 475                 480

Ala Asp Pro Tyr Arg Val Lys Met Lys Leu Cys Ile Leu Leu His Ala
            485                 490                 495

Phe Ser Thr Arg Val Val Thr Ile Asn Arg Val Met Gly Tyr Leu Ser
            500                 505                 510

Ser Ala His His His His His
            515                 520

<210> SEQ ID NO 45
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Ile Trp Glu Leu Lys Lys Asp Val Tyr Val Glu Leu Asp Trp Tyr
 1               5                  10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
 50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
            355                 360                 365

Asp His Glu Asp Ile Thr Lys Asp Lys Thr Ser Thr Val Glu Ala Cys
370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415
```

```
Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
            435                 440                 445

Lys Arg Gln Ile Phe Leu Asp Gln Asn Met Leu Ala Val Ile Asp Glu
450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
                500                 505                 510

Ser Tyr Leu Asn Ala Ser His His His His His
            515                 520

<210> SEQ ID NO 46
<211> LENGTH: 940
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gly Gly Gly Ser Gly Gly Gly Gly Ser Gly Gly Gly Gly Ser Gln Val
        115                 120                 125

Gln Leu Val Glu Ser Gly Gly Gly Val Val Gln Pro Gly Arg Ser Leu
    130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Phe
                165                 170                 175

Ile Arg Tyr Asp Gly Ser Asn Lys Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Lys Thr
    210                 215                 220

His Gly Ser His Asp Asn Trp Gly Gln Gly Thr Met Val Thr Val Ser
225                 230                 235                 240
```

-continued

```
Ser Gly Gly Gly Gly Ser Gly Gly Gly Ser Gly Gly Gly Ser
            245                 250                 255

Gly Gly Gly Gly Ser Gly Gly Gly Ser Gly Gly Gly Ser Ser
            260                 265                 270

Gly Gly Pro Gly Pro Ala Gly Met Lys Gly Leu Pro Gly Ser Ile Trp
            275                 280                 285

Glu Leu Lys Lys Asp Val Tyr Val Val Glu Leu Asp Trp Tyr Pro Asp
            290                 295                 300

Ala Pro Gly Glu Met Val Val Leu Thr Cys Asp Thr Pro Glu Glu Asp
305                 310                 315                 320

Gly Ile Thr Trp Thr Leu Asp Gln Ser Ser Glu Val Leu Gly Ser Gly
            325                 330                 335

Lys Thr Leu Thr Ile Gln Val Lys Glu Phe Gly Asp Ala Gly Gln Tyr
            340                 345                 350

Thr Cys His Lys Gly Gly Glu Val Leu Ser His Ser Leu Leu Leu Leu
            355                 360                 365

His Lys Lys Glu Asp Gly Ile Trp Ser Thr Asp Ile Leu Lys Asp Gln
            370                 375                 380

Lys Glu Pro Lys Asn Lys Thr Phe Leu Arg Cys Glu Ala Lys Asn Tyr
385                 390                 395                 400

Ser Gly Arg Phe Thr Cys Trp Trp Leu Thr Thr Ile Ser Thr Asp Leu
            405                 410                 415

Thr Phe Ser Val Lys Ser Ser Arg Gly Ser Ser Asp Pro Gln Gly Val
            420                 425                 430

Thr Cys Gly Ala Ala Thr Leu Ser Ala Glu Arg Val Arg Gly Asp Asn
            435                 440                 445

Lys Glu Tyr Glu Tyr Ser Val Glu Cys Gln Glu Asp Ser Ala Cys Pro
            450                 455                 460

Ala Ala Glu Glu Ser Leu Pro Ile Glu Val Met Val Asp Ala Val His
465                 470                 475                 480

Lys Leu Lys Tyr Glu Asn Tyr Thr Ser Ser Phe Phe Ile Arg Asp Ile
            485                 490                 495

Ile Lys Pro Asp Pro Pro Lys Asn Leu Gln Leu Lys Pro Leu Lys Asn
            500                 505                 510

Ser Arg Gln Val Glu Val Ser Trp Glu Tyr Pro Asp Thr Trp Ser Thr
            515                 520                 525

Pro His Ser Tyr Phe Ser Leu Thr Phe Cys Val Gln Val Gln Gly Lys
            530                 535                 540

Ser Lys Arg Glu Lys Lys Asp Arg Val Phe Thr Asp Lys Thr Ser Ala
545                 550                 555                 560

Thr Val Ile Cys Arg Lys Asn Ala Ser Ile Ser Val Arg Ala Gln Asp
            565                 570                 575

Arg Tyr Tyr Ser Ser Ser Trp Ser Glu Trp Ala Ser Val Pro Cys Ser
            580                 585                 590

Gly Gly Gly Gly Ser Gly Gly Gly Ser Gly Gly Gly Ser Arg
            595                 600                 605

Val Ile Pro Val Ser Gly Pro Ala Arg Cys Leu Ser Gln Ser Arg Asn
            610                 615                 620

Leu Leu Lys Thr Thr Asp Asp Met Val Lys Thr Ala Arg Glu Lys Leu
625                 630                 635                 640

Lys His Tyr Ser Cys Thr Ala Glu Asp Ile Asp His Glu Asp Ile Thr
            645                 650                 655
```

```
Arg Asp Gln Thr Ser Thr Leu Lys Thr Cys Leu Pro Leu Glu Leu His
              660                 665                 670

Lys Asn Glu Ser Cys Leu Ala Thr Arg Glu Thr Ser Ser Thr Thr Arg
        675                 680                 685

Gly Ser Cys Leu Pro Pro Gln Lys Thr Ser Leu Met Met Thr Leu Cys
    690                 695                 700

Leu Gly Ser Ile Tyr Glu Asp Leu Lys Met Tyr Gln Thr Glu Phe Gln
705                 710                 715                 720

Ala Ile Asn Ala Ala Leu Gln Asn His Asn His Gln Ile Ile Leu
                725                 730                 735

Asp Lys Gly Met Leu Val Ala Ile Asp Glu Leu Met Gln Ser Leu Asn
            740                 745                 750

His Asn Gly Glu Thr Leu Arg Gln Lys Pro Pro Val Gly Glu Ala Asp
        755                 760                 765

Pro Tyr Arg Val Lys Met Lys Leu Cys Ile Leu Leu His Ala Phe Ser
    770                 775                 780

Thr Arg Val Val Thr Ile Asn Arg Val Met Gly Tyr Leu Ser Ser Ala
785                 790                 795                 800

Ser Gly Gly Pro Gly Pro Ala Gly Met Lys Gly Leu Pro Gly Ser Glu
                805                 810                 815

Val Gln Leu Val Glu Ser Gly Gly Leu Val Gln Pro Gly Asn Ser
            820                 825                 830

Leu Arg Leu Ser Cys Ala Ala Ser Gly Phe Thr Phe Ser Lys Phe Gly
        835                 840                 845

Met Ser Trp Val Arg Gln Ala Pro Gly Lys Gly Leu Glu Trp Val Ser
    850                 855                 860

Ser Ile Ser Gly Ser Gly Arg Asp Thr Leu Tyr Ala Glu Ser Val Lys
865                 870                 875                 880

Gly Arg Phe Thr Ile Ser Arg Asp Asn Ala Lys Thr Thr Leu Tyr Leu
                885                 890                 895

Gln Met Asn Ser Leu Arg Pro Glu Asp Thr Ala Val Tyr Tyr Cys Thr
            900                 905                 910

Ile Gly Gly Ser Leu Ser Val Ser Ser Gln Gly Thr Leu Val Thr Val
        915                 920                 925

Ser Ser His His His His His His Glu Pro Glu Ala
    930                 935                 940

<210> SEQ ID NO 47
<211> LENGTH: 1069
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

-continued

```
Ala Glu Asp Glu Ala Asp Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gly Gly Gly Ser Gly Gly Gly Ser Gly Gly Gly Ser Gln Val
        115                 120                 125

Gln Leu Val Glu Ser Gly Gly Val Val Gln Pro Gly Arg Ser Leu
130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Phe
                165                 170                 175

Ile Arg Tyr Asp Gly Ser Asn Lys Tyr Tyr Ala Asp Ser Val Lys Gly
                180                 185                 190

Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Lys Thr
        210                 215                 220

His Gly Ser His Asp Asn Trp Gly Gln Gly Thr Met Val Thr Val Ser
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Ser Gly Gly Gly Gly Ser Ser
                260                 265                 270

Gly Gly Pro Gly Pro Ala Gly Met Lys Gly Leu Pro Gly Ser Ile Trp
        275                 280                 285

Glu Leu Lys Lys Asp Val Tyr Val Val Glu Leu Asp Trp Tyr Pro Asp
        290                 295                 300

Ala Pro Gly Glu Met Val Val Leu Thr Cys Asp Thr Pro Glu Glu Asp
305                 310                 315                 320

Gly Ile Thr Trp Thr Leu Asp Gln Ser Ser Glu Val Leu Gly Ser Gly
                325                 330                 335

Lys Thr Leu Thr Ile Gln Val Lys Glu Phe Gly Asp Ala Gly Gln Tyr
                340                 345                 350

Thr Cys His Lys Gly Gly Glu Val Leu Ser His Ser Leu Leu Leu Leu
        355                 360                 365

His Lys Lys Glu Asp Gly Ile Trp Ser Thr Asp Ile Leu Lys Asp Gln
        370                 375                 380

Lys Glu Pro Lys Asn Lys Thr Phe Leu Arg Cys Glu Ala Lys Asn Tyr
385                 390                 395                 400

Ser Gly Arg Phe Thr Cys Trp Trp Leu Thr Thr Ile Ser Thr Asp Leu
                405                 410                 415

Thr Phe Ser Val Lys Ser Ser Arg Gly Ser Ser Asp Pro Gln Gly Val
                420                 425                 430

Thr Cys Gly Ala Ala Thr Leu Ser Ala Glu Arg Val Arg Gly Asp Asn
        435                 440                 445

Lys Glu Tyr Glu Tyr Ser Val Glu Cys Gln Glu Asp Ser Ala Cys Pro
        450                 455                 460

Ala Ala Glu Glu Ser Leu Pro Ile Glu Val Met Val Asp Ala Val His
465                 470                 475                 480

Lys Leu Lys Tyr Glu Asn Tyr Thr Ser Ser Phe Phe Ile Arg Asp Ile
                485                 490                 495
```

```
Ile Lys Pro Asp Pro Pro Lys Asn Leu Gln Leu Lys Pro Leu Lys Asn
            500                 505                 510

Ser Arg Gln Val Glu Val Ser Trp Glu Tyr Pro Asp Thr Trp Ser Thr
        515                 520                 525

Pro His Ser Tyr Phe Ser Leu Thr Phe Cys Val Gln Val Gln Gly Lys
    530                 535                 540

Ser Lys Arg Glu Lys Lys Asp Arg Val Phe Thr Asp Lys Thr Ser Ala
545                 550                 555                 560

Thr Val Ile Cys Arg Lys Asn Ala Ser Ile Ser Val Arg Ala Gln Asp
                565                 570                 575

Arg Tyr Tyr Ser Ser Ser Trp Ser Glu Trp Ala Ser Val Pro Cys Ser
            580                 585                 590

Gly Gly Gly Gly Ser Gly Gly Gly Ser Gly Gly Gly Gly Ser Arg
            595                 600                 605

Val Ile Pro Val Ser Gly Pro Ala Arg Cys Leu Ser Gln Ser Arg Asn
        610                 615                 620

Leu Leu Lys Thr Thr Asp Asp Met Val Lys Thr Ala Arg Glu Lys Leu
625                 630                 635                 640

Lys His Tyr Ser Cys Thr Ala Glu Asp Ile Asp His Glu Asp Ile Thr
                645                 650                 655

Arg Asp Gln Thr Ser Thr Leu Lys Thr Cys Leu Pro Leu Glu Leu His
            660                 665                 670

Lys Asn Glu Ser Cys Leu Ala Thr Arg Glu Thr Ser Ser Thr Thr Arg
        675                 680                 685

Gly Ser Cys Leu Pro Pro Gln Lys Thr Ser Leu Met Met Thr Leu Cys
690                 695                 700

Leu Gly Ser Ile Tyr Glu Asp Leu Lys Met Tyr Gln Thr Glu Phe Gln
705                 710                 715                 720

Ala Ile Asn Ala Ala Leu Gln Asn His Asn His Gln Gln Ile Ile Leu
                725                 730                 735

Asp Lys Gly Met Leu Val Ala Ile Asp Glu Leu Met Gln Ser Leu Asn
            740                 745                 750

His Asn Gly Glu Thr Leu Arg Gln Lys Pro Pro Val Gly Glu Ala Asp
        755                 760                 765

Pro Tyr Arg Val Lys Met Lys Leu Cys Ile Leu Leu His Ala Phe Ser
770                 775                 780

Thr Arg Val Val Thr Ile Asn Arg Val Met Gly Tyr Leu Ser Ser Ala
785                 790                 795                 800

Ser Gly Gly Pro Gly Pro Ala Gly Met Lys Gly Leu Pro Gly Ser Glu
            805                 810                 815

Val Gln Leu Val Glu Ser Gly Gly Gly Leu Val Gln Pro Gly Asn Ser
        820                 825                 830

Leu Arg Leu Ser Cys Ala Ala Ser Gly Phe Thr Phe Ser Lys Phe Gly
            835                 840                 845

Met Ser Trp Val Arg Gln Ala Pro Gly Lys Gly Leu Glu Trp Val Ser
850                 855                 860

Ser Ile Ser Gly Ser Gly Arg Asp Thr Leu Tyr Ala Glu Ser Val Lys
865                 870                 875                 880

Gly Arg Phe Thr Ile Ser Arg Asp Asn Ala Lys Thr Thr Leu Tyr Leu
                885                 890                 895

Gln Met Asn Ser Leu Arg Pro Glu Asp Thr Ala Val Tyr Tyr Cys Thr
            900                 905                 910
```

```
Ile Gly Gly Ser Leu Ser Val Ser Ser Gln Gly Thr Leu Val Thr Val
            915                 920                 925

Ser Ser Gly Gly Gly Gly Ser Gly Gly Gly Ser Gly Gly Gly Gly
        930                 935                 940

Ser Gln Val Gln Leu Gln Glu Ser Gly Gly Leu Ala Gln Ala Gly
945                 950                 955                 960

Gly Ser Leu Ser Leu Ser Cys Ala Ala Ser Gly Phe Thr Val Ser Asn
                965                 970                 975

Ser Val Met Ala Trp Tyr Arg Gln Thr Pro Gly Lys Gln Arg Glu Phe
            980                 985                 990

Val Ala Ile Ile Asn Ser Val Gly  Ser Thr Asn Tyr Ala  Asp Ser Val
            995                 1000                 1005

Lys Gly Arg Phe Thr Ile Ser  Arg Asp Asn Ala Lys  Asn Thr Val
        1010                1015                1020

Tyr Leu  Gln Met Asn Asn Leu  Lys Pro Glu Asp Thr  Ala Val Tyr
    1025                1030                1035

Val Cys  Asn Arg Asn Phe Asp  Arg Ile Tyr Trp Gly  Gln Gly Thr
    1040                1045                1050

Gln Val  Thr Val Ser Ser His  His His His His His  Glu Pro Glu
    1055                1060                1065

Ala

<210> SEQ ID NO 48
<211> LENGTH: 1069
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Gln Glu Ser Gly Gly Gly Leu Ala Gln Ala Gly Gly
1               5                   10                  15

Ser Leu Ser Leu Ser Cys Ala Ala Ser Gly Phe Thr Val Ser Asn Ser
            20                  25                  30

Val Met Ala Trp Tyr Arg Gln Thr Pro Gly Lys Gln Arg Glu Phe Val
        35                  40                  45

Ala Ile Ile Asn Ser Val Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Val Cys Asn
                85                  90                  95

Arg Asn Phe Asp Arg Ile Tyr Trp Gly Gln Gly Thr Gln Val Thr Val
            100                 105                 110

Ser Ser Gly Gly Gly Gly Ser Gly Gly Gly Gly Ser Gly Gly Gly Gly
        115                 120                 125

Ser Gln Ser Val Leu Thr Gln Pro Pro Ser Val Ser Gly Ala Pro Gly
    130                 135                 140

Gln Arg Val Thr Ile Ser Cys Ser Gly Ser Arg Ser Asn Ile Gly Ser
145                 150                 155                 160

Asn Thr Val Lys Trp Tyr Gln Gln Leu Pro Gly Thr Ala Pro Lys Leu
                165                 170                 175

Leu Ile Tyr Tyr Asn Asp Gln Arg Pro Ser Gly Val Pro Asp Arg Phe
            180                 185                 190
```

```
Ser Gly Ser Lys Ser Gly Thr Ser Ala Ser Leu Ala Ile Thr Gly Leu
        195                 200                 205

Gln Ala Glu Asp Glu Ala Asp Tyr Tyr Cys Gln Ser Tyr Asp Arg Tyr
    210                 215                 220

Thr His Pro Ala Leu Leu Phe Gly Thr Gly Thr Lys Val Thr Val Leu
225                 230                 235                 240

Gly Gly Gly Gly Ser Gly Gly Gly Ser Gly Gly Gly Gly Ser Gln
                245                 250                 255

Val Gln Leu Val Glu Ser Gly Gly Val Val Gln Pro Gly Arg Ser
            260                 265                 270

Leu Arg Leu Ser Cys Ala Ala Ser Gly Phe Thr Phe Ser Ser Tyr Gly
    275                 280                 285

Met His Trp Val Arg Gln Ala Pro Gly Lys Gly Leu Glu Trp Val Ala
    290                 295                 300

Phe Ile Arg Tyr Asp Gly Ser Asn Lys Tyr Tyr Ala Asp Ser Val Lys
305                 310                 315                 320

Gly Arg Phe Thr Ile Ser Arg Asp Asn Ser Lys Asn Thr Leu Tyr Leu
                325                 330                 335

Gln Met Asn Ser Leu Arg Ala Glu Asp Thr Ala Val Tyr Tyr Cys Lys
        340                 345                 350

Thr His Gly Ser His Asp Asn Trp Gly Gln Gly Thr Met Val Thr Val
        355                 360                 365

Ser Ser Gly Gly Gly Gly Ser Gly Gly Gly Gly Ser Gly Gly Gly Gly
    370                 375                 380

Ser Gly Gly Gly Gly Ser Gly Gly Gly Gly Ser Gly Gly Gly Gly Ser
385                 390                 395                 400

Ser Gly Gly Pro Gly Pro Ala Gly Met Lys Gly Leu Pro Gly Ser Ile
                405                 410                 415

Trp Glu Leu Lys Lys Asp Val Tyr Val Val Glu Leu Asp Trp Tyr Pro
            420                 425                 430

Asp Ala Pro Gly Glu Met Val Val Leu Thr Cys Asp Thr Pro Glu Glu
        435                 440                 445

Asp Gly Ile Thr Trp Thr Leu Asp Gln Ser Ser Glu Val Leu Gly Ser
    450                 455                 460

Gly Lys Thr Leu Thr Ile Gln Val Lys Glu Phe Gly Asp Ala Gly Gln
465                 470                 475                 480

Tyr Thr Cys His Lys Gly Gly Glu Val Leu Ser His Ser Leu Leu Leu
                485                 490                 495

Leu His Lys Lys Glu Asp Gly Ile Trp Ser Thr Asp Ile Leu Lys Asp
        500                 505                 510

Gln Lys Glu Pro Lys Asn Lys Thr Phe Leu Arg Cys Glu Ala Lys Asn
    515                 520                 525

Tyr Ser Gly Arg Phe Thr Cys Trp Trp Leu Thr Thr Ile Ser Thr Asp
530                 535                 540

Leu Thr Phe Ser Val Lys Ser Ser Arg Gly Ser Ser Asp Pro Gln Gly
545                 550                 555                 560

Val Thr Cys Gly Ala Ala Thr Leu Ser Ala Glu Arg Val Arg Gly Asp
                565                 570                 575

Asn Lys Glu Tyr Glu Tyr Ser Val Glu Cys Gln Glu Asp Ser Ala Cys
        580                 585                 590

Pro Ala Ala Glu Glu Ser Leu Pro Ile Glu Val Met Val Asp Ala Val
    595                 600                 605
```

His Lys Leu Lys Tyr Glu Asn Tyr Thr Ser Ser Phe Phe Ile Arg Asp
610                 615                 620

Ile Ile Lys Pro Asp Pro Pro Lys Asn Leu Gln Leu Lys Pro Leu Lys
625                 630                 635                 640

Asn Ser Arg Gln Val Glu Val Ser Trp Glu Tyr Pro Asp Thr Trp Ser
            645                 650                 655

Thr Pro His Ser Tyr Phe Ser Leu Thr Phe Cys Val Gln Val Gln Gly
            660                 665                 670

Lys Ser Lys Arg Glu Lys Lys Asp Arg Val Phe Thr Asp Lys Thr Ser
    675                 680                 685

Ala Thr Val Ile Cys Arg Lys Asn Ala Ser Ile Ser Val Arg Ala Gln
690                 695                 700

Asp Arg Tyr Tyr Ser Ser Trp Ser Glu Trp Ala Ser Val Pro Cys
705                 710                 715                 720

Ser Gly Gly Gly Gly Ser Gly Gly Gly Ser Gly Gly Gly Gly Ser
            725                 730                 735

Arg Val Ile Pro Val Ser Gly Pro Ala Arg Cys Leu Ser Gln Ser Arg
            740                 745                 750

Asn Leu Leu Lys Thr Thr Asp Asp Met Val Lys Thr Ala Arg Glu Lys
            755                 760                 765

Leu Lys His Tyr Ser Cys Thr Ala Glu Asp Ile Asp His Glu Asp Ile
770                 775                 780

Thr Arg Asp Gln Thr Ser Thr Leu Lys Thr Cys Leu Pro Leu Glu Leu
785                 790                 795                 800

His Lys Asn Glu Ser Cys Leu Ala Thr Arg Glu Thr Ser Ser Thr Thr
            805                 810                 815

Arg Gly Ser Cys Leu Pro Pro Gln Lys Thr Ser Leu Met Met Thr Leu
            820                 825                 830

Cys Leu Gly Ser Ile Tyr Glu Asp Leu Lys Met Tyr Gln Thr Glu Phe
            835                 840                 845

Gln Ala Ile Asn Ala Ala Leu Gln Asn His Asn His Gln Ile Ile
850                 855                 860

Leu Asp Lys Gly Met Leu Val Ala Ile Asp Glu Leu Met Gln Ser Leu
865                 870                 875                 880

Asn His Asn Gly Glu Thr Leu Arg Gln Lys Pro Pro Val Gly Glu Ala
            885                 890                 895

Asp Pro Tyr Arg Val Lys Met Lys Leu Cys Ile Leu Leu His Ala Phe
            900                 905                 910

Ser Thr Arg Val Val Thr Ile Asn Arg Val Met Gly Tyr Leu Ser Ser
            915                 920                 925

Ala Ser Gly Gly Pro Gly Pro Ala Gly Met Lys Gly Leu Pro Gly Ser
930                 935                 940

Glu Val Gln Leu Val Glu Ser Gly Gly Gly Leu Val Gln Pro Gly Asn
945                 950                 955                 960

Ser Leu Arg Leu Ser Cys Ala Ala Ser Gly Phe Thr Phe Ser Lys Phe
            965                 970                 975

Gly Met Ser Trp Val Arg Gln Ala Pro Gly Lys Gly Leu Glu Trp Val
            980                 985                 990

Ser Ser Ile Ser Gly Ser Gly Arg Asp Thr Leu Tyr Ala Glu Ser Val
            995                 1000                1005

Lys Gly Arg Phe Thr Ile Ser Arg Asp Asn Ala Lys Thr Thr Leu
    1010                1015                1020

```
Tyr Leu Gln Met Asn Ser Leu Arg Pro Glu Asp Thr Ala Val Tyr
    1025                1030                1035

Tyr Cys Thr Ile Gly Gly Ser Leu Ser Val Ser Ser Gln Gly Thr
    1040                1045                1050

Leu Val Thr Val Ser Ser His His His His His His Glu Pro Glu
    1055                1060                1065

Ala

<210> SEQ ID NO 49
<211> LENGTH: 940
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Arg Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gln Ser Val Leu Thr Gln Pro Pro Ser Val Ser Gly Ala Pro
    130                 135                 140

Gly Gln Arg Val Thr Ile Ser Cys Ser Gly Ser Arg Ser Asn Ile Gly
145                 150                 155                 160

Ser Asn Thr Val Lys Trp Tyr Gln Gln Leu Pro Gly Thr Ala Pro Lys
                165                 170                 175

Leu Leu Ile Tyr Tyr Asn Asp Gln Arg Pro Ser Gly Val Pro Asp Arg
            180                 185                 190

Phe Ser Gly Ser Lys Ser Gly Thr Ser Ala Ser Leu Ala Ile Thr Gly
        195                 200                 205

Leu Gln Ala Glu Asp Glu Ala Asp Tyr Tyr Cys Gln Ser Tyr Asp Arg
    210                 215                 220

Tyr Thr His Pro Ala Leu Leu Phe Gly Thr Gly Thr Lys Val Thr Val
225                 230                 235                 240

Leu Gly Gly Gly Gly Ser Gly Gly Gly Gly Ser Gly Gly Gly Gly Ser
                245                 250                 255

Gln Val Gln Leu Val Glu Ser Gly Gly Gly Val Val Gln Pro Gly Arg
            260                 265                 270

Ser Leu Arg Leu Ser Cys Ala Ala Ser Gly Phe Thr Phe Ser Ser Tyr
        275                 280                 285

Gly Met His Trp Val Arg Gln Ala Pro Gly Lys Gly Leu Glu Trp Val
    290                 295                 300
```

```
Ala Phe Ile Arg Tyr Asp Gly Ser Asn Lys Tyr Tyr Ala Asp Ser Val
305                 310                 315                 320

Lys Gly Arg Phe Thr Ile Ser Arg Asp Asn Ser Lys Asn Thr Leu Tyr
            325                 330                 335

Leu Gln Met Asn Ser Leu Arg Ala Glu Asp Thr Ala Val Tyr Tyr Cys
        340                 345                 350

Lys Thr His Gly Ser His Asp Asn Trp Gly Gln Gly Thr Met Val Thr
    355                 360                 365

Val Ser Ser Gly Gly Gly Gly Ser Gly Gly Gly Ser Gly Gly Gly
370                 375                 380

Gly Ser Gly Gly Gly Gly Ser Gly Gly Gly Ser Gly Gly Gly Gly
385                 390                 395                 400

Ser Ser Gly Gly Pro Gly Pro Ala Gly Met Lys Gly Leu Pro Gly Ser
                405                 410                 415

Ile Trp Glu Leu Lys Lys Asp Val Tyr Val Val Glu Leu Asp Trp Tyr
            420                 425                 430

Pro Asp Ala Pro Gly Glu Met Val Val Leu Thr Cys Asp Thr Pro Glu
        435                 440                 445

Glu Asp Gly Ile Thr Trp Thr Leu Asp Gln Ser Ser Glu Val Leu Gly
    450                 455                 460

Ser Gly Lys Thr Leu Thr Ile Gln Val Lys Glu Phe Gly Asp Ala Gly
465                 470                 475                 480

Gln Tyr Thr Cys His Lys Gly Gly Glu Val Leu Ser His Ser Leu Leu
                485                 490                 495

Leu Leu His Lys Lys Glu Asp Gly Ile Trp Ser Thr Asp Ile Leu Lys
            500                 505                 510

Asp Gln Lys Glu Pro Lys Asn Lys Thr Phe Leu Arg Cys Glu Ala Lys
        515                 520                 525

Asn Tyr Ser Gly Arg Phe Thr Cys Trp Trp Leu Thr Thr Ile Ser Thr
    530                 535                 540

Asp Leu Thr Phe Ser Val Lys Ser Ser Arg Gly Ser Ser Asp Pro Gln
545                 550                 555                 560

Gly Val Thr Cys Gly Ala Ala Thr Leu Ser Ala Glu Arg Val Arg Gly
                565                 570                 575

Asp Asn Lys Glu Tyr Glu Tyr Ser Val Glu Cys Gln Glu Asp Ser Ala
            580                 585                 590

Cys Pro Ala Ala Glu Glu Ser Leu Pro Ile Glu Val Met Val Asp Ala
        595                 600                 605

Val His Lys Leu Lys Tyr Glu Asn Tyr Thr Ser Ser Phe Phe Ile Arg
    610                 615                 620

Asp Ile Ile Lys Pro Asp Pro Pro Lys Asn Leu Gln Leu Lys Pro Leu
625                 630                 635                 640

Lys Asn Ser Arg Gln Val Glu Val Ser Trp Glu Tyr Pro Asp Thr Trp
                645                 650                 655

Ser Thr Pro His Ser Tyr Phe Ser Leu Thr Phe Cys Val Gln Val Gln
            660                 665                 670

Gly Lys Ser Lys Arg Glu Lys Lys Asp Arg Val Phe Thr Asp Lys Thr
        675                 680                 685

Ser Ala Thr Val Ile Cys Arg Lys Asn Ala Ser Ile Ser Val Arg Ala
    690                 695                 700

Gln Asp Arg Tyr Tyr Ser Ser Ser Trp Ser Glu Trp Ala Ser Val Pro
705                 710                 715                 720
```

```
Cys Ser Gly Gly Gly Ser Gly Gly Gly Ser Gly Gly Gly
                725                 730                 735

Ser Arg Val Ile Pro Val Ser Gly Pro Ala Arg Cys Leu Ser Gln Ser
        740                 745                 750

Arg Asn Leu Leu Lys Thr Thr Asp Asp Met Val Lys Thr Ala Arg Glu
            755                 760                 765

Lys Leu Lys His Tyr Ser Cys Thr Ala Glu Asp Ile Asp His Glu Asp
770                 775                 780

Ile Thr Arg Asp Gln Thr Ser Thr Leu Lys Thr Cys Leu Pro Leu Glu
785                 790                 795                 800

Leu His Lys Asn Glu Ser Cys Leu Ala Thr Arg Glu Thr Ser Ser Thr
                805                 810                 815

Thr Arg Gly Ser Cys Leu Pro Pro Gln Lys Thr Ser Leu Met Met Thr
            820                 825                 830

Leu Cys Leu Gly Ser Ile Tyr Glu Asp Leu Lys Met Tyr Gln Thr Glu
        835                 840                 845

Phe Gln Ala Ile Asn Ala Ala Leu Gln Asn His Asn His Gln Gln Ile
    850                 855                 860

Ile Leu Asp Lys Gly Met Leu Val Ala Ile Asp Glu Leu Met Gln Ser
865                 870                 875                 880

Leu Asn His Asn Gly Glu Thr Leu Arg Gln Lys Pro Pro Val Gly Glu
                885                 890                 895

Ala Asp Pro Tyr Arg Val Lys Met Lys Leu Cys Ile Leu Leu His Ala
            900                 905                 910

Phe Ser Thr Arg Val Val Thr Ile Asn Arg Val Met Gly Tyr Leu Ser
        915                 920                 925

Ser Ala His His His His His His Glu Pro Glu Ala
    930                 935                 940

<210> SEQ ID NO 50
<211> LENGTH: 940
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Ser Gly Gly Pro Gly Pro Ala Gly Met Lys Gly Leu Pro
        115                 120                 125

Gly Ser Ile Trp Glu Leu Lys Lys Asp Val Tyr Val Val Glu Leu Asp
    130                 135                 140
```

```
Trp Tyr Pro Asp Ala Pro Gly Glu Met Val Val Leu Thr Cys Asp Thr
145                 150                 155                 160

Pro Glu Glu Asp Gly Ile Thr Trp Thr Leu Asp Gln Ser Ser Glu Val
            165                 170                 175

Leu Gly Ser Gly Lys Thr Leu Thr Ile Gln Val Lys Glu Phe Gly Asp
            180                 185                 190

Ala Gly Gln Tyr Thr Cys His Lys Gly Gly Glu Val Leu Ser His Ser
        195                 200                 205

Leu Leu Leu Leu His Lys Lys Glu Asp Gly Ile Trp Ser Thr Asp Ile
210                 215                 220

Leu Lys Asp Gln Lys Glu Pro Lys Asn Lys Thr Phe Leu Arg Cys Glu
225                 230                 235                 240

Ala Lys Asn Tyr Ser Gly Arg Phe Thr Cys Trp Trp Leu Thr Thr Ile
            245                 250                 255

Ser Thr Asp Leu Thr Phe Ser Val Lys Ser Ser Arg Gly Ser Ser Asp
            260                 265                 270

Pro Gln Gly Val Thr Cys Gly Ala Ala Thr Leu Ser Ala Glu Arg Val
        275                 280                 285

Arg Gly Asp Asn Lys Glu Tyr Glu Tyr Ser Val Glu Cys Gln Glu Asp
290                 295                 300

Ser Ala Cys Pro Ala Ala Glu Glu Ser Leu Pro Ile Glu Val Met Val
305                 310                 315                 320

Asp Ala Val His Lys Leu Lys Tyr Glu Asn Tyr Thr Ser Ser Phe Phe
            325                 330                 335

Ile Arg Asp Ile Ile Lys Pro Asp Pro Pro Lys Asn Leu Gln Leu Lys
            340                 345                 350

Pro Leu Lys Asn Ser Arg Gln Val Glu Val Ser Trp Glu Tyr Pro Asp
        355                 360                 365

Thr Trp Ser Thr Pro His Ser Tyr Phe Ser Leu Thr Phe Cys Val Gln
370                 375                 380

Val Gln Gly Lys Ser Lys Arg Glu Lys Lys Asp Arg Val Phe Thr Asp
385                 390                 395                 400

Lys Thr Ser Ala Thr Val Ile Cys Arg Lys Asn Ala Ser Ile Ser Val
            405                 410                 415

Arg Ala Gln Asp Arg Tyr Tyr Ser Ser Ser Trp Ser Glu Trp Ala Ser
            420                 425                 430

Val Pro Cys Ser Gly Gly Gly Ser Gly Gly Gly Ser Gly Gly
        435                 440                 445

Gly Gly Ser Arg Val Ile Pro Val Ser Gly Pro Ala Arg Cys Leu Ser
        450                 455                 460

Gln Ser Arg Asn Leu Leu Lys Thr Thr Asp Asp Met Val Lys Thr Ala
465                 470                 475                 480

Arg Glu Lys Leu Lys His Tyr Ser Cys Thr Ala Glu Asp Ile Asp His
            485                 490                 495

Glu Asp Ile Thr Arg Asp Gln Thr Ser Thr Leu Lys Thr Cys Leu Pro
            500                 505                 510

Leu Glu Leu His Lys Asn Glu Ser Cys Leu Ala Thr Arg Glu Thr Ser
        515                 520                 525

Ser Thr Thr Arg Gly Ser Cys Leu Pro Pro Gln Lys Thr Ser Leu Met
        530                 535                 540

Met Thr Leu Cys Leu Gly Ser Ile Tyr Glu Asp Leu Lys Met Tyr Gln
545                 550                 555                 560
```

```
Thr Glu Phe Gln Ala Ile Asn Ala Ala Leu Gln Asn His Asn His Gln
                565                 570                 575

Gln Ile Ile Leu Asp Lys Gly Met Leu Val Ala Ile Asp Glu Leu Met
            580                 585                 590

Gln Ser Leu Asn His Asn Gly Glu Thr Leu Arg Gln Lys Pro Pro Val
        595                 600                 605

Gly Glu Ala Asp Pro Tyr Arg Val Lys Met Lys Leu Cys Ile Leu Leu
    610                 615                 620

His Ala Phe Ser Thr Arg Val Val Thr Ile Asn Arg Val Met Gly Tyr
625                 630                 635                 640

Leu Ser Ser Ala Ser Gly Gly Pro Gly Pro Ala Gly Met Lys Gly Leu
                645                 650                 655

Pro Gly Ser Gly Gly Gly Gly Ser Gly Gly Gly Gly Ser Gly Gly Gly
            660                 665                 670

Gly Ser Gly Gly Gly Gly Ser Gly Gly Gly Gly Ser Gly Gly Gly Gly
        675                 680                 685

Ser Gln Ser Val Leu Thr Gln Pro Pro Ser Val Ser Gly Ala Pro Gly
    690                 695                 700

Gln Arg Val Thr Ile Ser Cys Ser Gly Ser Arg Ser Asn Ile Gly Ser
705                 710                 715                 720

Asn Thr Val Lys Trp Tyr Gln Leu Pro Gly Thr Ala Pro Lys Leu
                725                 730                 735

Leu Ile Tyr Tyr Asn Asp Gln Arg Pro Ser Gly Val Pro Asp Arg Phe
            740                 745                 750

Ser Gly Ser Lys Ser Gly Thr Ser Ala Ser Leu Ala Ile Thr Gly Leu
        755                 760                 765

Gln Ala Glu Asp Glu Ala Asp Tyr Tyr Cys Gln Ser Tyr Asp Arg Tyr
    770                 775                 780

Thr His Pro Ala Leu Leu Phe Gly Thr Gly Thr Lys Val Thr Val Leu
785                 790                 795                 800

Gly Gly Gly Gly Ser Gly Gly Gly Ser Gly Gly Gly Ser Gln
                805                 810                 815

Val Gln Leu Val Glu Ser Gly Gly Val Val Gln Pro Gly Arg Ser
            820                 825                 830

Leu Arg Leu Ser Cys Ala Ala Ser Gly Phe Thr Phe Ser Ser Tyr Gly
        835                 840                 845

Met His Trp Val Arg Gln Ala Pro Gly Lys Gly Leu Glu Trp Val Ala
    850                 855                 860

Phe Ile Arg Tyr Asp Gly Ser Asn Lys Tyr Tyr Ala Asp Ser Val Lys
865                 870                 875                 880

Gly Arg Phe Thr Ile Ser Arg Asp Asn Ser Lys Asn Thr Leu Tyr Leu
                885                 890                 895

Gln Met Asn Ser Leu Arg Ala Glu Asp Thr Ala Val Tyr Tyr Cys Lys
            900                 905                 910

Thr His Gly Ser His Asp Asn Trp Gly Gln Gly Thr Met Val Thr Val
        915                 920                 925

Ser Ser His His His His His Glu Pro Glu Ala
    930                 935                 940

<210> SEQ ID NO 51
<211> LENGTH: 940
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 51

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Gly
305                 310                 315                 320

Ser Arg Val Ile Pro Val Ser Gly Pro Ala Arg Cys Leu Ser Gln Ser
                325                 330                 335

Arg Asn Leu Leu Lys Thr Thr Asp Asp Met Val Lys Thr Ala Arg Glu
            340                 345                 350

Lys Leu Lys His Tyr Ser Cys Thr Ala Glu Asp Ile Asp His Glu Asp
            355                 360                 365

Ile Thr Arg Asp Gln Thr Ser Thr Leu Lys Thr Cys Leu Pro Leu Glu
370                 375                 380
```

```
Leu His Lys Asn Glu Ser Cys Leu Ala Thr Arg Glu Thr Ser Ser Thr
385                 390                 395                 400

Thr Arg Gly Ser Cys Leu Pro Pro Gln Lys Thr Ser Leu Met Met Thr
            405                 410                 415

Leu Cys Leu Gly Ser Ile Tyr Glu Asp Leu Lys Met Tyr Gln Thr Glu
        420                 425                 430

Phe Gln Ala Ile Asn Ala Ala Leu Gln Asn His Asn His Gln Gln Ile
        435                 440                 445

Ile Leu Asp Lys Gly Met Leu Val Ala Ile Asp Glu Leu Met Gln Ser
    450                 455                 460

Leu Asn His Asn Gly Glu Thr Leu Arg Gln Lys Pro Pro Val Gly Glu
465                 470                 475                 480

Ala Asp Pro Tyr Arg Val Lys Met Lys Leu Cys Ile Leu Leu His Ala
                485                 490                 495

Phe Ser Thr Arg Val Val Thr Ile Asn Arg Val Met Gly Tyr Leu Ser
            500                 505                 510

Ser Ala Ser Gly Gly Pro Gly Pro Ala Gly Met Lys Gly Leu Pro Gly
        515                 520                 525

Ser Gly Gly Gly Ser Gly Gly Gly Ser Gly Gly Gly Ser
530                 535                 540

Gly Gly Gly Gly Ser Gly Gly Gly Ser Gly Gly Gly Ser Gln
545                 550                 555                 560

Ser Val Leu Thr Gln Pro Pro Ser Val Ser Gly Ala Pro Gly Gln Arg
                565                 570                 575

Val Thr Ile Ser Cys Ser Gly Ser Arg Ser Asn Ile Gly Ser Asn Thr
            580                 585                 590

Val Lys Trp Tyr Gln Gln Leu Pro Gly Thr Ala Pro Lys Leu Leu Ile
            595                 600                 605

Tyr Tyr Asn Asp Gln Arg Pro Ser Gly Val Pro Asp Arg Phe Ser Gly
        610                 615                 620

Ser Lys Ser Gly Thr Ser Ala Ser Leu Ala Ile Thr Gly Leu Gln Ala
625                 630                 635                 640

Glu Asp Glu Ala Asp Tyr Tyr Cys Gln Ser Tyr Asp Arg Tyr Thr His
                645                 650                 655

Pro Ala Leu Leu Phe Gly Thr Gly Thr Lys Val Thr Val Leu Gly Gly
            660                 665                 670

Gly Gly Ser Gly Gly Gly Gly Ser Gly Gly Gly Gly Ser Gln Val Gln
        675                 680                 685

Leu Val Glu Ser Gly Gly Gly Val Val Gln Pro Gly Arg Ser Leu Arg
        690                 695                 700

Leu Ser Cys Ala Ala Ser Gly Phe Thr Phe Ser Ser Tyr Gly Met His
705                 710                 715                 720

Trp Val Arg Gln Ala Pro Gly Lys Gly Leu Glu Trp Val Ala Phe Ile
            725                 730                 735

Arg Tyr Asp Gly Ser Asn Lys Tyr Tyr Ala Asp Ser Val Lys Gly Arg
            740                 745                 750

Phe Thr Ile Ser Arg Asp Asn Ser Lys Asn Thr Leu Tyr Leu Gln Met
            755                 760                 765

Asn Ser Leu Arg Ala Glu Asp Thr Ala Val Tyr Tyr Cys Lys Thr His
            770                 775                 780

Gly Ser His Asp Asn Trp Gly Gln Gly Thr Met Val Thr Val Ser Ser
785                 790                 795                 800
```

```
Gly Gly Gly Gly Ser Gly Gly Gly Ser Gly Gly Gly Ser Glu
              805                 810                 815

Val Gln Leu Val Glu Ser Gly Gly Leu Val Gln Pro Gly Asn Ser
820                 825                 830

Leu Arg Leu Ser Cys Ala Ala Ser Gly Phe Thr Phe Ser Lys Phe Gly
            835                 840                 845

Met Ser Trp Val Arg Gln Ala Pro Gly Lys Gly Leu Glu Trp Val Ser
850                 855                 860

Ser Ile Ser Gly Ser Gly Arg Asp Thr Leu Tyr Ala Glu Ser Val Lys
865                 870                 875                 880

Gly Arg Phe Thr Ile Ser Arg Asp Asn Ala Lys Thr Thr Leu Tyr Leu
                885                 890                 895

Gln Met Asn Ser Leu Arg Pro Glu Asp Thr Ala Val Tyr Tyr Cys Thr
            900                 905                 910

Ile Gly Gly Ser Leu Ser Val Ser Ser Gln Gly Thr Leu Val Thr Val
        915                 920                 925

Ser Ser His His His His His His Glu Pro Glu Ala
    930                 935                 940

<210> SEQ ID NO 52
<211> LENGTH: 328
<212> TYPE: PRT
<213> ORGANISM: Homo sapiens

<400> SEQUENCE: 52

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240
```

```
Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 53
<211> LENGTH: 215
<212> TYPE: PRT
<213> ORGANISM: Mus musculus

<400> SEQUENCE: 53

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215

<210> SEQ ID NO 54
<211> LENGTH: 862
<212> TYPE: PRT
<213> ORGANISM: Unknown
<220> FEATURE:
<223> OTHER INFORMATION: Description of Unknown:
      IL12Rb-2 sequence
```

<400> SEQUENCE: 54

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
                20                  25                  30

Val Thr Val Lys Pro Ser His Val Ile Leu Gly Ser Thr Val Asn
            35                  40                  45

Ile Thr Cys Ser Leu Lys Pro Arg Gln Gly Cys Phe His Tyr Ser Arg
        50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
                100                 105                 110

Ile Cys Gly Ala Glu Ile Phe Val Gly Val Ala Pro Glu Gln Pro Gln
            115                 120                 125

Asn Leu Ser Cys Ile Gln Lys Gly Glu Gln Gly Thr Val Ala Cys Thr
130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380

Thr Val Ile Pro Arg Thr Gly Asn Trp Ala Val Ala Val Ser Ala Ala
385                 390                 395                 400

```
Asn Ser Lys Gly Ser Ser Leu Pro Thr Arg Ile Asn Ile Met Asn Leu
            405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
            435                 440                 445

Ser Ala Val Gln Glu Tyr Val Val Glu Trp Arg Glu Leu His Pro Gly
            450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
            485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
            515                 520                 525

Ala Ile Thr Glu Glu Lys Gly Ser Ile Leu Ile Ser Trp Asn Ser Ile
            530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
            565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
            595                 600                 605

His Gly Asn Glu Arg Glu Phe Cys Leu Gln Gly Lys Ala Asn Trp Met
610                 615                 620

Ala Phe Val Ala Pro Ser Ile Cys Ile Ala Ile Ile Met Val Gly Ile
625                 630                 635                 640

Phe Ser Thr His Tyr Phe Gln Gln Lys Val Phe Val Leu Leu Ala Ala
            645                 650                 655

Leu Arg Pro Gln Trp Cys Ser Arg Glu Ile Pro Asp Pro Ala Asn Ser
            660                 665                 670

Thr Cys Ala Lys Lys Tyr Pro Ile Ala Glu Glu Lys Thr Gln Leu Pro
            675                 680                 685

Leu Asp Arg Leu Leu Ile Asp Trp Pro Thr Pro Glu Asp Pro Glu Pro
            690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
            725                 730                 735

Gln Ala Ser Glu Lys Asp Met Met His Ser Ala Ser Ser Pro Pro Pro
            740                 745                 750

Pro Arg Ala Leu Gln Ala Glu Ser Arg Gln Leu Val Asp Leu Tyr Lys
            755                 760                 765

Val Leu Glu Ser Arg Gly Ser Asp Pro Lys Pro Glu Asn Pro Ala Cys
            770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
            805                 810                 815
```

-continued

```
Asp Ser Leu Glu Glu Leu Glu Pro Gln His Ile Ser Leu Ser Val Phe
            820                 825                 830

Pro Ser Ser Ser Leu His Pro Leu Thr Phe Ser Cys Gly Asp Lys Leu
            835                 840                 845

Thr Leu Asp Gln Leu Lys Met Arg Cys Asp Ser Leu Met Leu
            850                 855                 860

<210> SEQ ID NO 55
<211> LENGTH: 662
<212> TYPE: PRT
<213> ORGANISM: Unknown
<220> FEATURE:
<223> OTHER INFORMATION: Description of Unknown:
      IL12Rb-1 sequence

<400> SEQUENCE: 55

Met Glu Pro Leu Val Thr Trp Val Val Pro Leu Leu Phe Leu Phe Leu
 1               5                  10                  15

Leu Ser Arg Gln Gly Ala Ala Cys Arg Thr Ser Glu Cys Cys Phe Gln
                20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp
        50                  55                  60

Gln Tyr Glu Gly Pro Thr Ala Gly Val Ser His Phe Leu Arg Cys Cys
 65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320
```

-continued

```
Ser Asn Gln Phe Gly Pro Gly Leu Asn Gln Thr Trp His Ile Pro Ala
            325                 330                 335

Asp Thr His Thr Glu Pro Val Ala Leu Asn Ile Ser Val Gly Thr Asn
        340                 345                 350

Gly Thr Thr Met Tyr Trp Pro Ala Arg Ala Gln Ser Met Thr Tyr Cys
    355                 360                 365

Ile Glu Trp Gln Pro Val Gly Gln Asp Gly Gly Leu Ala Thr Cys Ser
370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
    610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
            660

<210> SEQ ID NO 56
<211> LENGTH: 328
<212> TYPE: PRT
<213> ORGANISM: Homo sapiens

<400> SEQUENCE: 56

Met Cys His Gln Gln Leu Val Ile Ser Trp Phe Ser Leu Val Phe Leu
1               5                   10                  15
```

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
            85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 57
<211> LENGTH: 335
<212> TYPE: PRT
<213> ORGANISM: Mus musculus

<400> SEQUENCE: 57

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
            35                  40                  45

Thr Cys Asp Thr Pro Glu Glu Asp Ile Thr Trp Thr Ser Asp Gln
            50                  55                  60

Arg His Gly Val Ile Gly Ser Gly Lys Thr Leu Thr Ile Thr Val Lys
 65                  70                  75                  80

Glu Phe Leu Asp Ala Gly Gln Tyr Thr Cys His Lys Gly Gly Glu Thr
                 85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 58
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Asp Met Arg Val Pro Ala Gln Leu Leu Gly Leu Leu Leu Leu Trp
 1               5                  10                  15

Leu Arg Gly Ala Arg Cys Glu Val Gln Leu Val Glu Ser Gly Gly Gly
                 20                  25                  30

Leu Val Gln Pro Gly Gly Ser Leu Arg Leu Ser Cys Ala Ala Ser Gly
            35                  40                  45

Phe Thr Phe Ser Ser Tyr Ala Met Ser Trp Val Arg Gln Ala Pro Gly
         50                  55                  60

```
Lys Gly Leu Glu Trp Val Ser Ala Ile Ser Gly Ser Gly Gly Ser Thr
 65                  70                  75                  80

Tyr Tyr Ala Asp Ser Val Lys Gly Arg Phe Thr Ile Ser Arg Asp Asn
             85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Gly Val Gly Ala Phe Arg Pro Tyr
            115                 120                 125

Arg Lys His Glu Trp Gly Gln Gly Thr Leu Val Thr Val Ser Arg Gly
        130                 135                 140

Gly Gly Gly Ser Gly Gly Gly Ser Gly Gly Gly Ser Ser
145                 150                 155                 160

Glu Leu Thr Gln Asp Pro Ala Val Ser Val Ala Leu Gly Gln Thr Val
                165                 170                 175

Arg Ile Thr Cys Gln Gly Asp Ser Leu Arg Ser Tyr Tyr Ala Ser Trp
            180                 185                 190

Tyr Gln Gln Lys Pro Gly Gln Ala Pro Val Leu Val Ile Tyr Gly Lys
        195                 200                 205

Asn Asn Arg Pro Ser Gly Ile Pro Asp Arg Phe Ser Gly Ser Ser Ser
210                 215                 220

Gly Asn Thr Ala Ser Leu Thr Thr Thr Gly Ala Gln Ala Glu Asp Glu
225                 230                 235                 240

Ala Asp Tyr Tyr Cys Asn Ser Ser Pro Phe Glu His Asn Leu Val Val
                245                 250                 255

Phe Gly Gly Gly Thr Lys Leu Thr Val Leu His His His His His His
                260                 265                 270

Glu Pro Glu Ala
        275

<210> SEQ ID NO 59
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Asp Met Arg Val Pro Ala Gln Leu Leu Gly Leu Leu Leu Leu Trp
 1               5                   10                  15

Leu Arg Gly Ala Arg Cys Arg Val Ile Pro Val Ser Gly Pro Ala Arg
             20                  25                  30

Cys Leu Ser Gln Ser Arg Asn Leu Leu Lys Thr Thr Asp Asp Met Val
         35                  40                  45

Lys Thr Ala Arg Glu Lys Leu Lys His Tyr Ser Cys Thr Ala Glu Asp
     50                  55                  60

Ile Asp His Glu Asp Ile Thr Arg Asp Gln Thr Ser Thr Leu Lys Thr
 65                  70                  75                  80

Cys Leu Pro Leu Glu Leu His Lys Asn Glu Ser Cys Leu Ala Thr Arg
             85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125
```

-continued

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala Ser Gly Gly Pro Gly Pro Ala Gly Met
    210                 215                 220

Lys Gly Leu Pro Gly Ser Met Trp Glu Leu Glu Lys Asp Val Tyr Val
225                 230                 235                 240

Val Glu Val Asp Trp Thr Pro Asp Ala Pro Gly Glu Thr Val Asn Leu
                245                 250                 255

Thr Cys Asp Thr Pro Glu Glu Asp Asp Ile Thr Trp Thr Ser Asp Gln
            260                 265                 270

Arg His Gly Val Ile Gly Ser Gly Lys Thr Leu Thr Ile Thr Val Lys
        275                 280                 285

Glu Phe Leu Asp Ala Gly Gln Tyr Thr Cys His Lys Gly Gly Glu Thr
    290                 295                 300

Leu Ser His Ser His Leu Leu Leu His Lys Lys Glu Asn Gly Ile Trp
305                 310                 315                 320

Ser Thr Glu Ile Leu Lys Asn Phe Lys Asn Lys Thr Phe Leu Lys Cys
                325                 330                 335

Glu Ala Pro Asn Tyr Ser Gly Arg Phe Thr Cys Ser Trp Leu Val Gln
            340                 345                 350

Arg Asn Met Asp Leu Lys Phe Asn Ile Lys Ser Ser Ser Ser Ser Pro
        355                 360                 365

Asp Ser Arg Ala Val Thr Cys Gly Met Ala Ser Leu Ser Ala Glu Lys
    370                 375                 380

Val Thr Leu Asp Gln Arg Asp Tyr Glu Lys Tyr Ser Val Ser Cys Gln
385                 390                 395                 400

Glu Asp Val Thr Cys Pro Thr Ala Glu Glu Thr Leu Pro Ile Glu Leu
                405                 410                 415

Ala Leu Glu Ala Arg Gln Gln Asn Lys Tyr Glu Asn Tyr Ser Thr Ser
            420                 425                 430

Phe Phe Ile Arg Asp Ile Ile Lys Pro Asp Pro Pro Lys Asn Leu Gln
        435                 440                 445

Met Lys Pro Leu Lys Asn Ser Gln Val Glu Val Ser Trp Glu Tyr Pro
    450                 455                 460

Asp Ser Trp Ser Thr Pro His Ser Tyr Phe Ser Leu Lys Phe Phe Val
465                 470                 475                 480

Arg Ile Gln Arg Lys Lys Glu Lys Met Lys Glu Thr Glu Glu Gly Cys
                485                 490                 495

Asn Gln Lys Gly Ala Phe Leu Val Glu Lys Thr Ser Thr Glu Val Gln
            500                 505                 510

Cys Lys Gly Gly Asn Val Cys Val Gln Ala Gln Asp Arg Tyr Tyr Asn
        515                 520                 525

Ser Ser Cys Ser Lys Trp Ala Cys Val Pro Cys Arg Val Arg Ser His
    530                 535                 540

His His His His His
545

<210> SEQ ID NO 60
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Met Asp Met Arg Val Pro Ala Gln Leu Leu Gly Leu Leu Leu Leu Trp
1               5                   10                  15

Leu Arg Gly Ala Arg Cys Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala Gly Gly Gly Ser Gly Gly Gly Gly
    210                 215                 220

Ser Gly Gly Gly Ser Ser Gly Gly Pro Gly Pro Ala Gly Met Lys
225                 230                 235                 240

Gly Leu Pro Gly Ser Gly Gly Gly Ser Gly Gly Gly Ser Gly
                245                 250                 255

Gly Gly Gly Ser Met Trp Glu Leu Glu Lys Asp Val Tyr Val Val Glu
            260                 265                 270

Val Asp Trp Thr Pro Asp Ala Pro Gly Glu Thr Val Asn Leu Thr Cys
        275                 280                 285

Asp Thr Pro Glu Glu Asp Asp Ile Thr Trp Thr Ser Asp Gln Arg His
    290                 295                 300

Gly Val Ile Gly Ser Gly Lys Thr Leu Thr Ile Thr Val Lys Glu Phe
305                 310                 315                 320

Leu Asp Ala Gly Gln Tyr Thr Cys His Lys Gly Gly Glu Thr Leu Ser
                325                 330                 335

His Ser His Leu Leu Leu His Lys Lys Glu Asn Gly Ile Trp Ser Thr
            340                 345                 350

```
Glu Ile Leu Lys Asn Phe Lys Asn Lys Thr Phe Leu Lys Cys Glu Ala
            355                 360                 365

Pro Asn Tyr Ser Gly Arg Phe Thr Cys Ser Trp Leu Val Gln Arg Asn
    370                 375                 380

Met Asp Leu Lys Phe Asn Ile Lys Ser Ser Ser Ser Pro Asp Ser
385                 390                 395                 400

Arg Ala Val Thr Cys Gly Met Ala Ser Leu Ser Ala Glu Lys Val Thr
                405                 410                 415

Leu Asp Gln Arg Asp Tyr Glu Lys Tyr Ser Val Ser Cys Gln Glu Asp
                420                 425                 430

Val Thr Cys Pro Thr Ala Glu Thr Leu Pro Ile Glu Leu Ala Leu
            435                 440                 445

Glu Ala Arg Gln Gln Asn Lys Tyr Glu Asn Tyr Ser Thr Ser Phe Phe
    450                 455                 460

Ile Arg Asp Ile Ile Lys Pro Asp Pro Pro Lys Asn Leu Gln Met Lys
465                 470                 475                 480

Pro Leu Lys Asn Ser Gln Val Glu Val Ser Trp Glu Tyr Pro Asp Ser
                485                 490                 495

Trp Ser Thr Pro His Ser Tyr Phe Ser Leu Lys Phe Phe Val Arg Ile
            500                 505                 510

Gln Arg Lys Lys Glu Lys Met Lys Glu Thr Glu Glu Gly Cys Asn Gln
    515                 520                 525

Lys Gly Ala Phe Leu Val Glu Lys Thr Ser Thr Glu Val Gln Cys Lys
    530                 535                 540

Gly Gly Asn Val Cys Val Gln Ala Gln Asp Arg Tyr Tyr Asn Ser Ser
545                 550                 555                 560

Cys Ser Lys Trp Ala Cys Val Pro Cys Arg Val Arg Ser His His His
                565                 570                 575

His His His

<210> SEQ ID NO 61
<211> LENGTH: 809
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Gln Pro Gly Asn Ser Leu Arg Leu Ser Cys Ala Ala Ser Gly
            35                  40                  45

Phe Thr Phe Ser Lys Phe Gly Met Ser Trp Val Arg Gln Ala Pro Gly
    50                  55                  60

Lys Gly Leu Glu Trp Val Ser Ser Ile Ser Gly Ser Gly Arg Asp Thr
65                  70                  75                  80

Leu Tyr Ala Glu Ser Val Lys Gly Arg Phe Thr Ile Ser Arg Asp Asn
                85                  90                  95

Ala Lys Thr Thr Leu Tyr Leu Gln Met Asn Ser Leu Arg Pro Glu Asp
            100                 105                 110

Thr Ala Val Tyr Tyr Cys Thr Ile Gly Gly Ser Leu Ser Val Ser Ser
        115                 120                 125
```

```
Gln Gly Thr Leu Val Thr Val Ser Ser Gly Gly Pro Gly Pro Ala
    130                 135                 140
Gly Met Lys Gly Leu Pro Gly Ser Met Trp Glu Leu Glu Lys Asp Val
145                 150                 155                 160
Tyr Val Val Glu Val Asp Trp Thr Pro Asp Ala Pro Gly Glu Thr Val
                165                 170                 175
Asn Leu Thr Cys Asp Thr Pro Glu Glu Asp Ile Thr Trp Thr Ser
            180                 185                 190
Asp Gln Arg His Gly Val Ile Gly Ser Gly Lys Thr Leu Thr Ile Thr
        195                 200                 205
Val Lys Glu Phe Leu Asp Ala Gly Gln Tyr Thr Cys His Lys Gly Gly
    210                 215                 220
Glu Thr Leu Ser His Ser His Leu Leu Leu His Lys Lys Glu Asn Gly
225                 230                 235                 240
Ile Trp Ser Thr Glu Ile Leu Lys Asn Phe Lys Asn Lys Thr Phe Leu
                245                 250                 255
Lys Cys Glu Ala Pro Asn Tyr Ser Gly Arg Phe Thr Cys Ser Trp Leu
            260                 265                 270
Val Gln Arg Asn Met Asp Leu Lys Phe Asn Ile Lys Ser Ser Ser Ser
        275                 280                 285
Ser Pro Asp Ser Arg Ala Val Thr Cys Gly Met Ala Ser Leu Ser Ala
    290                 295                 300
Glu Lys Val Thr Leu Asp Gln Arg Asp Tyr Glu Lys Tyr Ser Val Ser
305                 310                 315                 320
Cys Gln Glu Asp Val Thr Cys Pro Thr Ala Glu Glu Thr Leu Pro Ile
                325                 330                 335
Glu Leu Ala Leu Glu Ala Arg Gln Gln Asn Lys Tyr Glu Asn Tyr Ser
            340                 345                 350
Thr Ser Phe Phe Ile Arg Asp Ile Ile Lys Pro Asp Pro Pro Lys Asn
        355                 360                 365
Leu Gln Met Lys Pro Leu Lys Asn Ser Gln Val Glu Val Ser Trp Glu
    370                 375                 380
Tyr Pro Asp Ser Trp Ser Thr Pro His Ser Tyr Phe Ser Leu Lys Phe
385                 390                 395                 400
Phe Val Arg Ile Gln Arg Lys Lys Glu Lys Met Lys Glu Thr Glu Glu
                405                 410                 415
Gly Cys Asn Gln Lys Gly Ala Phe Leu Val Glu Lys Thr Ser Thr Glu
            420                 425                 430
Val Gln Cys Lys Gly Gly Asn Val Cys Val Gln Ala Gln Asp Arg Tyr
        435                 440                 445
Tyr Asn Ser Ser Cys Ser Lys Trp Ala Cys Val Pro Cys Arg Val Arg
    450                 455                 460
Ser Gly Gly Gly Ser Gly Gly Gly Ser Gly Gly Gly Ser
465                 470                 475                 480
Arg Val Ile Pro Val Ser Gly Pro Ala Arg Cys Leu Ser Gln Ser Arg
                485                 490                 495
Asn Leu Leu Lys Thr Thr Asp Asp Met Val Lys Thr Ala Arg Glu Lys
            500                 505                 510
Leu Lys His Tyr Ser Cys Thr Ala Glu Asp Ile Asp His Glu Asp Ile
        515                 520                 525
Thr Arg Asp Gln Thr Ser Thr Leu Lys Thr Cys Leu Pro Leu Glu Leu
    530                 535                 540
```

His Lys Asn Glu Ser Cys Leu Ala Thr Arg Glu Ser Ser Thr Thr
545                 550                 555                 560

Arg Gly Ser Cys Leu Pro Pro Gln Lys Thr Ser Leu Met Met Thr Leu
                565                 570                 575

Cys Leu Gly Ser Ile Tyr Glu Asp Leu Lys Met Tyr Gln Thr Glu Phe
                580                 585                 590

Gln Ala Ile Asn Ala Ala Leu Gln Asn His Asn His Gln Ile Ile
            595                 600                 605

Leu Asp Lys Gly Met Leu Val Ala Ile Asp Glu Leu Met Gln Ser Leu
    610                 615                 620

Asn His Asn Gly Glu Thr Leu Arg Gln Lys Pro Pro Val Gly Glu Ala
625                 630                 635                 640

Asp Pro Tyr Arg Val Lys Met Lys Leu Cys Ile Leu Leu His Ala Phe
                645                 650                 655

Ser Thr Arg Val Val Thr Ile Asn Arg Val Met Gly Tyr Leu Ser Ser
                660                 665                 670

Ala Ser Gly Gly Pro Gly Pro Ala Gly Met Lys Gly Leu Pro Gly Ser
                675                 680                 685

Glu Val Gln Leu Val Glu Ser Gly Gly Leu Val Gln Pro Gly Asn
690                 695                 700

Ser Leu Arg Leu Ser Cys Ala Ala Ser Gly Phe Thr Phe Ser Lys Phe
705                 710                 715                 720

Gly Met Ser Trp Val Arg Gln Ala Pro Gly Lys Gly Leu Glu Trp Val
                725                 730                 735

Ser Ser Ile Ser Gly Ser Gly Arg Asp Thr Leu Tyr Ala Glu Ser Val
                740                 745                 750

Lys Gly Arg Phe Thr Ile Ser Arg Asp Asn Ala Lys Thr Thr Leu Tyr
            755                 760                 765

Leu Gln Met Asn Ser Leu Arg Pro Glu Asp Thr Ala Val Tyr Tyr Cys
    770                 775                 780

Thr Ile Gly Gly Ser Leu Ser Val Ser Ser Gln Gly Thr Leu Val Thr
785                 790                 795                 800

Val Ser Ser His His His His His His
                805

<210> SEQ ID NO 62
<211> LENGTH: 938
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Arg Ile Phe Ser Ile Asp Ile Met Ser Trp Tyr Arg Gln Ala Pro Gly
    50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

```
Lys Asn Thr Val Tyr Leu Gln Met Asn Ser Leu Lys Pro Glu Asp Thr
                100                 105                 110

Gly Val Tyr Tyr Cys Asn Ala Leu Tyr Gly Thr Asp Tyr Trp Gly Lys
            115                 120                 125

Gly Thr Gln Val Thr Val Ser Ser Gly Gly Gly Gly Ser Gly Gly Gly
        130                 135                 140

Gly Ser Gly Gly Gly Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Lys Phe Gly Met Ser Trp Val Arg Gln Ala Pro
            180                 185                 190

Gly Lys Gly Leu Glu Trp Val Ser Ser Ile Ser Gly Ser Gly Arg Asp
        195                 200                 205

Thr Leu Tyr Ala Glu Ser Val Lys Gly Arg Phe Thr Ile Ser Arg Asp
    210                 215                 220

Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Val Ser
                245                 250                 255

Ser Gln Gly Thr Leu Val Thr Val Ser Ser Gly Gly Pro Gly Pro
            260                 265                 270

Ala Gly Met Lys Gly Leu Pro Gly Ser Met Trp Glu Leu Glu Lys Asp
        275                 280                 285

Val Tyr Val Val Glu Val Asp Trp Thr Pro Asp Ala Pro Gly Glu Thr
    290                 295                 300

Val Asn Leu Thr Cys Asp Thr Pro Glu Glu Asp Asp Ile Thr Trp Thr
305                 310                 315                 320

Ser Asp Gln Arg His Gly Val Ile Gly Ser Gly Lys Thr Leu Thr Ile
                325                 330                 335

Thr Val Lys Glu Phe Leu Asp Ala Gly Gln Tyr Thr Cys His Lys Gly
            340                 345                 350

Gly Glu Thr Leu Ser His Ser His Leu Leu Leu His Lys Lys Glu Asn
        355                 360                 365

Gly Ile Trp Ser Thr Glu Ile Leu Lys Asn Phe Lys Asn Lys Thr Phe
    370                 375                 380

Leu Lys Cys Glu Ala Pro Asn Tyr Ser Gly Arg Phe Thr Cys Ser Trp
385                 390                 395                 400

Leu Val Gln Arg Asn Met Asp Leu Lys Phe Asn Ile Lys Ser Ser Ser
                405                 410                 415

Ser Ser Pro Asp Ser Arg Ala Val Thr Cys Gly Met Ala Ser Leu Ser
            420                 425                 430

Ala Glu Lys Val Thr Leu Asp Gln Arg Asp Tyr Glu Lys Tyr Ser Val
        435                 440                 445

Ser Cys Gln Glu Asp Val Thr Cys Pro Thr Ala Glu Glu Thr Leu Pro
    450                 455                 460

Ile Glu Leu Ala Leu Glu Ala Arg Gln Gln Asn Lys Tyr Glu Asn Tyr
465                 470                 475                 480

Ser Thr Ser Phe Phe Ile Arg Asp Ile Ile Lys Pro Asp Pro Pro Lys
                485                 490                 495

Asn Leu Gln Met Lys Pro Leu Lys Asn Ser Gln Val Glu Val Ser Trp
            500                 505                 510
```

-continued

```
Glu Tyr Pro Asp Ser Trp Ser Thr Pro His Ser Tyr Phe Ser Leu Lys
    515                 520                 525

Phe Phe Val Arg Ile Gln Arg Lys Lys Glu Lys Met Lys Glu Thr Glu
    530                 535                 540

Glu Gly Cys Asn Gln Lys Gly Ala Phe Leu Val Glu Lys Thr Ser Thr
545                 550                 555                 560

Glu Val Gln Cys Lys Gly Gly Asn Val Cys Val Gln Ala Gln Asp Arg
                565                 570                 575

Tyr Tyr Asn Ser Ser Cys Ser Lys Trp Ala Cys Val Pro Cys Arg Val
            580                 585                 590

Arg Ser Gly Gly Gly Gly Ser Gly Gly Gly Gly Ser Gly Gly Gly Gly
    595                 600                 605

Ser Arg Val Ile Pro Val Ser Gly Pro Ala Arg Cys Leu Ser Gln Ser
    610                 615                 620

Arg Asn Leu Leu Lys Thr Thr Asp Asp Met Val Lys Thr Ala Arg Glu
625                 630                 635                 640

Lys Leu Lys His Tyr Ser Cys Thr Ala Glu Asp Ile Asp His Glu Asp
                645                 650                 655

Ile Thr Arg Asp Gln Thr Ser Thr Leu Lys Thr Cys Leu Pro Leu Glu
            660                 665                 670

Leu His Lys Asn Glu Ser Cys Leu Ala Thr Arg Glu Thr Ser Ser Thr
        675                 680                 685

Thr Arg Gly Ser Cys Leu Pro Pro Gln Lys Thr Ser Leu Met Met Thr
    690                 695                 700

Leu Cys Leu Gly Ser Ile Tyr Glu Asp Leu Lys Met Tyr Gln Thr Glu
705                 710                 715                 720

Phe Gln Ala Ile Asn Ala Ala Leu Gln Asn His Asn His Gln Gln Ile
                725                 730                 735

Ile Leu Asp Lys Gly Met Leu Val Ala Ile Asp Glu Leu Met Gln Ser
            740                 745                 750

Leu Asn His Asn Gly Glu Thr Leu Arg Gln Lys Pro Pro Val Gly Glu
        755                 760                 765

Ala Asp Pro Tyr Arg Val Lys Met Lys Leu Cys Ile Leu Leu His Ala
    770                 775                 780

Phe Ser Thr Arg Val Val Thr Ile Asn Arg Val Met Gly Tyr Leu Ser
785                 790                 795                 800

Ser Ala Ser Gly Gly Pro Gly Pro Ala Gly Met Lys Gly Leu Pro Gly
                805                 810                 815

Ser Glu Val Gln Leu Val Glu Ser Gly Gly Gly Leu Val Gln Pro Gly
            820                 825                 830

Asn Ser Leu Arg Leu Ser Cys Ala Ala Ser Gly Phe Thr Phe Ser Lys
        835                 840                 845

Phe Gly Met Ser Trp Val Arg Gln Ala Pro Lys Gly Leu Glu Trp
    850                 855                 860

Val Ser Ser Ile Ser Gly Ser Gly Arg Asp Thr Leu Tyr Ala Glu Ser
865                 870                 875                 880

Val Lys Gly Arg Phe Thr Ile Ser Arg Asp Asn Ala Lys Thr Thr Leu
                885                 890                 895

Tyr Leu Gln Met Asn Ser Leu Arg Pro Glu Asp Thr Ala Val Tyr Tyr
            900                 905                 910

Cys Thr Ile Gly Gly Ser Leu Ser Val Ser Ser Gln Gly Thr Leu Val
        915                 920                 925
```

```
Thr Val Ser Ser His His His His His His
    930                 935

<210> SEQ ID NO 63
<211> LENGTH: 938
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
                20                  25                  30

Leu Val Gln Ala Gly Gly Ser Leu Arg Leu Ser Cys Ala Ala Ser Gly
            35                  40                  45

Arg Ile Phe Ser Ile Asp Ile Met Ser Trp Tyr Arg Gln Ala Pro Gly
        50                  55                  60

Lys Gln Arg Glu Leu Val Ala Arg Ile Thr Arg Gly Gly Thr Ile Ser
65                  70                  75                  80

Tyr Asp Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Gly Val Tyr Tyr Cys Asn Ala Leu Tyr Gly Thr Asp Tyr Trp Gly Lys
        115                 120                 125

Gly Thr Gln Val Thr Val Ser Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Pro Gly Asn Ser Leu Arg Leu Ser Cys Ala Ala Ser
                165                 170                 175

Gly Phe Thr Phe Ser Lys Phe Gly Met Ser Trp Val Arg Gln Ala Pro
            180                 185                 190

Gly Lys Gly Leu Glu Trp Val Ser Ser Ile Ser Gly Ser Gly Arg Asp
        195                 200                 205

Thr Leu Tyr Ala Glu Ser Val Lys Gly Arg Phe Thr Ile Ser Arg Asp
    210                 215                 220

Asn Ala Lys Thr Thr Leu Tyr Leu Gln Met Asn Ser Leu Arg Pro Glu
225                 230                 235                 240

Asp Thr Ala Val Tyr Tyr Cys Thr Ile Gly Gly Ser Leu Ser Val Ser
                245                 250                 255

Ser Gln Gly Thr Leu Val Thr Val Ser Ser Gly Gly Pro Gly Pro
            260                 265                 270

Ala Gly Met Lys Gly Leu Pro Gly Ser Met Trp Glu Leu Glu Lys Asp
        275                 280                 285

Val Tyr Val Val Glu Val Asp Trp Thr Pro Asp Ala Pro Gly Glu Thr
    290                 295                 300

Val Asn Leu Thr Cys Asp Thr Pro Glu Glu Asp Asp Ile Thr Trp Thr
305                 310                 315                 320

Ser Asp Gln Arg His Gly Val Ile Gly Ser Gly Lys Thr Leu Thr Ile
                325                 330                 335
```

```
Thr Val Lys Glu Phe Leu Asp Ala Gly Gln Tyr Thr Cys His Lys Gly
            340                 345                 350

Gly Glu Thr Leu Ser His Ser His Leu Leu Leu His Lys Lys Glu Asn
            355                 360                 365

Gly Ile Trp Ser Thr Glu Ile Leu Lys Asn Phe Lys Asn Lys Thr Phe
370                 375                 380

Leu Lys Cys Glu Ala Pro Asn Tyr Ser Gly Arg Phe Thr Cys Ser Trp
385                 390                 395                 400

Leu Val Gln Arg Asn Met Asp Leu Lys Phe Asn Ile Lys Ser Ser Ser
            405                 410                 415

Ser Ser Pro Asp Ser Arg Ala Val Thr Cys Gly Met Ala Ser Leu Ser
            420                 425                 430

Ala Glu Lys Val Thr Leu Asp Gln Arg Asp Tyr Glu Lys Tyr Ser Val
            435                 440                 445

Ser Cys Gln Glu Asp Val Thr Cys Pro Thr Ala Glu Glu Thr Leu Pro
            450                 455                 460

Ile Glu Leu Ala Leu Glu Ala Arg Gln Gln Asn Lys Tyr Glu Asn Tyr
465                 470                 475                 480

Ser Thr Ser Phe Phe Ile Arg Asp Ile Ile Lys Pro Asp Pro Pro Lys
            485                 490                 495

Asn Leu Gln Met Lys Pro Leu Lys Asn Ser Gln Val Glu Val Ser Trp
            500                 505                 510

Glu Tyr Pro Asp Ser Trp Ser Thr Pro His Ser Tyr Phe Ser Leu Lys
            515                 520                 525

Phe Phe Val Arg Ile Gln Arg Lys Lys Glu Lys Met Lys Glu Thr Glu
            530                 535                 540

Glu Gly Cys Asn Gln Lys Gly Ala Phe Leu Val Glu Lys Thr Ser Thr
545                 550                 555                 560

Glu Val Gln Cys Lys Gly Gly Asn Val Cys Val Gln Ala Gln Asp Arg
            565                 570                 575

Tyr Tyr Asn Ser Ser Cys Ser Lys Trp Ala Cys Val Pro Cys Arg Val
            580                 585                 590

Arg Ser Gly Gly Gly Ser Gly Gly Gly Ser Gly Gly Gly Gly
            595                 600                 605

Ser Arg Val Ile Pro Val Ser Gly Pro Ala Arg Cys Leu Ser Gln Ser
            610                 615                 620

Arg Asn Leu Leu Lys Thr Thr Asp Asp Met Val Lys Thr Ala Arg Glu
625                 630                 635                 640

Lys Leu Lys His Tyr Ser Cys Thr Ala Glu Asp Ile Asp His Glu Asp
            645                 650                 655

Ile Thr Arg Asp Gln Thr Ser Thr Leu Lys Thr Cys Leu Pro Leu Glu
            660                 665                 670

Leu His Lys Asn Glu Ser Cys Leu Ala Thr Arg Glu Thr Ser Ser Thr
            675                 680                 685

Thr Arg Gly Ser Cys Leu Pro Pro Gln Lys Thr Ser Leu Met Met Thr
            690                 695                 700

Leu Cys Leu Gly Ser Ile Tyr Glu Asp Leu Lys Met Tyr Gln Thr Glu
705                 710                 715                 720

Phe Gln Ala Ile Asn Ala Ala Leu Gln Asn His Asn His Gln Gln Ile
            725                 730                 735

Ile Leu Asp Lys Gly Met Leu Val Ala Ile Asp Glu Leu Met Gln Ser
            740                 745                 750
```

```
Leu Asn His Asn Gly Glu Thr Leu Arg Gln Lys Pro Pro Val Gly Glu
        755                 760                 765

Ala Asp Pro Tyr Arg Val Lys Met Lys Leu Cys Ile Leu Leu His Ala
770                 775                 780

Phe Ser Thr Arg Val Val Thr Ile Asn Arg Val Met Gly Tyr Leu Ser
785                 790                 795                 800

Ser Ala Ser Gly Gly Pro Gly Pro Ala Gly Met Lys Gly Leu Pro Gly
            805                 810                 815

Ser Glu Val Gln Leu Val Glu Ser Gly Gly Leu Val Gln Pro Gly
            820                 825                 830

Asn Ser Leu Arg Leu Ser Cys Ala Ala Ser Gly Phe Thr Phe Ser Lys
        835                 840                 845

Phe Gly Met Ser Trp Val Arg Gln Ala Pro Gly Lys Gly Leu Glu Trp
850                 855                 860

Val Ser Ser Ile Ser Gly Ser Gly Arg Asp Thr Leu Tyr Ala Glu Ser
865                 870                 875                 880

Val Lys Gly Arg Phe Thr Ile Ser Arg Asp Asn Ala Lys Thr Thr Leu
                885                 890                 895

Tyr Leu Gln Met Asn Ser Leu Arg Pro Glu Asp Thr Ala Val Tyr Tyr
            900                 905                 910

Cys Thr Ile Gly Gly Ser Leu Ser Val Ser Gln Gly Thr Leu Val
        915                 920                 925

Thr Val Ser Ser His His His His His His
        930                 935

<210> SEQ ID NO 64
<211> LENGTH: 938
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Gln Pro Gly Asn Ser Leu Arg Leu Ser Cys Ala Ala Ser Gly
            35                  40                  45

Phe Thr Phe Ser Lys Phe Gly Met Ser Trp Val Arg Gln Ala Pro Gly
        50                  55                  60

Lys Gly Leu Glu Trp Val Ser Ser Ile Ser Gly Ser Gly Arg Asp Thr
65                  70                  75                  80

Leu Tyr Ala Glu Ser Val Lys Gly Arg Phe Thr Ile Ser Arg Asp Asn
                85                  90                  95

Ala Lys Thr Thr Leu Tyr Leu Gln Met Asn Ser Leu Arg Pro Glu Asp
            100                 105                 110

Thr Ala Val Tyr Tyr Cys Thr Ile Gly Gly Ser Leu Ser Val Ser Ser
        115                 120                 125

Gln Gly Thr Leu Val Thr Val Ser Ser Ser Gly Gly Pro Gly Pro Ala
    130                 135                 140

Gly Met Lys Gly Leu Pro Gly Ser Met Trp Glu Leu Glu Lys Asp Val
145                 150                 155                 160

Tyr Val Val Glu Val Asp Trp Thr Pro Asp Ala Pro Gly Glu Thr Val
                165                 170                 175
```

```
Asn Leu Thr Cys Asp Thr Pro Glu Glu Asp Ile Thr Trp Thr Ser
            180                 185                 190

Asp Gln Arg His Gly Val Ile Gly Ser Gly Lys Thr Leu Thr Ile Thr
            195                 200                 205

Val Lys Glu Phe Leu Asp Ala Gly Gln Tyr Thr Cys His Lys Gly Gly
210                 215                 220

Glu Thr Leu Ser His Ser His Leu Leu Leu His Lys Lys Glu Asn Gly
225                 230                 235                 240

Ile Trp Ser Thr Glu Ile Leu Lys Asn Phe Lys Asn Lys Thr Phe Leu
            245                 250                 255

Lys Cys Glu Ala Pro Asn Tyr Ser Gly Arg Phe Thr Cys Ser Trp Leu
            260                 265                 270

Val Gln Arg Asn Met Asp Leu Lys Phe Asn Ile Lys Ser Ser Ser Ser
            275                 280                 285

Ser Pro Asp Ser Arg Ala Val Thr Cys Gly Met Ala Ser Leu Ser Ala
            290                 295                 300

Glu Lys Val Thr Leu Asp Gln Arg Asp Tyr Glu Lys Tyr Ser Val Ser
305                 310                 315                 320

Cys Gln Glu Asp Val Thr Cys Pro Thr Ala Glu Glu Thr Leu Pro Ile
            325                 330                 335

Glu Leu Ala Leu Glu Ala Arg Gln Gln Asn Lys Tyr Glu Asn Tyr Ser
            340                 345                 350

Thr Ser Phe Phe Ile Arg Asp Ile Ile Lys Pro Asp Pro Pro Lys Asn
            355                 360                 365

Leu Gln Met Lys Pro Leu Lys Asn Ser Gln Val Glu Val Ser Trp Glu
            370                 375                 380

Tyr Pro Asp Ser Trp Ser Thr Pro His Ser Tyr Phe Ser Leu Lys Phe
385                 390                 395                 400

Phe Val Arg Ile Gln Arg Lys Lys Glu Lys Met Lys Glu Thr Glu Glu
            405                 410                 415

Gly Cys Asn Gln Lys Gly Ala Phe Leu Val Glu Lys Thr Ser Thr Glu
            420                 425                 430

Val Gln Cys Lys Gly Gly Asn Val Cys Val Gln Ala Gln Asp Arg Tyr
            435                 440                 445

Tyr Asn Ser Ser Cys Ser Lys Trp Ala Cys Val Pro Cys Arg Val Arg
450                 455                 460

Ser Gly Gly Gly Gly Ser Gly Gly Gly Ser Gly Gly Gly Gly Ser
465                 470                 475                 480

Arg Val Ile Pro Val Ser Gly Pro Ala Arg Cys Leu Ser Gln Ser Arg
            485                 490                 495

Asn Leu Leu Lys Thr Thr Asp Asp Met Val Lys Thr Ala Arg Glu Lys
            500                 505                 510

Leu Lys His Tyr Ser Cys Thr Ala Glu Asp Ile Asp His Glu Asp Ile
            515                 520                 525

Thr Arg Asp Gln Thr Ser Thr Leu Lys Thr Cys Leu Pro Leu Glu Leu
            530                 535                 540

His Lys Asn Glu Ser Cys Leu Ala Thr Arg Glu Thr Ser Ser Thr Thr
545                 550                 555                 560

Arg Gly Ser Cys Leu Pro Pro Gln Lys Thr Ser Leu Met Met Thr Leu
            565                 570                 575

Cys Leu Gly Ser Ile Tyr Glu Asp Leu Lys Met Tyr Gln Thr Glu Phe
            580                 585                 590
```

```
Gln Ala Ile Asn Ala Ala Leu Gln Asn His Asn His Gln Ile Ile
            595                 600                 605

Leu Asp Lys Gly Met Leu Val Ala Ile Asp Glu Leu Met Gln Ser Leu
610                 615                 620

Asn His Asn Gly Glu Thr Leu Arg Gln Lys Pro Pro Val Gly Glu Ala
625                 630                 635                 640

Asp Pro Tyr Arg Val Lys Met Lys Leu Cys Ile Leu Leu His Ala Phe
                645                 650                 655

Ser Thr Arg Val Val Thr Ile Asn Arg Val Met Gly Tyr Leu Ser Ser
            660                 665                 670

Ala Ser Gly Gly Pro Gly Pro Ala Gly Met Lys Gly Leu Pro Gly Ser
        675                 680                 685

Glu Val Gln Leu Val Glu Ser Gly Gly Gly Leu Val Gln Pro Gly Asn
690                 695                 700

Ser Leu Arg Leu Ser Cys Ala Ala Ser Gly Phe Thr Phe Ser Lys Phe
705                 710                 715                 720

Gly Met Ser Trp Val Arg Gln Ala Pro Gly Lys Gly Leu Glu Trp Val
                725                 730                 735

Ser Ser Ile Ser Gly Ser Gly Arg Asp Thr Leu Tyr Ala Glu Ser Val
            740                 745                 750

Lys Gly Arg Phe Thr Ile Ser Arg Asp Asn Ala Lys Thr Thr Leu Tyr
        755                 760                 765

Leu Gln Met Asn Ser Leu Arg Pro Glu Asp Thr Ala Val Tyr Tyr Cys
770                 775                 780

Thr Ile Gly Gly Ser Leu Ser Val Ser Ser Gln Gly Thr Leu Val Thr
785                 790                 795                 800

Val Ser Ser Gly Gly Gly Gly Ser Gly Gly Gly Gly Ser Gly Gly Gly
                805                 810                 815

Gly Ser Gln Val Gln Leu Gln Glu Ser Gly Gly Leu Val Gln Ala
            820                 825                 830

Gly Gly Ser Leu Arg Leu Ser Cys Ala Ala Ser Gly Arg Ile Phe Ser
        835                 840                 845

Ile Asp Ile Met Ser Trp Tyr Arg Gln Ala Pro Gly Lys Gln Arg Glu
850                 855                 860

Leu Val Ala Arg Ile Thr Arg Gly Gly Thr Ile Ser Tyr Asp Asp Ser
865                 870                 875                 880

Val Lys Gly Arg Phe Thr Ile Ser Arg Asp Asn Ala Lys Asn Thr Val
                885                 890                 895

Tyr Leu Gln Met Asn Ser Leu Lys Pro Glu Asp Thr Gly Val Tyr Tyr
            900                 905                 910

Cys Asn Ala Leu Tyr Gly Thr Asp Tyr Trp Gly Lys Gly Thr Gln Val
        915                 920                 925

Thr Val Ser Ser His His His His His
930                 935

<210> SEQ ID NO 65
<211> LENGTH: 962
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asp Met Arg Val Pro Ala Gln Leu Leu Gly Leu Leu Leu Leu Trp
1               5                   10                  15
```

```
Leu Arg Gly Ala Arg Cys Ile Trp Glu Leu Lys Lys Asp Val Tyr Val
             20                  25                  30

Val Glu Leu Asp Trp Tyr Pro Asp Ala Pro Gly Glu Met Val Val Leu
         35                  40                  45

Thr Cys Asp Thr Pro Glu Glu Asp Gly Ile Thr Trp Thr Leu Asp Gln
     50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
             100                 105                 110

Ser Thr Asp Ile Leu Lys Asp Gln Lys Glu Pro Lys Asn Lys Thr Phe
         115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Ser Gly Gly Gly
                325                 330                 335

Gly Ser Gly Gly Gly Gly Ser Arg Val Ile Pro Val Ser Gly Pro Ala
            340                 345                 350

Arg Cys Leu Ser Gln Ser Arg Asn Leu Leu Lys Thr Thr Asp Asp Met
        355                 360                 365

Val Lys Thr Ala Arg Glu Lys Leu Lys His Tyr Ser Cys Thr Ala Glu
    370                 375                 380

Asp Ile Asp His Glu Asp Ile Thr Arg Asp Gln Thr Ser Thr Leu Lys
385                 390                 395                 400

Thr Cys Leu Pro Leu Glu Leu His Lys Asn Glu Ser Cys Leu Ala Thr
                405                 410                 415

Arg Glu Thr Ser Ser Thr Thr Arg Gly Ser Cys Leu Pro Pro Gln Lys
            420                 425                 430
```

```
Thr Ser Leu Met Met Thr Leu Cys Leu Gly Ser Ile Tyr Glu Asp Leu
            435                 440                 445

Lys Met Tyr Gln Thr Glu Phe Gln Ala Ile Asn Ala Ala Leu Gln Asn
450                 455                 460

His Asn His Gln Gln Ile Ile Leu Asp Lys Gly Met Leu Val Ala Ile
465                 470                 475                 480

Asp Glu Leu Met Gln Ser Leu Asn His Asn Gly Glu Thr Leu Arg Gln
            485                 490                 495

Lys Pro Pro Val Gly Glu Ala Asp Pro Tyr Arg Val Lys Met Lys Leu
            500                 505                 510

Cys Ile Leu Leu His Ala Phe Ser Thr Arg Val Val Thr Ile Asn Arg
            515                 520                 525

Val Met Gly Tyr Leu Ser Ser Ala Gly Gly Gly Ser Gly Gly Gly Gly
            530                 535                 540

Gly Ser Gly Gly Gly Gly Ser Gly Gly Gly Ser Gly Gly Gly Gly
545                 550                 555                 560

Ser Gly Gly Gly Ser Gly Gly Gly Ser Gly Gly Gly Gly Ser
            565                 570                 575

Gly Gly Gly Gly Ser Gln Ser Val Leu Thr Gln Pro Pro Ser Val Ser
            580                 585                 590

Gly Ala Pro Gly Gln Arg Val Thr Ile Ser Cys Ser Gly Ser Arg Ser
            595                 600                 605

Asn Ile Gly Ser Asn Thr Val Lys Trp Tyr Gln Leu Pro Gly Thr
            610                 615                 620

Ala Pro Lys Leu Leu Ile Tyr Tyr Asn Asp Gln Arg Pro Ser Gly Val
625                 630                 635                 640

Pro Asp Arg Phe Ser Gly Ser Lys Ser Gly Thr Ser Ala Ser Leu Ala
            645                 650                 655

Ile Thr Gly Leu Gln Ala Glu Asp Glu Ala Asp Tyr Tyr Cys Gln Ser
            660                 665                 670

Tyr Asp Arg Tyr Thr His Pro Ala Leu Leu Phe Gly Thr Gly Thr Lys
            675                 680                 685

Val Thr Val Leu Gly Gly Gly Gly Ser Gly Gly Gly Gly Ser Gly Gly
            690                 695                 700

Gly Gly Ser Gln Val Gln Leu Val Glu Ser Gly Gly Val Val Gln
705                 710                 715                 720

Pro Gly Arg Ser Leu Arg Leu Ser Cys Ala Ala Ser Gly Phe Thr Phe
            725                 730                 735

Ser Ser Tyr Gly Met His Trp Val Arg Gln Ala Pro Gly Lys Gly Leu
            740                 745                 750

Glu Trp Val Ala Phe Ile Arg Tyr Asp Gly Ser Asn Lys Tyr Tyr Ala
            755                 760                 765

Asp Ser Val Lys Gly Arg Phe Thr Ile Ser Arg Asp Asn Ser Lys Asn
            770                 775                 780

Thr Leu Tyr Leu Gln Met Asn Ser Leu Arg Ala Glu Asp Thr Ala Val
785                 790                 795                 800

Tyr Tyr Cys Lys Thr His Gly Ser His Asp Asn Trp Gly Gln Gly Thr
            805                 810                 815

Met Val Thr Val Ser Ser Gly Gly Gly Ser Gly Gly Gly Gly Ser
            820                 825                 830

Gly Gly Gly Gly Ser Glu Val Gln Leu Val Glu Ser Gly Gly Gly Leu
            835                 840                 845
```

```
Val Gln Pro Gly Asn Ser Leu Arg Leu Ser Cys Ala Ala Ser Gly Phe
    850                 855                 860

Thr Phe Ser Lys Phe Gly Met Ser Trp Val Arg Gln Ala Pro Gly Lys
865                 870                 875                 880

Gly Leu Glu Trp Val Ser Ser Ile Ser Gly Ser Gly Arg Asp Thr Leu
                885                 890                 895

Tyr Ala Glu Ser Val Lys Gly Arg Phe Thr Ile Ser Arg Asp Asn Ala
            900                 905                 910

Lys Thr Thr Leu Tyr Leu Gln Met Asn Ser Leu Arg Pro Glu Asp Thr
        915                 920                 925

Ala Val Tyr Tyr Cys Thr Ile Gly Gly Ser Leu Ser Val Ser Ser Gln
    930                 935                 940

Gly Thr Leu Val Thr Val Ser Ser His His His His His His Glu Pro
945                 950                 955                 960

Glu Ala

<210> SEQ ID NO 66
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Met Arg Val Pro Ala Gln Leu Leu Gly Leu Leu Leu Leu Trp
1               5                   10                  15

Leu Arg Gly Ala Arg Cys Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240
```

-continued

```
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Ser Gly Gly Gly
                325                 330                 335
Gly Ser Gly Gly Gly Gly Ser Arg Val Ile Pro Val Ser Gly Pro Ala
            340                 345                 350
Arg Cys Leu Ser Gln Ser Arg Asn Leu Leu Lys Thr Thr Asp Asp Met
        355                 360                 365
Val Lys Thr Ala Arg Glu Lys Leu Lys His Tyr Ser Cys Thr Ala Glu
    370                 375                 380
Asp Ile Asp His Glu Asp Ile Thr Arg Asp Gln Thr Ser Thr Leu Lys
385                 390                 395                 400
Thr Cys Leu Pro Leu Glu Leu His Lys Asn Glu Ser Cys Leu Ala Thr
                405                 410                 415
Arg Glu Thr Ser Ser Thr Thr Arg Gly Ser Cys Leu Pro Pro Gln Lys
            420                 425                 430
Thr Ser Leu Met Met Thr Leu Cys Leu Gly Ser Ile Tyr Glu Asp Leu
        435                 440                 445
Lys Met Tyr Gln Thr Glu Phe Gln Ala Ile Asn Ala Ala Leu Gln Asn
    450                 455                 460
His Asn His Gln Gln Ile Ile Leu Asp Lys Gly Met Leu Val Ala Ile
465                 470                 475                 480
Asp Glu Leu Met Gln Ser Leu Asn His Asn Gly Glu Thr Leu Arg Gln
                485                 490                 495
Lys Pro Pro Val Gly Glu Ala Asp Pro Tyr Arg Val Lys Met Lys Leu
            500                 505                 510
Cys Ile Leu Leu His Ala Phe Ser Thr Arg Val Val Thr Ile Asn Arg
        515                 520                 525
Val Met Gly Tyr Leu Ser Ser Ala Ser Gly Gly Pro Gly Pro Ala Gly
    530                 535                 540
Met Lys Gly Leu Pro Gly Ser Gly Gly Gly Ser Gly Gly Gly Gly
545                 550                 555                 560
Ser Gly Gly Gly Ser Gly Gly Gly Gly Ser Gly Gly Gly Gly Ser
                565                 570                 575
Gly Gly Gly Gly Ser Gln Ser Val Leu Thr Gln Pro Pro Ser Val Ser
            580                 585                 590
Gly Ala Pro Gly Gln Arg Val Thr Ile Ser Cys Ser Gly Ser Arg Ser
        595                 600                 605
Asn Ile Gly Ser Asn Thr Val Lys Trp Tyr Gln Gln Leu Pro Gly Thr
    610                 615                 620
Ala Pro Lys Leu Leu Ile Tyr Tyr Asn Asp Gln Arg Pro Ser Gly Val
625                 630                 635                 640
Pro Asp Arg Phe Ser Gly Ser Lys Ser Gly Thr Ser Ala Ser Leu Ala
                645                 650                 655
```

-continued

```
Ile Thr Gly Leu Gln Ala Glu Asp Glu Ala Asp Tyr Tyr Cys Gln Ser
            660                 665                 670

Tyr Asp Arg Tyr Thr His Pro Ala Leu Leu Phe Gly Thr Gly Thr Lys
        675                 680                 685

Val Thr Val Leu Gly Gly Gly Gly Ser Gly Gly Gly Gly Ser Gly Gly
    690                 695                 700

Gly Gly Ser Gln Val Gln Leu Val Glu Ser Gly Gly Val Val Gln
705                 710                 715                 720

Pro Gly Arg Ser Leu Arg Leu Ser Cys Ala Ala Ser Gly Phe Thr Phe
                725                 730                 735

Ser Ser Tyr Gly Met His Trp Val Arg Gln Ala Pro Gly Lys Gly Leu
            740                 745                 750

Glu Trp Val Ala Phe Ile Arg Tyr Asp Gly Ser Asn Lys Tyr Tyr Ala
        755                 760                 765

Asp Ser Val Lys Gly Arg Phe Thr Ile Ser Arg Asp Asn Ser Lys Asn
    770                 775                 780

Thr Leu Tyr Leu Gln Met Asn Ser Leu Arg Ala Glu Asp Thr Ala Val
785                 790                 795                 800

Tyr Tyr Cys Lys Thr His Gly Ser His Asp Asn Trp Gly Gln Gly Thr
                805                 810                 815

Met Val Thr Val Ser Ser His His His His His His Glu Pro Glu Ala
            820                 825                 830

<210> SEQ ID NO 67
<211> LENGTH: 1091
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Met Arg Val Pro Ala Gln Leu Leu Gly Leu Leu Leu Leu Trp
1               5                   10                  15

Leu Arg Gly Ala Arg Cys Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190
```

-continued

```
Cys Gln Glu Asp Ser Ala Cys Pro Ala Ala Glu Ser Leu Pro Ile
    195                 200                 205
Glu Val Met Val Asp Ala Val His Lys Leu Lys Tyr Glu Asn Tyr Thr
210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Ser Gly Gly Gly
                325                 330                 335
Gly Ser Gly Gly Gly Gly Ser Arg Val Ile Pro Val Ser Gly Pro Ala
            340                 345                 350
Arg Cys Leu Ser Gln Ser Arg Asn Leu Leu Lys Thr Thr Asp Asp Met
        355                 360                 365
Val Lys Thr Ala Arg Glu Lys Leu Lys His Tyr Ser Cys Thr Ala Glu
    370                 375                 380
Asp Ile Asp His Glu Asp Ile Thr Arg Asp Gln Thr Ser Thr Leu Lys
385                 390                 395                 400
Thr Cys Leu Pro Leu Glu Leu His Lys Asn Glu Ser Cys Leu Ala Thr
                405                 410                 415
Arg Glu Thr Ser Ser Thr Thr Arg Gly Ser Cys Leu Pro Pro Gln Lys
            420                 425                 430
Thr Ser Leu Met Met Thr Leu Cys Leu Gly Ser Ile Tyr Glu Asp Leu
        435                 440                 445
Lys Met Tyr Gln Thr Glu Phe Gln Ala Ile Asn Ala Ala Leu Gln Asn
    450                 455                 460
His Asn His Gln Gln Ile Ile Leu Asp Lys Gly Met Leu Val Ala Ile
465                 470                 475                 480
Asp Glu Leu Met Gln Ser Leu Asn His Asn Gly Glu Thr Leu Arg Gln
                485                 490                 495
Lys Pro Pro Val Gly Glu Ala Asp Pro Tyr Arg Val Lys Met Lys Leu
            500                 505                 510
Cys Ile Leu Leu His Ala Phe Ser Thr Arg Val Val Thr Ile Asn Arg
        515                 520                 525
Val Met Gly Tyr Leu Ser Ser Ala Ser Gly Gly Pro Gly Pro Ala Gly
    530                 535                 540
Met Lys Gly Leu Pro Gly Ser Gly Gly Gly Ser Gly Gly Gly Gly
545                 550                 555                 560
Ser Gly Gly Gly Ser Gly Gly Gly Ser Gly Gly Gly Ser
                565                 570                 575
Gly Gly Gly Gly Ser Gln Ser Val Leu Thr Gln Pro Pro Ser Val Ser
            580                 585                 590
Gly Ala Pro Gly Gln Arg Val Thr Ile Ser Cys Ser Gly Ser Arg Ser
        595                 600                 605
```

```
Asn Ile Gly Ser Asn Thr Val Lys Trp Tyr Gln Gln Leu Pro Gly Thr
610                 615                 620

Ala Pro Lys Leu Leu Ile Tyr Tyr Asn Asp Gln Arg Pro Ser Gly Val
625                 630                 635                 640

Pro Asp Arg Phe Ser Gly Ser Lys Ser Gly Thr Ser Ala Ser Leu Ala
                645                 650                 655

Ile Thr Gly Leu Gln Ala Glu Asp Glu Ala Asp Tyr Tyr Cys Gln Ser
            660                 665                 670

Tyr Asp Arg Tyr Thr His Pro Ala Leu Leu Phe Gly Thr Gly Thr Lys
        675                 680                 685

Val Thr Val Leu Gly Gly Gly Gly Ser Gly Gly Gly Gly Ser Gly Gly
690                 695                 700

Gly Gly Ser Gln Val Gln Leu Val Glu Ser Gly Gly Gly Val Val Gln
705                 710                 715                 720

Pro Gly Arg Ser Leu Arg Leu Ser Cys Ala Ala Ser Gly Phe Thr Phe
                725                 730                 735

Ser Ser Tyr Gly Met His Trp Val Arg Gln Ala Pro Gly Lys Gly Leu
            740                 745                 750

Glu Trp Val Ala Phe Ile Arg Tyr Asp Gly Ser Asn Lys Tyr Tyr Ala
        755                 760                 765

Asp Ser Val Lys Gly Arg Phe Thr Ile Ser Arg Asp Asn Ser Lys Asn
770                 775                 780

Thr Leu Tyr Leu Gln Met Asn Ser Leu Arg Ala Glu Asp Thr Ala Val
785                 790                 795                 800

Tyr Tyr Cys Lys Thr His Gly Ser His Asp Asn Trp Gly Gln Gly Thr
                805                 810                 815

Met Val Thr Val Ser Ser Gly Gly Gly Gly Ser Gly Gly Gly Gly Ser
            820                 825                 830

Gly Gly Gly Gly Ser Glu Val Gln Leu Val Glu Ser Gly Gly Gly Leu
            835                 840                 845

Val Gln Pro Gly Asn Ser Leu Arg Leu Ser Cys Ala Ala Ser Gly Phe
850                 855                 860

Thr Phe Ser Lys Phe Gly Met Ser Trp Val Arg Gln Ala Pro Gly Lys
865                 870                 875                 880

Gly Leu Glu Trp Val Ser Ser Ile Ser Gly Ser Gly Arg Asp Thr Leu
                885                 890                 895

Tyr Ala Glu Ser Val Lys Gly Arg Phe Thr Ile Ser Arg Asp Asn Ala
            900                 905                 910

Lys Thr Thr Leu Tyr Leu Gln Met Asn Ser Leu Arg Pro Glu Asp Thr
        915                 920                 925

Ala Val Tyr Tyr Cys Thr Ile Gly Gly Ser Leu Ser Val Ser Ser Gln
            930                 935                 940

Gly Thr Leu Val Thr Val Ser Ser Gly Gly Gly Gly Ser Gly Gly Gly
945                 950                 955                 960

Gly Ser Gly Gly Gly Gly Ser Gln Val Gln Leu Gln Glu Ser Gly Gly
                965                 970                 975

Gly Leu Ala Gln Ala Gly Gly Ser Leu Ser Leu Ser Cys Ala Ala Ser
            980                 985                 990

Gly Phe Thr Val Ser Asn Ser Val Met Ala Trp Tyr Arg Gln Thr Pro
        995                 1000                1005

Gly Lys Gln Arg Glu Phe Val Ala Ile Ile Asn Ser Val Gly Ser
        1010                1015                1020
```

```
Thr Asn Tyr Ala Asp Ser Val Lys Gly Arg Phe Thr Ile Ser Arg
    1025                1030                1035

Asp Asn Ala Lys Asn Thr Val Tyr Leu Gln Met Asn Asn Leu Lys
    1040                1045                1050

Pro Glu Asp Thr Ala Val Tyr Val Cys Asn Arg Asn Phe Asp Arg
    1055                1060                1065

Ile Tyr Trp Gly Gln Gly Thr Gln Val Thr Val Ser Ser His His
    1070                1075                1080

His His His His Glu Pro Glu Ala
    1085                1090

<210> SEQ ID NO 68
<211> LENGTH: 1091
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Ala Gln Ala Gly Gly Ser Leu Ser Leu Ser Cys Ala Ala Ser Gly
        35                  40                  45

Phe Thr Val Ser Asn Ser Val Met Ala Trp Tyr Arg Gln Thr Pro Gly
    50                  55                  60

Lys Gln Arg Glu Phe Val Ala Ile Ile Asn Ser Val Gly Ser Thr Asn
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Asn Leu Lys Pro Glu Asp Thr
            100                 105                 110

Ala Val Tyr Val Cys Asn Arg Asn Phe Asp Arg Ile Tyr Trp Gly Gln
        115                 120                 125

Gly Thr Gln Val Thr Val Ser Ser Gly Gly Gly Ser Gly Gly Gly
    130                 135                 140

Gly Ser Gly Gly Gly Ser Ile Trp Glu Leu Lys Lys Asp Val Tyr
145                 150                 155                 160

Val Val Glu Leu Asp Trp Tyr Pro Asp Ala Pro Gly Glu Met Val Val
                165                 170                 175

Leu Thr Cys Asp Thr Pro Glu Glu Asp Gly Ile Thr Trp Thr Leu Asp
            180                 185                 190

Gln Ser Ser Glu Val Leu Gly Ser Gly Lys Thr Leu Thr Ile Gln Val
        195                 200                 205

Lys Glu Phe Gly Asp Ala Gly Gln Tyr Thr Cys His Lys Gly Gly Glu
    210                 215                 220

Val Leu Ser His Ser Leu Leu Leu Leu His Lys Lys Glu Asp Gly Ile
225                 230                 235                 240

Trp Ser Thr Asp Ile Leu Lys Asp Gln Lys Glu Pro Lys Asn Lys Thr
                245                 250                 255

Phe Leu Arg Cys Glu Ala Lys Asn Tyr Ser Gly Arg Phe Thr Cys Trp
            260                 265                 270
```

-continued

Trp Leu Thr Thr Ile Ser Thr Asp Leu Thr Phe Ser Val Lys Ser Ser
            275                 280                 285

Arg Gly Ser Ser Asp Pro Gln Gly Val Thr Cys Gly Ala Ala Thr Leu
        290                 295                 300

Ser Ala Glu Arg Val Arg Gly Asp Asn Lys Glu Tyr Glu Tyr Ser Val
305                 310                 315                 320

Glu Cys Gln Glu Asp Ser Ala Cys Pro Ala Ala Glu Glu Ser Leu Pro
                325                 330                 335

Ile Glu Val Met Val Asp Ala Val His Lys Leu Lys Tyr Glu Asn Tyr
            340                 345                 350

Thr Ser Ser Phe Phe Ile Arg Asp Ile Lys Pro Asp Pro Pro Lys
        355                 360                 365

Asn Leu Gln Leu Lys Pro Leu Lys Asn Ser Arg Gln Val Glu Val Ser
370                 375                 380

Trp Glu Tyr Pro Asp Thr Trp Ser Thr Pro His Ser Tyr Phe Ser Leu
385                 390                 395                 400

Thr Phe Cys Val Gln Val Gln Gly Lys Ser Lys Arg Glu Lys Lys Asp
                405                 410                 415

Arg Val Phe Thr Asp Lys Thr Ser Ala Thr Val Ile Cys Arg Lys Asn
            420                 425                 430

Ala Ser Ile Ser Val Arg Ala Gln Asp Arg Tyr Tyr Ser Ser Ser Trp
        435                 440                 445

Ser Glu Trp Ala Ser Val Pro Cys Ser Gly Gly Gly Ser Gly Gly
450                 455                 460

Gly Gly Ser Gly Gly Gly Ser Arg Val Ile Pro Val Ser Gly Pro
465                 470                 475                 480

Ala Arg Cys Leu Ser Gln Ser Arg Asn Leu Leu Lys Thr Thr Asp Asp
                485                 490                 495

Met Val Lys Thr Ala Arg Glu Lys Leu Lys His Tyr Ser Cys Thr Ala
            500                 505                 510

Glu Asp Ile Asp His Glu Asp Ile Thr Arg Asp Gln Thr Ser Thr Leu
        515                 520                 525

Lys Thr Cys Leu Pro Leu Glu Leu His Lys Asn Glu Ser Cys Leu Ala
530                 535                 540

Thr Arg Glu Thr Ser Ser Thr Thr Arg Gly Ser Cys Leu Pro Pro Gln
545                 550                 555                 560

Lys Thr Ser Leu Met Met Thr Leu Cys Leu Gly Ser Ile Tyr Glu Asp
                565                 570                 575

Leu Lys Met Tyr Gln Thr Glu Phe Gln Ala Ile Asn Ala Ala Leu Gln
            580                 585                 590

Asn His Asn His Gln Gln Ile Ile Leu Asp Lys Gly Met Leu Val Ala
        595                 600                 605

Ile Asp Glu Leu Met Gln Ser Leu Asn His Asn Gly Glu Thr Leu Arg
610                 615                 620

Gln Lys Pro Pro Val Gly Glu Ala Asp Pro Tyr Arg Val Lys Met Lys
625                 630                 635                 640

Leu Cys Ile Leu Leu His Ala Phe Ser Thr Arg Val Val Thr Ile Asn
                645                 650                 655

Arg Val Met Gly Tyr Leu Ser Ser Ala Ser Gly Gly Pro Gly Pro Ala
            660                 665                 670

Gly Met Lys Gly Leu Pro Gly Ser Gly Gly Gly Ser Gly Gly Gly
        675                 680                 685

```
Gly Ser Gly Gly Gly Gly Ser Gly Gly Gly Ser Gly Gly Gly
    690             695             700
Ser Gly Gly Gly Ser Gln Ser Val Leu Thr Gln Pro Ser Val
705             710             715             720
Ser Gly Ala Pro Gly Gln Arg Val Thr Ile Ser Cys Ser Gly Ser Arg
            725             730             735
Ser Asn Ile Gly Ser Asn Thr Val Lys Trp Tyr Gln Gln Leu Pro Gly
            740             745             750
Thr Ala Pro Lys Leu Leu Ile Tyr Tyr Asn Asp Gln Arg Pro Ser Gly
            755             760             765
Val Pro Asp Arg Phe Ser Gly Ser Lys Ser Gly Thr Ser Ala Ser Leu
770             775             780
Ala Ile Thr Gly Leu Gln Ala Glu Asp Glu Ala Asp Tyr Tyr Cys Gln
785             790             795             800
Ser Tyr Asp Arg Tyr Thr His Pro Ala Leu Leu Phe Gly Thr Gly Thr
            805             810             815
Lys Val Thr Val Leu Gly Gly Gly Ser Gly Gly Gly Ser Gly
    820             825             830
Gly Gly Gly Ser Gln Val Gln Leu Val Glu Ser Gly Gly Val Val
            835             840             845
Gln Pro Gly Arg Ser Leu Arg Leu Ser Cys Ala Ala Ser Gly Phe Thr
850             855             860
Phe Ser Ser Tyr Gly Met His Trp Val Arg Gln Ala Pro Gly Lys Gly
865             870             875             880
Leu Glu Trp Val Ala Phe Ile Arg Tyr Asp Gly Ser Asn Lys Tyr Tyr
            885             890             895
Ala Asp Ser Val Lys Gly Arg Phe Thr Ile Ser Arg Asp Asn Ser Lys
            900             905             910
Asn Thr Leu Tyr Leu Gln Met Asn Ser Leu Arg Ala Glu Asp Thr Ala
        915             920             925
Val Tyr Tyr Cys Lys Thr His Gly Ser His Asp Asn Trp Gly Gln Gly
    930             935             940
Thr Met Val Thr Val Ser Ser Gly Gly Gly Ser Gly Gly Gly Gly
945             950             955             960
Ser Gly Gly Gly Gly Ser Glu Val Gln Leu Val Glu Ser Gly Gly
            965             970             975
Leu Val Gln Pro Gly Asn Ser Leu Arg Leu Ser Cys Ala Ala Ser Gly
            980             985             990
Phe Thr Phe Ser Lys Phe Gly Met Ser Trp Val Arg Gln Ala Pro Gly
            995             1000            1005
Lys Gly Leu Glu Trp Val Ser Ser Ile Ser Gly Ser Gly Arg Asp
    1010            1015            1020
Thr Leu Tyr Ala Glu Ser Val Lys Gly Arg Phe Thr Ile Ser Arg
    1025            1030            1035
Asp Asn Ala Lys Thr Thr Leu Tyr Leu Gln Met Asn Ser Leu Arg
    1040            1045            1050
Pro Glu Asp Thr Ala Val Tyr Tyr Cys Thr Ile Gly Gly Ser Leu
    1055            1060            1065
Ser Val Ser Ser Gln Gly Thr Leu Val Thr Val Ser Ser His His
    1070            1075            1080
His His His His Glu Pro Glu Ala
    1085            1090
```

<210> SEQ ID NO 69
<211> LENGTH: 1091
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Gly Gly
            20                  25                  30

Leu Ala Gln Ala Gly Gly Ser Leu Ser Leu Ser Cys Ala Ala Ser Gly
        35                  40                  45

Phe Thr Val Ser Asn Ser Val Met Ala Trp Tyr Arg Gln Thr Pro Gly
    50                  55                  60

Lys Gln Arg Glu Phe Val Ala Ile Ile Asn Ser Val Gly Ser Thr Asn
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Asn Leu Lys Pro Glu Asp Thr
            100                 105                 110

Ala Val Tyr Val Cys Asn Arg Asn Phe Asp Arg Ile Tyr Trp Gly Gln
        115                 120                 125

Gly Thr Gln Val Thr Val Ser Ser Gly Gly Pro Gly Pro Ala Gly
    130                 135                 140

Met Lys Gly Leu Pro Gly Ser Ile Trp Glu Leu Lys Lys Asp Val Tyr
145                 150                 155                 160

Val Val Glu Leu Asp Trp Tyr Pro Asp Ala Pro Gly Glu Met Val Val
                165                 170                 175

Leu Thr Cys Asp Thr Pro Glu Glu Asp Gly Ile Thr Trp Thr Leu Asp
            180                 185                 190

Gln Ser Ser Glu Val Leu Gly Ser Gly Lys Thr Leu Thr Ile Gln Val
        195                 200                 205

Lys Glu Phe Gly Asp Ala Gly Gln Tyr Thr Cys His Lys Gly Gly Glu
    210                 215                 220

Val Leu Ser His Ser Leu Leu Leu Leu His Lys Lys Glu Asp Gly Ile
225                 230                 235                 240

Trp Ser Thr Asp Ile Leu Lys Asp Gln Lys Glu Pro Lys Asn Lys Thr
                245                 250                 255

Phe Leu Arg Cys Glu Ala Lys Asn Tyr Ser Gly Arg Phe Thr Cys Trp
            260                 265                 270

Trp Leu Thr Thr Ile Ser Thr Asp Leu Thr Phe Ser Val Lys Ser Ser
        275                 280                 285

Arg Gly Ser Ser Asp Pro Gln Gly Val Thr Cys Gly Ala Ala Thr Leu
    290                 295                 300

Ser Ala Glu Arg Val Arg Gly Asp Asn Lys Glu Tyr Glu Tyr Ser Val
305                 310                 315                 320

Glu Cys Gln Glu Asp Ser Ala Cys Pro Ala Ala Glu Glu Ser Leu Pro
                325                 330                 335

Ile Glu Val Met Val Asp Ala Val His Lys Leu Lys Tyr Glu Asn Tyr
            340                 345                 350

Thr Ser Ser Phe Phe Ile Arg Asp Ile Ile Lys Pro Asp Pro Pro Lys
        355                 360                 365
```

```
Asn Leu Gln Leu Lys Pro Leu Lys Asn Ser Arg Gln Val Glu Val Ser
    370                 375                 380

Trp Glu Tyr Pro Asp Thr Trp Ser Thr Pro His Ser Tyr Phe Ser Leu
385                 390                 395                 400

Thr Phe Cys Val Gln Val Gln Gly Lys Ser Lys Arg Glu Lys Lys Asp
                405                 410                 415

Arg Val Phe Thr Asp Lys Thr Ser Ala Thr Val Ile Cys Arg Lys Asn
            420                 425                 430

Ala Ser Ile Ser Val Arg Ala Gln Asp Arg Tyr Tyr Ser Ser Ser Trp
        435                 440                 445

Ser Glu Trp Ala Ser Val Pro Cys Ser Gly Gly Gly Ser Gly Gly
    450                 455                 460

Gly Gly Ser Gly Gly Gly Gly Ser Arg Val Ile Pro Val Ser Gly Pro
465                 470                 475                 480

Ala Arg Cys Leu Ser Gln Ser Arg Asn Leu Leu Lys Thr Thr Asp Asp
                485                 490                 495

Met Val Lys Thr Ala Arg Glu Lys Leu Lys His Tyr Ser Cys Thr Ala
            500                 505                 510

Glu Asp Ile Asp His Glu Asp Ile Thr Arg Asp Gln Thr Ser Thr Leu
        515                 520                 525

Lys Thr Cys Leu Pro Leu Glu Leu His Lys Asn Glu Ser Cys Leu Ala
    530                 535                 540

Thr Arg Glu Thr Ser Ser Thr Thr Arg Gly Ser Cys Leu Pro Pro Gln
545                 550                 555                 560

Lys Thr Ser Leu Met Met Thr Leu Cys Leu Gly Ser Ile Tyr Glu Asp
                565                 570                 575

Leu Lys Met Tyr Gln Thr Glu Phe Gln Ala Ile Asn Ala Ala Leu Gln
            580                 585                 590

Asn His Asn His Gln Gln Ile Ile Leu Asp Lys Gly Met Leu Val Ala
        595                 600                 605

Ile Asp Glu Leu Met Gln Ser Leu Asn His Asn Gly Glu Thr Leu Arg
    610                 615                 620

Gln Lys Pro Pro Val Gly Glu Ala Asp Pro Tyr Arg Val Lys Met Lys
625                 630                 635                 640

Leu Cys Ile Leu Leu His Ala Phe Ser Thr Arg Val Val Thr Ile Asn
                645                 650                 655

Arg Val Met Gly Tyr Leu Ser Ser Ala Ser Gly Gly Pro Gly Pro Ala
            660                 665                 670

Gly Met Lys Gly Leu Pro Gly Ser Gly Gly Gly Ser Gly Gly Gly
    675                 680                 685

Gly Ser Gly Gly Gly Ser Gly Gly Gly Ser Gly Gly Gly Gly
690                 695                 700

Ser Gly Gly Gly Ser Gln Ser Val Leu Thr Gln Pro Pro Ser Val
705                 710                 715                 720

Ser Gly Ala Pro Gly Gln Arg Val Thr Ile Ser Cys Ser Gly Ser Arg
            725                 730                 735

Ser Asn Ile Gly Ser Asn Thr Val Lys Trp Tyr Gln Gln Leu Pro Gly
        740                 745                 750

Thr Ala Pro Lys Leu Leu Ile Tyr Tyr Asn Asp Gln Arg Pro Ser Gly
    755                 760                 765

Val Pro Asp Arg Phe Ser Gly Ser Lys Ser Gly Thr Ser Ala Ser Leu
770                 775                 780
```

Ala Ile Thr Gly Leu Gln Ala Glu Asp Glu Ala Asp Tyr Tyr Cys Gln
785                 790                 795                 800

Ser Tyr Asp Arg Tyr Thr His Pro Ala Leu Leu Phe Gly Thr Gly Thr
                805                 810                 815

Lys Val Thr Val Leu Gly Gly Gly Ser Gly Gly Gly Gly Ser Gly
            820                 825                 830

Gly Gly Gly Ser Gln Val Gln Leu Val Glu Ser Gly Gly Val Val
        835                 840                 845

Gln Pro Gly Arg Ser Leu Arg Leu Ser Cys Ala Ala Ser Gly Phe Thr
850                 855                 860

Phe Ser Ser Tyr Gly Met His Trp Val Arg Gln Ala Pro Gly Lys Gly
865                 870                 875                 880

Leu Glu Trp Val Ala Phe Ile Arg Tyr Asp Gly Ser Asn Lys Tyr Tyr
                885                 890                 895

Ala Asp Ser Val Lys Gly Arg Phe Thr Ile Ser Arg Asp Asn Ser Lys
            900                 905                 910

Asn Thr Leu Tyr Leu Gln Met Asn Ser Leu Arg Ala Glu Asp Thr Ala
        915                 920                 925

Val Tyr Tyr Cys Lys Thr His Gly Ser His Asp Asn Trp Gly Gln Gly
930                 935                 940

Thr Met Val Thr Val Ser Ser Gly Gly Gly Ser Gly Gly Gly Gly
945                 950                 955                 960

Ser Gly Gly Gly Gly Ser Glu Val Gln Leu Val Glu Ser Gly Gly
            965                 970                 975

Leu Val Gln Pro Gly Asn Ser Leu Arg Leu Ser Cys Ala Ala Ser Gly
        980                 985                 990

Phe Thr Phe Ser Lys Phe Gly Met Ser Trp Val Arg Gln Ala Pro Gly
        995                 1000                1005

Lys Gly Leu Glu Trp Val Ser Ser Ile Ser Gly Ser Gly Arg Asp
    1010                1015                1020

Thr Leu Tyr Ala Glu Ser Val Lys Gly Arg Phe Thr Ile Ser Arg
    1025                1030                1035

Asp Asn Ala Lys Thr Thr Leu Tyr Leu Gln Met Asn Ser Leu Arg
    1040                1045                1050

Pro Glu Asp Thr Ala Val Tyr Tyr Cys Thr Ile Gly Gly Ser Leu
    1055                1060                1065

Ser Val Ser Ser Gln Gly Thr Leu Val Thr Val Ser Ser His His
    1070                1075                1080

His His His His Glu Pro Glu Ala
    1085                1090

<210> SEQ ID NO 70
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
            35                  40                  45

Phe Thr Phe Ser Ser Tyr Ala Met Ser Trp Val Arg Gln Ala Pro Gly
        50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Gly Val Gly Ala Phe Arg Pro Tyr
        115                 120                 125

Arg Lys His Glu Trp Gly Gln Gly Thr Leu Val Thr Val Ser Arg Gly
    130                 135                 140

Gly Gly Gly Ser Gly Gly Gly Ser Gly Gly Gly Ser Ser
145                 150                 155                 160

Glu Leu Thr Gln Asp Pro Ala Val Ser Val Ala Leu Gly Gln Thr Val
                165                 170                 175

Arg Ile Thr Cys Gln Gly Asp Ser Leu Arg Ser Tyr Tyr Ala Ser Trp
        180                 185                 190

Tyr Gln Gln Lys Pro Gly Gln Ala Pro Val Leu Val Ile Tyr Gly Lys
    195                 200                 205

Asn Asn Arg Pro Ser Gly Ile Pro Asp Arg Phe Ser Gly Ser Ser Ser
210                 215                 220

Gly Asn Thr Ala Ser Leu Thr Thr Thr Gly Ala Gln Ala Glu Asp Glu
225                 230                 235                 240

Ala Asp Tyr Tyr Cys Asn Ser Ser Pro Phe Glu His Asn Leu Val Val
                245                 250                 255

Phe Gly Gly Gly Thr Lys Leu Thr Val Leu His His His His His His
        260                 265                 270

Glu Pro Glu Ala
        275

<210> SEQ ID NO 71
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

```
Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
            115                 120                 125

Lys Pro Leu Gly Leu Gln Ala Arg Val Val Gly Gly Gly Thr Gln
            130                 135                 140

Thr Val Val Thr Gln Glu Pro Ser Leu Thr Val Ser Pro Gly Gly Thr
145                     150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
            195                 200                 205

Gly Ser Leu Leu Gly Gly Lys Ala Ala Leu Thr Leu Ser Gly Val Gln
            210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
            275                 280                 285

Cys Ala Ala Ser Gly Phe Thr Phe Asn Lys Tyr Ala Ile Asn Trp Val
            290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
            355                 360                 365

Ala Asn Phe Gly Asn Ser Tyr Ile Ser Tyr Trp Ala Tyr Trp Gly Gln
            370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Gly Arg Thr Phe Ser Ser
            420                 425                 430

Tyr Ala Met Gly Trp Phe Arg Gln Ala Pro Gly Lys Glu Arg Glu Phe
            435                 440                 445

Val Val Ala Ile Asn Trp Ala Ser Gly Ser Thr Tyr Tyr Ala Asp Ser
            450                 455                 460

Val Lys Gly Arg Phe Thr Ile Ser Arg Asp Asn Ser Lys Asn Thr Leu
465                 470                 475                 480

Tyr Leu Gln Met Asn Ser Leu Arg Ala Glu Asp Thr Ala Val Tyr Tyr
                485                 490                 495

Cys Ala Ala Gly Tyr Gln Ile Asn Ser Gly Asn Tyr Asn Phe Lys Asp
            500                 505                 510
```

```
Tyr Glu Tyr Asp Tyr Trp Gly Gln Gly Thr Leu Val Thr Val Ser Ser
            515                 520                 525

His His His His His His
    530

<210> SEQ ID NO 72
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
            195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335
```

```
Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
        355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Ser Gly Gly Gly
385                 390                 395                 400

Ser Glu Val Gln Leu Val Glu Ser Gly Gly Gly Leu Val Gln Pro Gly
                405                 410                 415

Gly Ser Leu Thr Leu Ser Cys Ala Ala Ser Gly Arg Thr Phe Ser Ser
            420                 425                 430

Tyr Ala Met Gly Trp Phe Arg Gln Ala Pro Gly Lys Glu Arg Glu Phe
        435                 440                 445

Val Val Ala Ile Asn Trp Ala Ser Gly Ser Thr Tyr Tyr Ala Asp Ser
    450                 455                 460

Val Lys Gly Arg Phe Thr Ile Ser Arg Asp Asn Ser Lys Asn Thr Leu
465                 470                 475                 480

Tyr Leu Gln Met Asn Ser Leu Arg Ala Glu Asp Thr Ala Val Tyr Tyr
                485                 490                 495

Cys Ala Ala Gly Tyr Gln Ile Asn Ser Gly Asn Tyr Asn Phe Lys Asp
            500                 505                 510

Tyr Glu Tyr Asp Tyr Trp Gly Gln Gly Thr Leu Val Thr Val Ser Ser
        515                 520                 525

His His His His His His
    530

<210> SEQ ID NO 73
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Val Val Gly Gly Gly Gly Thr Gln Thr Val Val Thr Gln Glu Pro Ser
1               5                   10                  15

Leu Thr Val Ser Pro Gly Gly Thr Val Thr Leu Thr Cys Ala Ser Ser
            20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
            100                 105                 110

Leu Thr Val Leu Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140
```

```
Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
            165                 170                 175

Glu Trp Val Ala Arg Ile Arg Ser Lys Tyr Asn Asn Tyr Ala Thr Tyr
        180                 185                 190

Tyr Ala Asp Gln Val Lys Asp Arg Phe Thr Ile Ser Arg Asp Asp Ser
    195                 200                 205

Lys Asn Thr Ala Tyr Leu Gln Met Asn Asn Leu Lys Thr Glu Asp Thr
210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
            245                 250                 255

Gly Gly Gly Gly Ser Gly Gly Ser Glu Val Gln Leu Val Glu Ser
            260                 265                 270

Gly Gly Gly Leu Val Gln Pro Gly Gly Ser Leu Thr Leu Ser Cys Ala
            275                 280                 285

Ala Ser Gly Arg Thr Phe Ser Ser Tyr Ala Met Gly Trp Phe Arg Gln
290                 295                 300

Ala Pro Gly Lys Glu Arg Glu Phe Val Ala Ile Asn Trp Ala Ser
305                 310                 315                 320

Gly Ser Thr Tyr Tyr Ala Asp Ser Val Lys Gly Arg Phe Thr Ile Ser
            325                 330                 335

Arg Asp Asn Ser Lys Asn Thr Leu Tyr Leu Gln Met Asn Ser Leu Arg
            340                 345                 350

Ala Glu Asp Thr Ala Val Tyr Tyr Cys Ala Ala Gly Tyr Gln Ile Asn
            355                 360                 365

Ser Gly Asn Tyr Asn Phe Lys Asp Tyr Glu Tyr Asp Tyr Trp Gly Gln
            370                 375                 380

Gly Thr Leu Val Thr Val Ser Ser His His His His His His
385                 390                 395

<210> SEQ ID NO 74
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
            35                  40                  45

Glu Glu Pro Gly Gly Leu Glu Trp Val Ser Ser Ile Ser Gly Ser Gly
        50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
            85                  90                  95
```

```
Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
            115                 120                 125

Lys Pro Leu Gly Leu Gln Ala Arg Val Val Gly Gly Gly Thr Gln
            130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
            195                 200                 205

Gly Ser Leu Leu Gly Gly Lys Ala Ala Leu Thr Leu Ser Gly Val Gln
            210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Ser Glu Val Gln Leu Val
            260                 265                 270

Glu Ser Gly Gly Gly Leu Val Gln Pro Gly Gly Ser Leu Lys Leu Ser
            275                 280                 285

Cys Ala Ala Ser Gly Phe Thr Phe Asn Lys Tyr Ala Ile Asn Trp Val
            290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
            355                 360                 365

Ala Asn Phe Gly Asn Ser Tyr Ile Ser Tyr Trp Ala Tyr Trp Gly Gln
            370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Leu Val Gln Pro Gly
            405                 410                 415

Gly Ser Leu Thr Leu Ser Cys Ala Ala Ser Arg Phe Met Ile Ser Glu
            420                 425                 430

Tyr His Met His Trp Val Arg Gln Ala Pro Gly Lys Gly Leu Glu Trp
            435                 440                 445

Val Ser Thr Ile Asn Pro Ala Gly Thr Thr Asp Tyr Ala Glu Ser Val
            450                 455                 460

Lys Gly Arg Phe Thr Ile Ser Arg Asp Asn Ala Lys Asn Thr Leu Tyr
465                 470                 475                 480

Leu Gln Met Asn Ser Leu Lys Pro Glu Asp Thr Ala Val Tyr Tyr Cys
                485                 490                 495

Asp Ser Tyr Gly Tyr Arg Gly Gln Gly Thr Gln Val Thr Val Ser Ser
            500                 505                 510
```

His His His His His His
        515

<210> SEQ ID NO 75
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser Gly Gly Gly Gly
        115                 120                 125

Ser Gly Gly Gly Gly Ser Gly Gly Val Val Gly Gly Gly Thr Gln
    130                 135                 140

Thr Val Val Thr Gln Glu Pro Ser Leu Thr Val Ser Pro Gly Gly Thr
145                 150                 155                 160

Val Thr Leu Thr Cys Ala Ser Ser Thr Gly Ala Val Thr Ser Gly Asn
                165                 170                 175

Tyr Pro Asn Trp Val Gln Gln Lys Pro Gly Gln Ala Pro Arg Gly Leu
            180                 185                 190

Ile Gly Gly Thr Lys Phe Leu Val Pro Gly Thr Pro Ala Arg Phe Ser
        195                 200                 205

Gly Ser Leu Leu Gly Gly Lys Ala Ala Leu Thr Leu Ser Gly Val Gln
    210                 215                 220

Pro Glu Asp Glu Ala Glu Tyr Tyr Cys Thr Leu Trp Tyr Ser Asn Arg
225                 230                 235                 240

Trp Val Phe Gly Gly Gly Thr Lys Leu Thr Val Leu Gly Gly Gly Gly
                245                 250                 255

Ser Gly Gly Gly Gly Ser Gly Gly Gly Ser Glu Val Gln Leu Val
            260                 265                 270

Glu Ser Gly Gly Gly Leu Val Gln Pro Gly Gly Ser Leu Lys Leu Ser
        275                 280                 285

Cys Ala Ala Ser Gly Phe Thr Phe Asn Lys Tyr Ala Ile Asn Trp Val
    290                 295                 300

Arg Gln Ala Pro Gly Lys Gly Leu Glu Trp Val Ala Arg Ile Arg Ser
305                 310                 315                 320

Lys Tyr Asn Asn Tyr Ala Thr Tyr Tyr Ala Asp Gln Val Lys Asp Arg
                325                 330                 335

Phe Thr Ile Ser Arg Asp Asp Ser Lys Asn Thr Ala Tyr Leu Gln Met
            340                 345                 350

Asn Asn Leu Lys Thr Glu Asp Thr Ala Val Tyr Tyr Cys Val Arg His
                355                 360                 365

Ala Asn Phe Gly Asn Ser Tyr Ile Ser Tyr Trp Ala Tyr Trp Gly Gln
    370                 375                 380

Gly Thr Leu Val Thr Val Ser Ser Gly Gly Gly Gly Ser Gly Gly Gly
385                 390                 395                 400

Ser Glu Val Gln Leu Val Glu Ser Gly Gly Leu Val Gln Pro Gly
                405                 410                 415

Gly Ser Leu Thr Leu Ser Cys Ala Ala Ser Arg Phe Met Ile Ser Glu
                420                 425                 430

Tyr His Met His Trp Val Arg Gln Ala Pro Gly Lys Gly Leu Glu Trp
                435                 440                 445

Val Ser Thr Ile Asn Pro Ala Gly Thr Thr Asp Tyr Ala Glu Ser Val
                450                 455                 460

Lys Gly Arg Phe Thr Ile Ser Arg Asp Asn Ala Lys Asn Thr Leu Tyr
465                 470                 475                 480

Leu Gln Met Asn Ser Leu Lys Pro Glu Asp Thr Ala Val Tyr Tyr Cys
                485                 490                 495

Asp Ser Tyr Gly Tyr Arg Gly Gln Gly Thr Gln Val Thr Val Ser Ser
                500                 505                 510

His His His His His His
        515

<210> SEQ ID NO 76
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Val Val Gly Gly Gly Thr Gln Thr Val Thr Gln Glu Pro Ser
1               5                   10                  15

Leu Thr Val Ser Pro Gly Gly Thr Val Thr Leu Thr Cys Ala Ser Ser
                20                  25                  30

Thr Gly Ala Val Thr Ser Gly Asn Tyr Pro Asn Trp Val Gln Gln Lys
        35                  40                  45

Pro Gly Gln Ala Pro Arg Gly Leu Ile Gly Gly Thr Lys Phe Leu Val
    50                  55                  60

Pro Gly Thr Pro Ala Arg Phe Ser Gly Ser Leu Leu Gly Gly Lys Ala
65                  70                  75                  80

Ala Leu Thr Leu Ser Gly Val Gln Pro Glu Asp Glu Ala Glu Tyr Tyr
                85                  90                  95

Cys Thr Leu Trp Tyr Ser Asn Arg Trp Val Phe Gly Gly Gly Thr Lys
                100                 105                 110

Leu Thr Val Leu Gly Gly Gly Gly Ser Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Lys Leu Ser Cys Ala Ala Ser Gly Phe Thr Phe
145                 150                 155                 160

Asn Lys Tyr Ala Ile Asn Trp Val Arg Gln Ala Pro Gly Lys Gly Leu
                165                 170                 175

Glu Trp Val Ala Arg Ile Arg Ser Lys Tyr Asn Asn Tyr Ala Thr Tyr
            180                 185                 190

Tyr Ala Asp Gln Val Lys Asp Arg Phe Thr Ile Ser Arg Asp Asp Ser
        195                 200                 205

Lys Asn Thr Ala Tyr Leu Gln Met Asn Asn Leu Lys Thr Glu Asp Thr
210                 215                 220

Ala Val Tyr Tyr Cys Val Arg His Ala Asn Phe Gly Asn Ser Tyr Ile
225                 230                 235                 240

Ser Tyr Trp Ala Tyr Trp Gly Gln Gly Thr Leu Val Thr Val Ser Ser
            245                 250                 255

Gly Gly Gly Gly Ser Gly Gly Gly Ser Glu Val Gln Leu Val Glu Ser
            260                 265                 270

Gly Gly Gly Leu Val Gln Pro Gly Gly Ser Leu Thr Leu Ser Cys Ala
            275                 280                 285

Ala Ser Arg Phe Met Ile Ser Glu Tyr His Met His Trp Val Arg Gln
290                 295                 300

Ala Pro Gly Lys Gly Leu Glu Trp Val Ser Thr Ile Asn Pro Ala Gly
305                 310                 315                 320

Thr Thr Asp Tyr Ala Glu Ser Val Lys Gly Arg Phe Thr Ile Ser Arg
            325                 330                 335

Asp Asn Ala Lys Asn Thr Leu Tyr Leu Gln Met Asn Ser Leu Lys Pro
            340                 345                 350

Glu Asp Thr Ala Val Tyr Tyr Cys Asp Ser Tyr Gly Tyr Arg Gly Gln
            355                 360                 365

Gly Thr Gln Val Thr Val Ser Ser His His His His His His
            370                 375                 380

<210> SEQ ID NO 77
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
            85                  90                  95

Asn Val Asn Val Gly Phe Glu Tyr Trp Gly Gln Gly Thr Gln Val Thr
            100                 105                 110

Val Ser Ser Gly Gly Gly Gly Ser Gly Gly Gly Ser Glu Val Gln Leu
        115                 120                 125

Val Glu Ser Gly Gly Gly Leu Val Gln Pro Gly Asn Ser Leu Arg Leu
    130                 135                 140

Ser Cys Ala Ala Ser Gly Phe Thr Phe Ser Lys Phe Gly Met Ser Trp
145                 150                 155                 160

Val Arg Gln Ala Pro Gly Lys Gly Leu Glu Trp Val Ser Ser Ile Ser
            165                 170                 175

Gly Ser Gly Arg Asp Thr Leu Tyr Ala Asp Ser Val Lys Gly Arg Phe
        180                 185                 190

Thr Ile Ser Arg Asp Asn Ala Lys Thr Thr Leu Tyr Leu Gln Met Asn
    195                 200                 205

Ser Leu Arg Pro Glu Asp Thr Ala Val Tyr Tyr Cys Thr Ile Gly Gly
210                 215                 220

Ser Leu Ser Val Ser Ser Gln Gly Thr Leu Val Thr Val Ser Ser Gly
225                 230                 235                 240

Gly Gly Gly Ser Gly Gly Ser Glu Val Gln Leu Val Glu Ser Gly
                245                 250                 255

Gly Gly Leu Val Gln Pro Gly Gly Ser Leu Lys Leu Ser Cys Ala Ala
        260                 265                 270

Ser Gly Phe Thr Phe Asn Lys Tyr Ala Ile Asn Trp Val Arg Gln Ala
    275                 280                 285

Pro Gly Lys Gly Leu Glu Trp Val Ala Arg Ile Arg Ser Lys Tyr Asn
290                 295                 300

Asn Tyr Ala Thr Tyr Tyr Ala Asp Gln Val Lys Asp Arg Phe Thr Ile
305                 310                 315                 320

Ser Arg Asp Asp Ser Lys Asn Thr Ala Tyr Leu Gln Met Asn Asn Leu
            325                 330                 335

Lys Thr Glu Asp Thr Ala Val Tyr Tyr Cys Val Arg His Ala Asn Phe
        340                 345                 350

Gly Asn Ser Tyr Ile Ser Tyr Trp Ala Tyr Trp Gly Gln Gly Thr Leu
    355                 360                 365

Val Thr Val Ser Ser Gly Gly Gly Ser Gly Gly Gly Ser Gly
370                 375                 380

Gly Gly Gly Ser Gln Thr Val Val Thr Gln Glu Pro Ser Leu Thr Val
385                 390                 395                 400

Ser Pro Gly Gly Thr Val Thr Leu Thr Cys Ala Ser Ser Thr Gly Ala
            405                 410                 415

Val Thr Ser Gly Asn Tyr Pro Asn Trp Val Gln Gln Lys Pro Gly Gln
        420                 425                 430

Ala Pro Arg Gly Leu Ile Gly Gly Thr Lys Phe Leu Val Pro Gly Thr
    435                 440                 445

Pro Ala Arg Phe Ser Gly Ser Leu Leu Gly Gly Lys Ala Ala Leu Thr
450                 455                 460

Leu Ser Gly Val Gln Pro Glu Asp Glu Ala Glu Tyr Tyr Cys Thr Leu
465                 470                 475                 480

Trp Tyr Ser Asn Arg Trp Val Phe Gly Gly Gly Thr Lys Leu Thr Val
            485                 490                 495

Leu His His His His His His
            500

<210> SEQ ID NO 78
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Gly Ser Gly Gly Val
        115                 120                 125

Val Gly Gly Gly Thr Gln Thr Val Val Thr Gln Glu Pro Ser Leu
130                 135                 140

Thr Val Ser Pro Gly Gly Thr Val Thr Leu Thr Cys Ala Ser Ser Thr
145                 150                 155                 160

Gly Ala Val Thr Ser Gly Asn Tyr Pro Asn Trp Val Gln Gln Lys Pro
                165                 170                 175

Gly Gln Ala Pro Arg Gly Leu Ile Gly Gly Thr Lys Phe Leu Val Pro
            180                 185                 190

Gly Thr Pro Ala Arg Phe Ser Gly Ser Leu Leu Gly Gly Lys Ala Ala
        195                 200                 205

Leu Thr Leu Ser Gly Val Gln Pro Glu Asp Glu Ala Glu Tyr Tyr Cys
    210                 215                 220

Thr Leu Trp Tyr Ser Asn Arg Trp Val Phe Gly Gly Gly Thr Lys Leu
225                 230                 235                 240

Thr Val Leu Gly Gly Gly Gly Ser Gly Gly Gly Ser Gly Gly Gly
            245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
            275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
            325                 330                 335

Asn Thr Ala Tyr Leu Gln Met Asn Asn Leu Lys Thr Glu Asp Thr Ala
        340                 345                 350

Val Tyr Tyr Cys Val Arg His Ala Asn Phe Gly Asn Ser Tyr Ile Ser
    355                 360                 365

Tyr Trp Ala Tyr Trp Gly Gln Gly Thr Leu Val Thr Val Ser Ser Gly
        370                 375                 380

Gly Gly Gly Ser Gly Gly Gly Ser Glu Val Gln Leu Val Glu Ser Gly
385                 390                 395                 400

Gly Gly Leu Val Gln Pro Gly Gly Ser Leu Thr Leu Ser Cys Ala Ala
            405                 410                 415

```
Ser Arg Phe Met Ile Ser Glu Tyr His Met His Trp Val Arg Gln Ala
                420                 425                 430

Pro Gly Lys Gly Leu Glu Trp Val Ser Thr Ile Asn Pro Ala Gly Thr
            435                 440                 445

Thr Asp Tyr Ala Glu Ser Val Lys Gly Arg Phe Thr Ile Ser Arg Asp
450                 455                 460

Asn Ala Lys Asn Thr Leu Tyr Leu Gln Met Asn Ser Leu Lys Pro Glu
465                 470                 475                 480

Asp Thr Ala Val Tyr Tyr Cys Asp Ser Tyr Gly Tyr Arg Gly Gln Gly
                485                 490                 495

Thr Gln Val Thr Val Ser Ser His His His His His
            500                 505

<210> SEQ ID NO 79
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Val
            20                  25                  30

Ser Gly Ala Pro Gly Gln Arg Val Thr Ile Ser Cys Ser Gly Ser Arg
        35                  40                  45

Ser Asn Ile Gly Ser Asn Thr Val Lys Trp Tyr Gln Gln Leu Pro Gly
    50                  55                  60

Thr Ala Pro Lys Leu Leu Ile Tyr Tyr Asn Asp Gln Arg Pro Ser Gly
65                  70                  75                  80

Val Pro Asp Arg Phe Ser Gly Ser Lys Ser Gly Thr Ser Ala Ser Leu
                85                  90                  95

Ala Ile Thr Gly Leu Gln Ala Glu Asp Glu Ala Asp Tyr Tyr Cys Gln
            100                 105                 110

Ser Tyr Asp Arg Tyr Thr His Pro Ala Leu Leu Phe Gly Thr Gly Thr
        115                 120                 125

Lys Val Thr Val Leu Gly Gly Gly Gly Ser Gly Gly Gly Gly Ser Gly
    130                 135                 140

Gly Gly Ser Gln Val Gln Leu Val Glu Ser Gly Gly Gly Val Val
145                 150                 155                 160

Gln Pro Gly Arg Ser Leu Arg Leu Ser Cys Ala Ala Ser Gly Phe Thr
                165                 170                 175

Phe Ser Ser Tyr Gly Met His Trp Val Arg Gln Ala Pro Gly Lys Gly
            180                 185                 190

Leu Glu Trp Val Ala Phe Ile Arg Tyr Asp Gly Ser Asn Lys Tyr Tyr
        195                 200                 205

Ala Asp Ser Val Lys Gly Arg Phe Thr Ile Ser Arg Asp Asn Ser Lys
    210                 215                 220

Asn Thr Leu Tyr Leu Gln Met Asn Ser Leu Arg Ala Glu Asp Thr Ala
225                 230                 235                 240

Val Tyr Tyr Cys Lys Thr His Gly Ser His Asp Asn Trp Gly Gln Gly
                245                 250                 255
```

Thr Met Val Thr Val Ser Ser His His His His His His
            260                 265

<210> SEQ ID NO 80
<211> LENGTH: 5
<212> TYPE: PRT
<213> ORGANISM: Unknown
<220> FEATURE:
<223> OTHER INFORMATION: Description of Unknown:
      Sortase A cleavage site
<220> FEATURE:
<221> NAME/KEY: MOD_RES
<222> LOCATION: (3)..(3)
<223> OTHER INFORMATION: Any amino acid

<400> SEQUENCE: 80

Leu Pro Xaa Thr Gly
1               5

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 'Gly Gly Gly
      Gly Ser' repeating units

<400> SEQUENCE: 81

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-5 'Gly Gly Gly
      Ser' repeating units

<400> SEQUENCE: 82

Gly Gly Gly Ser Gly Gly Gly Ser Gly Gly Gly Ser Gly Gly Gly Ser
1               5                   10                  15

Gly Gly Gly Ser
            20

<210> SEQ ID NO 83
<211> LENGTH: 7
<212> TYPE: PRT
<213> ORGANISM: Unknown
<220> FEATURE:
<223> OTHER INFORMATION: Description of Unknown:
      protease-cleavable sequence

<400> SEQUENCE: 83

Gly Pro Leu Gly Val Arg Gly
1               5

```
<210> SEQ ID NO 84
<211> LENGTH: 8
<212> TYPE: PRT
<213> ORGANISM: Unknown
<220> FEATURE:
<223> OTHER INFORMATION: Description of Unknown:
      protease-cleavable sequence

<400> SEQUENCE: 84

Ile Pro Val Ser Leu Arg Ser Gly
1               5

<210> SEQ ID NO 85
<211> LENGTH: 8
<212> TYPE: PRT
<213> ORGANISM: Unknown
<220> FEATURE:
<223> OTHER INFORMATION: Description of Unknown:
      protease-cleavable sequence

<400> SEQUENCE: 85

Val Pro Leu Ser Leu Tyr Ser Gly
1               5

<210> SEQ ID NO 86
<211> LENGTH: 10
<212> TYPE: PRT
<213> ORGANISM: Unknown
<220> FEATURE:
<223> OTHER INFORMATION: Description of Unknown:
      protease-cleavable sequence

<400> SEQUENCE: 86

Ser Gly Glu Ser Pro Ala Tyr Tyr Thr Ala
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Gly Gly Ser
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Gly Ser Gly Ser
1               5

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 89

Gly Ser Gly Gly Gly Ser Gly Gly Ser Gly Gly Thr
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Gly Gly Ser Gly Gly Gly Ser Gly Gly Gly Gly Ser
1               5                   10                  15

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 91

His His His His His His
1               5

<210> SEQ ID NO 92
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Gly Gly Gly Gly Leu Asp Gly Asn
        35                  40                  45

Glu Glu Pro Gly Gly Leu Glu Trp Val Ser Ser Ile Ser Gly Ser Gly
    50                  55                  60

Arg Asp Thr Leu Tyr Ala Asp Ser Val Lys Gly Arg Phe Thr Ile Ser
65                  70                  75                  80

Arg Asp Asn Ala Lys Thr Thr Leu Tyr Leu Gln Met Asn Ser Leu Arg
                85                  90                  95

Pro Glu Asp Thr Ala Val Tyr Tyr Cys Thr Ile Gly Gly Ser Leu Ser
            100                 105                 110

Val Ser Ser Gln Gly Thr Leu Val Thr Val Ser Ser
        115                 120

ACTIVATABLE INTERLEUKIN 12 POLYPEPTIDES AND METHODS OF USE THEREOF

RELATED APPLICATIONS

This application is a continuation of Ser. No. 16/438,166, filed Jun. 11, 2019, which is a continuation-in-part of International Patent Application No. PCT/US2019/032322, filed May 14, 2019, which claims the benefit of U.S. Provisional Application 62/671,225, filed on May 14, 2018, U.S. Provisional Application No. 62/756,504, filed on Nov. 6, 2018, U.S. Provisional Application No. 62/756,507, filed on Nov. 6, 2018, and U.S. Provisional Application No. 62/756,515, filed on Nov. 6, 2018. The entire teachings of the above applications are incorporated herein by reference.

SEQUENCE LISTING

The instant application contains a Sequence Listing, which has been submitted electronically in ASCII format and is hereby incorporated by reference in its entirety. Said ASCII copy, created on May 31, 2019, is named 761146_000139_SL.txt and is 230,489 bytes in size.

BACKGROUND

The development of mature immunocompetent lymphoid cells from less-committed precursors, their subsequent antigen-driven immune responses, and the suppression of these and unwanted autoreactive responses are highly dependent and regulated by cytokines (including interleukin-2 [IL-2], IL-4, IL-7, IL-9, IL-15, and IL-21) that utilize receptors in the common γ-chain (γc) family (Rochman et al., 2009) and family members including IL-12, 18 and 23. IL-2 is essential for thymic development of Treg cells and critically regulates several key aspects of mature peripheral Treg and antigen-activated conventional T cells. Because of its potent T cell growth factor activity in vitro, IL-2 has been extensively studied in part because this activity offered a potential means to directly boost immunity, e.g., in cancer and AIDS-HIV patients, or a target to antagonize unwanted responses, e.g., transplantation rejection and autoimmune diseases. Although in vitro studies with IL-2 provided a strong rationale for these studies, the function of IL-2 in vivo is clearly much more complex as first illustrated in IL-2-deficient mice, where a rapid lethal autoimmune syndrome, not lack of immunity, was observed (Sadlack et al., 1993, 1995). Similar observations were later made when the gene encoding IL-2Rα (Il2ra) and IL-2Rβ(Il2rb) were individually ablated (Suzuki et al., 1995; Willerford et al., 1995).

The present invention refers to conditionally active and/or targeted cytokines for use in the treatment of cancer and other diseases dependent on immune up or down regulation. For example, the antitumoral activity of some cytokines is well known and described and some cytokines have already been used therapeutically in humans. Cytokines such as interleukin-2 (IL-2) and interferon α (IFNα) have shown positive antitumoral activity in patients with different types of tumors, such as kidney metastatic carcinoma, hairy cell leukemia, Kaposi sarcoma, melanoma, multiple myeloma, and the like. Other cytokines like IFNβ, the Tumor Necrosis Factor (TNF) α, TNFβ, IL-1, 4, 6, 12, 15 and the CSFs have shown a certain antitumoral activity on some types of tumors and therefore are the object of further studies.

SUMMARY

Provided herein are therapeutic proteins, nucleic acids that encode the proteins, and compositions and methods of using the proteins and nucleic acids for the treatment of a disease or disorder, such as proliferative disease, a tumorous disease, an inflammatory disease, an immunological disorder, an autoimmune disease, an infectious disease, a viral disease, an allergic reaction, a parasitic reaction, graft-versus-host disease and the like.

The invention features fusion proteins that are conditionally active variants of IL-12. In one aspect, the full-length polypeptides of the invention have reduced or minimal IL-12-receptor activating activity even though they contain a functional IL-12 polypeptide. Upon activation, e.g., by cleavage of a linker that joins a blocking moiety, e.g., a steric blocking polypeptide, in sequence to the active cytokine, IL-12, or a functional fragment or mutein thereof, can bind its receptor and effect signaling. If desired, the full-length polypeptides can include a blocking polypeptide moiety that also provides additional advantageous properties. For example, the full-length polypeptide can contain a blocking polypeptide moiety that also extends the serum half-life and/or targets the full-length polypeptide to a desired site of cytokine activity. Alternatively, the full-length fusion polypeptides can contain a serum half-life extension element and/or targeting domain that are distinct from the blocking polypeptide moiety. Preferably, the fusion protein contains at least one element or domain capable of extending in vivo circulating half-life. Preferably, this element is removed enzymatically in the desired body location (e.g., protease cleavage in the tumor microenvironment), restoring pharmacokinetic properties to the payload molecule (e.g., IL-12) substantially similar to the naturally occurring payload molecule. The fusion proteins may be targeted to a desired cell or tissue. As described herein targeting is accomplished through the action of a blocking polypeptide moiety that also binds to a desired target, or through a targeting domain. The domain that recognizes a target antigen on a preferred target (for example a tumor-specific antigen), may be attached to the cytokine via a cleavable or non-cleavable linker. If attached by a non-cleavable linker, the targeting domain may further aid in retaining the cytokine in the tumor, and may be considered a retention domain. The targeting domain does not necessarily need to be directly linked to the payload molecule, and may be linked directly to another element of the fusion protein. This is especially true if the targeting domain is attached via a cleavable linker.

In one aspect is provided a fusion polypeptide comprising an IL-12 polypeptide, or functional fragment or mutein thereof, and a blocking moiety, e.g., a steric blocking domain. The blocking moiety is fused to the IL-12 polypeptide, directly or through a linker, and can be separated from the IL-12 polypeptide by cleavage (e.g., protease-mediated cleavage) of the fusion polypeptide at or near the fusion site or linker or in the blocking moiety. For example, when the IL-12 polypeptide is fused to a blocking moiety through a linker that contains a protease cleavage site, the IL-12 polypeptide is released from the blocking moiety and can bind its receptor, upon protease mediated cleavage of the linker. The linker is designed to be cleaved at the site of desired cytokine activity, for example in the tumor microenvironment, avoiding off-target cytokine activity and reducing overall toxicity of cytokine therapy.

In one embodiment, a fusion polypeptide is provided that includes at least one of each of an interleukin 12 (IL-12) polypeptide [A], a half-life extension domain [B], an IL-12 blocking moiety [D], and a protease-cleavable polypeptide linker [L], wherein the IL-12 polypeptide and the IL-12 blocking moiety are operably linked by the protease-cleavable polypeptide linker and the fusion polypeptide has attenuated IL-12-receptor activating activity. Typically, the IL-12-receptor activating activity of the fusion polypeptide is at least about 10 fold less than the IL-12-receptor activating activity of the polypeptide that includes the IL-12 polypeptide that is produced by cleavage of the protease-cleavable polypeptide linker. The serum half-life of the IL-12-comprising polypeptide that is produced by protease cleavage of the protease-cleavable polypeptide linker is typically comparable to the half-life of naturally occurring IL-12.

The fusion polypeptide can have the formula:

[A]-[L1]-[D],

[A]-[L1]-[D]-[L2]-[B], or

[B]-[L1]-[A]-[L1]-[D], where [A] is an interleukin 12 (IL-12) polypeptide, [B] is a half-life extension element, [L1] and [L2] are each independently a polypeptide linker, wherein [L1] is a protease-cleavable polypeptide linker and [L2] is polypeptide linker that is optionally protease-cleavable, and [D] is an IL-12 blocking moiety. In one embodiment, the fusion polypeptide has attenuated IL-12-receptor activating activity, but the IL-12 comprising polypeptide that is produced upon (i) cleavage of the L1 protease-cleavable polypeptide linker, or (ii) cleavage of both L1 and L2 when L2 is a protease-cleavable polypeptide linker, has comparable IL-12-receptor activating activity and half-life to naturally occurring IL-12. The interleukin 12 (IL-12) polypeptide [A] can be further defined by the formula:

[A1]-[L3]-[A2], or

[A2]-[L3]-[A1], where [A1] is an IL-12 p40 subunit polypeptide, [A2] is an IL-12 p35 subunit polypeptide, and [L3] is a polypeptide linker that is optionally protease cleavable.

The fusion polypeptide can further include a tumor-specific antigen binding peptide. For example, the tumor-specific antigen binding peptide can be linked to any one of [A], [B], or [D] by a non-cleavable linker. The tumor-specific antigen binding peptide can be linked to any one of [A], [B], or [D] by a cleavable linker. The tumor-specific antigen binding peptide can be linked to the IL-12 polypeptide by a non-cleavable linker and the IL-12 polypeptide can be linked to the half-life extension element or the IL-12 blocking moiety by a cleavable linker.

The IL-12-receptor activating activity of the fusion polypeptide can be assessed, for example, using a HEK Blue reporter cell assay and using equal amounts on a mole basis of the IL-12 polypeptide and the fusion polypeptide.

The fusion polypeptide of the invention may include protease-cleavable polypeptide linkers, where each protease-cleavable polypeptide linker independently comprises at least one sequence that is capable of being cleaved by a protease selected from the group consisting of a kallikrein, thrombin, chymase, carboxypeptidase A, cathepsin G, cathepsin L, an elastase, PR-3, granzyme M, a calpain, a matrix metalloproteinase (MMP), a fibroblast activation protein (FAP), an ADAM metalloproteinase, a plasminogen activator, a cathepsin, a caspase, a tryptase, and a tumor cell surface protease. Each protease-cleavable polypeptide of the fusion polypeptide can independently comprise two or more cleavage sites for the same protease, or two or more cleavage sites that can be cleaved by different proteases, or at least one of the protease-cleavable polypeptides comprises a cleavage site for two or more different proteases.

In some embodiments, the IL-12 blocking moiety of the fusion polypeptides of the invention inhibits activation of the IL-12 receptor by the fusion polypeptide. In some embodiments, the IL-12 blocking moiety of the fusion polypeptide can comprise, for example, a ligand-binding domain or fragment of a cognate receptor for the IL-12, a single domain antibody, Fab or scFv that binds the IL-12 polypeptide, or an antibody or antibody fragment selected from a single domain antibody, an Fab and an scFv that binds a receptor of the IL-12.

The half-life extension element of the fusion polypeptide can be, for example, human serum albumin, an antigen-binding polypeptide that binds human serum albumin, or an immunoglobulin Fc.

In some embodiments, the blocking moiety can also function as a serum half-life extension element. In some other embodiments, the fusion polypeptide further comprises a separate serum half-life extension element. In some embodiments, the fusion polypeptide further comprises a targeting domain. In various embodiments, the serum half-life extension element is a water-soluble polypeptide such as optionally branched or multi-armed polyethylene glycol (PEG), full length human serum albumin (HSA) or a fragment that preserves binding to FcRn, an Fc fragment, or a nanobody that binds to FcRn directly or to human serum albumin.

In addition to serum half-life extension elements, the pharmaceutical compositions described herein preferably comprise at least one, or more targeting domains that bind to one or more target antigens or one or more regions on a single target antigen. It is contemplated herein that a polypeptide construct of the invention is cleaved, for example, in a disease-specific microenvironment or in the blood of a subject at the protease cleavage site and that the targeting domain(s) will bind to a target antigen on a target cell. At least one target antigen is involved in and/or associated with a disease, disorder or condition. Exemplary target antigens include those associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

Target antigens, in some cases, are expressed on the surface of a diseased cell or tissue, for example a tumor or a cancer cell. Target antigens for tumors include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, c-Met, FOLR1, and CEA. Pharmaceutical compositions disclosed herein, also include proteins comprising two antigen binding domains that bind to two different target antigens known to be expressed on a diseased cell or tissue. Exemplary pairs of antigen binding domains include but are not limited to EGFR/CEA, EpCAM/CEA, and HER-2/HER-3.

In some embodiments, the targeting polypeptides independently comprise a scFv, a VH domain, a VL domain, a non-Ig domain, or a ligand that specifically binds to the target antigen. In some embodiments, the targeting polypeptides specifically bind to a cell surface molecule. In some embodiments, the targeting polypeptides specifically bind to a tumor antigen. In some embodiments, the targeting polypeptides specifically and independently bind to a tumor antigen selected from at least one of EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1. In some embodiments, the targeting polypeptide serves as a retention domain and is attached to the cytokine via a non-cleavable linker.

As described herein, the IL-12 blocking moiety can bind to IL-12 and thereby block activation of the cognate IL-12 receptor.

This disclosure also related to nucleic acids, e.g., DNA, RNA, mRNA, that encode the conditionally active proteins described herein, as well as vectors and host cells that contain such nucleic acids.

This disclosure also relates to pharmaceutical compositions that contain a conditionally active protein, nucleic acid that encodes the conditionally active protein, and vectors and host cells that contain such nucleic acids. Typically, the pharmaceutical composition contains one or more physiologically acceptable carriers and/or excipients.

The disclosure also relates to methods of making a pharmaceutical composition that include culturing host cell that contain nucleic acids encoding the fusion polypeptides of the invention under suitable conditions for expression and collection of the fusion polypeptides.

The disclosure also relates to therapeutic methods that include administering to a subject in need thereof an effective amount of a conditionally active protein, nucleic acid that encodes the conditionally active protein, vector or host cells that contain such a nucleic acid, and pharmaceutical compositions of any of the foregoing. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure further relates methods for treating a tumor or cancer that include administering to a subject in need thereof an effective amount of a fusion polypeptide of the invention. In some embodiments, the method for treating a tumor or cancer can include administering effective amount of the fusion polypeptide intravenously. In some embodiments, the method can further include administration of an additional chemotherapeutic agent.

The disclosure also relates to the use of a conditionally active protein, nucleic acid that encodes the conditionally active protein, vector or host cells that contain such a nucleic acid, and pharmaceutical compositions of any of the foregoing, for treating a subject in need thereof. Typically the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid for the manufacture of a medicament for treating a disease, such as a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

BRIEF DESCRIPTION OF THE DRAWINGS

FIG. 2 is a schematic illustrating a protease-activated cytokine or chemokine comprising a cytokine or chemokine polypeptide, a blocking moiety, and a serum half-life extending domain connected by at least one protease-cleavable linker. To the left of the arrow the drawing shows that a cytokine is connected to a blocking moiety via protease-cleavable linkers, thus blocking its ability to bind to its receptor. It is also bound to a separate half-life extension element, which extends half-life in serum. To the right of the arrow the drawing shows that in an inflammatory or tumor environment a protease cleaves at a protease-cleavage site on linker, thus releasing the serum half-life extension element and the blocking moiety and allowing the cytokine to bind to its receptor. The cytokine now has similar pK properties as compared to the native cytokine (e.g., a short half-life).

FIGS. 11a-11d are graphs depicting results from a HEK-Blue assay performed on human p40/murine p35 IL-12 fusion proteins before and after protease cleavage. Results confirm that IL-12 protein fusion proteins are active. Each proliferation assay was performed with HSA or without HSA. Constructs tested were ACP36 (FIG. 11a and FIG. 11b) and ACP37 (FIG. 11c and FIG. 11d).

FIG. 12a is a graph showing analysis of ACP11 (a human p40/murine p35 IL-12 fusion protein). Squares depict activity of the uncut ACP11 polypeptide and triangles depict the activity of the cut polypeptide (ACP11+MMP9). EC50 values for each are shown in the table. FIG. 12b is a graph showing analysis of ACP91 (a non-cleavable chimeric IL-12 fusion protein). Squares depict activity of the uncut ACP91 polypeptide and triangles depict the activity of the cut polypeptide (ACP91+MMP9). EC50 values for each are shown in the table. FIG. 12c is a graph showing analysis of ACP136 (a chimeric IL-12 fusion protein). Squares depict activity of the uncut ACP136 polypeptide and triangles depict the activity of the cut polypeptide (ACP136+MMP9). EC50 values for each are shown in the table insert.

FIGS. 14a-14f are "spaghetti" plots showing tumor volume over time in a mouse xenograft tumor model in mice each treated with vehicle alone (top left), 2 µg ACP04 (top middle), 10 µg ACP04 (top right), 17.5 µg ACP11 (bottom left), 175 µg ACP11 (bottom middle), and 525 µg ACP11 (bottom right). Each line represents a single mouse.

FIG. 16 illustrates differential activities of ProTriTAC proteins measured by ELISA, flow cytometry, and T cell-dependent cellular cytotoxicity assay.

FIG. 20 demonstrates functional masking and stability of ProTriTAC in cynomolgus monkey pharmacokinetic study.

DETAILED DESCRIPTION

Figure 1A:
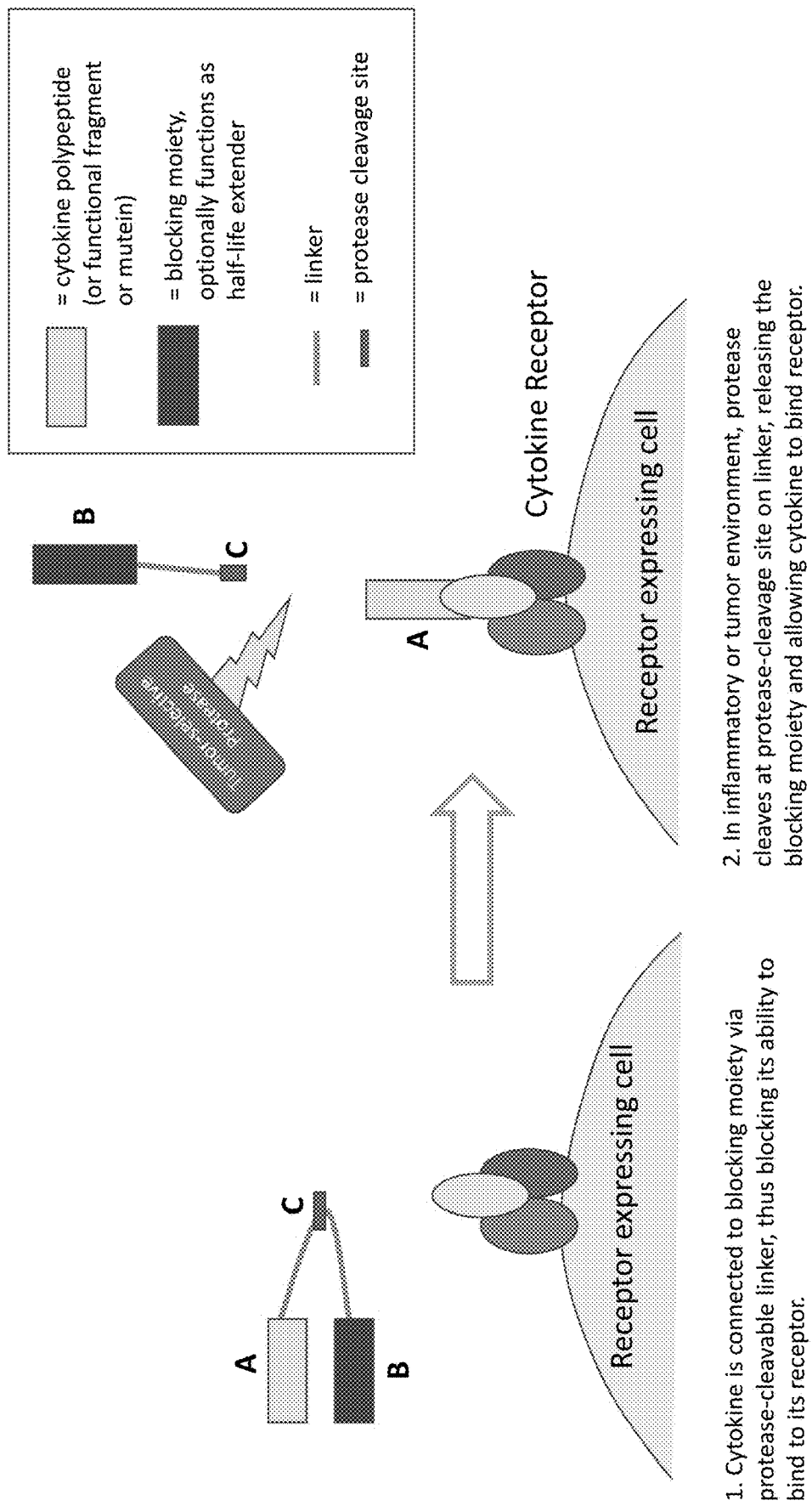
FIG. 1a is a schematic illustrating a protease-activated cytokine or chemokine that includes a blocking moiety. The blocking moiety may optionally function as a serum half-life extending domain. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease-cleavage site on the linker, releasing the blocking moiety and allowing the cytokine to bind to its receptor.
Figure 1B:
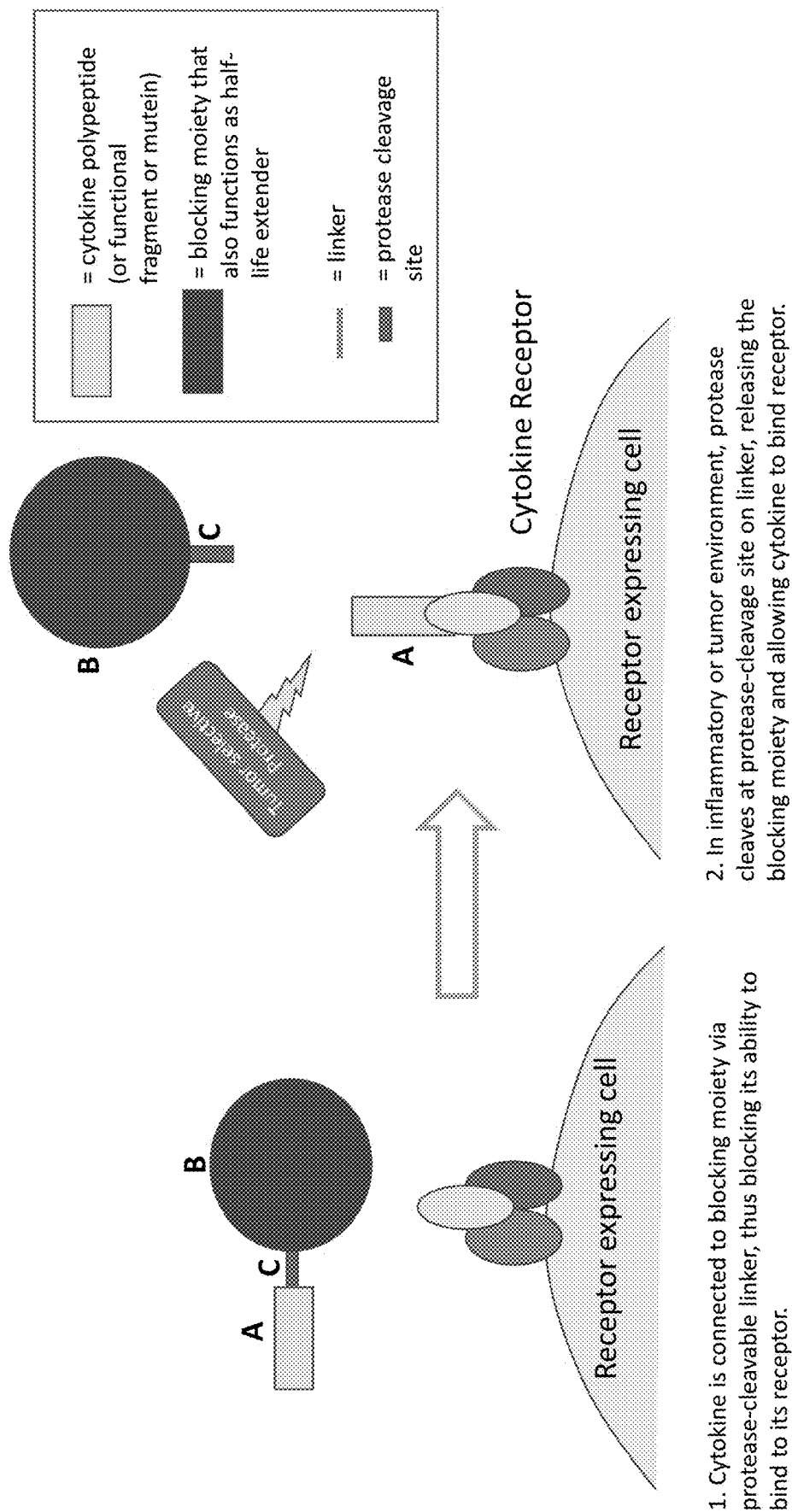
FIG. 1b is a schematic illustrating a protease-activated cytokine or chemokine wherein HSA (blocking moiety) is directly bound to the cytokine or chemokine of interest, with a protease cleavage site between the HSA and a cytokine or chemokine of interest. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, the protease cleaves at a protease-cleavage site on linker, releasing the blocking moiety and allowing the cytokine to bind to its receptor.
Figure 1C:
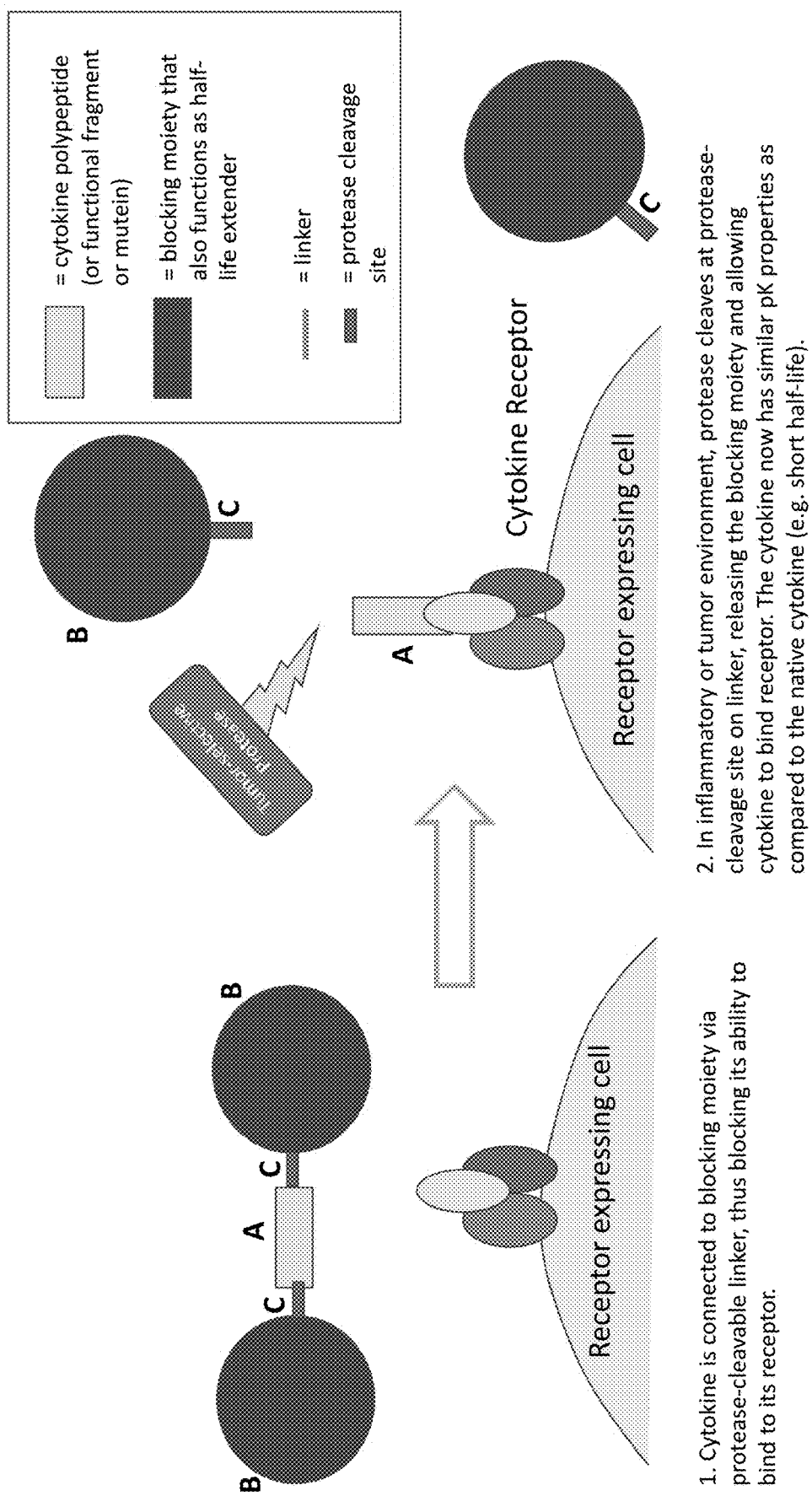
FIG. 1c is a schematic illustrating a protease-activated cytokine or chemokine wherein more than one HSA (blocking moiety) is bound directly to the molecule of interest. If desired, one or more of the HSA can be bonded to the cytokine or chemokine through a linker, such as a linker that contains a protease cleavage site. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, protease cleaves at protease-cleavage site on linker, releasing the blocking moiety and allowing cytokine to bind receptor. The cytokine now has similar pK properties as compared to the native cytokine (e.g., has a short half-life).
Figure 1D:
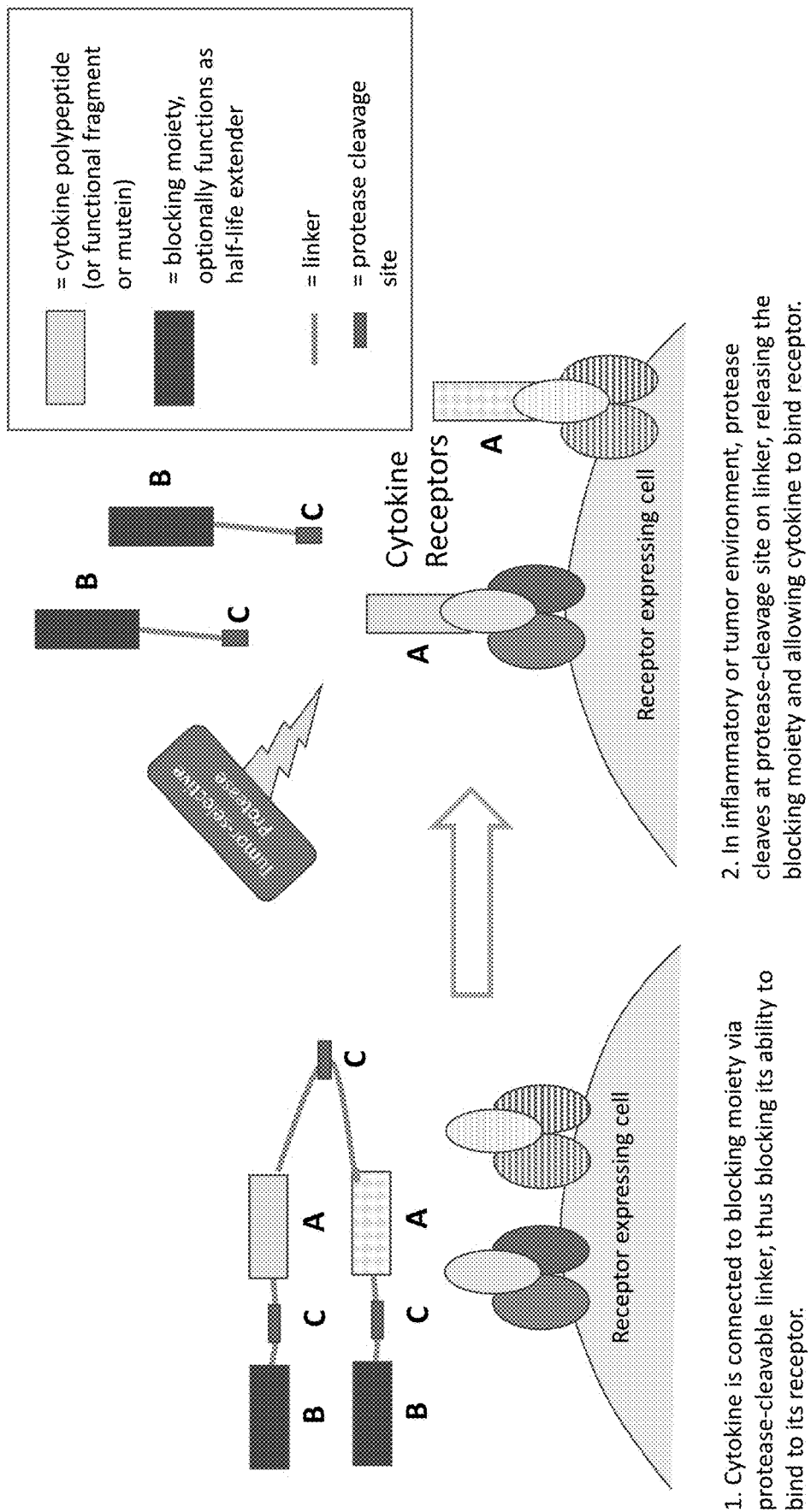
FIG. 1d is a schematic illustrating a protease-activated cytokine or chemokine comprising more than one cytokine, of the same type or different type, each of which is bonded to a binding domain through a protease-cleavable linker. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease cleavage site on linker, releasing the blocking moiety and allowing the cytokine to bind to its receptor.
Figure 3:
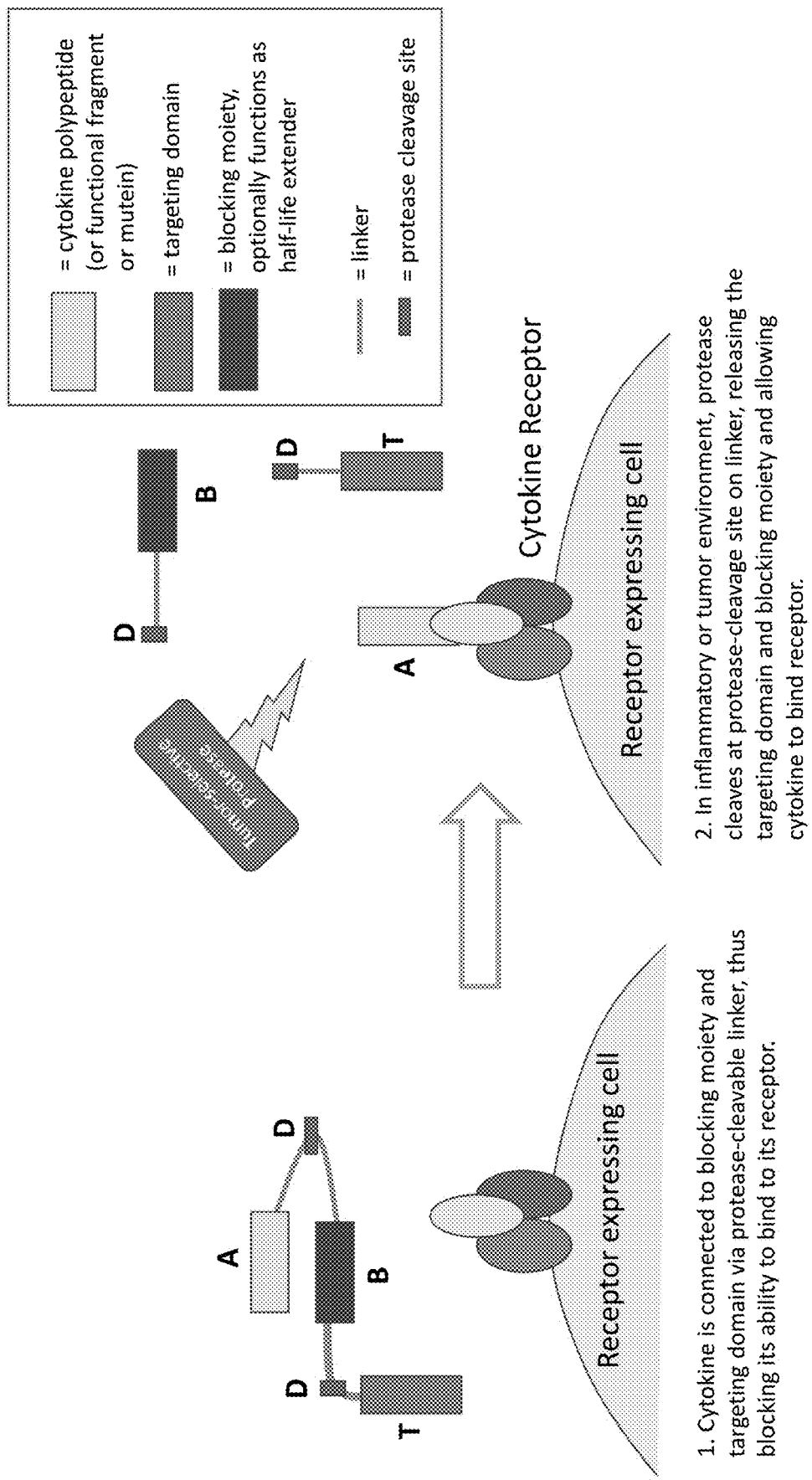
FIG. 3 is a schematic illustrating a protease-activated cytokine or chemokine comprising a cytokine or chemokine polypeptide, a blocking moiety, and a targeting domain connected by at least one protease-cleavable linker. To the left of the arrow the drawing shows that a cytokine is connected to a blocking moiety and a targeting domain via a protease-cleavable linker, thus blocking its ability to bind to its receptor. To the right of the arrow the drawing shows that in an inflammatory or tumor microenvironment a protease cleaves at the protease cleavage site in the linker, releasing the targeting domain and the blocking moiety and allowing the cytokine to bind to its receptor.
Figure 4A:
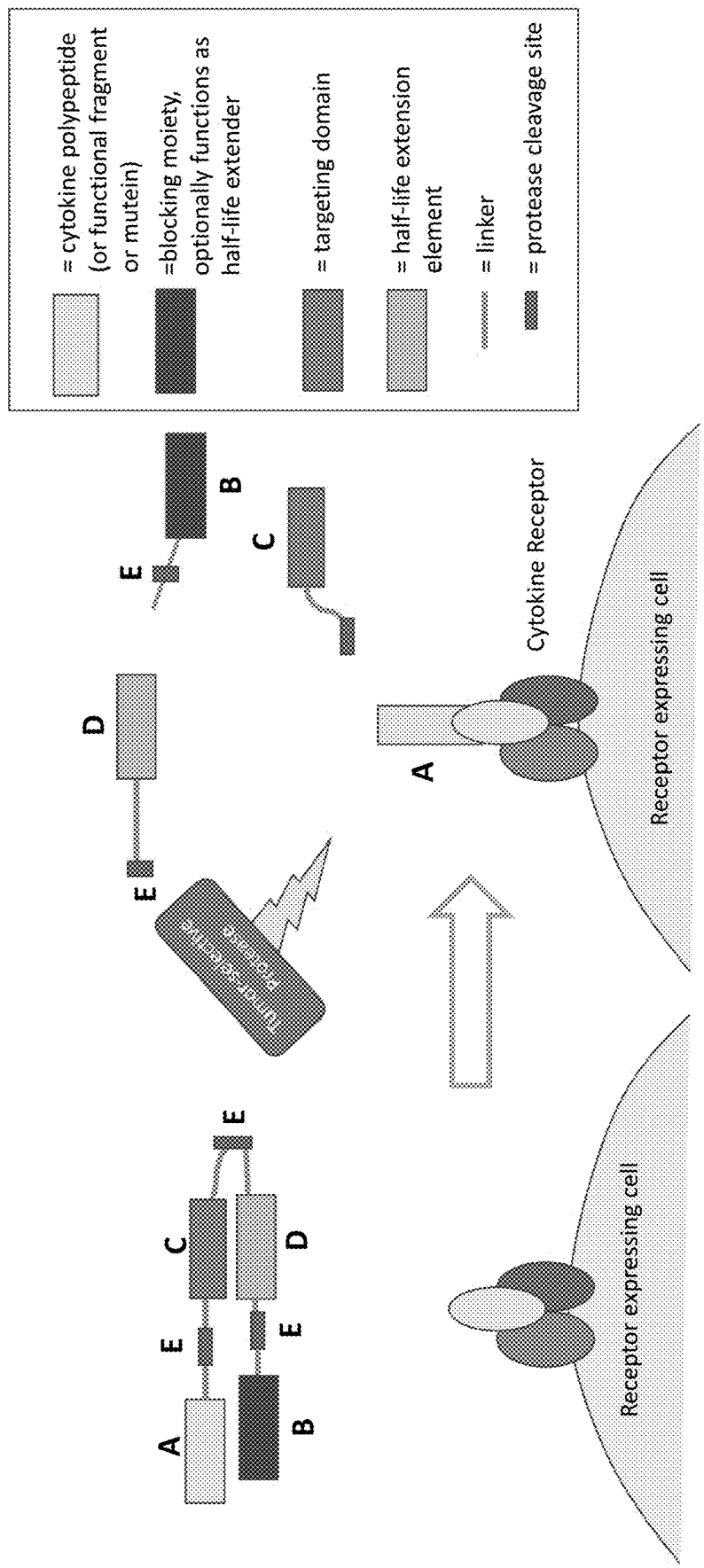
FIG. 4a is a schematic illustrating a protease-activated cytokine or chemokine comprising a cytokine or chemokine polypeptide, a blocking moiety, a targeting domain, and a serum half-life extending domain connected by at least one protease-cleavable linker, wherein the cytokine polypeptide and the targeting domain are connected by a protease-cleavable linker. To the left of the arrow, the drawing shows that a cytokine is connected to targeting domain, blocking moiety, and half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element, the targeting domain, and the blocking moiety, and allowing the cytokine to bind to its receptor. The cytokine now has similar pK properties as compared to the native cytokine (e.g., short half-life).
Figure 4B:
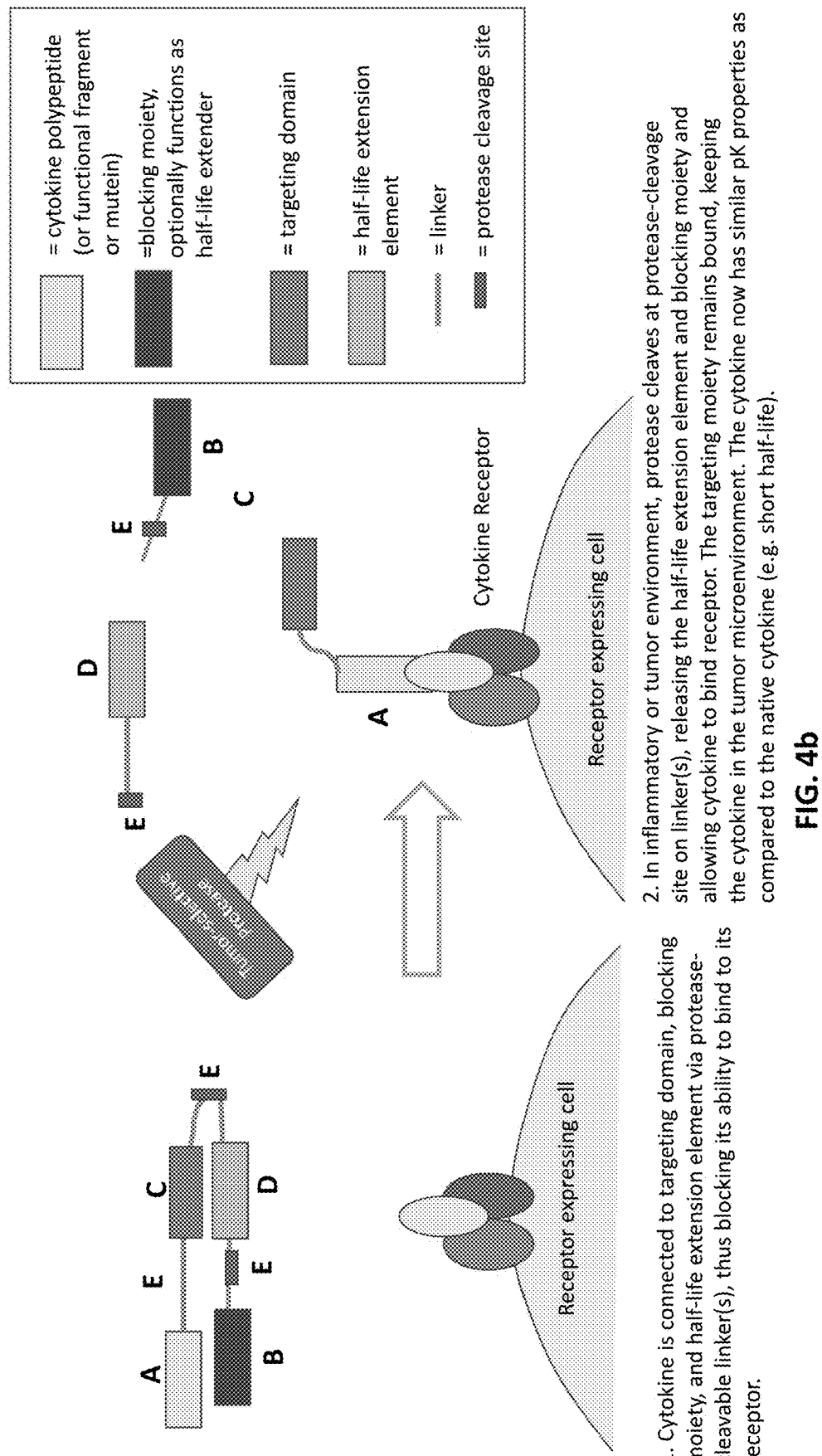
FIG. 4b is a schematic illustrating a protease-activated cytokine or chemokine comprising a cytokine or chemokine polypeptide, a blocking moiety, a targeting domain, and a serum half-life extending domain connected by at least one protease-cleavable linker. To the left of the arrow, the drawing shows that a cytokine is connected to targeting domain, a blocking moiety, and a half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element and the blocking moiety and allowing the cytokine to bind to the receptor. The targeting moiety remains bound, keeping the cytokine in the tumor microenvironment. The cytokine now has similar pK properties as compared to the native cytokine (e.g., a short half-life).

Disclosed herein are methods and compositions to engineer and use constructs comprising inducible IL-12. IL-12 is a potent immune agonist, which lead to it being considered a promising therapeutic agent for oncology. However, IL-12 and other cytokines proved to have a very narrow therapeutic window. Cytokines, such as IL-12, have short serum half-lives and are also considered to be highly potent. Consequently, therapeutic administration of cytokines produced undesirable systemic effects and toxicities. These were exacerbated by the need to administer large quantities of cytokine in order to achieve the desired levels of cytokine at the intended site of cytokine action (e.g., a tumor). Unfortunately, due to the biology of cytokines and inability to effectively target and control their activity, cytokines did not achieve the hoped-for clinical advantages in the treatment of tumors.

Disclosed herein are fusion proteins that overcome the toxicity and short half-life problems that have severely limited the clinical use of IL-12 in oncology. The fusion proteins contain IL-12 polypeptides that have receptor agonist activity. But in the context of the fusion protein, the IL-12 receptor agonist activity is attenuated and the circulating half-life is extended. The fusion proteins include protease cleave sites, which are cleaved by proteases that are associated with a desired site of IL-12 activity (e.g., a tumor), and are typically enriched or selectively present at the site of desired activity. Thus, the fusion proteins are preferentially (or selectively) and efficiently cleaved at the desired site of activity to limit cytokine activity substantially to the desired site of activity, such as the tumor microenvironment. Protease cleavage at the desired site of activity, such as in a tumor microenvironment, releases a form of IL-12 from the fusion protein that is much more active as an IL-12 receptor agonist than the fusion protein (typically at least about 100× more active than the fusion protein). The form of IL-12 that is released upon cleavage of the fusion protein typically has a short half-life, which is often substantially similar to the half-life of naturally occurring IL-12, further restricting IL-12 cytokine activity to the tumor microenvironment. Even though the half-life of the fusion protein is extended, toxicity is dramatically reduced or eliminated because the circulating fusion protein is attenuated and active cytokine is targeted to the tumor microenvironment. The fusion proteins described herein, for the first time, enable the administration of an effective therapeutic dose of a cytokine to treat tumors with the activity of the cytokine substantially limited to the tumor microenvironment, and dramatically reduces or eliminates unwanted systemic effects and toxicity of the cytokine.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

"Cytokine" is a well-known term of art that refers to any of a class of immunoregulatory proteins (such as interleukin or interferon) that are secreted by cells especially of the immune system and that are modulators of the immune system. Cytokine polypeptides that can be used in the fusion proteins disclosed herein include, but are not limited to transforming growth factors, such as TGF-α and TGF-β (e.g., TGFbeta1, TGFbeta2, TGFbeta3); interferons, such as interferon-α, interferon-β, interferon-γ, interferon-kappa and interferon-omega; interleukins, such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25; tumor necrosis factors, such as tumor necrosis factor alpha and lymphotoxin; chemokines (e.g., C—X—C motif chemokine 10 (CXCL10), CCL19, CCL20, CCL21), and granulocyte macrophage-colony stimulating factor (GM-CS), as well as fragments of such polypeptides that active the cognate receptors for the cytokine (i.e., functional fragments of the foregoing). "Chemokine" is a term of art that refers to any of a family of small cytokines with the ability to induce directed chemotaxis in nearby responsive cells.

Cytokines are well-known to have short serum half-lives that frequently are only a few minutes or hours. Even forms of cytokines that have altered amino acid sequences intended to extend the serum half-life yet retain receptor agonist activity typically also have short serum half-lives. As used herein, a "short-half-life cytokine" refers to a cytokine that has a substantially brief half-life circulating in the serum of a subject, such as a serum half-life that is less than 10, less than 15, less than 30, less than 60, less than 90, less than 120, less than 240, or less than 480 minutes. As used herein, a short half-life cytokine includes cytokines which have not been modified in their sequence to achieve a longer than usual half-life in the body of a subject and polypeptides that have altered amino acid sequences intended to extend the serum half-life yet retain receptor agonist activity. This latter case is not meant to include the addition of heterologous protein domains, such as a bona fide half-life extension element, such as serum albumin. Typically a short half-life cytokine polypeptide, such as an IL-12 polypeptide, has a serum half-life that is comparable to naturally occurring IL-12, e.g., within 5 fold, 4 fold, 3 fold or 2 fold of naturally occurring IL-12.

"Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO: 80) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

As used herein, the term "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. A steric blocker may also block by virtue of recruitment of a large protein-binding partner. An example of this is an antibody, which binds to serum albumin; while the antibody itself may or may not be large enough to block activation or binding on its own, recruitment of albumin allows for sufficient steric blocking.

As used herein, the term "operably linked" in the context of a fusion polypeptide refers to orientation of the components of a fusion polypeptide that permits the components to function in their intended manner. For example, an IL-12 polypeptide and an IL-12 blocking moiety are operably linked by a protease-cleavable polypeptide linker in a fusion polypeptide when the IL-12 blocking moiety is capable of inhibiting the IL-12 receptor-activating activity of the IL-12 polypeptide in the fusion polypeptide, for example by binding to the IL-12 polypeptide, but upon cleavage of the protease-cleavable polypeptide linker the inhibition of the IL-12 receptor-activating activity of the IL-12 polypeptide by the IL-12 blocking moiety is decreased or eliminated, for example because the IL-12 blocking moiety can diffuse away from the IL-12 polypeptide.

As used and described herein, a "half-life extension element" is a part of the chimeric polypeptide that increases the serum half-life and improve pK, for example, by altering its size (e.g., to be above the kidney filtration cutoff), shape, hydrodynamic radius, charge, or parameters of absorption, biodistribution, metabolism, and elimination.

As used herein, the terms "activatable," "activate," "induce," and "inducible" refer to the ability of a protein, i.e. a cytokine, that is part of a fusion protein, to bind its receptor and effectuate activity upon cleavage of additional elements from the fusion protein.

As used herein, "plasmids" or "viral vectors" are agents that transport the disclosed nucleic acids into the cell without degradation and include a promoter yielding expression of the nucleic acid molecule and/or polypeptide in the cells into which it is delivered.

As used herein, the terms "peptide", "polypeptide", or "protein" are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, "subject" can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered.

As used herein, "patient" or "subject" may be used interchangeably and can refer to a subject with a disease or disorder (e.g., cancer). The term patient or subject includes human and veterinary subjects.

As used herein the terms "treatment", "treat", or "treating" refers to a method of reducing the effects of a disease or condition or symptom of the disease or condition. Thus, in the disclosed method, treatment can refer to at least about 10%, at least about 20%, at least about 30%, at least about 40%, at least about 50%, at least about 60%, at least about 70%, at least about 80%, at least about 90%, or substantially complete reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent", "preventing", and "prevention" of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder.

As used herein, references to "decreasing", "reducing", or "inhibiting" include a change of at least about 10%, of at least about 20%, of at least about 30%, of at least about 40%, of at least about 50%, of at least about 60%, of at least about 70%, of at least about 80%, of at least about 90% or greater as compared to a suitable control level. Such terms can include but do not necessarily include complete elimination of a function or property, such as agonist activity.

An "attenuated cytokine receptor agonist" is a cytokine receptor agonist that has decreased receptor agonist activity as compared to the cytokine receptor's naturally occurring agonist. An attenuated cytokine agonist may have at least about 10×, at least about 50×, at least about 100×, at least about 250×, at least about 500×, at least about 1000× or less agonist activity as compared to the receptor's naturally occurring agonist. When a fusion protein that contains a cytokine polypeptide as described herein is described as "attenuated" or having "attenuated activity", it is meant that the fusion protein is an attenuated cytokine receptor agonist.

An "intact fusion protein" is a fusion protein in which no domain has been removed, for example by protease cleavage. A domain may be removable by protease cleavage or other enzymatic activity, but when the fusion protein is "intact", this has not occurred.

As used herein "moiety" refers to a portion of a molecule that has a distinct function within that molecule, and that function may be performed by that moiety in the context of another molecule. A moiety may be a chemical entity with a particular function, or a portion of a biological molecule with a particular function. For example, a "blocking moiety" within a fusion protein is a portion of the fusion protein which is capable of blocking the activity of some or all of the fusion polypeptide. This may be a protein domain, such as serum albumin. Blocking may be accomplished by a steric blocker or a specific blocker. A steric blocker blocks by virtue of size and position and not based upon specific binding; an examples is serum albumin. A specific blocker blocks by virtue of specific interactions with the moiety to be blocked. A specific blocker must be tailored to the particular cytokine or active domain; a steric blocker can be used regardless of the payload, as long as it is large enough.

In general, the therapeutic use of cytokines is strongly limited by their systemic toxicity. TNF, for example, was originally discovered for its capacity of inducing the hemorrhagic necrosis of some tumors, and for its in vitro cytotoxic effect on different tumoral lines, but it subsequently proved to have strong pro-inflammatory activity, which can, in case of overproduction conditions, dangerously affect the human body. As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

Interleukin-12 (IL-12) is a disulfide-linked heterodimer of two separately encoded subunits (p35 and p40), which are linked covalently to give rise to the so-called bioactive heterodimeric (p70) molecule (Lieschke et al., 1997; Jana et al., 2014). Apart from forming heterodimers (IL-12 and IL-23), the p40 subunit is also secreted as a monomer (p40) and a homodimer ($p40_2$). It is known in the art that synthesis of the heterodimer as a single chain with a linker connecting the p35 to the p40 subunit preserves the full biological activity of the heterodimer. IL-12 plays a critical role in the early inflammatory response to infection and in the generation of Th1 cells, which favor cell-mediated immunity. It has been found that overproduction of IL-12 can be dangerous to the host because it is involved in the pathogenesis of a number of autoimmune inflammatory diseases (e.g., MS, arthritis, type 1 diabetes).

The IL-12 receptor (IL-12R) is a heterodimeric complex consisting of IL-12Rβ1 and IL-12Rβ2 chains expressed on the surface of activated T-cells and natural killer cells (Trinchieri et al., 2003). The IL-12Rβ1 chain binds to the IL-12p40 subunit, whereas IL-12p35 in association with IL-12Rβ2 confers an intracellular signaling ability (Benson et al., 2011). Signal transduction through IL-12R induces phosphorylation of Janus kinase (Jak2) and tyrosine kinase (Tyk2), that phosphorylate and activate signal transducer and activator of transcription (STAT)1, STAT3, STAT4, and STAT5. The specific cellular effects of IL-12 are due mainly to activation of STAT4. IL-12 induces natural killer and T-cells to produce cytokines, in particular interferon (IFN)γ, that mediate many of the proinflammatory activities of IL-12, including CD4+ T-cell differentiation toward the Th1 phenotype (Montepaone et al., 2014).

IL-12 is a pleiotropic cytokine, the actions of which create an interconnection between the innate and adaptive immunity. IL-12 was first described as a factor secreted from PMA-induced EBV-transformed B-cell lines. Based on its actions, IL-12 has been designated as cytotoxic lymphocyte maturation factor and natural killer cell stimulatory factor. Due to bridging the innate and adaptive immunity and potently stimulating the production of IFNγ, a cytokine coordinating natural mechanisms of anticancer defense, IL-12 seemed ideal candidate for tumor immunotherapy in humans. However, severe side effects associated with systemic administration of IL-12 in clinical investigations and the very narrow therapeutic index of this cytokine markedly tempered enthusiasm for the use of this cytokine in cancer patients (Lasek et. al., 2014). Approaches to IL-12 therapy in which delivery of the cytokine is tumor-targeted, which may diminish some of the previous issues with IL-12 therapy, are currently in clinical trials for cancers.

The present invention is designed to address the shortcomings of direct IL-12 therapy and therapy using other cytokines, for example using cytokine blocking moieties, e.g., steric blocking polypeptides, serum half-life extending polypeptides, targeting polypeptides, linking polypeptides, including protease-cleavable linkers, and combinations thereof. Cytokines, including interleukins (e.g., IL-2, IL-7, IL-12, IL-15, IL-18, IL-21 IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (C-X-C motif chemokine 10 (CXCL10), CCL19, CCL20, CCL21), and granulocyte macrophage-colony stimulating factor (GM-CS) are highly potent when administered to patients. As used herein, "chemokine" means a family of small cytokines with the ability to induce directed chemotaxis in nearby responsive cells Cytokines can provide powerful therapy, but are accompanied by undesired effects that are difficult to control clinically and which have limited the clinical use of cytokines. This disclosure relates to new forms of cytokines that can be used in patients with reduced or eliminated undesired effects. In particular, this disclosure relates to pharmaceutical compositions including chimeric polypeptides (fusion proteins), nucleic acids encoding fusion proteins and pharmaceutical formulations of the foregoing that contain cytokines or active fragments or muteins of cytokines that have decreased cytokine receptor activating activity in comparison to the corresponding cytokine. However, under selected conditions or in a selected biological environment the chimeric polypeptides activate their cognate receptors, often with the same or higher potency as the corresponding naturally occurring cytokine. As described herein, this is typically achieved using a cytokine blocking moiety that blocks or inhibits the receptor activating function of the cytokine, active fragment or mutein thereof under general conditions but not under selected conditions, such as those present at the desired site of cytokine activity (e.g., an inflammatory site or a tumor).

The chimeric polypeptides and nucleic acids encoding the chimeric polypeptides can be made using any suitable method. For example, nucleic acids encoding a chimeric polypeptide can be made using recombinant DNA techniques, synthetic chemistry or combinations of these techniques, and expressed in a suitable expression system, such as in CHO cells. Chimeric polypeptides can similarly be made, for example by expression of a suitable nucleic acid, using synthetic or semi-synthetic chemical techniques, and the like. In some embodiments, the blocking moiety can be attached to the cytokine polypeptide via sortase-mediated conjugation. "Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO: 80) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

To form the cytokine-blocking moiety fusion protein, the cytokine polypeptide is first tagged at the N-terminus with a polyglycine sequence, or alternatively, with at the C-terminus with a LPXTG motif (SEQ ID NO: 80). The blocking moiety or other element has respective peptides attached that serve as acceptor sites for the tagged polypeptides. For conjugation to domains carrying a LPXTG (SEQ ID NO: 80) acceptor peptide attached via its N-terminus, the polypeptide will be tagged with an N-terminal poly-glycine stretch. For conjugation to domain carrying a poly-glycine peptide attached via its C-terminus, the polypeptide will be tagged at its C-terminus with a LPXTG (SEQ ID NO: 80) sortase recognition sequence. Recognizing poly-glycine and LPXTG (SEQ ID NO: 80) sequences, sortase will form a peptide bond between polymer-peptide and tagged polypeptides. The sortase reaction cleaves off glycine residues as intermediates and occurs at room temperature.

A variety of mechanisms can be exploited to remove or reduce the inhibition caused by the blocking moiety. For example, the pharmaceutical compositions can include an IL-12 polypeptide and a blocking moiety, e.g., a steric blocking moiety, with a protease-cleavable linker comprising a protease cleavage site located between the IL-12 polypeptide and IL-12 blocking moiety or within the IL-12 blocking moiety. When the protease cleavage site is cleaved, the blocking moiety can dissociate from cytokine, and the cytokine can then activate cytokine receptor. An IL-12 cytokine moiety can also be blocked by a specific blocking moiety, such as an antibody, which binds an epitope found on the relevant cytokine.

Any suitable linker can be used. For example, the linker can comprise glycine-glycine, a sortase-recognition motif, or a sortase-recognition motif and a peptide sequence (Gly$_4$Ser)$_n$(SEQ ID NO: 81) or (Gly$_3$Ser)$_n$(SEQ ID NO: 82), wherein n is 1, 2, 3, 4 or 5. Typically, the sortase-recognition motif comprises a peptide sequence LPXTG (SEQ ID NO: 80), where X is any amino acid. In some embodiments, the covalent linkage is between a reactive lysine residue attached to the C-terminal of the cytokine polypeptide and a reactive aspartic acid attached to the N-terminal of the blocker or other domain. In other embodiments, the covalent linkage is between a reactive aspartic acid residue attached to the N-terminal of the cytokine polypeptide and a reactive lysine residue attached to the C-terminal of said blocker or other domain.

Accordingly, as described in detail herein, the cytokine blocking moieties (IL-12 blocking moieties) used can be steric blockers. As used herein, a "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. The steric inhibition of the cytokine moiety can be removed by spatially separating the cytokine moiety from the steric blocker, such as by enzymatically cleaving a fusion protein that contains a steric blocker and a cytokine polypeptide at a site between the steric blocker and the cytokine polypeptide.

As described in greater detail herein, the blocking function can be combined with or due to the presence of additional functional components in the pharmaceutical composition, such as a targeting domain, a serum half-life extension element, and protease-cleavable linking polypeptides. For example, a serum half-life extending polypeptide can also be a steric blocker.

Various elements ensure the delivery and activity of IL-12 preferentially at the site of desired IL-12 activity and to severely limit systemic exposure to the interleukin via a blocking and/or a targeting strategy preferentially linked to a serum half-life extension strategy. In this serum half-life extension strategy, the blocked version of interleukin circulates for extended times (preferentially 1-2 or more weeks) but the activated version has the typical serum half-life of the interleukin.

In some embodiments of this invention, the half-life extension element is linked to the interleukin via a linker which is cleaved at the site of action (e.g., by inflammation-specific or tumor-specific proteases) releasing the interleukin's full activity at the desired site and also separating it from the half-life extension of the uncleaved version. In such embodiments, the fully active and free interleukin would have very different pharmacokinetic (pK) properties—a half-life of hours instead of weeks. In addition, exposure to active cytokine is limited to the site of desired cytokine activity (e.g., an inflammatory site or tumor) and systemic exposure to active cytokine, and associated toxicity and side effects, are reduced.

Blocking moieties, described in further detail below, can also be used to favor binding to or activation of one or more receptors. This blocking may be relievable by removal of the blocking moieties in a particular environment, for example by proteolytic cleavage of a linker linking one or more blocking moieties to the cytokine.

In another aspect, a similar approach can be applied to improve other cytokines, particularly for use as immunostimulatory agents, for example for treating cancer. For example, in this aspect, the pharmacokinetics and/or pharmacodynamics of the cytokine (e.g., IL-2, IL-7, IL-12, IL-15, IL-18, IL-21 IL-23, IFNalpha, IFNbeta and IFNgamma, TNFalpha, lymphotoxin, TGFbeta1, TGFbeta2, TGFbeta3 GM-CSF, CXCL10, CCL19, CCL20, and CCL21 can be tailored to maximally activate effector cells (e.g., effect T cells, NK cells) and/or cytotoxic immune response promoting cells (e.g., induce dendritic cell maturation) at a site of desired activity, such as in a tumor, but preferably not systemically.

Thus, provided herein are pharmaceutical compositions comprising at least one cytokine polypeptide, such as interleukins (e.g., IL-2, IL-7, IL-12, IL-15, IL-18, IL-21, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (e.g., CXCL10, CCL19, CCL20, CCL21) and granulocyte macrophage-colony stimulating factor (GM-CS) or a functional fragment or mutein of any of the foregoing. The polypeptide typically also includes at least one linker amino acid sequence, wherein the amino acid sequence is in certain embodiments capable of being cleaved by an endogenous protease. In one embodiment, the linker comprises an amino acid sequence comprising HSSKLQ (SEQ ID NO: 24), GPLGVRG (SEQ ID NO: 83), IPVSLRSG (SEQ ID NO: 84), VPLSLYSG (SEQ ID NO: 85), or SGESPAYYTA (SEQ ID NO: 86). In other embodiments, the chimeric polypeptide further contains a blocking moiety, e.g., a steric blocking polypeptide moiety, capable of blocking the activity of the interleukin polypeptide. The blocking moiety, for example, can comprise a human serum albumin (HSA) binding domain or an optionally branched or multi-armed polyethylene glycol (PEG). Alternatively, the pharmaceutical composition comprises a first cytokine polypeptide or a fragment thereof, and blocking moiety, e.g., a steric blocking polypeptide moiety, wherein the blocking moiety blocks the activity of the cytokine polypeptide on the cytokine receptor, and wherein the blocking moiety in certain embodiments comprises a protease-cleavable domain. In some embodiments, blockade and reduction of cytokine activity is achieved simply by attaching additional domains with very short linkers to the N or C terminus of the interleukin domain. In such embodiments, it is anticipated the blockade is relieved by protease digestion of the blocking moiety or of the short linker that tethers the blocker to the interleukin. Once the domain is clipped or is released, it will no longer be able to achieve blockade of cytokine activity.

The pharmaceutical composition e.g., chimeric polypeptide can comprise two or more cytokines, which can be the same cytokine polypeptide or different cytokine polypeptides. For example, the two or more different types of cytokines have complementary functions. In some examples, a first cytokine is IL-12 and a second cytokine is IL-2. In some embodiments, each of the two or more different types of cytokine polypeptides have activities that modulate the activity of the other cytokine polypeptides. In some examples of chimeric polypeptides that contain two cytokine polypeptides, a first cytokine polypeptide is T-cell activating, and a second cytokine polypeptide is non-T-cell-activating. In some examples of chimeric polypeptides that contain two cytokine polypeptides, a first cytokine is a chemoattractant, e.g., CXCL10, and a second cytokine is an immune cell activator.

Preferably, the IL-12 polypeptides (including functional fragments) that are included in the fusion proteins disclosed herein are not mutated or engineered to alter the properties of the naturally occurring cytokine, including receptor binding affinity and specificity or serum half-life. However, changes in amino acid sequence from naturally occurring (including wild type) cytokine are acceptable to facilitate cloning and to achieve desired expression levels, for example.

Blocking Moiety

The blocking moiety can be any moiety that inhibits the ability of the cytokine to bind and/or activate its receptor. The blocking moiety can inhibit the ability of the cytokine to bind and/or activate its receptor sterically blocking and/or by noncovalently binding to the cytokine. Examples of suitable blocking moieties include the full length or a cytokine-binding fragment or mutein of the cognate receptor of the cytokine. Antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like that bind the cytokine can also be used. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of suitable blocking polypeptides include polypeptides that sterically inhibit or block binding of the cytokine to its cognate receptor. Advantageously, such moieties can also function as half-life extending elements. For example, a peptide that is modified by conjugation to a water-soluble polymer, such as PEG, can sterically inhibit or prevent binding of the cytokine to its receptor. Polypeptides, or fragments thereof, that have long serum half-lives can also be used, such as serum albumin (human serum albumin), immunoglobulin Fc, transferrin and the like, as well as fragments and muteins of such polypeptides. Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. Examples of such antigen-binding polypeptides include a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds.

In illustrative examples, when IL-12 is the cytokine in the chimeric polypeptide, the blocking moiety can be the full length or fragment or mutein of the first molecule of IL-12 receptor (IL-12Rβ1) or beta (IL-12Rβ2), an anti-IL-2 single-domain antibody (dAb) or scFv, an anti-IL-12Rβ1 antibody or fragment thereof, an anti-IL-12Rβ2 antibody or fragment thereof, and anti-HSA dAb or scFv, and the like.

Additional Aspects of the Invention

1. A fusion protein comprising a cytokine moiety that is operably linked to a binding moiety, the binding moiety comprising a non-CDR loop and a cleavable linker, wherein the binding moiety is capable of masking the binding the cytokine to its receptor and/or the activation of the receptor by the cytokine.
2. The fusion protein of aspect 1, wherein the binding moiety is a natural peptide, a synthetic peptide, an engineered scaffold, or an engineered bulk serum protein.
3. The fusion protein of aspect 1 or 2, wherein the engineered scaffold comprises a sdAb, a scFv, a Fab, a VHH, a fibronectin type III domain, immunoglobulin-like scaffold, DARPin, cystine knot peptide, lipocalin, three-helix bundle scaffold, protein G-related albumin-binding module, or a DNA or RNA aptamer scaffold.
4. The fusion protein of any one of aspects 1-2, wherein the binding moiety is capable of binding to a bulk serum protein.
5. The fusion protein of any one of aspects 1-3, wherein the non-CDR loop is from a variable domain, a constant domain, a C1-set domain, a C2-set domain, an I-domain, or any combinations thereof.
6. The fusion protein of any one of aspects 1-4, wherein the binding moiety further comprises complementarity determining regions (CDRs).
7. The fusion protein of aspect 5, wherein the binding moiety is capable of binding to the bulk serum protein.
8. The fusion protein of aspect 6, wherein the bulk serum protein is a half-life extending protein.

9. The fusion protein of aspect 6 or 7, wherein the bulk serum protein is albumin, transferrin, Factor XIII, or Fibrinogen.
10. The fusion protein of any one of aspects 5-8, wherein the CDR loop provides the binding site specific for the bulk serum protein or the immunoglobulin light chain, or any combinations thereof.
11. The fusion protein of any one of aspects 1-9, wherein the cleavable linker comprises a cleavage site.
12. The fusion protein of aspect 10, wherein the cleavage site is recognized by a protease.
13. The fusion protein of aspect 11, wherein the binding moiety is bound to the cytokine.
14. The fusion protein of aspect 11 or 13, wherein the binding moiety is covalently linked to the cytokine.
15. The fusion protein of aspect 11, 13, or 14, wherein the binding moiety is capable of masking the binding of the cytokine to its target via specific intermolecular interactions between the binding moiety and the cytokine.
16. The fusion protein of any one of aspects 11-14, wherein the non-CDR loop provides a binding site specific for binding of the moiety to the cytokine.
17. The fusion protein of any one of aspects 11-15, wherein upon cleavage of the cleavable linker, the binding moiety is separated from the cytokine and the cytokine binds to its target.
18. The fusion protein of any one of aspects 1-16, wherein the cytokine binds to a cytokine receptor.
19. The fusion protein of aspect 17, wherein the cytokine receptor comprises a type I cytokine receptor, a type I IL receptor, a type II IL receptor, a chemokine receptor, or a tumor necrosis receptor superfamily receptor.
20. The fusion protein of any one of aspects 1-18, wherein the cleavable linker comprises a cleavage site.
21. The fusion protein of aspect 20, wherein the cleavage site is recognized by a protease.
22. The fusion protein of aspect 21, wherein the protease cleavage site is recognized by a serine protease, a cysteine protease, an aspartate protease, a threonine protease, a glutamic acid protease, a metalloproteinase, a gelatinase, or a asparagine peptide lyase.
23. The fusion protein of aspect 21, wherein the protease cleavage site is recognized by a Cathepsin B, a Cathepsin C, a Cathepsin D, a Cathepsin E, a Cathepsin K, a Cathepsin L, a kallikrein, a hK1, a hK10, a hK15, a plasmin, a collagenase, a Type IV collagenase, a stromelysin, a Factor Xa, a chymotrypsin-like protease, a trypsin-like protease, a elastase-like protease, a subtilisin-like protease, an actinidain, a bromelain, a calpain, a caspase, a caspase-3, a Mir1-CP, a papain, a HIV-1 protease, a HSV protease, a CMV protease, a chymosin, a renin, a pepsin, a matriptase, a legumain, a plasmepsin, a nepenthesin, a metalloexopeptidase, a metalloendopeptidase, a matrix metalloprotease (MMP), a MMP1, a MMP2, a MMP3, a MMP8, a MMP9, a MMP10, a MMP11, a MMP12, a MMP13, a MMP14, an ADAM10, an ADAM17, an ADAM12, an urokinase plasminogen activator (uPA), an enterokinase, a prostate-specific target (PSA, hK3), an interleukin-1β converting enzyme, a thrombin, a FAP (FAP-α), a dipeptidyl peptidase, or dipeptidyl peptidase IV (DPPIV/CD26), a type II transmembrane serine protease (TTSP), a neutrophil elastase, a cathepsin G, a proteinase 3, a neutrophil serine protease 4, a mast cell chymase, a mast cell tryptase, a dipeptidyl peptidase, and a dipeptidyl peptidase IV (DPPIV/CD26).
24. A conditionally active binding protein comprising a binding moiety (M) which comprises a non-CDR loop, a cytokine, and a cleavable linker (L), wherein the non-CDR loop is capable of binding to the cytokine, and wherein the binding moiety is capable of inhibiting the binding of the cytokine to its receptor and/or inhibiting activation of the receptor by the cytokine.
25. The conditionally active binding protein of aspect 24, wherein the binding moiety is capable of binding to a half-life extending protein.
26. The conditionally active binding protein of aspect 24 or 25, wherein the binding moiety is a natural peptide, a synthetic peptide, an engineered scaffold, or an engineered serum bulk protein.
27. The conditionally active binding protein of aspect 26, wherein the engineered scaffold comprises a sdAb, a scFv, a Fab, a VHH, a fibronectin type III domain, immunoglobulin-like scaffold, DARPin, cystine knot peptide, lipocalin, three-helix bundle scaffold, protein G-related albumin-binding module, or a DNA or RNA aptamer scaffold.
28. The conditionally active binding protein of any one of aspects 24-27, wherein the non-CDR-loop is from a variable domain, a constant domain, a C1-set domain, a C2-set domain, an I-domain, or any combinations thereof.
29. The conditionally active binding protein of any one of aspects 24-28, wherein the binding moiety further comprises complementarity determining regions (CDRs).
30. The conditionally active binding protein of any one of aspects 24-29, wherein the binding moiety comprises a binding site specific for a bulk serum protein.
31. The conditionally active binding protein of aspect 30, wherein the bulk serum protein is albumin, transferrin, Factor XIII, or Fibrinogen.
32. The conditionally active binding protein of any one of aspects 29-31, wherein the CDRs provide the binding site specific for the bulk serum protein or the immunoglobulin light chain, or any combinations thereof.
33. The conditionally active binding protein of any one of aspects 29-32, wherein the binding moiety is capable of masking the binding of the cytokine to its target via specific intermolecular interactions between the binding moiety and the cytokine.
34. The conditionally active binding protein of any one of aspects 29-33, wherein the non-CDR loop provides a binding site specific for binding of the binding moiety to the cytokine.
35. The conditionally active binding protein of any one of aspects 24-34, wherein the cytokine binds to a cytokine receptor.
36. The conditionally active binding protein of aspect 35, wherein the cytokine receptor comprises a type I cytokine receptor, a type I IL receptor, a type II IL receptor, a chemokine receptor, or a tumor necrosis receptor superfamily receptor.
37. The conditionally active binding protein of aspect 24-36, wherein the cleavable linker comprises a cleavage site.
38. The conditionally active binding protein of aspect 37, wherein the cleavage site is recognized by a protease.
39. The conditionally active binding protein of aspect 38, wherein the protease cleavage site is recognized by a serine protease, a cysteine protease, an aspartate protease, a threonine protease, a glutamic acid protease, a metalloproteinase, a gelatinase, or a asparagine peptide lyase.

40. The conditionally active binding protein of aspect 38, wherein the protease cleavage site is recognized by a Cathepsin B, a Cathepsin C, a Cathepsin D, a Cathepsin E, a Cathepsin K, a Cathepsin L, a kallikrein, a hK1, a hK10, a hK15, a plasmin, a collagenase, a Type IV collagenase, a stromelysin, a Factor Xa, a chymotrypsin-like protease, a trypsin-like protease, a elastase-like protease, a subtilisin-like protease, an actinidain, a bromelain, a calpain, a caspase, a caspase-3, a Mir1-CP, a papain, a HIV-1 protease, a HSV protease, a CMV protease, a chymosin, a renin, a pepsin, a matriptase, a legumain, a plasmepsin, a nepenthesin, a metalloexopeptidase, a metalloendopeptidase, a matrix metalloprotease (MMP), a MMP1, a MMP2, a MMP3, a MMP8, a MMP9, a MMP10, a MMP11, a MMP12, a MMP13, a MMP14, an ADAM10, an ADAM17, an ADAM12, an urokinase plasminogen activator (uPA), an enterokinase, a prostate-specific target (PSA, hK3), an interleukin-1β converting enzyme, a thrombin, a FAP (FAP-α), a dipeptidyl peptidase, or dipeptidyl peptidase IV (DPPIV/CD26), a type II transmembrane serine protease (TTSP), a neutrophil elastase, a cathepsin G, a proteinase 3, a neutrophil serine protease 4, a mast cell chymase, a mast cell tryptase, a dipeptidyl peptidase, and a dipeptidyl peptidase IV (DPPIV/CD26).

41. The conditionally active binding protein of aspect 24, further comprising a half-life extension domain bound to the binding moiety, wherein the half-life extension domain provides the binding protein with a safety switch, and wherein upon cleavage of the linker the binding protein is activated by separation of the binding moiety and the half-life extension domain from the cytokine, and the binding protein is thereby separated from the safety switch.

42. The conditionally active binding protein of aspect 41, wherein the cleavage of the linker is in a tumor microenvironment.

43. A conditionally active binding protein, comprising a binding moiety that binds a cytokine via a non-CDR loop within the binding moiety, wherein the binding moiety is further linked to a half-life extension domain and comprises a cleavable linker, wherein the binding protein has an extended half-life prior to its activation by cleavage of the linker, and wherein upon activation the binding moiety and the half-life extension domain are separated from the cytokine, and wherein the binding protein, in its activated state, does not have an extended half-life.

44. The conditionally active binding protein of aspect 43, wherein the cleavage of the linker is in a tumor microenvironment.

In Vivo Half-Life Extension Elements

Preferably, the chimeric polypeptides comprise an in vivo half-life extension element. Increasing the in vivo half-life of therapeutic molecules with naturally short half-lives allows for a more acceptable and manageable dosing regimen without sacrificing effectiveness. As used herein, a "half-life extension element" is a part of the chimeric polypeptide that increases the in vivo half-life and improve pK, for example, by altering its size (e.g., to be above the kidney filtration cutoff), shape, hydrodynamic radius, charge, or parameters of absorption, biodistribution, metabolism, and elimination. An exemplary way to improve the pK of a polypeptide is by expression of an element in the polypeptide chain that binds to receptors that are recycled to the plasma membrane of cells rather than degraded in the lysosomes, such as the FcRn receptor on endothelial cells and transferrin receptor. Three types of proteins, e.g., human IgGs, HSA (or fragments), and transferrin, persist for much longer in human serum than would be predicted just by their size, which is a function of their ability to bind to receptors that are recycled rather than degraded in the lysosome. These proteins, or fragments of them that retain the FcRn binding are routinely linked to other polypeptides to extend their serum half-life. In one embodiment, the half-life extension element is a human serum albumin (HSA) binding domain. HSA (SEQ ID NO: 1) may also be directly bound to the pharmaceutical compositions or bound via a short linker. Fragments of HSA may also be used. HSA and fragments thereof can function as both a blocking moiety and a half-life extension element. Human IgGs and Fc fragments can also carry out a similar function.

The serum half-life extension element can also be antigen-binding polypeptide that binds to a protein with a long serum half-life such as serum albumin, transferrin and the like. Examples of such polypeptides include antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocalin and CTLA4 scaffolds. Further examples of antigen-binding polypeptides include a ligand for a desired receptor, a ligand-binding portion of a receptor, a lectin, and peptides that binds to or associates with one or more target antigens.

Figure 5:
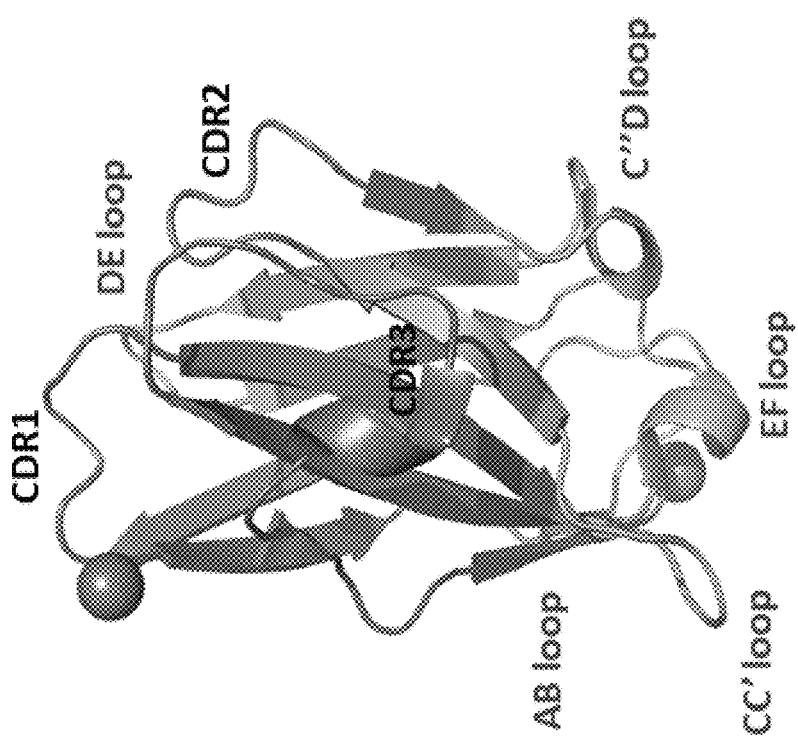
FIG. 5 is a schematic illustrating the structure of a variable domain of an immunoglobulin molecule. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops.

Some preferred serum half-life extension elements are polypeptides that comprise complementarity determining regions (CDRs), and optionally non-CDR loops. Advantageously, such serum half-life extension elements can extend the serum half-life of the cytokine, and also function as inhibitors of the cytokine (e.g., via steric blocking, non-covalent interaction or combination thereof) and/or as targeting domains. In some instances, the serum half-life extension elements are domains derived from an immunoglobulin molecule (Ig molecule) or engineered protein scaffolds that mimic antibody structure and/or binding activity. The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. As shown in FIG. 5, a variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I(Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain. The serum half-life extension domain (e.g., a domain that comprises CDRs) can comprise at least one non-CDR loop. In some embodiments, a non-CDR loop provides a binding site for binding to a cytokine, bulk serum protein or other target antigen.

The serum half-life extension element, in addition to or alternatively to containing CDRs, comprises a non-CDR loop. In some embodiments, the non-CDR loop is modified to generate an antigen binding site specific for a desired target antigen, such as a bulk serum protein, such as albumin, or for the cytokine moiety or other targeting antigen. It is contemplated that various techniques can be used for modifying the non-CDR loop, e.g., site-directed mutagenesis, random mutagenesis, insertion of at least one amino acid that is foreign to the non-CDR loop amino acid sequence, amino acid substitution. An antigen peptide is inserted into a non-CDR loop, in some examples. In some examples, an antigenic peptide is substituted for the non-CDR loop. The modification, to generate an antigen binding site, is in some cases in only one non-CDR loop. In other instances, more than one non-CDR loop are modified. For instance, the modification is in any one of the non-CDR loops shown in FIG. 5, i.e., AB, CC', C" D, EF, and D-E. In some cases, the modification is in the DE loop. In other cases the modifications are in all four of AB, CC', C"-D, E-F loops.

In some examples, the serum half-life extension element has dual binding specificity and contains CDRs that specifically bind a bulk serum proteins, such as serum albumin, and non-CDR loops that specifically bind and block the cytokine domain. In other examples, the serum half-life extension element contains CDRs that specifically bind a target antigen, such as the cytokine domain or other target antigen, and non-CDR loops that specifically bind a bulk serum protein, such as serum albumin. Preferably, the serum half-life extension element inhibits binding of the cytokine domain to the cognate cytokine receptor, e.g., via steric occlusion, via specific intermolecular interactions, or a combination of both.

In some embodiments, the serum half-life extension element noncovalently binds directly to the cytokine and inhibit its activity.

In certain examples, the binding moiety binds to a cytokine via one or more of AB, CC', C" D, and E-F loop and binds to a bulk-serum protein, such as albumin, via one or more of BC, C'C", and FG loop. In certain examples, the binding moiety binds to a bulk serum protein, such as albumin, via its AB, CC', C" D, or EF loop and binds to a cytokine via its BC, C'C", or FG loop. In certain examples, the binding moiety of the binds to a bulk serum protein, such as albumin, via its AB, CC', C" D, and EF loop and is bound to a cytokine via its BC, C'C", and FG loop. In certain examples, the binding moiety binds to a bulk serum protein, such as albumin, via one or more of AB, CC', C" D, and E-F loop and binds to a cytokine, via one or more of BC, C'C", and FG loop.

The binding moieties are any kinds of polypeptides. For example, in certain instances the binding moieties are natural peptides, synthetic peptides, or fibronectin scaffolds, or engineered bulk serum proteins. The bulk serum protein comprises, for example, albumin, fibrinogen, or a globulin. In some embodiments, the binding moieties are an engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the serum half-life extension element binds to the cytokine domain via its non-CDR loops and the cytokine domain is further connected to a targeting domain as described herein. In some cases, the serum half-life extending element comprises a binding site for a bulk serum protein. In some embodiments, the CDRs provide the binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the CDR form a binding site for an immunoglobulin light chain, such as an Igκ free light chain or an Igλ free light chain.

Figure 6:
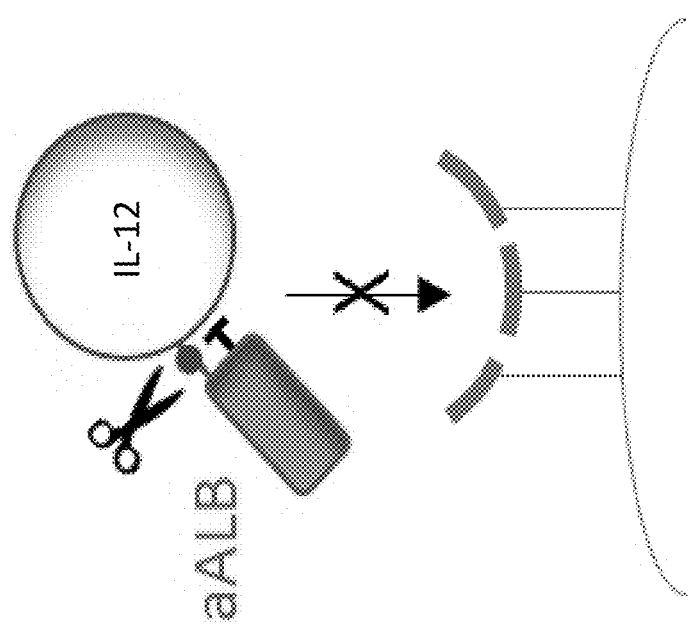
FIG. 6 is a schematic illustrating a protease-activated cytokine or chemokine comprising a cytokine or chemokine polypeptide, a blocking moiety that is a serum albumin binding domain (e.g., a dAb), and a protease-cleavable linker. In the illustrated example, the non-CDR loops in a serum albumin binding domain (e.g., a sdAb) can form a binding site for the cytokine IL-12. In this example, the binding site for serum albumin can be formed by the CDRs of the serum albumin binding domain.
Figure 7B:
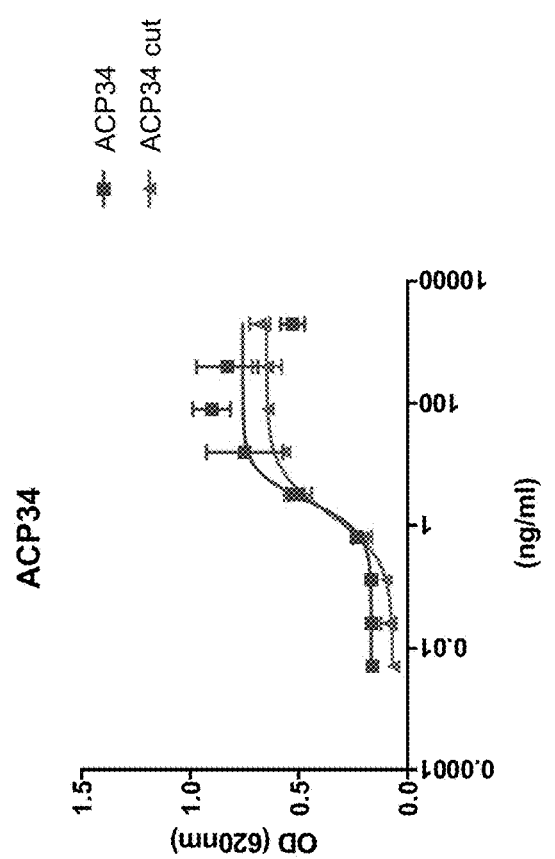
FIG. 7a and FIG. 7b are graphs depicting results from a HEK-Blue IL-12 reporter assay performed on human p40/murine p35 IL-12 fusion proteins before and after protease cleavage. Analysis was performed based on quantification of Secreted Alkaline Phosphatase (SEAP) activity using the reagent QUANTI-Blue® (InvivoGen). Results confirm that IL-12 protein fusion proteins are active.
Figure 7A:
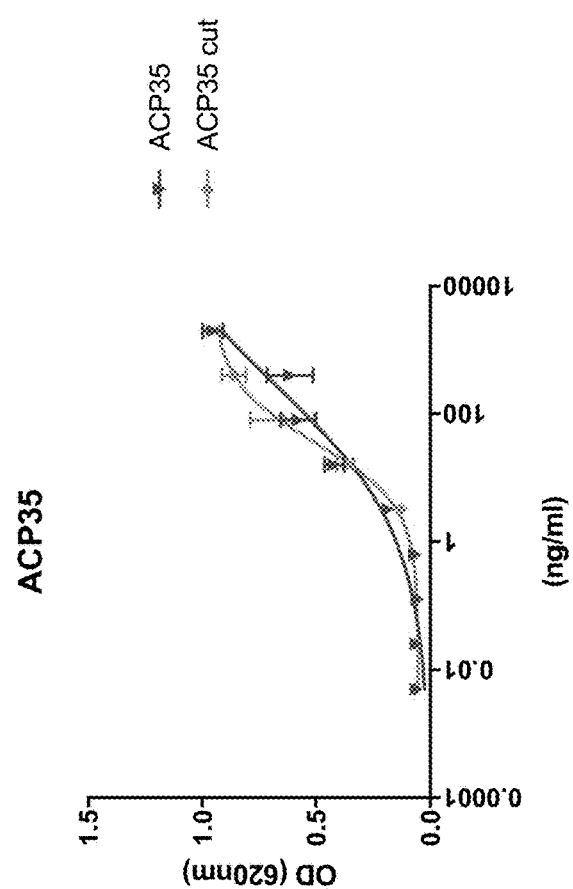
Figure 8A:
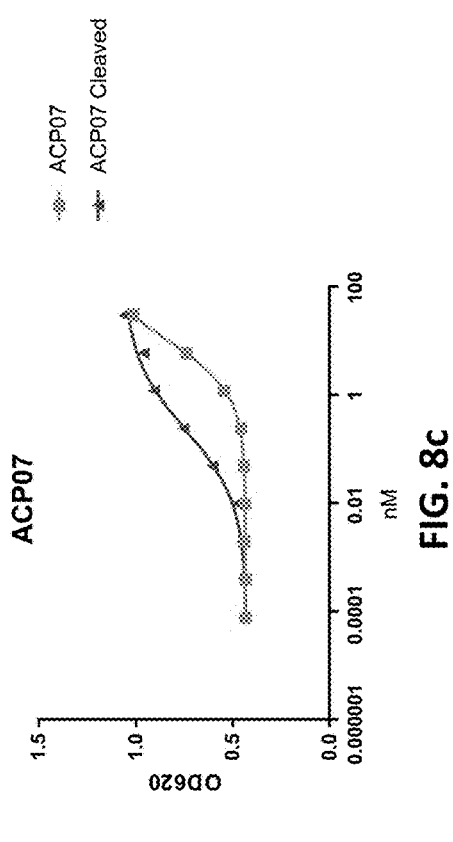
FIGS. 8a-8f show a series of graphs depicting the results of HEK-blue assay of IL-12 fusion proteins, before and after cleavage by MMP9. Analysis was performed based on quantification of Secreted Alkaline Phosphatase (SEAP) activity using the reagent QUANTI-Blue (InvivoGen). The data show greater activity in the cleaved IL-12 than in the full fusion protein. Constructs tested were ACP06 (FIG. 8a), ACP07 (FIG. 8b), ACP08 (FIG. 8c), ACP09 (FIG. 8d), ACP10 (FIG. 8e), ACP11 (FIG. 8f).
Figure 8C:
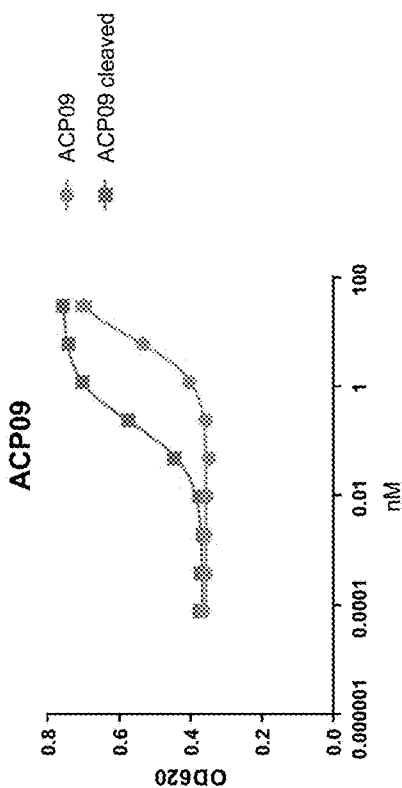
Figure 8B:
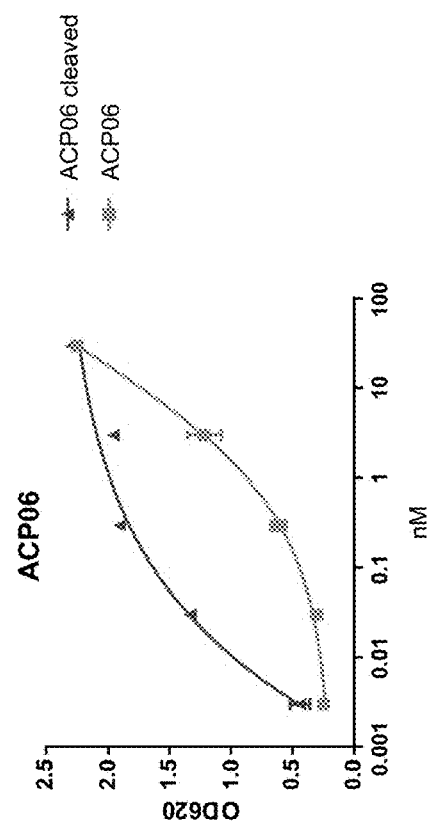
Figure 8D:
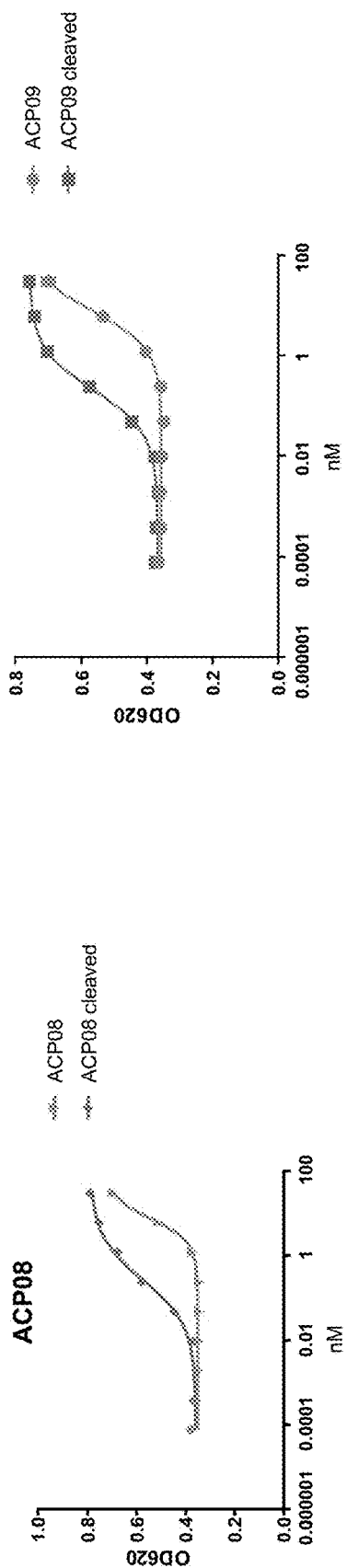
Figures 8E, 8F:
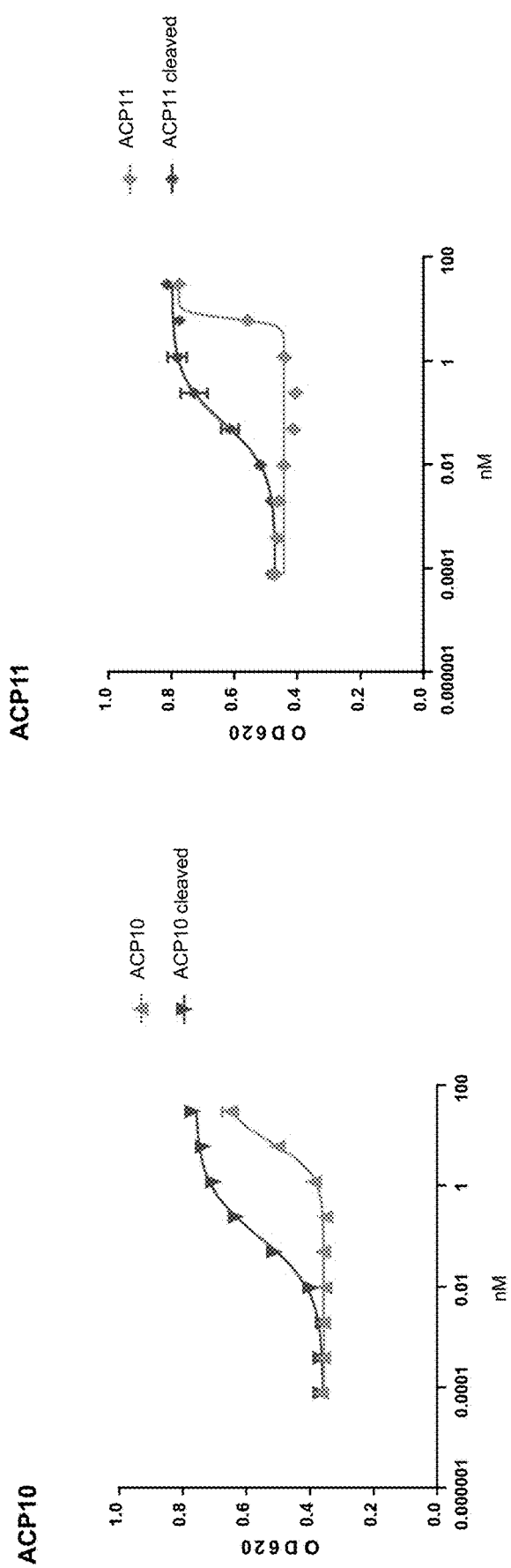

One exemplary conditionally active protein is shown in FIG. 6. In the illustrated example, the non-CDR loops in a serum albumin binding domain (e.g., a dAb) can form a binding site for the cytokine IL-12. In this example, the binding site for serum albumin can be formed by the CDRs of the serum albumin binding domain.

The serum half-life extension element can be any type of binding domain, including but not limited to, domains from a monoclonal antibody, a polyclonal antibody, a recombinant antibody, a human antibody, a humanized antibody. In some embodiments, the binding moiety is a single chain variable fragment (scFv), single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

In other embodiments, the serum half-life extension element can be a water-soluble polymer or a peptide that is conjugated to a water-soluble polymer, such as PEG. "PEG," "polyethylene glycol" and "poly(ethylene glycol)" as used herein, are interchangeable and encompass any nonpeptidic water-soluble poly(ethylene oxide). The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below. The PEG is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the PEG can be organized in any number of different repeat patterns and can be selected from the group consisting of homopolymer, alternating copolymer, random copolymer, block copolymer, alternating tripolymer, random tripolymer, and block tripolymer. PEGs can be conjugated to polypeptide and peptides through any suitable method. Typically a reactive PEG derivative, such as N-hydroxysuccinamidyl ester PEG, is reacted with a peptide or polypeptide that includes amino acids with a side chain that contains an amine, sulfhydryl, carboxylic acid or hydroxyl functional group, such as cysteine, lysine, asparagine, glutamine, theonine, tyrosine, serine, aspartic acid, and glutamic acid.

Targeting and Retention Domains

For certain applications, it may be desirable to maximize the amount of time the construct is present in its desired location in the body. This can be achieved by including one further domain in the chimeric polypeptide (fusion protein) to influence its movements within the body. For example, the chimeric nucleic acids can encode a domain that directs the polypeptide to a location in the body, e.g., tumor cells or a site of inflammation; this domain is termed a "targeting domain" and/or encode a domain that retains the polypeptide in a location in the body, e.g., tumor cells or a site of inflammation; this domain is termed a "retention domain". In some embodiments a domain can function as both a targeting and a retention domain. In some embodiments, the targeting domain and/or retention domain are specific to a protease-rich environment. In some embodiments, the encoded targeting domain and/or retention domain are specific for regulatory T cells (Tregs), for example targeting the CCR4 or CD39 receptors. Other suitable targeting and/or retention domains comprise those that have a cognate ligand that is overexpressed in inflamed tissues, e.g., the IL-1 receptor, or the IL-6 receptor. In other embodiments, the suitable targeting and/or retention domains comprise those who have a cognate ligand that is overexpressed in tumor tissue, e.g., Epcam, CEA or mesothelin. In some embodiments, the targeting domain is linked to the interleukin via a linker which is cleaved at the site of action (e.g., by inflammation or cancer specific proteases) releasing the interleukin full activity at the desired site. In some embodiments, the targeting and/or retention domain is linked to the interleukin via a linker which is not cleaved at the site of action (e.g., by inflammation or cancer specific proteases), causing the cytokine to remain at the desired site.

Antigens of choice, in some cases, are expressed on the surface of a diseased cell or tissue, for example a tumor or a cancer cell. Antigens useful for tumor targeting and retention include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, EpCAM, EGFR, HER-2, HER-3, c-Met, FOLR1, and CEA. Pharmaceutical compositions disclosed herein, also include proteins comprising two targeting and/or retention domains that bind to two different target antigens known to be expressed on a diseased cell or tissue. Exemplary pairs of antigen binding domains include but are not limited to EGFR/CEA, EpCAM/CEA, and HER-2/HER-3.

Suitable targeting and/or retention domains include antigen-binding domains, such as antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocallin and CTLA4 scaffolds. Further examples of antigen-binding polypeptides include a ligand for a desired receptor, a ligand-binding portion of a receptor, a lectin, and peptides that binds to or associates with one or more target antigens.

In some embodiments, the targeting and/or retention domains specifically bind to a cell surface molecule. In some embodiments, the targeting and/or retention domains specifically bind to a tumor antigen. In some embodiments, the targeting polypeptides specifically and independently bind to a tumor antigen selected from at least one of Fibroblast activation protein alpha (FAPa), Trophoblast glycoprotein (5T4), Tumor-associated calcium signal transducer 2 (Trop2), Fibronectin EDB (EDB-FN), FOLR1, fibronectin EIIIB domain, EpCAM, EGFR, HER-2, HER-3, cMet, CEA, and FOLR1. In some embodiments, the targeting polypeptides specifically and independently bind to two different antigens, wherein at least one of the antigens is a tumor antigen selected from Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, EpCAM, EGFR, HER-2, HER-3, cMet, CEA, and FOLR1.

The targeting and/or retention antigen can be a tumor antigen expressed on a tumor cell. Tumor antigens are well known in the art and include, for example, Fibroblast activation protein alpha (FAPa), Trophoblast glycoprotein (5T4), Tumor-associated calcium signal transducer 2 (Trop2), Fibronectin EDB (EDB-FN), FOLR1, fibronectin EIIIB domain, EpCAM, EGFR, HER-2, HER-3, c-Met, PSMA, CD38, BCMA, and CEA. 5T4, AFP, B7-H3, Cadherin-6, CAIX, CD117, CD123, CD138, CD166, CD19, CD20, CD205, CD22, CD30, CD33, CD352, CD37, CD44, CD52, CD56, CD70, CD71, CD74, CD79b, DLL3, EphA2, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1, Muc16, NaPi2b, Nectin-4, P-cadherin, NY-ESO-1, PRLR, PSCA, PTK7, ROR1, SLC44A4, SLTRK5, SLTRK6, STEAP1, TIM1, Trop2, WT1.

The targeting and/or retention antigen can be an immune checkpoint protein. Examples of immune checkpoint proteins include but are not limited to CD27, CD137, 2B4, TIGIT, CD155, ICOS, HVEM, CD40L, LIGHT, TIM-1, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDO1, IDO2, TDO, KIR, LAG-3, TIM-3, or VISTA.

The targeting and/or retention antigen can be a cell surface molecule such as a protein, lipid or polysaccharide. In some embodiments, a targeting and/or retention antigen is a on a tumor cell, virally infected cell, bacterially infected cell, damaged red blood cell, arterial plaque cell, inflamed or fibrotic tissue cell. The targeting and/or retention antigen can comprise an immune response modulator. Examples of immune response modulator include but are not limited to granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), GITRL, CD3, or GITR.

The targeting and/or retention antigen can be a cytokine receptor. Examples, of cytokine receptors include but are not limited to Type I cytokine receptors, such as GM-CSF receptor, G-CSF receptor, Type I IL receptors, Epo receptor, LIF receptor, CNTF receptor, TPO receptor; Type II Cytokine receptors, such as IFN-alpha receptor (IFNAR1, IFNAR2), IFB-beta receptor, IFN-gamma receptor (IFNGR1, IFNGR2), Type II IL receptors; chemokine receptors, such as CC chemokine receptors, CXC chemokine receptors, CX3C chemokine receptors, XC chemokine receptors; tumor necrosis receptor superfamily receptors, such as TNFRSF5/CD40, TNFRSF8/CD30, TNFRSF7/CD27, TNFRSF1A/TNFR1/CD120a, TNFRSF1B/TNFR2/CD120b; TGF-beta receptors, such as TGF-beta receptor 1, TGF-beta receptor 2; Ig super family receptors, such as IL-1 receptors, CSF-1R, PDGFR (PDGFRA, PDGFRB), SCFR.

Linkers

As stated above, the pharmaceutical compositions comprise one or more linker sequences. A linker sequence serves to provide flexibility between polypeptides, such that, for example, the blocking moiety is capable of inhibiting the activity of the cytokine polypeptide. The linker sequence can be located between any or all of the cytokine polypeptide, the serum half-life extension element, and/or the blocking moiety. As described herein at least one of the linkers is protease cleavable, and contains a (one or more) cleavage site for a (one or more) desired protease. Preferably, the desired protease is enriched or selectively expressed at the desired site of cytokine activity (e.g., the tumor microenvironment). Thus, the fusion protein is preferentially or selectively cleaved at the site of desired cytokine activity.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

The orientation of the components of the pharmaceutical composition, are largely a matter of design choice and it is recognized that multiple orientations are possible and all are intended to be encompassed by this disclosure. For example, a blocking moiety can be located C-terminally or N-terminally to a cytokine polypeptide.

Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mir1-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-β converting enzyme, thrombin, FAP (FAP-a), dipeptidyl peptidase, meprins, granzymes and dipeptidyl peptidase IV (DPPIV/CD26). Proteases capable of cleaving amino acid sequences encoded by the chimeric nucleic acid sequences provided herein can, for example, be selected from the group consisting of a prostate specific antigen (PSA), a matrix metalloproteinase (MMP), an A Disintigrin and a Metalloproteinase (ADAM), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Proteases useful in the methods disclosed herein are presented in Table 1, and exemplary proteases and their cleavage site are presented in Table 1a:

TABLE 1

| Proteases relevant to inflammation and cancer | | |
|---|---|---|
| Protease | Specificity | Other aspects |
| Secreted by killer T cells: | | |
| Granzyme B (grB) | Cleaves after Asp residues (asp-ase) | Type of serine protease; strongly implicated in inducing perforin-dependent target cell apoptosis |
| Granzyme A (grA) | trypsin-like, cleaves after basic residues | Type of serine protease; |
| Granzyme H (grH) | Unknown substrate specificity | Type of serine protease; Other granzymes are also secreted by |

TABLE 1-continued

Proteases relevant to inflammation and cancer

| Protease | Specificity | Other aspects |
|---|---|---|
| | | killer T cells, but not all are present in humans |
| Caspase-8 | Cleaves after Asp residues | Type of cysteine protease; plays essential role in TCR-induced cellular expansion-exact molecular role unclear |
| Mucosa-associated lymphoid tissue (MALT1) | Cleaves after arginine residues | Type of cysteine protease; likely acts both as a scaffold and proteolytically active enzyme in the CBM-dependent signaling pathway |
| Tryptase | Targets: angiotensin I, fibrinogen, prourokinase, TGFβ; preferentially cleaves proteins after lysine or arginine residues | Type of mast cell-specific serine protease; trypsin-like; resistant to inhibition by macromolecular protease inhibitors expressed in mammals due to their tetrameric structure, with all sites facing narrow central pore; also associated with inflammation |

Associated with inflammation:

| Protease | Specificity | Other aspects |
|---|---|---|
| Thrombin | Targets: FGF-2, HB-EGF, Osteo-pontin, PDGF, VEGF | Type of serine protease; modulates activity of vascular growth factors, chemokines and extracellular proteins; strengthens VEGF-induced proliferation; induces cell migration; angiogenic factor; regulates hemostasis |
| Chymase | Exhibit chymotrypsin-like specificity, cleaving proteins after aromatic amino acid residues | Type of mast cell-specific serine protease |
| Carboxypeptidase A (MC-CPA) | Cleaves amino acid residues from C-terminal end of peptides and proteins | Type of zinc-dependent metalloproteinase |
| Kallikreins | Targets: high molecular weight kininogen, pro-urokinase | Type of serine protease; modulate relaxation response; contribute to inflammatory response; fibrin degradation |
| Elastase | Targets: E-cadherin, GM-CSF, IL-1, IL-2, IL-6, IL8, p38$^{MAPK}$, TNFα, VE-cadherin | Type of neutrophil serine protease; degrades ECM components; regulates inflammatory response; activates pro-apoptotic signaling |
| Cathepsin G | Targets: EGF, ENA-78, IL-8, MCP-1, MMP-2, MT1-MMP, PAI-1, RANTES, TGFβ, TNFα | Type of serine protease; degrades ECM components; chemo-attractant of leukocytes; regulates inflammatory response; promotes apoptosis |
| PR-3 | Targets: ENA-78, IL-8, IL-18, JNK, p38$^{MAPK}$, TNFα | Type of serine protease; promotes inflammatory response; activates pro-apoptotic signaling |
| Granzyme M (grM) | Cleaves after Met and other long, unbranched hydrophobic residues | Type of serine protease; only expressed in NK cells |
| Calpains | Cleave between Arg and Gly | Family of cysteine proteases; calcium-dependent; activation is involved in the process of numerous inflammation-associated diseases |

TABLE 1a

Exemplary Proteases and Protease Recognition Sequences

| Protease | Cleavage Domain Sequence | SEQ ID NO: |
|---|---|---|
| MMP7 | KRALGLPG | 2 |
| MMP7 | (DE)₈RPLALWRS(DR)₈ | 3 |
| MMP9 | PR(S/T)(L/I)(S/T) | 4 |
| MMP9 | LEATA | 5 |
| MMP11 | GGAANLVRGG | 6 |
| MMP14 | SGRIGFLRTA | 7 |
| MMP | PLGLAG | 8 |
| MMP | PLGLAX | 9 |
| MMP | PLGC(me)AG | 10 |
| MMP | ESPAYYTA | 11 |
| MMP | RLQLKL | 12 |
| MMP | RLQLKAC | 13 |
| MMP2, MMP9, MMP14 | EP(Cit)G(Hof)YL | 14 |
| Urokinase plasminogen activator (uPA) | SGRSA | 15 |
| Urokinase plasminogen activator (uPA) | DAFK | 16 |
| Urokinase plasminogen activator (uPA) | GGGRR | 17 |
| Lysosomal Enzyme | GFLG | 18 |
| Lysosomal Enzyme | ALAL | 19 |
| Lysosomal Enzyme | FK | 20 |

TABLE 1a-continued

Exemplary Proteases and Protease Recognition Sequences

| Protease | Cleavage Domain Sequence | SEQ ID NO: |
|---|---|---|
| Cathepsin B | NLL | 21 |
| Cathepsin D | PIC(Et)FF | 22 |
| Cathepsin K | GGPRGLPG | 23 |
| Prostate Specific Antigen | HSSKLQ | 24 |
| Prostate Specific Antigen | HSSKLQL | 25 |
| Prostate Specific Antigen | HSSKLQEDA | 26 |
| Herpes Simplex Virus Protease | LVLASSSFGY | 27 |
| HIV Protease | GVSQNYPIVG | 28 |
| CMV Protease | GVVQASCRLA | 29 |
| Thrombin | F(Pip)RS | 30 |
| Thrombin | DPRSFL | 31 |
| Thrombin | PPRSFL | 32 |
| Caspase-3 | DEVD | 33 |
| Caspase-3 | DEVDP | 34 |
| Caspase-3 | KGSGDVEG | 35 |
| Interleukin 1β converting enzyme | GWEHDG | 36 |
| Enterokinase | EDDDDKA | 37 |
| FAP | KQEQNPGST | 38 |
| Kallikrein 2 | GKAFRR | 39 |
| Plasmin | DAFK | 40 |
| Plasmin | DVLK | 41 |
| Plasmin | DAFK | 42 |
| TOP | ALLLALL | 43 |

Provided herein are pharmaceutical compositions comprising polypeptide sequences. As with all peptides, polypeptides, and proteins, including fragments thereof, it is understood that additional modifications in the amino acid sequence of the chimeric polypeptides (amino acid sequence variants) can occur that do not alter the nature or function of the peptides, polypeptides, or proteins. Such modifications include conservative amino acid substitutions and are discussed in greater detail below.

The compositions provided herein have a desired function. The compositions are comprised of at least an IL-12 cytokine polypeptide, a blocking moiety, e.g., a steric blocking polypeptide, and an optional serum half-life extension element, and an optional targeting polypeptide, with one or more linkers connecting each polypeptide in the composition. The first polypeptide, e.g., an IL-12 polypeptide, is provided to be an active agent. The blocking moiety is provided to block the activity of the interleukin. The linker polypeptide, e.g., a protease-cleavable polypeptide, is provided to be cleaved by a protease that is specifically expressed at the intended target of the active agent. Optionally, the blocking moiety blocks the activity of the first polypeptide by binding the interleukin polypeptide. In some embodiments, the blocking moiety, e.g., a steric blocking peptide, is linked to the interleukin via a protease-cleavable linker which is cleaved at the site of action (e.g., by inflammation or tumor specific proteases) releasing the cytokine full activity at the desired site.

The protease cleavage site may be a naturally occurring protease cleavage site or an artificially engineered protease cleavage site. The artificially engineered protease cleavage site can be cleaved by more than one protease specific to the desired environment in which cleavage will occur, e.g., a tumor. The protease cleavage site may be cleavable by at least one protease, at least two proteases, at least three proteases, or at least four proteases.

In some embodiments, the linker comprises glycine-glycine, a sortase-recognition motif, or a sortase-recognition motif and a peptide sequence (Gly$_4$Ser)$_n$(SEQ ID NO: 81) or (Gly$_3$Ser)$_n$(SEQ ID NO: 82), wherein n is 1, 2, 3, 4 or 5. In one embodiment, the sortase-recognition motif comprises a peptide sequence LPXTG (SEQ ID NO: 80), where X is any amino acid. In one embodiment, the covalent linkage is between a reactive lysine residue attached to the C-terminal of the cytokine polypeptide and a reactive aspartic acid attached to the N-terminal of the blocking or other moiety. In one embodiment, the covalent linkage is between a reactive aspartic acid residue attached to the N-terminal of the cytokine polypeptide and a reactive lysine residue attached to the C-terminal of the blocking or other moiety.

Cleavage and Inducibility

As described herein, the activity of the cytokine polypeptide the context of the fusion protein is attenuated, and protease cleavage at the desired site of activity, such as in a tumor microenvironment, releases a form of the cytokine from the fusion protein that is much more active as a cytokine receptor agonist than the fusion protein. For example, the cytokine-receptor activating (agonist) activity of the fusion polypeptide can be at least about 10x, at least about 50x, at least about 100x, at least about 250x, at least about 500x, or at least about 1000x less than the cytokine receptor activating activity of the cytokine polypeptide as a separate molecular entity. The cytokine polypeptide that is part of the fusion protein exists as a separate molecular entity when it contains an amino acid that is substantially identical to the cytokine polypeptide and does not substantially include additional amino acids and is not associated (by covalent or non-covalent bonds) with other molecules. If necessary, a cytokine polypeptide as a separate molecular entity may include some additional amino acid sequences, such as a tag or short sequence to aid in expression and/or purification.

In other examples, the cytokine-receptor activating (agonist) activity of the fusion polypeptide is at least about 10x, at least about 50x, at least about 100x, at least about 250x, at least about 500x, or about 1000x less than the cytokine receptor activating activity of the polypeptide that contains the cytokine polypeptide that is produced by cleavage of the protease-cleavable linker in the fusion protein. In other words, the cytokine receptor activating (agonist) activity of the polypeptide that contains the cytokine polypeptide that is produced by cleavage of the protease-cleavable linker in the fusion protein is at least about 10x, at least about 50x, at least about 100x, at least about 250x, at least about 500x, or at least about 1000x greater than the cytokine receptor activating activity of the fusion protein.

Polypeptide Substitutions

The polypeptides described herein can include components (e.g., the cytokine, the blocking moiety) that have the same amino acid sequence of the corresponding naturally occurring protein (e.g., IL-2, IL-15, HSA) or can have an amino acid sequence that differs from the naturally occurring protein so long as the desired function is maintained. It is understood that one way to define any known modifications and derivatives or those that might arise, of the disclosed proteins and nucleic acids that encode them is through defining the sequence variants in terms of identity to specific known reference sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the sequence of any of the nucleic acids or polypeptides described herein. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 2 and are referred to as conservative substitutions.

TABLE 2

Exemplary amino acid substitutions

| Amino Acid | Exemplary Substitutions |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. For example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the complementarity determining regions (CDRs). Such random mutations can be introduced using a variety of techniques, including radiation, chemical mutagens or error-prone PCR. Multiple rounds of mutation and selection can be performed using, for example, phage display.

The disclosure also relates to nucleic acids that encode the chimeric polypeptides described herein, and to the use of such nucleic acids to produce the chimeric polypeptides and for therapeutic purposes. For example, the invention includes DNA and RNA molecules (e.g., mRNA, self-replicating RNA) that encode a chimeric polypeptide and to the therapeutic use of such DNA and RNA molecules.

Exemplary Compositions

Exemplary fusion proteins of the invention combine the above described elements in a variety of orientations. The orientations described in this section are meant as examples and are not to be considered limiting.

In some embodiments, the fusion protein comprises an IL-12 polypeptide, a blocking moiety and a half-life extension element. In some embodiments, the IL-12 polypeptide, is positioned between the half-life extension element and the blocking moiety. In some embodiments, the IL-12 polypeptide, is N-terminal to the blocking moiety and the half-life extension element. In some such embodiments, IL-12 polypeptide, is proximal to the blocking moiety; in some such embodiments, the IL-12 polypeptide, is proximal to the half-life extension element. At least one protease-cleavable linker must be included in all embodiments, such that the IL-12 polypeptide, may be active upon cleavage. In some embodiments, the IL-12 polypeptide, is C-terminal to the blocking moiety and the half-life extension element. Additional elements may be attached to one another by a cleavable linker, a non-cleavable linker, or by direct fusion. In some cases, it is beneficial to include two of the same cytokine to facilitate dimerization.

In some embodiments, the blocking domains used are capable of extending half-life, and the IL-12 polypeptide, is positioned between two such blocking domains. In some embodiments, the IL-12 polypeptide, is positioned between two blocking domains, one of which is capable of extending half-life.

In some embodiments, two cytokines are included in the same construct. In some embodiments, the cytokines are connected to two blocking domains each (three in total in one molecule), with a blocking domain between the two cytokine domains. In some embodiments, one or more additional half-life extension domains may be included to optimize pharmacokinetic properties.

In some embodiments, three cytokines are included in the same construct. In some embodiments, the third cytokine may function to block the other two in place of a blocking domain between the two cytokines.

Preferred half-life extension elements for use in the fusion proteins are human serum albumin (HSA), an antibody or antibody fragment (e.g., scFV, dAb) which binds serum albumin, a human or humanized IgG, or a fragment of any of the foregoing. In some preferred embodiments, the blocking moiety is human serum albumin (HSA), or an antibody or antibody fragment which binds serum albumin, an antibody which binds the cytokine and prevents activation of binding or activation of the cytokine receptor, another cytokine, or a fragment of any of the foregoing. In preferred embodiments comprising an additional targeting domain, the targeting domain is an antibody which binds a cell surface protein which is enriched on the surface of cancer cells, such as EpCAM, FOLR1, and Fibronectin.

Methods of Treatment and Pharmaceutical Compositions

Further provided are methods of treating a subject with or at risk of developing an of a disease or disorder, such as proliferative disease, a tumorous disease, an inflammatory disease, an immunological disorder, an autoimmune disease, an infectious disease, a viral disease, an allergic reaction, a parasitic reaction, or graft-versus-host disease. The methods administering to a subject in need thereof an effective amount of a fusion protein as disclosed herein that is typically administered as a pharmaceutical composition. In some embodiments, the method further comprises selecting a subject with or at risk of developing a disease or disorder. The pharmaceutical composition preferably comprises a blocked IL-12 polypeptide, fragment or mutein thereof that is activated at a site of inflammation or a tumor. In one embodiment, the chimeric polypeptide comprises an IL-12 polypeptide, fragment or mutein thereof and a serum half-life extension element. In another embodiment, the chimeric polypeptide comprises an IL-12 polypeptide, fragment or mutein thereof and a blocking moiety, e.g., a steric blocking polypeptide, wherein the steric blocking polypeptide is capable of sterically blocking the activity of the IL-12 polypeptide, fragment or mutein thereof. In another embodiment, the chimeric polypeptide comprises an IL-12 polypeptide, fragment or mutein thereof, a blocking moiety, and a serum half-life extension element.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Inflammation can occur from infection, as a symptom or a disease, e.g., cancer, atherosclerosis, allergies, myopathies, HIV, obesity, or an autoimmune disease. An autoimmune disease is a chronic condition arising from an abnormal immune response to a self-antigen. Autoimmune diseases that may be treated with the polypeptides disclosed herein include but are not limited to lupus, celiac disease, diabetes mellitus type 1, Graves disease, inflammatory bowel disease, multiple sclerosis, psoriasis, rheumatoid arthritis, and systemic lupus erythematosus.

The pharmaceutical composition can comprise one or more protease-cleavable linker sequences. The linker sequence serves to provide flexibility between polypeptides, such that each polypeptide is capable of inhibiting the activity of the first polypeptide. The linker sequence can be located between any or all of the cytokine polypeptide, fragment or mutein thereof, the blocking moiety, and serum half-life extension element. Optionally, the composition comprises, two, three, four, or five linker sequences. The linker sequence, two, three, or four linker sequences can be the same or different linker sequences. In one embodiment, the linker sequence comprises GGGGS (SEQ ID NO: 87), GSGSGS (SEQ ID NO: 88), or G(SGGG)$_2$SGGT (SEQ ID NO: 89). In another embodiment, the linker comprises a protease-cleavable sequence selected from group consisting of HSSKLQ (SEQ ID NO: 24), GPLGVRG (SEQ ID NO: 83), IPVSLRSG (SEQ ID NO: 84), VPLSLYSG (SEQ ID NO: 85), and SGESPAYYTA (SEQ ID NO: 86).

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

In some embodiments, the linker is cleaved by a protease selected from the group consisting of a kallikrein, thrombin, chymase, carboxypeptidase A, cathepsin G, an elastase, PR-3, granzyme M, a calpain, a matrix metalloproteinase (MMP), a plasminogen activator, a cathepsin, a caspase, a tryptase, or a tumor cell surface protease.

Further provided are methods of treating a subject with or at risk of developing cancer. The methods comprise administering to the subject in need thereof an effective amount of a chimeric polypeptide (a fusion protein) as disclosed herein that is typically administered as a pharmaceutical composition. In some embodiments, the method further comprises selecting a subject with or at risk of developing cancer. The pharmaceutical composition preferably comprises a blocked cytokine, fragment or mutein thereof that is activated at a tumor site. Preferably, the tumor is a solid tumor. The cancer may be a colon cancer, a lung cancer, a melanoma, a sarcoma, a renal cell carcinoma, and a breast cancer.

The method can further involve the administration of one or more additional agents to treat cancer, such as chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2), cellular therapies (e.g., CAR-T, T-cell therapy), oncolytic viruses and the like.

Provided herein are pharmaceutical formulations or compositions containing the chimeric polypeptides and a pharmaceutically acceptable carrier. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical formulation or composition in which it is contained. The carrier is selected to minimize degradation of the active ingredient and to minimize adverse side effects in the subject.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic, although the formulate can be hypertonic or hypotonic if desired. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The pharmaceutical formulations or compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. In some embodiments, the compositions are administered locally (non-systemically), including intratumorally, intra-articularly, intrathecally, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Such compositions and methods can be used to transfect or transduce cells in vitro or in vivo, for example, to produce cell lines that express and preferably secrete the encoded chimeric polypeptide or to therapeutically deliver nucleic acids to a subject. The components of the chimeric nucleic acids disclosed herein typically are operably linked in frame to encode a fusion protein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Such vectors can also be used to make the chimeric polypeptides by expression is a suitable host cell, such as CHO cells.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g., β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g., chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or inflammation) or during early onset (e.g., upon initial signs and symptoms of cancer or inflammation). Prophylactic administration can occur for several days to years prior to the manifestation of symptoms of cancer or inflammation. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or inflammation (e.g., an autoimmune disease). Prophylactic use may also apply when a patient is undergoing a treatment, e.g., a chemotherapy, in which inflammation is expected.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following are examples of methods and compositions of the invention. It is understood that various other embodiments may be practiced, given the general description provided herein.

Example 1: Protease Cleavage of IL-12 Fusion Protein by MMP9 Protease

Figure 9:
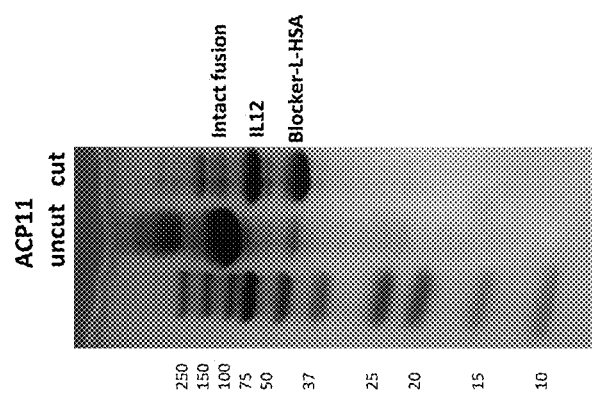
FIG. 9 shows results of protein cleavage assay. Fusion protein ACP11 was run on an SDS-PAGE gel in both cleaved and uncleaved form. As can be seen in the gel, cleavage was complete.
Figure 10:
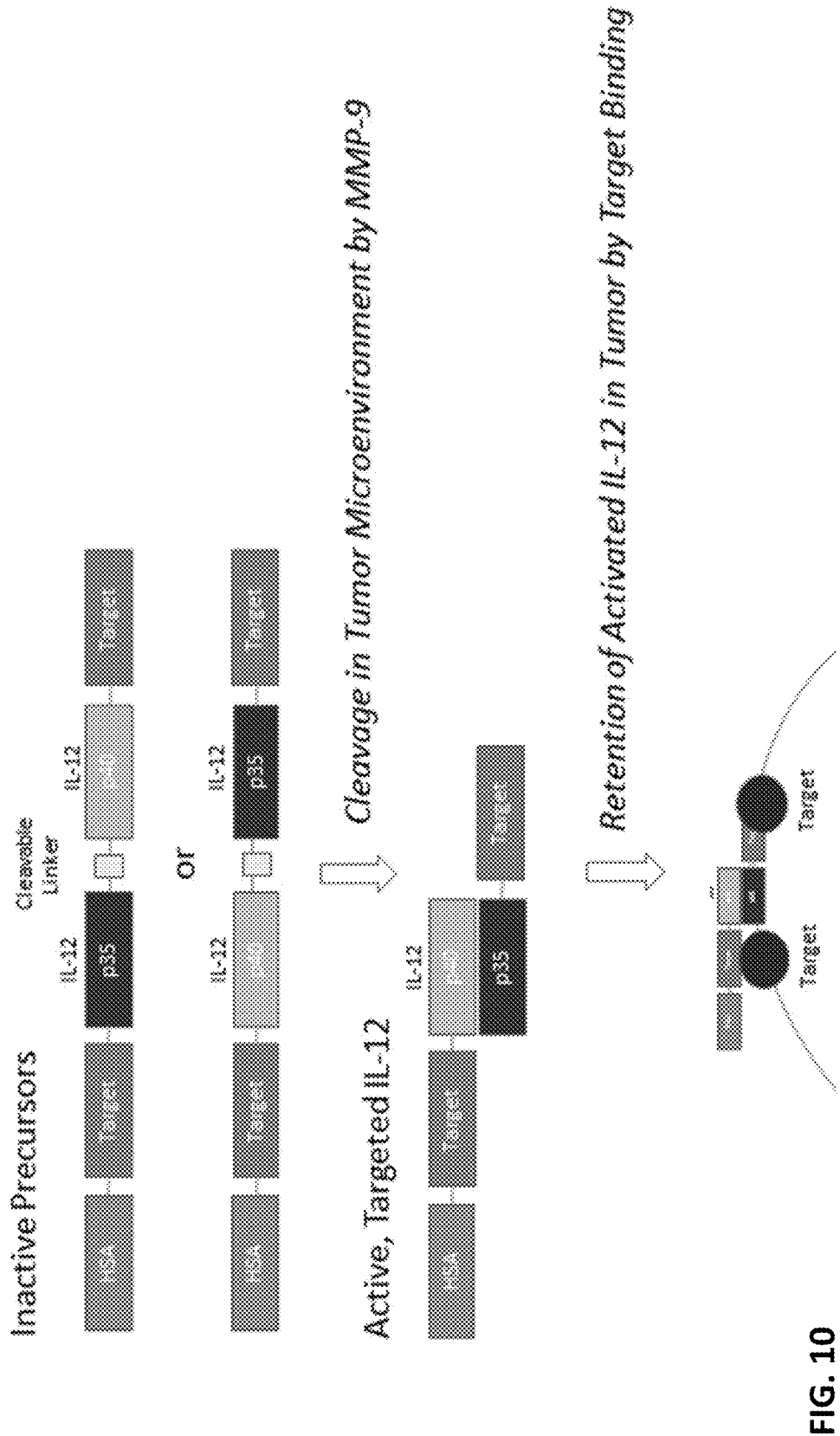
FIG. 10 is a schematic, which depicts a non-limiting example of an inducible IL-12 protein, wherein the construct is activated upon protease cleavage of a linker between two subunits of IL-12.
Figure 12A:
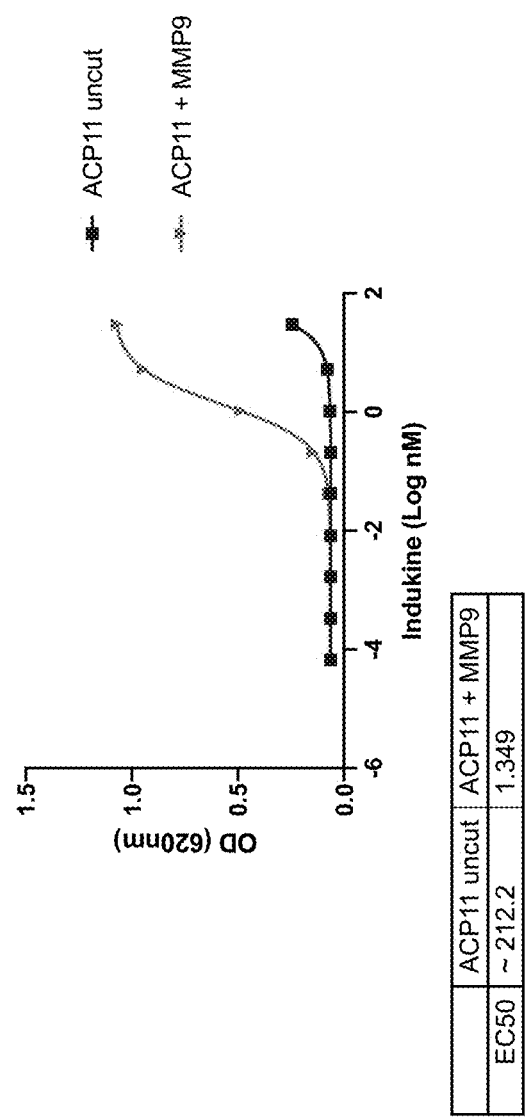
FIGS. 12a-12c is a series of graphs showing activity of fusion proteins in an HEK Blue IL-12 reporter assay.
Figure 12B:
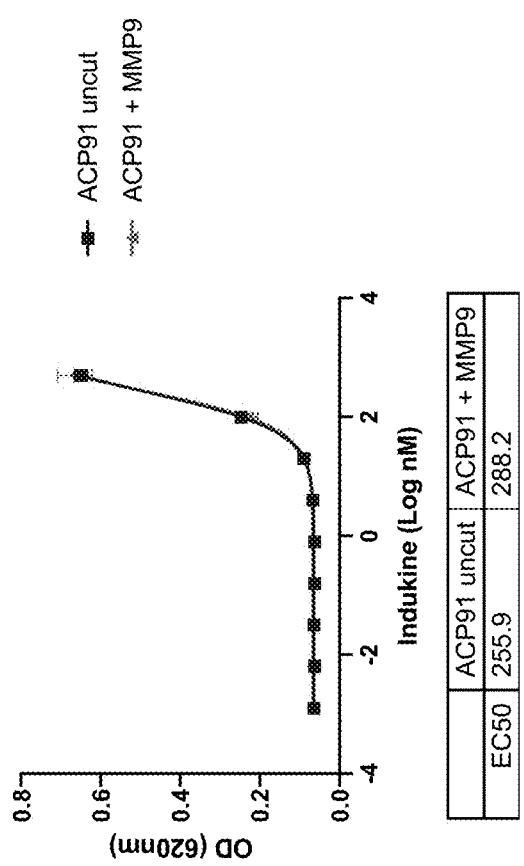
Figure 12C:
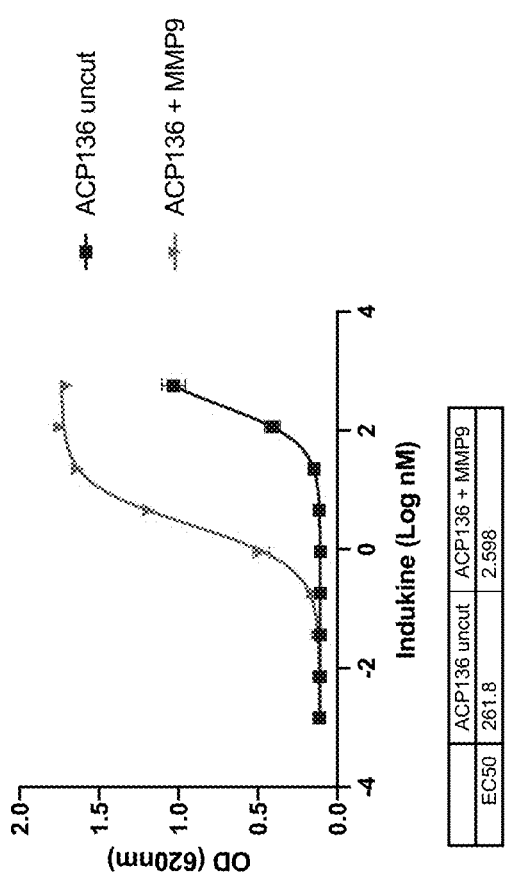
Figure 13:
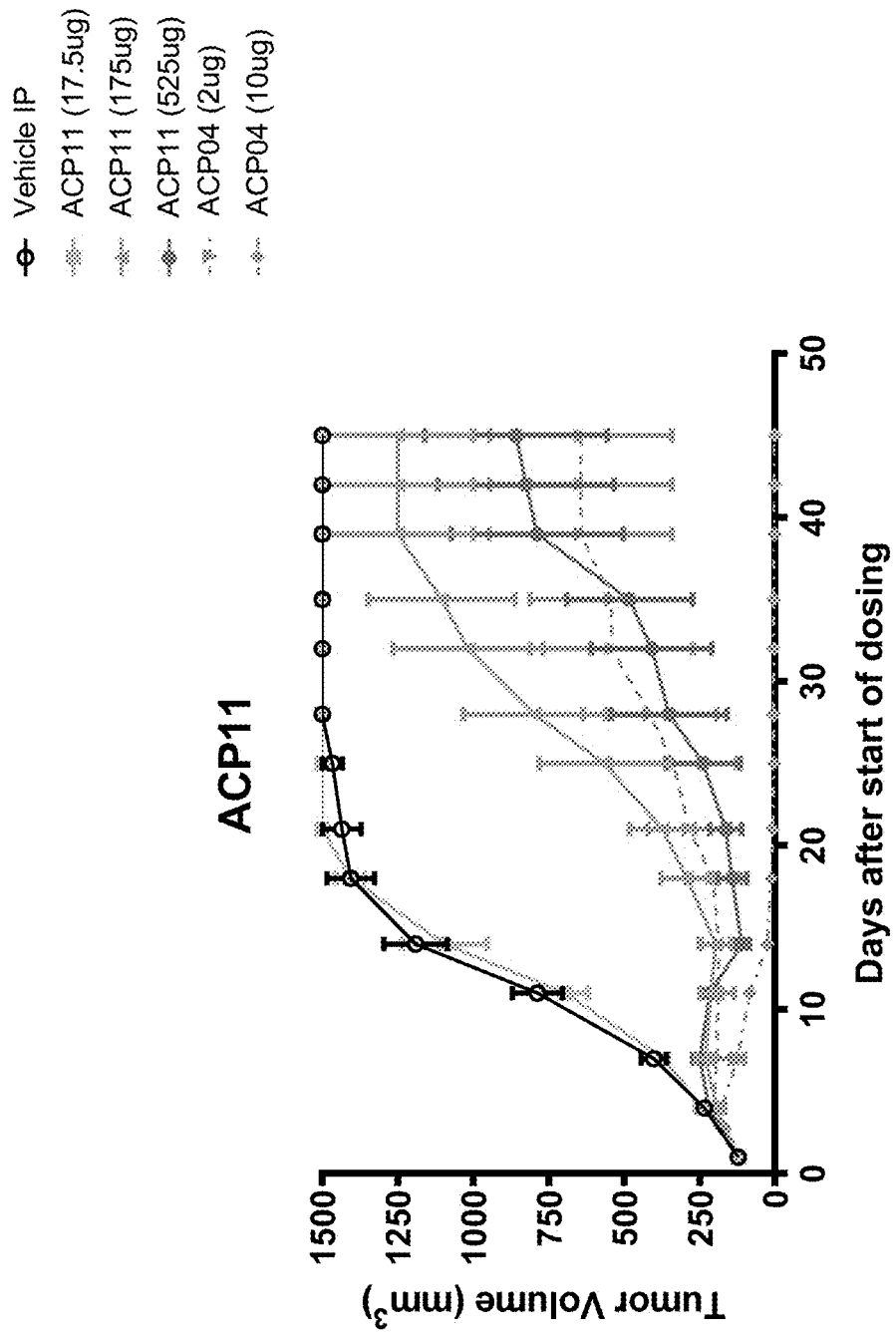
FIG. 13 is a graph showing tumor volume over time in mice treated with 17.5 µg ACP11 (squares), 175 µg ACP11 (triangles), 525 µg ACP11 (circles), and as controls 2 µg ACP04 (dashed line, triangles) and 10 µg ACP04 (dashed line, diamonds). Vehicle alone is indicated by large open circles. The data show tumor volume decreasing over time in a dose-dependent manner in mice treated with both ACP11 and ACP04 (a human p40/murine p35 IL-12 fusion protein).
Figure 15:
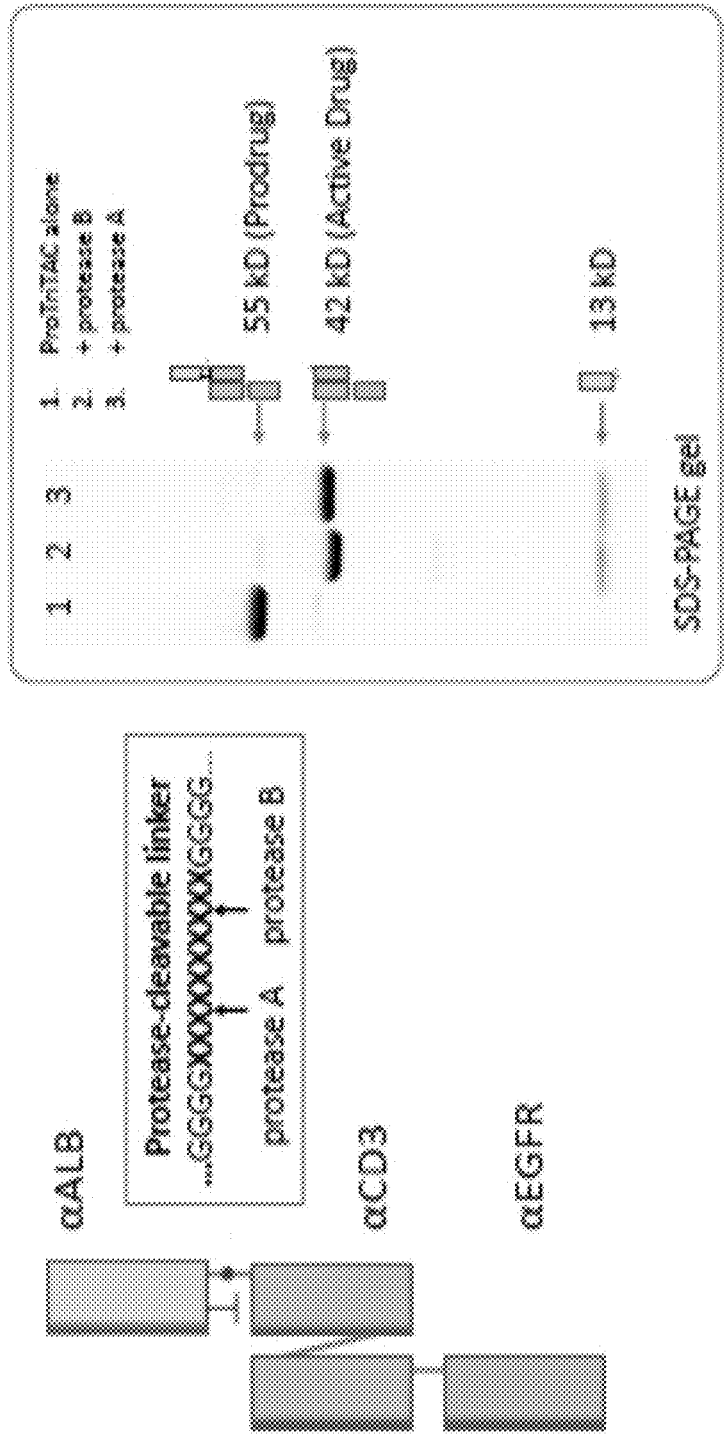
FIG. 15 illustrates the properties of ProTriTac polypeptides, which serve as exemplary protease-cleavable fusion proteins.
Figure 17:
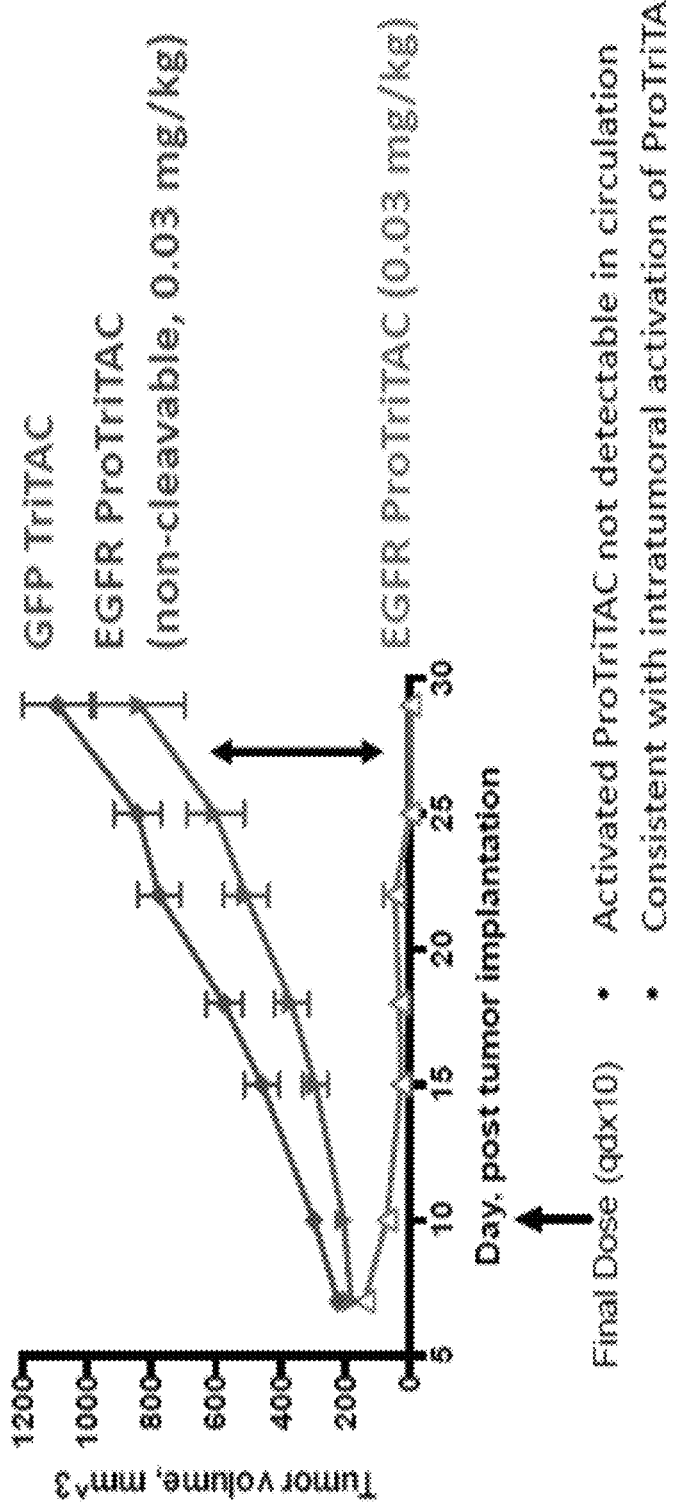
FIG. 17 illustrates ProTriTAC exhibits potent, protease-dependent, anti-tumor activity in a rodent tumor xenograft model.
Figure 18:
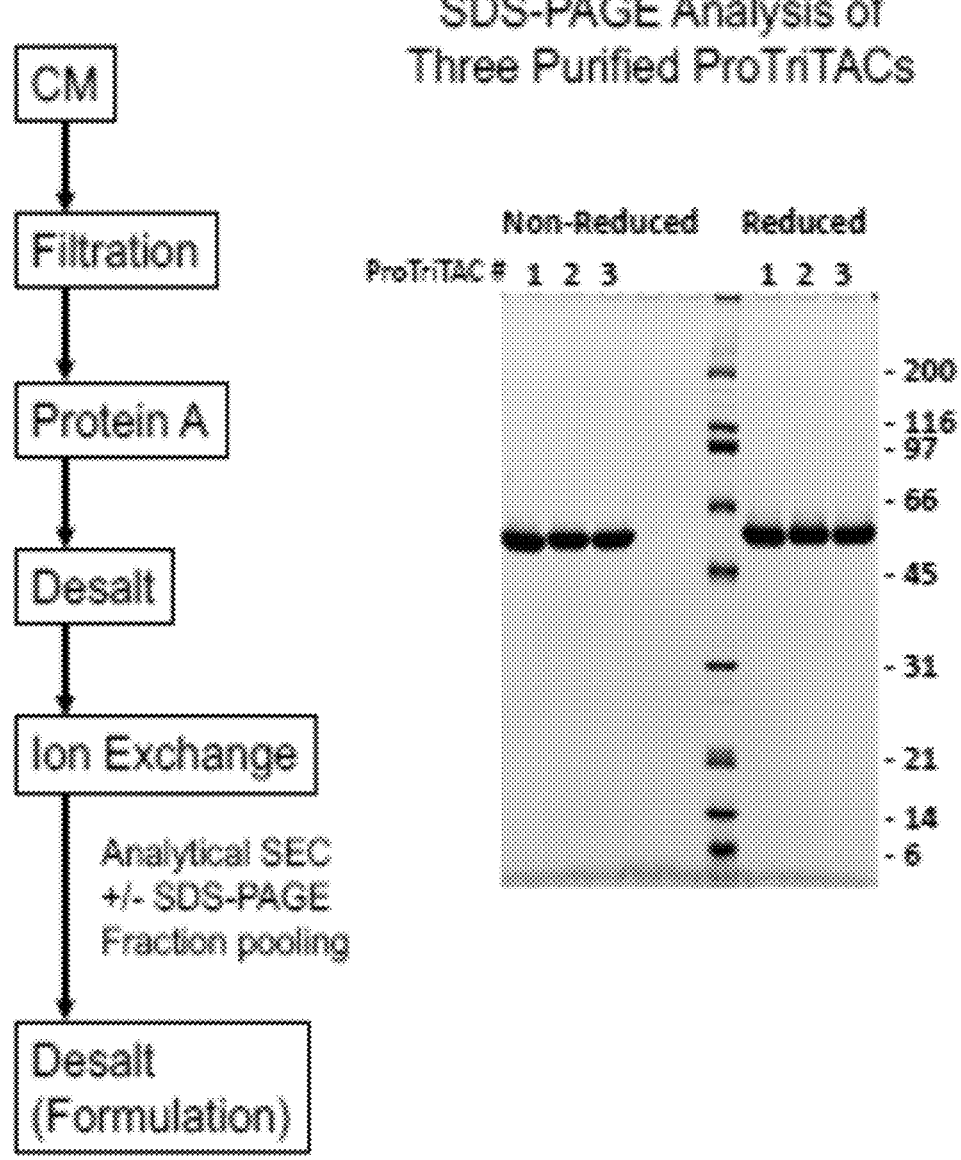
FIG. 18 illustrates SDS-PAGE analysis of purified ProTriTAC proteins.
Figure 19:
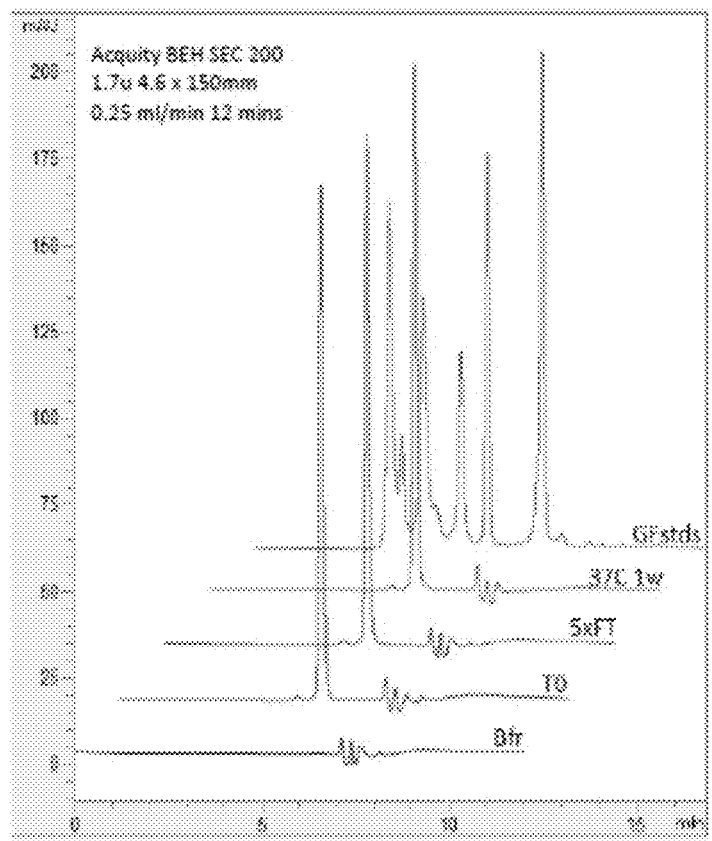
FIG. 19 illustrates analytical SEC of a ProTriTAC protein after different stress conditions.

One of skill in the art would be familiar with methods of setting up protein cleavage assay. 100 ug of protein in 1×PBS pH 7.4 were cleaved with 1 ug active MMP9 (Sigma catalog # SAE0078-50 or Enzo catalog BML-SE360) and incubated at room temperature for up to 16 hours. Digested protein can be subsequently used in functional assays or stored at −80° C. prior to testing. Extent of cleavage was monitored by SDS PAGE using methods well known in the art. As shown in FIG. 9, the ACP11 fusion protein was cleaved by MMP9 protease.

Example 2: HEK Blue Assay

HEK-Blue IL-12 cells (InvivoGen) were plated in suspension at a concentration of 250,000 cells/well in culture media with or without 40 mg/ml human serum albumin (HSA) and stimulated with a dilution series of recombinant hIL-12, chimeric IL-12 (mouse p35/human p40) or activatable hIL-12 for 24 hours at 37° C. and 5% $CO_2$. Activity of uncleaved and cleaved activatable hIL-12 was tested. Cleaved inducible hIL-12 was generated by incubation with active MMP9. IL-12 activity was assessed by quantification of Secreted Alkaline Phosphatase (SEAP) activity using the reagent QUANTI-Blue (InvivoGen), a colorimetric based assay. Results are shown in FIGS. 7a, 7b, 8a-8f, and 11a-11d.

Example 3: Splenocyte T-Blast Assay

T-Blasts were induced from murine splenocytes with a 6-day incubation with PHA and a 24 hr incubation with recombinant hIL-12. Tblasts were then plated in suspension at a concentration of 200,000 cells/well in culture media with or without 40 mg/ml human serum albumin (HSA) and stimulated with a dilution series of recombinant hIL-12 or chimeric IL-12 (mouse p35/human p40) or mouse IL-12 for 72 hours at 37° C. and 5% $CO_2$. Activity of uncleaved and cleaved IL-12 was tested. Cleaved inducible hIL-12 was generated by incubation with active MMP9. IL-12 activity was assessed by downstream quantification of IFNγ production using a mIFNγ alphaLISA.

Example 4: In Vivo Delivery of a Protease Activated IL-12 Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 5: Construction of an Exemplary Activatable IL-12 Protein Targeting CD20

Generation of an Activatable IL-12 Domain

The human IL-12p35 chain canonical sequence is Uniprot Accession No. P29459. The human IL-12p40 chain canonical sequence is Uniprot Accession No. P29460. IL-12p35 and IL-12p40 are cloned into an expression construct. A protease cleavage site is included between the IL-12p35 and IL-12p40 domains. An IL-12 polypeptide capable of binding to CD20 polypeptide present in a tumor or on a tumor cell is produced as follows. A nucleic acid is produced that contains nucleic acid sequences: (1) encoding an IFNg polypeptide sequence and (2) one or more polypeptide linkers. Activatable IL-12 plasmid constructs can have optional Flag, His or other affinity tags, and are electroporated into HEK293 or other suitable human or mammalian cell lines and purified. Validation assays include T cell activation assays using T cells responsive to IL-12 stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable IL-12 protein. DNA sequences coding for human or humanized VL and VH domains are obtained, and the codons for the constructs are, optionally, optimized for expression in cells from Homo sapiens. The order in which the VL and VH domains appear in the scFv is varied (i.e., VL-VH, or VH-VL orientation), and three copies of the "G4S" (SEQ ID NO: 87) or "G$_4$S" (SEQ ID NO: 87) subunit (G$_4$S)$_3$ (SEQ ID NO: 90) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IL-12 Protein

The activatable IL-12 construct with protease cleavage site domains are used to construct an activatable interleukin protein in combination with an anti-CD20 scFv domain and a serum half-life extension element (e.g., a HSA binding peptide or VH domain). For expression of an activatable IL-12 protein in CHO cells, coding sequences of all protein domains are cloned into a mammalian expression vector system. In brief, gene sequences encoding the activatable IL-12 domain, serum half-life extension element, and CD20 binding domain along with peptide linkers L1 and L2 are separately synthesized and subcloned. The resulting constructs are then ligated together in the order of CD20 binding domain-L1-IL-12p35-L2-protease cleavage domain-L3-IL-12p40-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO: 91) to facilitate protein secretion and purification, respectively.

Expression of Activatable IL-12 Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable IL-12 proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable IL-12 proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IL-12 proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IL-12 Proteins

Activatable IL-12 proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 6: Determination of Antigen Affinity by Flow Cytometry

The activatable IL-12 proteins are tested for their binding affinities to human CD20$^+$ cells and cynomolgus CD20$^+$ cells.

CD20$^+$ cells are incubated with 100 μL of serial dilutions of the activatable IL-12 proteins and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IL-12 proteins. The cells were then washed again and resuspended in 0.2 mL of FACS buffer containing 2 μg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla Calif. USA).

CD20 binding and crossreactivity are assessed on the human CD20$^+$ tumor cell lines. The $K_D$ ratio of crossreactivity is calculated using the $K_D$ values determined on the CHO cell lines expressing either recombinant human or recombinant cynomolgus antigens.

Example 7: Cytotoxicity Assay

The activatable IL-12 protein is evaluated in vitro on its mediation of immune response to CD20$^+$ target cells.

Fluorescence labeled CD20$^+$ REC-1 cells (a Mantle cell lymphoma cell line, ATCC CRL-3004) are incubated with isolated PBMC of random donors or CB15 T-cells (standardized T-cell line) as effector cells in the presence of the activatable IL-12 protein and at least one protease. After incubation for 4 h at 37° C. in a humidified incubator, the release of the fluorescent dye from the target cells into the supernatant is determined in a spectrofluorimeter. Target cells incubated without the activatable IL-12 protein and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/number of living targets$_{(spontaneous)}$)]×100%. Sigmoidal dose response curves and EC$_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 8: Pharmacokinetics of Activatable IL-12 Proteins

The activatable IL-12 protein is evaluated for half-time elimination in animal studies.

The activatable IL-12 protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a IL-12 construct with serum half-life extension elements and a IL-12 construct with CD20 and serum half-life extension elements respectively, and both comparable in size to the activatable IL-12 protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and α and β are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications*, 5th edition, American Pharmaceutical Assoc., Washington, D.C.

It is expected that the activatable IL-12 protein has improved pharmacokinetic parameters such as an increase in elimination half-time as compared to proteins lacking a serum half-life extension element.

Example 9: Xenograft Tumor Model

The activatable IL-12 protein is evaluated in a xenograft model. Female immune-deficient NOD/scid mice are sublethally irradiated (2 Gy) and subcutaneously inoculated with 4×10⁶ Ramos RA1 cells into the right dorsal flank. When tumors reach 100 to 200 mm³, animals are allocated into 3 treatment groups. Groups 2 and 3 (8 animals each) are intraperitoneally injected with 1.5×10⁷ activated human T-cells. Three days later, animals from Group 3 are subsequently treated with a total of 9 intravenous doses of 50 µg activatable IL-12 protein (qd×9d). Groups 1 and 2 are only treated with vehicle. Body weight and tumor volume are determined for 30 days.

It is expected that animals treated with the activatable IL-12 protein has a statistically significant delay in tumor growth in comparison to the respective vehicle-treated control group.

Example 10: MC38 Experiments

The MC38 cell line, a rapidly growing colon adenocarcinoma cell line that expresses MMP9 in vitro, was used. Using this tumor model, the ability of fusion proteins to affect tumor growth was examined.

Example 10a: MC38 IL-12 Fusion Protein Treatment

Agents and Treatment:

| Gr. | N | Agent | Formulation dose | Route | Schedule |
|---|---|---|---|---|---|
| 1# | 12 | Vehicle | — | ip | biwk x 3 |
| 2 | 8 | ACP11 | 17.5 µg/animal | ip | biwk x 3 |
| 3 | 8 | ACP11 | 175 µg/animal | ip | biwk x 3 |
| 4 | 8 | ACP11 | 525 µg/animal | ip | biwk x 3 |
| 13 | 8 | ACP04 | 2 µg/animal | ip | bid x 5 then 2-day pause then bid x 5 then 2-day pause |
| 14 | 8 | ACP04 | 10 µg/animal | ip | bid x 5 then 2-day pause then bid x 5 then 2-day pause |

Control Group

Procedures:

Mice were anaesthetized with isoflurane for implant of cells to reduce the ulcerations. CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and treatment was started. Body weights were taken at initiation and then biweekly to the end. Caliper measurements were taken biweekly to the end. Any adverse reactions were to be reported immediately. Any individual animal with a single observation of > than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized.

Results are shown in FIGS. 13 and 14a-14f. The results show efficacy in tumor growth inhibition (TGI) with IL-12 fusion protein treatments in a dose-dependent manner compared to the IL-12 control ACP04.

Example 11: Conditionally Active Fusion Proteins that Contain a Blocking Moiety that is a Serum Albumin Binding Domain This example describes the production and activity of fusion proteins, preferably cytokines, that have inducible activity, i.e., they are inactive until induced, typically by separation of a blocking moiety from the active moiety upon cleavage of a linker between the blocking moiety and the active moiety. The fusion proteins contain a single antibody variable domain (a dAb) that binds serum albumin via the CDR loops, and binds to an active moiety (here an anti-CD3 scFV) via one or more non-CDR loops (e.g., the C loop). The serum albumin-binding blocking moiety is operably linked to the active moiety through a protease-cleavable linker, and active moiety is operably linked to a targeting domain (here an anti-epidermal growth factor receptor (EGFR) dAb or anti-prostate-specific membrane antigen (PSMA) dAb) through a linker that is not protease-cleavable. These fusion proteins can be administered as inactive proteins that become activated upon cleavage of the protease-cleavable linker and subsequent release of the inhibitory albumin-binding domain. The anti-CD3 scFV in the fusion proteins is a surrogate for a desired cytokine in the fusion proteins described in this disclosure. Similar fusion proteins that contain a desired cytokine (e.g., IL-2, IL-12, an Interferon) or functional fragment or mutein thereof, a targeting domain and an albumin-binding dAb that also binds and inhibits the cytokine or functional fragment or mutein thereof can be prepared using the methods described and exemplified herein. Anti-serum albumin dAb that bind and inhibit the activity of a desired cytokine or functional fragment or mutein thereof can provide both steric masking of the cytokine (through the cytokines proximity to bound serum albumin) and specific masking of the cytokine (through binding to cytokine via the non-CDR loop (e.g., the C loop)). Anti-serum albumin dAb that bind and inhibit the activity of a desired cytokine or functional fragment or mutein thereof can be obtained using suitable methods, such as by introducing amino acid sequence diversity into the non-CDR loops (e.g., C loop) of an anti-serum albumin binding dAb and screening for binding to the desired cytokine. Any suitable methods can be used for the selection, such as phage display. For example, an exemplary anti-serum albumin dab that can be used has the following sequence, and the amino acid sequence in the C loop (Bold Underlined) can be diversified (e.g., randomized) and resulting dAbs screened for binding to serum albumin via CDR interaction and to cytokine via non-CDR loop interaction. If desired, the amino acid sequence of a known cytokine binding peptide can be grafted into the C loop.

(SEQ ID NO: 92)
EVQLVESGGGLVQPGNSLRLSCAASGFTFSKFGMSWVRQGGGGGLDGN

EEPGGLEWVSSISGSGRDTLYADSVKGRFTISRDNAKTTLYLQMNSLR

PEDTAVYYCTIGGSLSVSSQGTLVTVSS

A. Protease Activation of ProTriTAC Leads to Significantly Enhanced Activity In Vitro Purified ProTriTAC (prodrug), non-cleavable ProTriTAC [prodrug (non-cleavable)], and recombinant active drug fragment mimicking the protease-activated ProTriTAC (active drug) were tested for binding to recombinant human CD3 in an ELISA assay, binding to purified human primary T cells in a flow cytometry assay, and functional potency in a T cell-dependent cellular cytotoxicity assay.

For ELISA, soluble ProTriTAC proteins at the indication concentrations were incubated with immobilized recombinant human CD3e (R&D Systems) for 1 h at room temperature in PBS supplemented with 15 mg/ml human serum albumin. Plates were blocked using SuperBlock (Thermo Fisher), washed using PBS with 0.05% Tween-20, and detected using a non-competitive anti-CD3 idiotype monoclonal antibody 11D3 followed by peroxidase-labeled secondary antibody and TMB-ELISA substrate solution (Thermo Fisher).

For flow cytometry, soluble ProTriTAC proteins at the indicated concentrations were incubated with purified human primary T cells for 1 h at 4° C. in the presence of PBS with 2% fetal bovine serum and 15 mg/ml human serum albumin. Plates were washed with PBS with 2% fetal bovine serum, detected using AlexaFluor 647-labeled non-competitive anti-CD3 idiotype monoclonal antibody 11D3, and data was analyzed using FlowJo 10 (FlowJo, LLC).

For functional potency in a T cell-dependent cellular cytotoxicity assays, soluble ProTriTAC proteins at the indicated concentrations were incubated with purified resting human T cells (effector cell) and HCT116 cancer cell (target cell) at 10:1 effector:target cell ratio for 48 h at 37° C. The HCT116 target cell line has been stably transfected with a luciferase reporter gene to allow specific T cell-mediated cell killing measurement by ONE-Glo (Promega).

B. ProTriTAC Exhibits Potent, Protease-Dependent, Anti-Tumor Activity in a Rodent Tumor Xenograft Model ProTriTAC was evaluated for their anti-tumor activity in vivo in an HCT116 subcutaneous xenograft tumor admixed with expanded human T cells in immunocompromised NCG mice. Specifically, 5×106 HCT116 cells were admixed with 2.5×106 expanded T cells per mouse on day 0. Dosing of ProTriTACs were performed starting on the following day with a q.d.×10 schedule via intraperitoneal injection. Tumor volume measurements were determined using caliper measurements and calculated using the formula V=(length× width×width)/2 at the indicated times.

C. Expression, Purification and Stability of Exemplary ProTriTAC Trispecific Molecules Protein Production Sequences encoding inducible fusion protein molecules were cloned into mammalian expression vector pcDNA 3.4 (Invitrogen) preceded by a leader sequence and followed by a 6×Histidine Tag (SEQ ID NO: 91). Expi293F cells (Life Technologies A14527) were maintained in suspension in Optimum Growth Flasks (Thomson) between 0.2 to 8×1e6 cells/ml in Expi 293 media. Purified plasmid DNA was transfected into Expi293 cells in accordance with Expi293 Expression System Kit (Life Technologies, A14635) protocols, and maintained for 4-6 days post transfection. Alternatively sequences encoding the fusion protein molecules were cloned into mammalian expression vector pDEF38 (CMC ICOS) transfected into CHO-DG44 dhfr− cells, stable pools generated, and cultured in production media for up to 12 days prior to purification. The amount of exemplary fusion proteins in conditioned media was quantified using an Octet RED 96 instrument with Protein A tips (ForteBio/Pall) using a control fusion protein for a standard curve. Conditioned media from either host cell was filtered and partially purified by affinity and desalting chromatography. Fusion proteins were subsequently polished by ion exchange and upon fraction pooling formulated in a neutral buffer containing excipients. Final purity was assessed by SDS-PAGE and analytical SEC using an Acquity BEH SEC 200 1.7 u 4.6×150 mm column (Waters Corporation) resolved in an aqueous/organic mobile phase with excipients at neutral pH on a 1290 LC system and peaks integrated with Chemstation CDS software (Agilent). Fusion proteins purified from CHO host cells are shown in the SDS-PAGE depicted below.

Stability Assessment

Purified fusion proteins in two formulations were sub-aliquoted into sterile tubes and stressed by five freeze-thaw cycles each comprising greater than 1 hour at −80° C. and room temperature or by incubation at 37° C. for 1 week. Stressed samples were evaluated for concentration and turbidity by UV spectrometry using UV transparent 96 well plates (Corning 3635) with a SpectraMax M2 and SoftMax-Pro Software (Molecular Devices), SDS-PAGE, and analytical SEC and compared to the same analysis of control non-stressed samples. An overlay of chromatograms from analytical SEC of control and stressed samples for a single exemplary ProTriTAC molecule purified from 293 host cells is depicted below.

The results show that ProTriTACs were produced in comparable yields to regular TriTACs from CHO stable pools; and that the proteins were stable after repeated freeze-thaws and 37° C. for 1 week.

D. Demonstration of Functional Masking and Stability of ProTriTAC In Vivo in a Three-Week Cynomolgus Monkey Pharmacokinetic Study Single dose of PSMA-targeting ProTriTAC (SEQ ID NO: 74), non-cleavable ProTriTAC (SEQ ID NO: 75), non-masked/non-cleavable TriTAC (SEQ ID NO: 78), and active drug mimicking protease-activated ProTriTAC (SEQ ID NO: 76) was dosed into cynomolgus monkeys at 0.1 mg/kg via intravenous injection. Plasma samples were collected at the indicated time points. ProTriTAC concentrations were determined using ligand binding assays with biotinylated recombinant human PSMA (R&D systems) and sulfo-tagged anti-CD3 idiotype antibody cloned 11D3 in a MSD assay (Meso Scale Diagnostic, LLC). Pharmacokinetic parameters were estimated using Phoenix WinNonlin pharmacokinetic software using a non-compartmental approach consistent with the intravenous bolus route of administration.

To calculate the rate of in vivo prodrug conversion, the concentration of active drug in circulation was estimated by solving the following system of differential equations where P is the concentration of prodrug, A is the concentration of active drug, $k_a$ is the rate of prodrug activation in circulation, $k_{c,P}$ is the clearance rate of the prodrug, and $k_{c,A}$ is the clearance rate of the active drug.

$$\frac{dP}{dt} = -k_{c,P}P$$

$$\frac{dA}{dt} = k_a P - k_{c,A} A$$

The clearance rates of the prodrug, active drug, and a non-cleavable prodrug control ($k_{c,NCLV}$) were determined empirically in cynomolgus monkeys. To estimate the rate of prodrug activation in circulation, we assumed that the difference between the clearance rate of cleavable prodrug and non-cleavable prodrug arose solely from non-specific activation in circulation. Therefore, the rate of prodrug conversion to active drug in circulation was estimated by subtracting the clearance rate of the cleavable prodrug from the non-cleavable prodrug.

$$k_a = k_{c,NCLV} - k_{c,P}$$

The initial concentration of prodrug in circulation was determined empirically and the initial concentration of active drug was assumed to be zero.

Results and Discussion

The results of this Example 11 show that fusion proteins that contain a polypeptide with desired therapeutic activity, such as a cytokine or functional fragment or mutein thereof or anti-CD3 scFV, can be prepared in which the therapeutic activity is masked by a masking domain that binds to both serum albumin and to the active polypeptide. The masking domain is operably linked to the active domain through a protease-cleavable linker. The results show that this type of fusion protein can be administered as an inactive protein that becomes activated upon protease cleavage at the desired location of therapeutic activity, such as, at a tumor.

Amino acid sequences of fusion proteins used in Example 11 are given SEQ ID NOs: 71-78.

Sample fusion protein constructs are detailed in Table 3. In Table 3, "L" is an abbreviation of "linker", "cleav. link." and "XL" are abbreviations of different cleavable linkers, and HSA indicates human serum albumin (HSA).

TABLE 3

CONSTRUCT PERMUTATION TABLE

| Construct Name | Construct Description |
| --- | --- |
| ACP63 | anti-FN CGS-2 scFv (Vh/Vl)-6xHis |
| ACP04 | human p40-murine p35-6xHis |
| ACP05 | human p40-human p35-6xHis |
| ACP34 | mouse p35-(cleav. link.)-mouse p40-6xHis |
| ACP35 | mouse p35-GS-(cleav. link.)-GS-mouse p40-6xHis |
| ACP36 | (anti-HSA)-(cleav. link.)-mouse p40-mouse p35-(cleav. link.)-(anti-HSA)-6xHis |
| ACP37 | (anti-EpCAM)-(anti-HSA)-(cleav. link.)-mouse p40-mouse p35-(cleav. link.)-(anti-HSA)-6xHis |
| ACP79 | (anti-EpCAM)-Linker-(anti-HSA)-(cleav. link.)-mIL12-(cleav. link.)-(Anti-HSA)-6xHis |
| ACP80 | (anti-HSA)-(cleav. link.)-mIL12-(cleav. link.)-(anti-HSA)-Linker-(anti-EpCAM)-6xHis |
| ACP06 | Blocker12-Linker-(cleav. link.)-human p40-Linker-mouse p35-(cleav. link.)-(anti-HSA)-6xHis |
| ACP07 | Blocker12-Linker-(cleav. link)-human p40-Linker-mouse p35-(cleav. link.)-(anti-HSA)-Linker-(anti-FOLR1)-6xHis |
| ACP08 | (anti-FOLR1)-Linker-Blocker12-Linker-(cleav. link.)-human p40-Linker-mouse p35-(cleav. link.)-(anti-HSA)-6xHis |
| ACP09 | (anti-HSA)-Linker-Blocker12-Linker-(cleav. link.)-human p40-Linker-mouse p35-6xHis |
| ACP10 | (anti-HSA)-(cleav. link.)-human p40-L-mouse p35-(cleav. link.)-Linker-Blocker12-6xHis |
| ACP11 | hp40-Linker-mp35-(cleav. link.)-Linker-Blocker12-Linker-(anti-HSA)-6xHis |
| ACP91 | human_p40-Linker-mouse_p35-Linker-Linker-Blocker-Linker-(anti-HSA)_(non-cleavable control) |
| ACP136 | human p40-L-mouse p35-XL-Blocker |
| ACP138 | human_p40-L-mouse_p35-XL-Blocker-L-HSA-L-FOLR1 |
| ACP139 | FOLR1-L-human_p40-L-mouse_p35-XL-Blocker-L-HSA |
| ACP140 | FOLR1-(cleav. link.)-human_p40-L-mouse_p35-XL-Blocker-L-HSA |
| ACP117 | anti-FN CGS-2 scFv (Vh/Vl)-6xHis |

TABLE 4

SEQUENCE TABLE

| SEQ ID NO. | Name | Sequence |
| --- | --- | --- |
| 1 | Human serum albumin | MKWVTFISLL FLFSSAYSRG VFRRDAHKSE VAHRFKDLGE ENFKALVLIA FAQYLQQCPF EDHVKLVNEV TEFAKTCVAD ESAENCDKSL HTLFGDKLCT VATLRETYGE MADCCAKQEP ERNECFLQHK DDNPNLPRLV RPEVDVMCTA FHDNEETFLK KYLYEIARRH PYFYAPELLF FAKRYKAAFT ECCQAADKAA CLLPKLDELR DEGKASSAKQ GLKCASLQKF GERAFKAWAV ARLSQRFPKA EFAEVSKLVT DLTKVHTECC HGDLLECADD RADLAKYICE NQDSISSKLK ECCEKPLLEK SHCIAEVEND EMPADLPSLA ADFVGSKDVC KNYAEAKDVF LGMFLYEYAR RHPDYSVVLL LRLAKTYETT LEKCCAAADP HECYAKVFDE FKPLVEEPQN LIKQNCELFE QLGEYKFQNA LLVRYTKKVP QVSTPTLVEV SRNLGKVGSK CCKHPEAKRM PCAEDCLSVF LNQLCVLHEK TPVSDRVTKC CTESLVNGRPCFSALEVDETYVPKEFNAETFTFHADICTLSEKERQIKK QTALV ELVKHK PKATKEQLKAVMDDFAAFVEKCCKADDKET CFAEEGKKLVAASQAALGL |
| 44 | ACP04 (human p40/murine p35 IL-12 fusion protein) | iwelkkdvyvveldwypdapgemvvltcdtpeedgitwtldqssevlgsgktltiqvkefgdagqytchk ggevlshslllhkkedgiwstdilkdqkepknktflrceaknysgrftcwwlttistdltfsvkssrgssdpqg vtcgaatlsaervrgdnkeyeysvecqedsacpaaeeslpievmvdavhklkyenytssffirdiikpdppk nlqlkplknsrqvevsweypdtwstphsyfsltfcvqvqgkskrekkdrvftdktsatvicrknasisvraqd ryyssswsewasvpcsgggsggggsggggsrvipvsgparclsqsrnllkttddmvktareklkhyscta edidheditrdqtstlktclplelhknesclatretssttrgsclppqktslmmtlclgsiyedlkmyqtefqai naalqnhnhqqiildkgmlvaidelmqslnhngetlrqkppvgeadpyrvkmklcillhafstrvvtinrvmg ylssaHHHHHH |

TABLE 4-continued

SEQUENCE TABLE

| SEQ ID NO. | Name | Sequence |
|---|---|---|
| 45 | ACP05 (human p40/murine p35 IL-12 fusion protein) | iwelkkdvyvveldwypdapgemvvltcdtpeedgitwtldqssevlgsgktltiqvkefgdagqytchk ggevlshllllhkkedgiwstdilkdqkepknktflrceaknysgrftcwwlttistdltfsvkssrgssdpqg vtcgaatlsaervrgdnkeyeysvecqedsacpaaeeslpievmvdavhklkyenytssffirdiikpdppk nlqlkplknsrqvevsweypdtwstphsyfsltfcvqvqgkskrekkdrvftdktsatvicrknasisvraqd rryyssswsewasvpcsgggsgggsgggsgggsrnlpvatpdpgmfpclhhsqnllravsnmlqkarqtlef ypctseeidheditkdktstveaclpleltknesclnsretsfitngsclasrktsfmmalclssiyedlkmyqve fktmnakllmdpkrqifldqnmlavidelmqalnfnsetvpqksleepdfyktkiklcillhafriravtidr vmsylnasHHHHHH |
| 46 | ACP06 (human p40/murine p35 IL-12 fusion protein) | QSVLTQPPSVSGAPGQRVTISCSGSRSNIGSNTVKWYQQLPGTAPKLLI YYNDQRPSGVPDRFSGSKSGTSASLAITGLQAEDEADYYCQSYDRYTH PALLFGTGTKVTVLggggsggggsggggsQVQLVESGGGVVQPGRSLRLSCA ASGFTFSSYGMHWVRQAPGKGLEWVAFIRYDGSNKYYADSVKGRFTI SRDNSKNTLYLQMNSLRAEDTAVYYCKTHGSHDNWGQGTMVTVSSg gggsgggsggggsggggsggggsggggsggggsSGGPGPAGMKGLPGSiwelkkdvyvveldwy pdapgemvvltcdtpeedgitwtldqssevlgsgktltiqvkefgdagqytchkggevlshsllllhkkedgi wstdilkdqkepknktflrceaknysgrftcwwlttistdltfsvkssrgssdpqgvtcgaatlsaervrgdnke yeysvecqedsacpaaeeslpievmvdavhklkyenytssffirdiikpdppknlqlkplknsrqvevswe ypdtwstphsyfsltfcvqvqgkskrekkdrvftdktsatvicrknasisvraqdryyssswsewasvpcsg gggsggggsggggsrvipvsgparclsqsrnllkttddmvktareklkhysctaedidheditrdqtstlktcl plelhknesclatretssttrgsclppqktslmmtlclgsiyedlkmyqtefqainaalqnhnhqqiildkgml vaidelmqslnhngetlrqkppvgeadpyrvkmklcillhafstrvvtinrvmgylssaSGGPGPAG MKGLPGSEVQLVESGGGLVQPGNSLRLSCAASGFTFSKFGMSWVRQA PGKGLEWVSSISGSGRDTLYAESVKGRFTISRDNAKTTLYLQMNSLRP EDTAVYYCTIGGSLSVSSQGTLVTVSSHHHHHHEPEA |
| 47 | ACP07 (human p40/murine p35 IL-12 fusion protein) | QSVLTQPPSVSGAPGQRVTISCSGSRSNIGSNTVKWYQQLPGTAPKLLI YYNDQRPSGVPDRFSGSKSGTSASLAITGLQAEDEADYYCQSYDRYTH PALLFGTGTKVTVLggggsggggsggggsQVQLVESGGGVVQPGRSLRLSCA ASGFTFSSYGMHWVRQAPGKGLEWVAFIRYDGSNKYYADSVKGRFTI SRDNSKNTLYLQMNSLRAEDTAVYYCKTHGSHDNWGQGTMVTVSSg gggsgggsggggsggggsggggsggggsggggsSGGPGPAGMKGLPGSiwelkkdvyvveldwy pdapgemvvltcdtpeedgitwtldqssevlgsgktltiqvkefgdagqytchkggevlshsllllhkkedgi wstdilkdqkepknktflrceaknysgrftcwwlttistdltfsvkssrgssdpqgvtcgaatlsaervrgdnke yeysvecqedsacpaaeeslpievmvdavhklkyenytssffirdiikpdppknlqlkplknsrqvevswe ypdtwstphsyfsltfcvqvqgkskrekkdrvftdktsatvicrknasisvraqdryyssswsewasvpcsg gggsggggsggggsrvipvsgparclsqsrnllkttddmvktareklkhysctaedidheditrdqtstlktcl plelhknesclatretssttrgsclppqktslmmtlclgsiyedlkmyqtefqainaalqnhnhqqiildkgml vaidelmqslnhngetlrqkppvgeadpyrvkmklcillhafstrvvtinrvmgylssaSGGPGPAG MKGLPGSEVQLVESGGGLVQPGNSLRLSCAASGFTFSKFGMSWVRQA PGKGLEWVSSISGSGRDTLYAESVKGRFTISRDNAKTTLYLQMNSLRP EDTAVYYCTIGGSLSVSSQGTLVTVSSggggsggggsggggsggggsQVQLQESGGG LAQAGGSLSLSCAASGFTVSNSVMAWYRQTPGKQREFVAIINSVGSTN YADSVKGRFTISRDNAKNTVYLQMNNLKPEDTAVYVCNRNFDRIYW GQGTQVTVSSHHHHHHEPEA |
| 48 | ACP08 (human p40/murine p35 IL-12 fusion protein) | QVQLQESGGGLAQAGGSLSLSCAASGFTVSNSVMAWYRQTPGKQREF VAIINSVGSTNYADSVKGRFTISRDNAKNTVYLQMNNLKPEDTAVYVC NRNFDRIYWGQGTQVTVSSggggsggggsggggsggggsQSVLTQPPSVSGAPGQRV TISCSGSRSNIGSNTVKWYQQLPGTAPKLLIYYNDQRPSGVPDRFSGSK SGTSASLAITGLQAEDEADYYCQSYDRYTHPALLFGTGTKVTVLggggsg gggsggggsQVQLVESGGGVVQPGRSLRLSCAASGFTFSSYGMHWVRQA PGKGLEWVAFIRYDGSNKYYADSVKGRFTISRDNSKNTLYLQMNSLR AEDTAVYYCKTHGSHDNWGQGTMVTVSSggggsggggsggggsggggsggggs ggggsSGGPGPAGMKGLPGSiwelkkdvyvveldwypdapgemvvltcdtpeedgitwtld qssevlgsgktltiqvkefgdagqytchkggevlshsllllhkkedgiwstdilkdqkepknktfirceaknys grftcwwlttistdltfsvkssrgssdpqgvtcgaatlsaervrgdnkeyeysvecqedsacpaaeeslpievm vdavhklkyenytssffirdiikpdppknlqlkplknsrqvevsweypdtwstphsyfsltfcvqvqgkskr ekkdrvftdktsatvicrknasisvraqdryyssswsewasvpcsgggsggggsggggsrvipvsgparcl sqsrnllkttddmvktareklkhysctaedidheditrdqtstlktclplelhknesclatretssttrgsclp pqktslmmtlclgsiyedlkmyqtefqainaalqnhnhqqiildkgmlvaidelmqslnhngetlrqkppvgea dpyrvkmklcillhafstrwtinrvmgylssaSGGPGPAGMKGLPGSEVQLVESGGGLV QPGNSLRLSCAASGFTFSKFGMSWVRQAPGKGLEWVSSISGSGRDTLY AESVKGRFTISRDNAKTTLYLQMNSLRPEDTAVYYCTIGGSLSVSSQGT LVTVSSHHHHHHEPEA |
| 49 | ACP09 (human p40/murine p35 IL-12 fusion protein) | EVQLVESGGGLVQPGNSLRLSCAASGFTFSKFGMSWVRQAPGKGLEW VSSISGSGRDTLYAESVKGRFTISRDNAKTTLYLQMNSLRPEDTAVYY CTIGGSLSVSSQGTLVTVSSggggsggggsggggsggggsQSVLTQPPSVSGAPGQRV TISCSGSRSNIGSNTVKWYQQLPGTAPKLLIYYNDQRPSGVPDRFSGSK SGTSASLAITGLQAEDEADYYCQSYDRYTHPALLFGTGTKVTVLggggsg gggsggggsQVQLVESGGGVVQPGRSLRLSCAASGFTFSSYGMHWVRQA PGKGLEWVAFIRYDGSNKYYADSVKGRFTISRDNSKNTLYLQMNSLR AEDTAVYYCKTHGSHDNWGQGTMVTVSSggggsggggsggggsggggsggggs |

TABLE 4-continued

SEQUENCE TABLE

| SEQ ID NO. | Name | Sequence |
|---|---|---|
| | | ggggsSGGPGPAGMKGLPGSiwelkkdvyvveldwypdapgemvvltcdtpeedgitwtld qssevlgsgktltiqvkefgdagqytchkggevlshsllllhkkedgiwstdilkdqkepknktfirceakenys grftcwwltttistdltfsvkssrgssdpqgyvtcgaatlsaervrgdnkeyeysvecqedsacpaaeeslpievm vdavhklkyenytssffirdiikpdppknlqlkplknsrqvevsweypdtwstphsyfsltfcvqvqgkskr ekkdrvftdktsatvicrknasisvraqdryyssswsewasvpcsggggsggggsggggsrvipvsgparcl sqsrnllkttddmvktareklkhysctaedidheditrdqtstlktclplelhknesclatretsstrgsclp pqktslmmtlclgsiyedlkmyqtefqainaaalqnhnhqqiildkgmlvaidelmqslnhngetlrqkppvgea dpyrvkmklcillhafstrvvtinrvmgylssaHHHHHHEPEA |
| 50 | ACP10 (human p40/murine p35 IL-12 fusion protein) | EVQLVESGGGLVQPGNSLRLSCAASGFTFSKFGMSWVRQAPGKGLEW VSSISGSGRDTLYAESVKGRFTISRDNAKTTLYLQMNSLRPEDTAVYY CTIGGSLSVSSQGTLVTVSSSGGPGPAGMKGLPGSiwelkkdvyvveldwypda pgemvvltcdtpeedgitwtldqssevlgsgktltiqvkefgdagqytchkggevlshsllllhkkedgiwst dilkdqkepknktflrceaknysgrftcwwlttistdltfsvkssrgssdpqgytcgaatlsaervrgdnkeyey svecqedsacpaaeeslpievmvdavhklkyenytssffirdiikpdppknlqlkplknsrqvevsweypd twstphsyfsltfcvqvqgkskrekkdrvftdktsatvicrknasisvraqdryyssswsewasvpcsgggg sggggsggggsrvipvsgparclsqsrnllkttddmvktareklkhysctaedidheditrdqtstlktclplel hknesclatretsstrgsclppqktslmmtlclgsiyedlkmyqtefqainaalqnhnhqqiildkgmlvaid elmqslnhngetlrqkppvgeadpyrvkmklcillhafstrwtinrvmgylssaSGGPGPAGMKG LPGSggggsggggsggggsggggsggggsggggsQSVLTQPPSVSGAPGQRVTISCS GSRSNIGSNTVKWYQQLPGTAPKLLIYYNDQRPSGVPDRFSGSKSGTS ASLAITGLQAEDEADYYCQSYDRYTHPALLFGTGTKVTVLggggsggggsg gggsQVQLVESGGGVVQPGRSLRLSCAASGFTFSSYGMHWVRQAPGKG LEWVAFIRYDGSNKYYADSVKGRFTISRDNSKNTLYLQMNSLRAEDT AVYYCKTHGSHDNWGQGTMVTVSSHHHHHHEPEA |
| 51 | ACP11 (human p40/murine p35 IL-12 fusion protein) | iwelkkdvyvveldwypdapgemvvltcdtpeedgitwtldqssevlgsgktltiqvkefgdagqytchk ggevlshsllllhkkedgiwstdilkdqkepknktfirceaknysgrftcwwlttistdltfsvkssrgssdpqg vtcgaatlsaervrgdnkeyeysvecqedsacpaaeeslpievmvdavhklkyenytssffirdiikpdppk nlqlkplknsrqvevsweypdtwstphsyfsltfcvqvqgkskrekkdrvftdktsatvicrknasisvraqd ryyssswsewasvpcsggggsggggsggggsrvipvsgparclsqsrnllkttddmvktareklkhyscta edidheditrdqtstlktclplelhknesclatretsstrgsclppqktslmmtlclgsiyedlkmyqtefqai naalqnhnhqqiildkgmlvaidelmqslnhngetlrqkppvgeadpyrvkmklcillhafstrvvtinrvmg ylssaSGGPGPAGMKGLPGSggggsggggsggggsggggsggggsggggsQSVLTQPP SVSGAPGQRVTISCSGSRSNIGSNTVKWYQQLPGTAPKLLIYYNDQRPS GVPDRFSGSKSGTSASLAITGLQAEDEADYYCQSYDRYTHPALLFGTG TKVTVLggggsggggsggggsQVQLVESGGGVVQPGRSLRLSCAASGFTFSS YGMHWVRQAPGKGLEWVAFIRYDGSNKYYADSVKGRFTISRDNSKN TLYLQMNSLRAEDTAVYYCKTHGSHDNWGQGTMVTVSSggggsggggsg gggsEVQLVESGGGLVQPGNSLRLSCAASGFTFSKFGMSWVRQAPGKG LEWVSSISGSGRDTLYAESVKGRFTISRDNAKTTLYLQMNSLRPEDTA VYYCTIGGSLSVSSQGTLVTVSSHHHHHHEPEA |
| 52 | IL-12p40 human (Uniprot Accession No. P29460) | 10 20 30 40 50<br>MCHQQLVISW FSLVFLASPL VAIWELKKDV YVVELDWYPD APGEMVVLTC<br>60 70 80 90 100<br>DTPEEDGITW TLDQSSEVLG SGKTLTIQVW EFGDAGQYTC HKGGEVLSHS<br>110 120 130 140 150<br>LLLLHKKEDG IWSTDILKDQ KEPKNKTFLR CEAKNYSGRF TCWWLTTIST<br>160 170 180 190 200<br>DLTFSVKSSR GSSDPQGCTC GAATLSAERV RGDNKEYEYS VECQEDSACP<br>210 220 230 240 250<br>AAEESLPIEV MVDAVHKLKY ENYTSSFFIR DIIKPDPPKN LQLKPLKNSR<br>260 270 280 290 300<br>QVEVSWEYPD TWSTPHSYFS LTFCVQVQGK SKREKKDRVF TDKTSATVIC<br>310 320<br>RKNASISVRA QDRYYSsSWS EWASVPCS |
| 53 | IL-12p35 mouse (Uniprot Accession No. P43431) | 10 20 30 40 50<br>MCQSRYLLFL ATLALLNHLS LARVIPVSGP ARCLSQSRNL LKTTDDMVKT<br>60 70 80 90 100<br>AREKLKHYSC TAEDIDHEDI TRDQTSTLKT CLPLELHKNE SCLATRETSS<br>110 120 130 140 150<br>TTRGSCLPPQ KTSLMMTLCL GSIYEDLKMY QTEFQAINAA LQNHNHQQII<br>160 170 180 190 200<br>LDKGMLVAID ELMQSLNHNG ETLRQKPPVG EADPYRVKMK LCILLHAFST<br>210<br>TVVTINRVMG YLSSA |
| 54 | IL12Rb-2 | 10 20 30 40 50<br>MAHTFRGCSL AFMFIITHLL IKAKIDACKR GDVTVKPSHV ILLGSTVNLT<br>60 70 80 90 100<br>CSLKPRQGCF HYSRRNKLIL YKFDRRINFH HGHSLNSQVT GLPLGTTLFV |

TABLE 4-continued

SEQUENCE TABLE

| SEQ ID NO. | Name | Sequence |
|---|---|---|

|   |   | 110 120 130 140 150 |
|---|---|---|
|   |   | CKLACINSDE IQICGAEIEV GVAPEQPQNL SCIQKGEQGI VACTWERGRD |
|   |   | 160 170 180 190 200 |
|   |   | THLYTEYTLQ LSGPKNLTWQ KQCKDIYCDY LPEGINLTPE SPESNETAKV |
|   |   | 210 220 230 240 250 |
|   |   | TAVNSIGSSS SLPSTFTFLD IVRPLPPWDI RIKFQKASVS RCTLYWRDEG |
|   |   | 260 270 280 290 300 |
|   |   | LVLLNRLRYR PSNSRLWNMV NVTKAKGRHD LLDLKPETEY EFQISSKLHL |
|   |   | 310 320 330 340 350 |
|   |   | YKGSNSDWSE SLRAQTREEE PTGMLDVWYM KRHIDYSRQQ ISLFWKNLSV |
|   |   | 360 370 380 390 400 |
|   |   | SEARGKILHY QVTLQELIGG KAMTQNITGH ISWTTVIPRI GNWAVAVSAA |
|   |   | 410 420 430 440 450 |
|   |   | NSKGSSLPTR INIMNLCEAG LLAPRQYSAN SEGMDNILVI WQPRRKDPSA |
|   |   | 460 470 480 490 500 |
|   |   | VQEYVVEWRE LHPGGDTQVP LNWLRSRPYN VSALISENIK SYICYEIRVY |
|   |   | 510 520 530 540 550 |
|   |   | ALSGDQGGCS SILGNSKHKA PLSGPHINAI TEEKGSILIS WNSIPVQEQM |
|   |   | 560 570 580 590 600 |
|   |   | GCLLHYRIYW KERDSNSQPQ LCEIPYRVSQ NSHPINSLQP RVTYVLWMTA |
|   |   | 610 620 630 640 650 |
|   |   | LTAAGESSHG NEREFCLQGK ANWMAFVAPS ICIAIIMVGI FSTHYFQQKV |
|   |   | 660 670 680 690 700 |
|   |   | FVLLAALRPQ WCSREIPDPA NSTCAKKYPI AEEKTQLPLD RLLIDWPTPE |
|   |   | 710 720 730 740 750 |
|   |   | DPEPLVISEV LHQVTPVERH PPCSNWPQRE KGIQGHQASE KDMMHSASSP |
|   |   | 760 770 780 790 800 |
|   |   | PPPRALQAES RQLVDLYKVL ESRGSDPKPE NPACPWTVLP AGDLPTHDGY |
|   |   | 810 820 830 840 850 |
|   |   | LPSNIDDLPS HEAPLADSLE ELEPQHISLS VPRSSSLHPL TFSCGDKLTL |
|   |   | 860 |
|   |   | DQLKMRCDSL ML |
| 55 | IL12Rb-1 | 10 20 30 40 50 |
|   |   | MEPLVTWVVP LLFLFLLSRQ GAACRTSECC FQDPPYPDAD SGSASGPRDL |
|   |   | 60 70 80 90 100 |
|   |   | RCYRISSDRY ECSWQYEGPT AGVSHFLRCC LSSGRCCYFA AGSATRLQFS |
|   |   | 110 120 130 140 150 |
|   |   | DQAGVSVLYT VTLWVESWAR NQTEKSPEVT LQLYNSVKYE PPLGDIKVSK |
|   |   | 160 170 180 190 200 |
|   |   | LAGQLRMEWE TPDNQVGAEV QFRHRTPSSP WKLGDCGPQD DDTESCLCPL |
|   |   | 210 220 230 240 250 |
|   |   | EMNVAQEFQL RRRQLGSQGS SNSKWSSPVC VPPENPPQPQ VRFSVEQLGQ |
|   |   | 260 270 280 290 300 |
|   |   | DGRRRLTLKE QPTQLELPEG CQGLAPGTEV TYRLQLHMLS CPCKAKATRI |
|   |   | 310 320 330 340 350 |
|   |   | LHLGKMPYLS GAAYNVAVIS SNQFGPGLNQ TWHIPADTHT EPVALNISVG |
|   |   | 360 370 380 390 400 |
|   |   | TNGTTMYWPA RAQSMTYCIE WQPVGQDGGL ATCSLTAPQD PDPAGMATYS |
|   |   | 410 420 430 440 450 |
|   |   | WSRESGAMGQ EKCYYITIFA SAHPEKLTLW STVLSTYHFG GNASAAGTPH |
|   |   | 460 470 480 490 500 |
|   |   | HVSVKNHSLD SVSVDWAPSL LSTCPGVLKE YVVRCRDEDS KQVSEHPVAP |
|   |   | 510 520 530 540 550 |
|   |   | TETQVTLSGL RAGVAYTVQV RADTAWLRGV WSQPQRFSIE VQVSDWLIFF |
|   |   | 560 570 580 590 600 |
|   |   | ASLGSFLSIL LVGVLGYLGL NRAARHLCPP LPTPCASSAI EFPGGKETWQ |
|   |   | 610 620 630 640 650 |
|   |   | WINPVDFQEE ASLQEALVVE MSWDKGERTE PLEKTELPEG APELALDTEL |
|   |   | 660 |
|   |   | SLEDGDRCKA KM |
| 56 | IL-12p35 human (Uniprot accession no. P29459) | 10 20 30 40 50 |
|   |   | MCHQQLVISW FSLVFLASPL VAIWELKKDV YVVELDWYPD APGEMVVLTC |
|   |   | 60 70 80 90 100 |
|   |   | DTPEEDGITW TLDQSSEVLG SGKTLTIQVK EFGDAGQYTC HKGGEVLSHS |
|   |   | 110 120 130 140 150 |
|   |   | LLLLHKKEDG IWSTDILKDQ KEPKNKTFLR CEAKNYSGRF TCWWLTTIST |
|   |   | 160 170 180 190 200 |

TABLE 4-continued

SEQUENCE TABLE

| SEQ ID NO. | Name | Sequence |
|---|---|---|
| | | DLTFSVKSSR GSSDPQGVTC GAATLSAERV RGDNKEYEYS VECQEDSACP<br>      210            220            230            240            250<br>AAEESLPIEV MVDAVHKLKY ENYTSSFFIR DIIKPDPPKN LQLKPLKNSR<br>      260            270            280            290            300<br>QVEVSWEYPD TWSTPHSYFS LTFCVQVQGK SKREKKDRVF TDKTSATVIC<br>      310            320<br>RKNASISVRA QDRYYSSSWS EWASVPCS |
| 57 | IL-12p40 mouse (Uniprot accession no. P43432) |        10             20             30             40             50<br>MCPQKLTISQ FAIVLLVSPL MAMWELEKDV YVVEVDWTPD APGETVNLTC<br>       60             70             80             90            100<br>DTPEEDDITW TSDQRHGVIG SKGTLTITVK EFLDAGQYTC HKGGETLSHS<br>      110            120            130            140            150<br>HLLLHKKENG IWSTEILKNF KNKTFLKCEA PNYSGRFTCS WLVQRNMDLK<br>      160            170            180            190            200<br>FNIKSSSSSP DSRAVTCGMA SLSAEKVTLD QRDYEKYSVS CQEDVTCPTA<br>      210            220            230            240            250<br>EETLPIELAL EARQQNKYEN YSTSFFIRDI IKPDPPKNLQ MKPLKNSQVE<br>      260            270            280            290            300<br>VSWEYPDSWS TPHSYFSLKF FVRIQRKKEK MKETEEGCNQ KGAGLVEKTS<br>      310            320            330<br>TEVQCKGGNV CVQAQDRYYN SSCSKWACVP CRVRS |
| 58 | ACP63 (Anti-FN CGS-2 scFv) | mdmrvpaqllglllllwlrgarcEVQLVESGGGLVQPGGSLRLSCAASGFTFSSYA<br>MSWVRQAPGKGLEWVSAISGSGGSTYYADSVKGRFTISRDNSKNTLY<br>LQMNSLRAEDTAVYYCARGVGAFRPYRKHEWGQGTLVTVSRggggsgg<br>ggsggggsSSELTQDPAVSVALGQTVRITCQGDSLRSYYASWYQQKPGQA<br>PVLVIYGKNNRPSGIPDRFSGSSGNTASLTTTGAQAEDEADYYCNSSP<br>FEHNLVVFGGGTKLTVLHHHHHHEPEA |
| 59 | ACP34 (Mouse IL-12 fusion protein) | mdmrvpaqllglllllwlrgarcrvipvsgparclsqsrnallkttddmvktareklkhysctaediheditrdqt<br>stlktclplelhknesclatretssttrgsclppqktslmmtlclgsiyedlkmyqtefgainaalqnhnhqqiil<br>dkgmlvaidelmqslnhngetlrqkppvgeadpyrvkmklcillhafstrvvtinrvmgylssaSGGPG<br>PAGMKGLPGSmwelekdvyvvevdwtpdapgetvnltcdtpeedditwtsdqrhgvigsgktltit<br>vkefldagqytchkggetlshshlllhkkengiwsteilknfknktflkceapnysgrftcswlvqrnmdlkf<br>niksssspdsravtcgmaslsaekvadqrdyekysyscqedvtcptaeetlpielalearqqnkyenystsf<br>firdiikpdppknlqmkplknsqvevsweypdswstphsyfaffvriqrkkekmketeegcnqkgafl<br>vektstevqckggnvcvqaqdryynsscskwacvpcmsHHHHHH |
| 60 | ACP35 (Mouse IL-12 fusion protein) | mdmrvpaqllglllllwlrgarcrvipvsgparclsqsrnallkttddmvktareklkhysctaediheditrdqt<br>stlktclplelhknesclatretssttrgsclppqktslmmtlclgsiyedlkmyqtefgainaalqnhnhqqiil<br>dkgmlvaidelmqslnhngetlrqkppvgeadpyrvkmklcillhafstrvvtinrvmgylssaggggsgg<br>ggsggggsSGGPGPAGMKGLPGSggggsggggsggggsmwelekdvyvvevdwtpdapg<br>etvnltcdtpeedditwtsdqrhgvigsgktltitvkefldagqytchkggetlshshlllhkkengiwsteilkn<br>fknktflkceapnysgrftcswlvqrnmdlkfniksssspdsravtcgmaslsaekvtldqrdyekysysc<br>qedvtcptaeetlpielalearqqnkyenystsffirdiikpdppknlqmkplknsqvevsweypdswstph<br>syfslkffvriqrkkekmketeegcnqkgaflvektstevqckggnvcvqaqdryynsscskwacvpervr<br>sHHHHHH |
| 61 | ACP36 (Mouse IL-12 fusion protein) | mdmrvpaqllglllllwlrgarcEVQLVESGGGLVQPGNSLRLSCAASGFTFSKFG<br>MSWVRQAPGKGLEWVSSISGSGRDTLYAESVKGRFTISRDNAKTTLYL<br>QMNSLRPEDTAVYYCTIGGSLSVSSQGTLVTVSSSGGPGPAGMKGLPGS<br>Smwelekdvyvvevdwtpdapgetvnltcdtpeedditwtsdqrhgvigsgktltitvkefldagqytchk<br>ggetlshshlllhkkengiwsteilknfknktflkceapnysgrftcswlvqrnmdlkfniksssspdsravt<br>cgmaslsaekvtldqrdyekysyscqedvtcptaeetlpielalearqqnkyenystsffirdiikpdppknlq<br>mkplknsqvevsweypdswstphsyfslkffvriqrkkekmketeegcnqkgaflvektstevqckggn<br>vcvqaqdryynsscskwacvpcrvrsggggsggggsggggsrvipvsgparclsqsmllkttddmvktar<br>eklkhysctaediheditrdqtstlktclplelhknesclatretssttrgsclppqktslmmtlclgsiyed<br>lkmyqtefgainaalqnhnhqqiildkgmlvaidelmqslnhngetlrqkppvgeadpyrvkmklcillhafst<br>rvvtinrvmgylssaSGGPGPAGMKGLPGSEVQLVESGGGLVQPGNSLRLSCA<br>ASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSHHHH<br>HH |
| 62 | ACP37 (Mouse IL-12 fusion protein) | mdmrvpaqllglllllwlrgarcQVQLQESGGGLVQAGGSLRLSCAASGRIFSIDIM<br>SWYRQAPGKQRELVARITRGGTISYDDSVKGRFTISRDNAKNTVYLQ<br>MNSLKPEDTGVYYCNALYGTDYWGKGTQVTVSSggggsggggsggggsEV<br>QLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTI<br>GGSLSVSSQGTLVTVSSSGGPGPAGMKGLPGSmwelekdvyvvevdwtpdapg<br>etvnltcdtpeedditwtsdqrhgvigsgktltitvkefldagqytchkggetlshshlllhkkengiwsteilkn<br>fknktflkceapnysgrftcswlvqrnmdlkfniksssspdsravtcgmaslsaekvtldqrdyekysysc<br>qedvtcptaeetlpielalearqqnkyenystsffirdiikpdppknlqmkplknsqvevsweypdswstph<br>syfslkffvriqrkkekmketeegcnqkgaflvektstevqckggnvcvqaqdryynsscskwacvpcrvr |

TABLE 4-continued

SEQUENCE TABLE

| SEQ ID NO. | Name | Sequence |
|---|---|---|
| | | sggggsggggsggggsggggsrvipvsgparclsqsrnllkttddmvktareklkhysctaedidheditrdqtstlkt clplelhknesclatretssttrgsclppqktslmmtlclgsiyedlkmyqtefqainaalqnhnhqqiildkg mlvaidelmqslnhngetlrqkppvgeadpyrvkmklcillhafstrvvtinrvmgylssaSGGPGPA GMKGLPGSEVQLVESGGGLVQPGNSLRLSCAASGFTFSKFGMSWVRQ APGKGLEWVSSISGSGRDTLYAESVKGRFTISRDNAKTTLYLQMNSLR PEDTAVYYCTIGGSLSVSSQGTLVTVSSHHHHHH |
| 63 | ACP79 (Mouse IL-12 fusion protein) | mdmrvpaqllglllllwlrgarcQVQLQESGGGLVQAGGSLRLSCAASGRIFSIDIM SWYRQAPGKQRELVARITRGGTISYDDSVKGRFTISRDNAKNTVYLQ MNSLKPEDTGVYYCNALYGTDYWGKGTQVTVSSggggsggggsggggsEV QLVESGGGLVQPGNSLRLSCAASGFTFSKFGMSWVRQAPGKGLEWVS SISGSGRDTLYAESVKGRFTISRDNAKTTLYLQMNSLRPEDTAVYYCTI GGSLSVSSQGTLVTVSSSGGPGPAGMKGLPGSmwelekdvyvvevdwtpdapg etvnltcdtpeedditwtsdqrhgvigsgktltitvkefldagqytchkggetlshshlllhkkengiwsteilkn fknktflkceapnysgrftcswlvqrnmdlkfnikssssspdsravtcgmaslsaekvtldqrdyekysyc qedvtcptaeeetlpielalearqqnkyenystsffirdiikpdppknlqmkplknsqvevsweypdswstph syfslkffvriqrkkekmketeegcnqkgaflvektstevqckggnvcvqaqdryynsscskwacvpcrvr sggggsggggsggggsrvipvsgparclsqsrnllkttddmvktareklkhysctaedidheditrdqtstlkt clplelhknesclatretssttrgsclppqktslmmtlclgsiyedlkmyqtefqainaalqnhnhqqiildkg mlvaidelmqslnhngetlrqkppvgeadpyrvkmklcillhafstrvvtinrvmgylssaSGGPGPA GMKGLPGSEVQLVESGGGLVQPGNSLRLSCAASGFTFSKFGMSWVRQ APGKGLEWVSSISGSGRDTLYAESVKGRFTISRDNAKTTLYLQMNSLR PEDTAVYYCTIGGSLSVSSQGTLVTVSSHHHHHH |
| 64 | ACP80 (Mouse IL-12 fusion protein) | mdmrvpaqllglllllwlrgarcEVQLVESGGGLVQPGNSLRLSCAASGFTFSKFG MSWVRQAPGKGLEWVSSISGSGRDTLYAESVKGRFTISRDNAKTTLYL QMNSLRPEDTAVYYCTIGGSLSVSSQGTLVTVSSSGGPGPAGMKGLPGS Smwelekdvyvvevdwtpdapgetvnltcdtpeedditwtsdqrhgvigsgktltitvkefldagqytchk ggetlshshlllhkkengiwsteilknfknktflkceapnysgrftcswlvqrnmdlkfnikssssspdsravt cgmaslsaekvtldqrdyekysycqedvtcptaeeetlpielalearqqnkyenystsffirdiikpdppknlq mkplknsqvevsweypdswstphsyfslkffvriqrkkekmketeegcnqkgaflvektstevqckggn vcvqaqdryynsscskwacvpervrsggggsggggsggggsrvipvsgparclsqsrnllkttddmvktar eklkhysctaedidheditrdqtstlktclplelhknesclatretssttrgsclppqktslmmtlclgsiyed lkmyqtefqainaalqnhnhqqiildkgmlvaidelmqslnhngetlrqkppvgeadpyrvkmklcillhafst rvvtinrvmgylssaSGGPGPAGMKGLPGSEVQLVESGGGLVQPGNSLRLSCA ASGFTFSKFGMSWVRQAPGKGLEWVSSISGSGRDTLYAESVKGRFTIS RDNAKTTLYLQMNSLRPEDTAVYYCTIGGSLSVSSQGTLVTVSSggggsg ggggsggggsQVQLQESGGGLVQAGGSLRLSCAASGRIFSIDIMSWYRQAPG KQRELVARITRGGTISYDDSVKGRFTISRDNAKNTVYLQMNSLKPEDT GVYYCNALYGTDYWGKGTQVTVSSHHHHHH |
| 65 | ACP91 (Chimeric IL-12 fusion protein) | mdmrvpaqllglllllwlrgarciwelkkdvyvveldwypdapgemvvltcdtpeedgitwtldqssevlg sgkltltiqvkefgdagqytchkggevlshsllllhkkedgiwstdilkdqkepknktflrceaknysgrftcw wlttistdltfsvkssrgssdpqgvtcgaatlsaervrgdnkeyeysvecqedsacpaaeeslpievmvdavh klkyenytssffirdiikpdppknlqlkplknsrqvevsweypdtwstphsyfsltfcvqvqgkskrekkdr vftdktsatvicrknasisvraqdryyssswewasvpcsggggsggggsggggsrvipvsgparclsqsrn llkttddmvktareklkhysctaedidheditrdqtstlktclplelhknesclatretssttrgsclppqkts lmmtlclgsiyedlkmyqtefqainaalqnhnhqqiildkgmlvaidelmqslnhngetlrqkppvgeadpyrv kmklcillhafstrvvtinrvmgylssaggggsggggsggggsggggsggggsggggsggggsggggsgg ggsQSVLTQPPSVSGAPGQRVTISCSGSRSNIGSNTVKWYQQLPGTAPKL LIYYNDQRPSGVPDRFSGSKSGTSASLAITGLQAEDEADYYCQSYDRY THPALLFGTGTKVTVLggggsggggsggggsQVQLVESGGGVVQPGRSLRLS CAASGFTFSSYGMHWVRQAPGKGLEWVAFIRYDGSNKYYADSVKGR FTISRDNSKNTLYLQMNSLRAEDTAVYYCKTHGSHDNWGQGTMVTV SSggggsggggsggggsEVQLVESGGGLVQPGNSLRLSCAASGFTFSKFGMS WVRQAPGKGLEWVSSISGSGRDTLYAESVKGRFTISRDNAKTTLYLQ MNSLRPEDTAVYYCTIGGSLSVSSQGTLVTVSSHHHHHHEPEA |
| 66 | ACP 136 (Chimeric IL-12 fusion protein) | mdmrvpaqllglllllwlrgarciwelkkdvyvveldwypdapgemvvltcdtpeedgitwtldqssevlg sgkltltiqvkefgdagqytchkggevlshsllllhkkedgiwstdilkdqkepknktflrceaknysgrftcw wlttistdltfsvkssrgssdpqgvtcgaatlsaervrgdnkeyeysvecqedsacpaaeeslpievmvdavh klkyenytssffirdiikpdppknlqlkplknsrqvevsweypdtwstphsyfsltfcvqvqgkskrekkdr vftdktsatvicrknasisvraqdryyssswewasvpcsggggsggggsggggsrvipvsgparclsqsrn llkttddmvktareklkhysctaedidheditrdqtstlktclplelhknesclatretssttrgsclppqkts lmmtlclgsiyedlkmyqtefqainaalqnhnhqqiildkgmlvaidelmqslnhngetlrqkppvgeadpyrv kmklcillhafstrvvtinrvmgylssaSGGPGPAGMKGLPGSggggsggggsggggsggggsg gggsggggsQSVLTQPPSVSGAPGQRVTISCSGSRSNIGSNTVKWYQQLPG TAPKLLIYYNDQRPSGVPDRFSGSKSGTSASLAITGLQAEDEADYYCQS YDRYTHPALLFGTGTKVTVLggggsggggsggggsggggsQVQLVESGGGVVQPGR SLRLSCAASGFTFSSYGMHWVRQAPGKGLEWVAFIRYDGSNKYYADS VKGRFTISRDNSKNTLYLQMNSLRAEDTAVYYCKTHGSHDNWGQGT MVTVSSHHHHHHEPEA |

TABLE 4-continued

SEQUENCE TABLE

| SEQ ID NO. | Name | Sequence |
|---|---|---|
| 67 | ACP 138 (Chimeric IL-12 fusion protein) | mdmrvpaqllglllllwlrgarciwelkkdvyvveldwypdapgemvvltcdtpeedgitwtldqssevlg sgkltltiqvkefgdagqytchkggevlshsllllhkkedgiwstdilkdqkepknktflrceaknysgrftcw wltttistdltfsvkssrgssdpqgvtcgaatlsaervrgdnkeyeysvecqedsacpaaeeslpievmvdavh klkyenytssffirdiikpdppknlqlkplknsrqvevsweypdtwstphsyfsltfcvqvqgkskrekkdr vftdktsatvicrknasisvraqdryyssswsewasvpcsggggsggggsggggsrvipvsgparclsqsrn llkttddmvktareklkhysctaedidheditrdqtstlktclplelhknesclatretssttrgsclppqkts lmmtlclgsiyedlkmyqtefqainaalqnhnhqqiildkgmlvaidelmqslnhngetlrqkppvgeadpyrv kmklcillhafstrvvtinrvmgylssaSGGPGPAGMKGLPGSggggsggggsggggsggggsg gggsggggsQSVLTQPPSVSGAPGQRVTISCSGSRSNIGSNTVKWYQQLPG TAPKLLIYYNDQRPSGVPDRFSGSKSGTSASLAITGLQAEDEADYYCQS YDRYTHPALLFGTGTKVTVLggggsggggsggggsQVQLVESGGGVVQPGR SLRLSCAASGFTFSSYGMHWVRQAPGKGLEWVAFIRYDGSNKYYADS VKGRFTISRDNSKNTLYLQMNSLRAEDTAVYYCKTHGSHDNWGQGT MVTVSSggggsggggsggggsEVQLVESGGGLVQPGNSLRLSCAASGFTFSK FGMSWVRQAPGKGLEWVSSISGSGRDTLYAESVKGRFTISRDNAKTTL YLQMNSLRPEDTAVYYCTIGGSLSVSSQGTLVTVSSggggsggggsggggsQ VQLQESGGGLAQAGGSLSLSCAASGFTVSNSVMAWYRQTPGKQREFV AIINSVGSTNYADSVKGRFTISRDNAKNTVYLQMNNLKPEDTAVYVCN RNFDRIYWGQGTQVTVSSHHHHHHEPEA |
| 68 | ACP139 (Chimeric IL-12 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSggggsggggsggggsiw elkkdvyvveldwypdapgemvvltcdtpeedgitwtldqssevlgsgktltiqvkefgdagqytchkgge vlshslllllhkkedgiwstdilkdqkepknktfIrceaknysgrftcwwlttistdlifsvkssrgssdpqgvtcg aatlsaervrgdnkeyeysvecqedsacpaaeeslpievmvdavhklkyenytssffirdiikpdppknlql kplknsrqvevsweypdtwstphsyfsltfcvqvqgkskrekkdrvftdktsatvicrknasisvraqdryys ssswsewasvpcsggggsggggsggggsrvipvsgparclsqsrnllkttddmvktareklkhysctaedid heditrdqtstlktclplelhknesclatretssttrgsclppqktslmmtlclgsiyedlkmyqtefqainaalq nhnhqqiildkgmlvaidelmqslnhngetlrqkppvgeadpyrvkmklcillhafstrvvtinrvmgylssa SGGPGPAGMKGLPGSggggsggggsggggsggggsggggsQSVLTQPPSVS GAPGQRVTISCSGSRSNIGSNTVKWYQQLPGTAPKLLIYYNDQRPSGVP DRFSGSKSGTSASLAITGLQAEDEADYYCQSYDRYTHPALLFGTGTKV TVLggggsggggsggggsQVQLVESGGGVVQPGRSLRLSCAASGFTFSSYGM HWVRQAPGKGLEWVAFIRYDGSNKYYADSVKGRFTISRDNSKNTLYL QMNSLRAEDTAVYYCKTHGSHDNWGQGTMVTVSSggggsggggsggggsE VQLVESGGGLVQPGNSLRLSCAASGFTFSKFGMSWVRQAPGKGLEWV SSISGSGRDTLYAESVKGRFTISRDNAKTTLYLQMNSLRPEDTAVYYCT IGGSLSVSSQGTLVTVSSHHHHHHEPEA |
| 69 | ACP140 (Chimeric IL-12 fusion protein) | mdmrvpaqllglllllwlrgarcQVQLQESGGGLAQAGGSLSLSCAASGFTVSNSV MAWYRQTPGKQREFVAIINSVGSTNYADSVKGRFTISRDNAKNTVYL QMNNLKPEDTAVYVCNRNFDRIYWGQGTQVTVSSSGGPGPAGMKGL PGSiwelkkdvyvveldwypdapgemvvltcdtpeedgitwtldqssevlgsgktltiqvkefgdagqyt chkggevlshsllllhkkedgiwstdilkdqkepknktfIrceaknysgrftcwwlttistdlifsvkssrgssd pqgvtcgaatlsaervrgdnkeyeysvecqedsacpaaeeslpievmvdavhklkyenytssffirdiikpd ppknlqlkplknsrqvevsweypdtwstphsyfsltfcvqvqgkskrekkdrvftdktsatvicrknasisvr aqdryyssswsewasvpcsggggsggggsggggsrvipvsgparclsqsrnllkttddmvktareklkhys ctaedidheditrdqtstlktclplelhknesclatretssttrgsclppqktslmmtlclgsiyedlkmyqtef qainaalqnhnhqqiildkgmlvaidelmqslnhngetlrqkppvgeadpyrvkmklcillhafstrvvtinrv mgylssaSGGPGPAGMKGLPGSggggsggggsggggsggggsggggsggggsQSVLTQ PPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGT GTKVTVLggggsggggsggggsQVQLVESGGGVVQPGRSLRLSCAASGFTFS SYGMHWVRQAPGKGLEWVAFIRYDGSNKYYADSVKGRFTISRDNSK NTLYLQMNSLRAEDTAVYYCKTHGSHDNWGQGTMVTVSSggggsggggs ggggsEVQLVESGGGLVQPGNSLRLSCAASGFTFSKFGMSWVRQAPGK GLEWVSSISGSGRDTLYAESVKGRFTISRDNAKTTLYLQMNSLRPEDT AVYYCTIGGSLSVSSQGTLVTVSSHHHHHHEPEA |
| 70 | ACP117 (Anti-FN CGS-2 scFv) | mdmrvpaqllglllllwlrgarcEVQLVESGGGLVQPGGSLRLSCAASGFTFSSYA MSWVRQAPGKGLEWVSAISGSGGSTYYADSVKGRFTISRDNSKNTLY LQMNSLRAEDTAVYYCARGVGAFRPYRKHEWGQGTLVTVSRggggsgg ggsggggsSSELTQDPAVSVALGQTVRITCQGDSLRSYYASWYQQKPGQA PVLVIYGKNNRPSGIPDRFSGSSSGNTASLTTTGAQAEDEADYYCNSSP FEHNLVVFGGGTKLTVLHHHHHHEPEA |
| 71 | EGFR (G8) Prodrug C1486 | EVQLVESGGGLVQPGNSLRLSCAASGFTFSKFGMSWVRQ<u>GGGGGLDG</u> <u>NEEPGG</u>LEWVSSISGSGRDTLYADSVKGRFTISRDNAKTTLYLQMNSL RPEDTAVYYCTIGGSLSVSSQGTLVTVSSGGGGGKPLGLQARVVGGGGT QTVVTQEPSLTVSPGGTVTLTCASSTGAVTSGNYPNWVQQKPGQAPR GLIGGTKFLVPGTPARFSGSLLGGKAALTLSGVQPEDEAEYYCTLWYS NRWVFGGGTKLTVLGGGGSGGGGSGGGGSEVQLVESGGGLVQPGGS |

TABLE 4-continued

SEQUENCE TABLE

| SEQ ID NO. | Name | Sequence |
|---|---|---|
| | | LKLSCAASGFTFNKYAINWVRQAPGKGLEWVARIRSKYNNYATYYAD QVKDRFTISRDDSKNTAYLQMNNLKTEDTAVYYCVRHANFGNSYISY WAYWGQGTLVTVSSGGGGSGGGGS*EVQLVESGGGLVQPGGSLTLSCAAS GRTFSSYAMGWERQAPGKEREFVVAINWASGSTYYADSVKGRFTISRDNSK NTLYLQMNSLRAEDTAVYYCAAGYQINSGNYNFIWYEYDYWGQGTLVTVSS*HHHHHH |
| 72 | EGFR (G8) Non-cleavable Prodrug C1756 | EVQLVESGGGLVQPGNSLRLSCAASGFTFSKFGMSWVRQ<u>GGGGGLDG NEEPGG</u>LEWVSSISGSGRDTLYADSVKGRFTISRDNAKTTLYLQMNSL RPEDTAVYYCTIGGSLSVSSQGTLVTVSS<u>GGGGSGGGGSGGVVGGGG TQ</u>TVVTQEPSLTVSPGGTVTLTCASSTGAVTSGNYPNWVQQKPGQAP RGLIGGTKFLVPGTPARFSGSLLGGKAALTLSGVQPEDEAEYYCTLWY SNRWVFGGGTKLTVLGGGGSGGGGSGGGGSEVQLVESGGGLVQPGG SLKLSCAASGFTFNKYAINWVRQAPGKGLEWVARIRSKYNNYATYYA DQVKDRFTISRDDSKNTAYLQMNNLKTEDTAVYYCVRHANFGNSYIS YWAYWGQGTLVTVSSGGGGSGGGS*EVQLVESGGGLVQPGGSLTLSCAA SGRTESSYAMGWERQAPGKEREFVVAINWASGSTYYADSVKGRFTISRDNS KNTLYLQMNSLRAEDTAVYYCAAGYQINSGNYNFIWYEYDYWGQGTLVTVS*SHHHHHH |
| 73 | EGFR (G8) Active Drug C1300 | <u>VVGGGGTQ</u>TVVTQEPSLTVSPGGTVTLTCASSTGAVTSGNYPNWVQQ KPGQAPRGLIGGTKFLVPGTPARFSGSLLGGKAALTLSGVQPEDEAEY YCTLWYSNRWVFGGGTKLTVLGGGGSGGGGSGGGGSEVQLVESGG LVQPGGSLKLSCAASGFTFNKYAINWVRQAPGKGLEWVARIRSKYNN YATYYADQVKDRFTISRDDSKNTAYLQMNNLKTEDTAVYYCVRHAN FGNSYISYWAYWGQGTLVTVSSGGGGSGGGS*EVQLVESGGGLVQPGG SLTLSCAASGRTESSYAMGWFRQAPGKEREFVVAINWASGSTYYADSVKGR FTISRDNSKNTLYLQMNSLRAEDTAVYYCAAGYQINSGNYNEKDYEYDYWG QGTLVTVS*SHHHHHH |
| 74 | PSMA Prodrug C1872 | EVQLVESGGGLVQPGNSLRLSCAASGFTFSKFGMSWVRQ<u>GGGGGLDG NEEPGG</u>LEWVSSISGSGRDTLYADSVKGRFTISRDNAKTTLYLQMNSL RPEDTAVYYCTIGGSLSVSSQGTLVTVSSGGGGKPLGLQARVVGGGGT QTVVTQEPSLTVSPGGTVTLTCASSTGAVTSGNYPNWVQQKPGQAPR GLIGGTKFLVPGTPARFSGSLLGGKAALTLSGVQPEDEAEYYCTLWYS NRWVFGGGTKLTVLGGGGSGGGGSGGGGSEVQLVESGGGLVQPGGS LKLSCAASGFTFNKYAINWVRQAPGKGLEWVARIRSKYNNYATYYAD QVKDRFTISRDDSKNTAYLQMNNLKTEDTAVYYCVRHANFGNSYISY WAYWGQGTLVTVSSGGGGSGGGS*EVQLVESGGGLVQPGGSLTLSCAAS RFMISEYHMHWVRQAPGKGLEWVSTINPAGTTDYAESVKGRFTISRDNAKN TLYLQMNSLKPEDTAVYYCDSYGYRGQGTQVTVSS*HHHHHH |
| 75 | PSMA Non-cleavable Prodrug C1873 | EVQLVESGGGLVQPGNSLRLSCAASGFTFSKFGMSWVRQ<u>GGGGGLDG NEEPGG</u>LEWVSSISGSGRDTLYADSVKGRFTISRDNAKTTLYLQMNSL RPEDTAVYYCTIGGSLSVSSQGTLVTVSS<u>GGGGSGGGGSGGVVGGGG TQ</u>TVVTQEPSLTVSPGGTVTLTCASSTGAVTSGNYPNWVQQKPGQAP RGLIGGTKFLVPGTPARFSGSLLGGKAALTLSGVQPEDEAEYYCTLWY SNRWVFGGGTKLTVLGGGGSGGGGSGGGGSEVQLVESGGGLVQPGG SLKLSCAASGFTFNKYAINWVRQAPGKGLEWVARIRSKYNNYATYYA DQVKDRFTISRDDSKNTAYLQMNNLKTEDTAVYYCVRHANFGNSYIS YWAYWGQGTLVTVSSGGGGSGGGS*EVQLVESGGGLVQPGGSLTLSCAA SRFMISEYHMHWVRQAPGKGLEWVSTINPAGTTDYAESVKGRFTISRDNAK NTLYLQMNSLKPEDTAVYYCDSYGYRGQGTQVTVSS*HHHHHH |
| 76 | PSMA Active Drug C1875 | <u>VVGGGGTQ</u>TVVTQEPSLTVSPGGTVTLTCASSTGAVTSGNYPNWVQQ KPGQAPRGLIGGTKFLVPGTPARFSGSLLGGKAALTLSGVQPEDEAEY YCTLWYSNRWVFGGGTKLTVLGGGGSGGGGSGGGGSEVQLVESGG LVQPGGSLKLSCAASGFTFNKYAINWVRQAPGKGLEWVARIRSKYNN YATYYADQVKDRFTISRDDSKNTAYLQMNNLKTEDTAVYYCVRHAN FGNSYISYWAYWGQGTLVTVSSGGGGSGGGS*EVQLVESGGGLVQPGG SLTLSCAASRFMISEYHMHWVRQAPGKGLEWVSTINPAGTTDYAESVKGRF TISRDNAKNTLYLQMNSLKPEDTAVYYCDSYGYRGQGTQVTVSS*HHHHHH |
| 77 | GFP TriTAC C646 | *QVQLVESGGALVQPGGSLRLSCAASGFPVNRYSMRWYRQAPGKEREWVAG MSSAGDRSSYEDSVKGRFTISRDDARNTVYLQMNSLKPEDTAVYYCNVNVG FEYWGQGTQVTVSS*GGGGSGGGGS EVQLVESGGGLVQPGNSLRLSCAAS GFTFSKFGMSWVRQAPGKGLEWVSSISGSGRDTLYADSVKGRFTISRD NAKTTLYLQMNSLRPEDTAVYYCTIGGSLSVSSQGTLVTVSSGGGGSG GGSEVQLVESGGGLVQPGGSLKLSCAASGFTFNKYAINWVRQAPGKG LEWVARIRSKYNNYATYYADQVKDRFTISRDDSKNTAYLQMNNLKTE DTAVYYCVRHANFGNSYISYWAYWGQGTLVTVSSGGGGSGGGGSGG GGSQTVVTQEPSLTVSPGGTVTLTCASSTGAVTSGNYPNWVQQKPGQ APRGLIGGTKFLVPGTPARFSGSLLGGKAALTLSGVQPEDEAEYYCTL WYSNRWVFGGGTKLTVLHHHHHH |

TABLE 4-continued

SEQUENCE TABLE

| SEQ ID NO. | Name | Sequence |
|---|---|---|
| 78 | non-masked/non-cleavable TriTAC C1874 | EVQLVESGGGLVQPGNSLRLSCAASGFTFSKFGMSWVRQAPGKGLEW VSSISGSGRDTLYADSVKGRFTISRDNAKTTLYLQMNSLRPEDTAVYY CTIGGSLSVSSQGTLVTVSSGGGGSGGGGSGGVVGGGGTQTVVTQEPS LTVSPGGTVTLTCASSTGAVTSGNYPNWVQQKPGQAPRGLIGGTKFLV PGTPARFSGSLLGGKAALTLSGVQPEDEAEYYCTLWYSNRWVFGGGT KLTVLGGGSGGGGSGGGGSEVQLVESGGGLVQPGGSLKLSCAASGF TFNKYAINWVRQAPGKGLEWVARIRSKYNNYATYYADQVKDRFTISR DDSKNTAYLQMNNLKTEDTAVYYCVRHANFGNSYISYWAYWGQGT LVTVSSGGGGSGGGSEVQLVESGGGLVQPGGSLTLSCAASRFMISEYH MHWVRQAPGKGLEWVSTINPAGTTDYAESVKGRFTISRDNAKNTLYL QMNSLKPEDTAVYYCDSYGYRGQGTQVTVSSHHHHHH |
| 79 | Blocker 12 (IL-12 blocker) | mdmrvpaqllglllwlrgarcQSVLTQPPSVSGAPGQRVTISCSGSRSNIGSNTVK WYQQLPGTAPKLLIYYNDQRPSGVPDRFSGSKSGTSASLAITGLQAED EADYYCQSYDRYTHPALLFGTGTKVTVLggggsggggsggggsQVQLVESG GGVVQPGRSLRLSCAASGFTFSSYGMHWVRQAPGKGLEWVAFIRYDG SNKYYADSVKGRFTISRDNSKNTLYLQMNSLRAEDTAVYYCKTHGSH DNWGQGTMVTVSSHHHHHH |

INCORPORATION BY REFERENCE

The entire disclosures of all patent and non-patent publications cited herein are each incorporated by reference in their entireties for all purposes.

OTHER EMBODIMENTS

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

The invention claimed is:

1. A pharmaceutical composition comprising at least one of each of:
   a) a human interleukin 12 (IL-12) polypeptide comprising an IL-12 subunit polypeptide selected from IL-12p35 and IL-12p40;
   b) an IL-12 blocking moiety, wherein the IL-12 blocking moiety comprises a ligand-binding domain or fragment of a cognate receptor for the IL-12 polypeptide, or an antibody or antigen-binding fragment of an antibody that binds the IL-12 polypeptide;
   c) a protease-cleavable polypeptide linker; and
   d) a half-life extension element wherein the half-life extension element is human serum albumin, an antigen-binding polypeptide that binds human serum albumin, or an immunoglobulin Fc;
      wherein the IL-12 subunit polypeptide and the IL-12 blocking moiety are operably linked by the protease-cleavable polypeptide linker, the IL-12 polypeptide has attenuated IL-12-receptor activating activity at least about 10 fold less than the IL-12-receptor activating activity of the polypeptide that comprises the IL-12 polypeptide that is produced by cleavage of the protease-cleavable polypeptide linker, and wherein the IL-12 receptor activating activity is assessed using a using a HEK Blue reporter cell assay, with equal amounts on a mole basis of the IL-12 polypeptide and the pharmaceutical composition.

2. The pharmaceutical composition of claim 1, wherein the half-life extension element is operably linked to IL-12p35.

3. The pharmaceutical composition of claim 1, wherein the half-life extension element is operably linked to IL-12p40.

4. The pharmaceutical composition of claim 1, comprising a first polypeptide comprising at least one of each of: a) a human interleukin 12 (IL-12) subunit polypeptide selected from IL-12p35 and IL-12p40; b) an IL-12 blocking moiety; and c) a protease-cleavable polypeptide linker, wherein the IL-12 subunit polypeptide and the IL-12 blocking moiety are operably linked by the protease-cleavable polypeptide linker.

5. The pharmaceutical composition of claim 1, comprising a first polypeptide and a second polypeptide, wherein the first polypeptide comprises at least one of each of: a) a human interleukin 12 (IL-12) subunit polypeptide selected from IL-12p35 and IL-12p40; b) an IL-12 blocking moiety; and c) a protease-cleavable polypeptide linker, wherein the IL-12 subunit polypeptide and the IL-12 blocking moiety are operably linked by the protease-cleavable polypeptide linker; and wherein the second polypeptide comprises a human interleukin 12 (IL-12) subunit polypeptide selected from IL-12p35 and IL-12p40.

6. The pharmaceutical composition of claim 1, further comprising a tumor-specific antigen binding peptide.

7. The pharmaceutical composition of claim 1, comprising a human IL-12p35 subunit polypeptide and a human IL-12p40 subunit polypeptide.

8. The pharmaceutical composition of claim 1, wherein the protease-cleavable polypeptide linker comprises at least one sequence that is capable of being cleaved by a protease selected from the group consisting of a kallikrein, thrombin, chymase, carboxypeptidase A, cathepsin G, cathepsin L, an elastase, PR-3, granzyme M, a calpain, a matrix metalloproteinase (MMP), a fibroblast activation protein (FAP), an ADAM metalloproteinase, a plasminogen activator, a cathepsin, a caspase, a tryptase, and a tumor cell surface protease.

9. The pharmaceutical composition of claim 1, wherein IL-12 blocking moiety inhibits activation of the IL-12 receptor by the human IL-12 polypeptide.

10. The pharmaceutical composition of claim 1, wherein the antibody fragment that binds to IL-12 is a single domain antibody, Fab or scFv.

11. The pharmaceutical composition of claim 1, wherein the IL-12 polypeptide comprises a naturally-occurring IL-12 polypeptide sequence or a functional fragment thereof.

12. The pharmaceutical composition of claim 1, wherein the protease cleavable polypeptide linker comprises a sequence that is cleaved by cathepsin selected from the group consisting of cathepsin B, cathepsin C, cathepsin D, cathepsin E, cathepsin K, cathepsin L, and cathepsin G.

13. The pharmaceutical composition of claim 1, wherein the protease cleavable polypeptide linker comprises a sequence that is cleaved by a matrix metalloprotease (MMP) is selected from the group consisting of MMP1, MMP2, MMP3, MMP8, MMP9, MMP10, MMP11, MMP12, MMP13, and MMP14.

14. The pharmaceutical composition of claim 1, wherein the serum half-life of the IL-12 polypeptide that is produced by cleavage of the protease-cleavable polypeptide linker is comparable to the half-life of naturally occurring IL-12.

15. The pharmaceutical composition of claim 1, wherein the IL-12 polypeptide that is produced by cleavage if the protease-cleavable polypeptide linker does not comprise the half-life extension element or IL-12 blocking moiety.

16. The pharmaceutical composition of claim 1, wherein the cognate receptor for the IL-12 is IL-12R beta 1 (IL-12Rβ1) or IL12R beta 2 (IL-12Rβ2).

* * * * *